(12) United States Patent
Chenard et al.

(10) Patent No.: US 9,440,972 B2
(45) Date of Patent: Sep. 13, 2016

(54) PYRIDO[2,3-D]PYRIMIDINE-2,4(1H,3H)-DIONE DERIVATIVES

(71) Applicant: Hydra Biosciences, Inc., Cambridge, MA (US)

(72) Inventors: Bertrand L. Chenard, Waterford, CT (US); Randall J. Gallaschun, Lebanon, CT (US)

(73) Assignee: Hydra Biosciences, Inc., Cambridge, MA (US)

( * ) Notice: Subject to any disclaimer, the term of this patent is extended or adjusted under 35 U.S.C. 154(b) by 0 days.

(21) Appl. No.: 14/822,135

(22) Filed: Aug. 10, 2015

(65) Prior Publication Data

US 2016/0046624 A1 Feb. 18, 2016

Related U.S. Application Data

(60) Provisional application No. 62/035,581, filed on Aug. 11, 2014.

(51) Int. Cl.
*A61K 31/519* (2006.01)
*C07D 471/04* (2006.01)

(52) U.S. Cl.
CPC ........... *C07D 471/04* (2013.01); *A61K 31/519* (2013.01)

(58) Field of Classification Search
CPC ................................................. C07D 471/04
See application file for complete search history.

(56) References Cited

U.S. PATENT DOCUMENTS

| | | | | |
|---|---|---|---|---|
| 4,536,518 A * | 8/1985 | Welch, Jr. | ............... | C07C 43/21 514/555 |
| 2009/0069347 A1* | 3/2009 | Bakthavatchalam | | C07D 471/04 514/260.1 |
| 2012/0041004 A1* | 2/2012 | Chaudhari | ............ | A61K 31/519 514/262.1 |
| 2012/0178766 A1* | 7/2012 | Chaudhari | ............ | C07D 495/04 514/260.1 |
| 2015/0190366 A1* | 7/2015 | Housley | ................ | A61K 31/352 514/6.5 |
| 2016/0039772 A1* | 2/2016 | Chenard | ............... | C07D 235/26 514/266.31 |
| 2016/0039815 A1* | 2/2016 | Chenard | ............... | C07D 471/04 514/264.1 |
| 2016/0039831 A1* | 2/2016 | Chenard | ............... | C07D 487/04 514/265.1 |
| 2016/0039841 A1* | 2/2016 | Chenard | ............... | C07D 495/04 514/260.1 |
| 2016/0046624 A1* | 2/2016 | Chenard | ............... | C07D 471/04 514/264.1 |

FOREIGN PATENT DOCUMENTS

WO WO 02064572 A1 * 8/2002 ........... A61K 31/517
WO WO-2010017368 A2   2/2010

OTHER PUBLICATIONS

N.A. Lack et al., 54 Journal of Medicinal Chemistry, 8563-8573 (2011).*
CAS Registry Numbers (Indexed 2007).*
C. Hong et al., 138 Brain, 3030-3047 (2015).*
K.D. Phelan et al., 83 Molecular Pharmacology, 429-438 (2013).*
M. Raychaudhuri et al., 2011 International Journal of Alzheimer's Disease, 1-5 (2011).*
J. Richter et al., 171 British Journal of Pharmacology, 158-170 (2014).*
U.S. Appl. No. 14/822,135, Alexander R. Pagano.*
C-O Wong et al., 159 British Journal of Pharmacology, 1486-1496 (2010).*
Miller et al. "Identification of ML204, a Novel Potent Antagonist that Selectively Modulates Native TRPC4/C5 Ion Channels," J Bio Chem, 286(38):33436-33446 (2011).

* cited by examiner

*Primary Examiner* — Alexander R Pagano
(74) *Attorney, Agent, or Firm* — McCarter & English, LLP; Steven G. Davis; Kathryn M. Kizer

(57) ABSTRACT

This invention relates to novel Pyrido[2,3-d]pyrimidine-2,4(1H,3H)-dione derivatives of Formula (I):

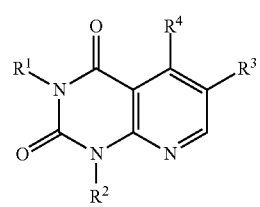

and their use as TRPC5 modulators, pharmaceutical compositions containing the same, and methods of using the same as agents for the treatment of TRPC5 receptor mediated disorders or conditions. $R^1$, $R^2$, $R^3$ and $R^4$ have meanings given in the description.

16 Claims, No Drawings

PYRIDO[2,3-D]PYRIMIDINE-2,4(1H,3H)-DIONE DERIVATIVES

RELATED APPLICATIONS

The present application is a U.S. Non-Provisional Application which claims priority to U.S. Provisional Patent Application No. 62/035,581, filed Aug. 11, 2014, the entirety of which application is hereby incorporated herein by reference.

FIELD OF THE INVENTION

This invention relates to novel Pyrido[2,3-d]pyrimidine-2,4(1H,3H)-dione derivatives and their use as TRPC5 modulators, pharmaceutical compositions containing the same, and methods of using the same as agents for the treatment of TRPC5 receptor mediated disorders or conditions.

BACKGROUND

A variety of ion channel proteins exist to mediate ion flux across cellular membranes. The proper expression and function of ion channel proteins is essential for the maintenance of cell function, intracellular communication, and the like. Numerous diseases are the result of misregulation of membrane potential or aberrant calcium handling. Given the central importance of ion channels in modulating membrane potential and ion flux in cells, identification of agents that can promote or inhibit particular ion channels are of great interest as research tools and as possible therapeutic agents.

Cation channels such as TRPC5 modulate the flux of calcium and sodium ions across cellular membranes. Sodium and calcium influx leads to a depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPC5 also alters the intracellular free calcium concentration. Calcium is a ubiquitous second messenger molecule within the cell and the alterations in intracellular calcium levels have profound effects on signal transduction and gene expression. Thus, activation of non-selective cation channels such as TRPC5 can lead to changes in gene expression and cellular phenotype. Gene expression events include, but are not limited to, production of mRNAs encoding cell surface receptors, ion channels, and kinases. These changes in gene expression can lead to hyperexcitability in that cell.

Transient receptor potential (TRP) homomeric TRPC5 ion channels are signal transduction gated, $Ca^{2+}$-permeable channels predominantly expressed in the neurons. TRPC5 forms homomultimeric structures such as tetramers (i.e., TRPC5 homomultimers) and heteromultimeric structures such as tetramers (i.e., TRPC5-TRPC1 heteromultimers). Unless expressly stated otherwise, when the term TRPC5 is used herein, for example, when identifying a modulator of TRPC5 such as a TRPC5 antagonist, the term TRPC5 is used generically so as to include either or both of a TRPC5 homomultimer or a heteromultimer (e.g., TRPC5-TPRC1 or TRPC5-TRPC4 heteromultimer). Examples of TRPC5 in the literature include the following: Nature. 2008 Jan. 3; 451 (7174):69-72; Mol Pharmacol. 2008 January; 73 (1):42-9; J Biol Chem. 2007 Nov. 16; 282 (46):33868-78; Biochem Biophys Res Commun. 2008 Jan. 11; 365 (2):239-45; J Biol Chem. 2006 Nov. 3; 281 (44):33487-96; Eur J Pharmacol. 2005 Mar. 14; 510 (3):217-22; J Biol Chem. 2006 Feb. 24; 281 (8):4977-82; Biochem Soc Trans. 2007 February; 35 (Pt 1):101-4; Handb Exp Pharmacol. 2007; (179):109-23; J Biol Chem. 2005 Mar. 25; 280 (12):10997-1006; J Physiol. 2006 Jan. 15; 570 (Pt 2):219-35; and Nat Neurosci. (2003) 6: 837-45.

Modulating the function of TRPC5 proteins provides a means of modulating calcium homeostasis, sodium homeostasis, membrane polarization, and/or intracellular calcium levels, and compounds that can modulate TRPC5 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

SUMMARY OF THE INVENTION

The present invention provides compounds of Formula (I):

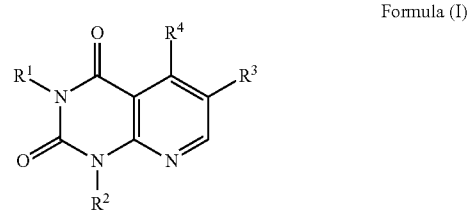

Formula (I)

or a pharmaceutically acceptable salt thereof, wherein constituent members are provided herein.

The present invention further provides methods of treating a TRPC5 mediated disorder in a subject, e.g. a human subject, comprising administering to the subject a compound or composition of a compound of Formula (I) or a pharmaceutically acceptable salt thereof, to thereby treat the subject, e.g., a human subject.

The present invention provides methods and compositions for treating conditions such as a neuropsychiatric disorder, a neurodegenerative disorder, nephropathy, and seizure disorder by modulating the activity of the transient receptor potential cation channel subfamily C, member 5 (TRPC5), which can exist in homomultimeric form as well as heteromultimeric form with other ion channels such as TRPC1 or TRPC3 (i.e., TRPC5-TRPC1 and TRPC1-TRPC3-TRPC5). The compound of Formula (I) modulate the function of TRPC5 by inhibiting a TRPC5-mediated ion flux or by inhibiting the inward current, the outward current, or both currents mediated by TRPC5. The inhibition of a particular current is the ability to inhibit or reduce such current (e.g., inward and/or outward) in an in vitro or an in vivo assay. The activation of a particular current is the ability to activate or increase such current (e.g., inward and/or outward) in an in vitro or an in vivo assay.

DETAILED DESCRIPTION OF THE INVENTION

The present invention provides a compound of Formula (I):

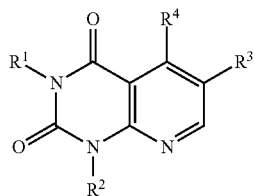

Formula (I)

or a pharmaceutically acceptable salt thereof, wherein:

$R^1$ is $C_2$-$C_{10}$ hydroxyalkyl, optionally substituted with 1-3 $R^6$;

$R^2$ is H, $C_1$-$C_6$ alkyl, $C_1$-$C_6$ hydroxyalkyl, $C_3$-$C_{10}$ cycloalkyl, $C_2$-$C_6$ alkenyl, $C_2$-$C_6$ alkynyl, or $C_1$-$C_6$ alkoxy;

$R^3$ is $C_1$-$C_6$ alkyl, $C_2$-$C_6$ alkenyl, $C_2$-$C_6$ alkynyl, $C_1$-$C_6$ acyl, $C_3$-$C_{10}$ cycloalkyl, $C_1$-$C_6$ alkoxy, $C_4$-$C_{10}$ cycloalkyloxy, halo, $C_1$-$C_6$haloalkyl, $C_1$-$C_6$haloalkoxy, hydroxyl, $C_1$-$C_{10}$ hydroxyalkyl, alkylthio, thionyl, sulfonyl, sulfonamidyl, $C_6$-$C_{12}$ aryl, 5-14-membered heteroaryl, $C_6$-$C_{12}$ aryl-$C_1$-$C_6$ alkyl, 5-14-membered heteroaryl-$C_1$-$C_6$ alkyl, $C_6$-$C_{12}$ aryloxy, —O—$C_6$-$C_{12}$ aryl-$C_1$-$C_6$ alkyl, —O—$C_1$-$C_6$ alkyl-$C_6$-$C_{12}$ aryl, —$C_6$-$C_{12}$ aryl-$C_1$-$C_6$ alley-O, 5-14-membered heteroaryloxy, 3-18-membered heterocycloalkyl, amino, $C_1$-$C_6$ alkylamino, $C_2$-$C_{12}$ dialkylamino,—C(O)NH—,—C(O)N—$C_1$-$C_6$ alkyl-, —NHC(O)—, —N— $C_1$-$C_6$ alkyl C(O)—, urea, sulfonylurea, nitro, or cyano, optionally substituted with 1-5 $R^5$;

$R^4$ is $C_1$-$C_6$ alkyl, $C_1$-$C_6$ acyl, $C_3$-$C_{10}$ cycloalkyl, $C_1$-$C_6$ alkoxy, $C_4$-$C_{10}$ cycloalkyloxy, halo, $C_1$-$C_6$haloalkyl, $C_1$-$C_6$haloalkoxy, hydroxyl, alkylthio, thionyl, sulfonyl, sulfonamidyl, $C_6$-$C_{12}$ aryl, 5-14-membered heteroaryl, $C_6$-$C_{12}$ aryl-$C_1$-$C_6$ alkyl, 5-14-membered heteroaryl-$C_1$-$C_6$ alkyl, $C_6$-$C_{12}$ aryloxy, —O—$C_6$-$C_{12}$ aryl-$C_1$-$C_6$ alkyl, —O—$C_1$-$C_6$ alkyl-$C_6$-$C_{12}$ aryl, —$C_6$-$C_{12}$ aryl-$C_1$-$C_6$ alky-O, 5-14-membered heteroaryl-$C_1$-$C_6$ alkyl, 5-14-membered heteroaryloxy, 3-18-membered heterocycloalkyl, amino, $C_1$-$C_6$ alkylamino, $C_2$-$C_{12}$ dialkylamino, —C(O)NH—,—C(O)N—$C_1$-$C_6$ alkyl-,—NHC(O)—, —N— $C_1$-$C_6$ alkyl C(O)—, urea, sulfonylurea, nitro, or cyano, optionally substituted with 1-5 $R^5$;

each $R^5$ is independently $C_1$-$C_6$ alkyl, $C_2$-$C_6$ alkenyl, $C_2$-$C_6$ alkynyl, $C_1$-$C_6$ acyl, $C_1$-$C_6$ alkoxy, $C_4$-$C_{10}$ cycloalkyloxy, halo, $C_1$-$C_6$haloalkyl, $C_1$-$C_6$haloalkoxy, hydroxy, $C_1$-$C_{10}$ hydroxyalkyl, amino, $C_6$-$C_{12}$ aryl, 5-14-membered heteroaryl, $C_6$-$C_{12}$ aryl-$C_1$-$C_6$ alkyl, $C_6$-$C_{12}$ aryloxy, O—$C_6$-$C_{12}$ aryl-$C_1$-$C_6$ alkyl, —O— $C_1$-$C_6$ alkyl-$C_6$-$C_{12}$ aryl, —$C_6$-$C_{12}$ aryl-$C_1$-$C_6$ alky-O, or 5-14-membered heteroaryloxy, each of which is optionally substituted with 1-5 $R^6$; and each $R^6$ is independently $C_1$-$C_6$ alkyl, $C_1$-$C_6$ alkoxy, $C_3$-$C_{10}$ cycloalkyl, halo, $C_1$-$C_6$ haloalkyl, $C_1$-$C_6$ haloalkoxy, hydroxyl, amino, $C_1$-$C_6$ alkylamino, $C_2$-$C_{12}$ dialkylamino, cyano, nitro, —C(O)NH—, —C(O)N—$C_1$-$C_6$ alkyl-,—NHC(O)—, —N—$C_1$-$C_6$ alkyl C(O)—, —C(O)O—$C_1$-$C_6$ alkyl, —C(O)OH, —C(O)O—$C_1$-$C_6$ alkyl, —C(O)—$C_1$-$C_6$ alkyl, acyl, nitro, or cyano.

In a second embodiment, in the general formula I, $R^2$, $R^3$, $R^4$, $R^5$, and $R^6$ have the same meaning as defined in the preceding embodiment and $R^1$ is 3-hydroxypropyl; or a pharmaceutically acceptable salt thereof.

In another embodiment, in the general formula I, $R^1$, $R^3$, $R^4$, $R^5$, and $R^6$ have the same meaning as defined in the preceding embodiment and $R^2$ is $C_1$-$C_4$ alkyl.

In another embodiment, in the general formula I, $R^1$, $R^3$, $R^4$, $R^5$, and $R^6$ have the same meaning as defined in the preceding embodiment and $R^2$ is methyl.

In another embodiment, in the general formula I, $R^1$, $R^2$, and $R^4$ have the same meaning as defined in the preceding embodiment and $R^3$ is $C_1$-$C_4$ alkoxy, $C_2$ arylalkoxy, $C_2$ arylalkyl, or aryl, the latter three groups optionally substituted with one or more halogens, —$CF_3$, —$OCF_3$.

In another embodiment, in the general formula I, $R^1$, $R^2$, and $R^4$ have the same meaning as defined in the preceding embodiment and $R^3$ is, propyloxy, methoxypyridine, phenoxy, propyloxy, phenyl or benzyl, the latter five groups optionally substituted with one or more halogens, —$CF_3$, —$OCF_3$ In another embodiment, in the general formula I, $R^1$, $R^2$, and $R^4$ have the same meaning as defined in the preceding embodiment and $R^3$ is

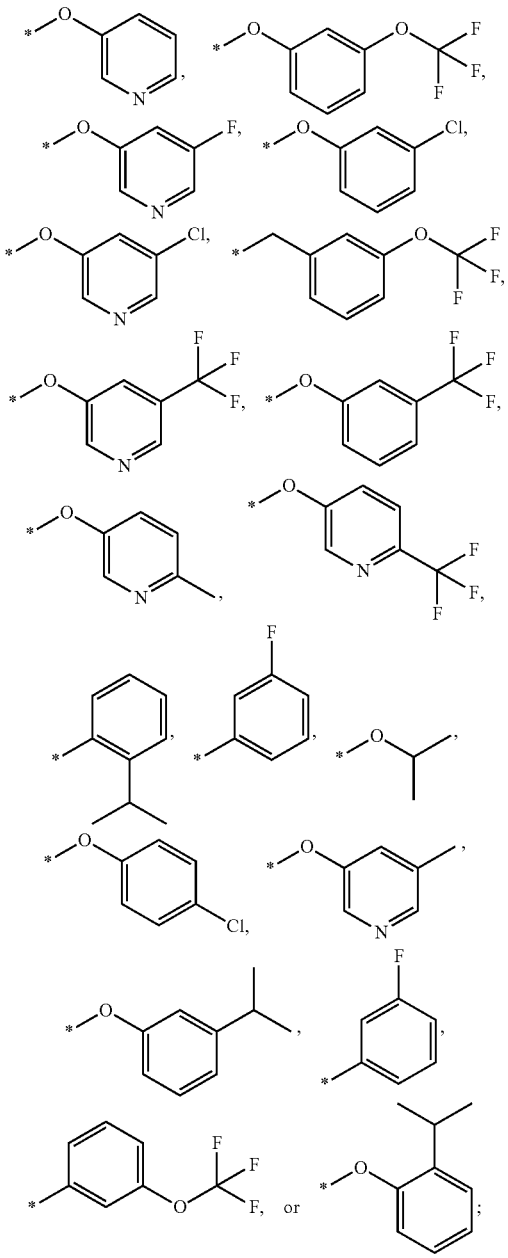

or a pharmaceutically acceptable salt thereof.

In another embodiment, in the general formula I, $R^1$, $R^2$, and $R^3$ have the same meaning as defined in the preceding embodiment and R⁴ is C₂-C₆ alkyl, C₂-C₆ alkoxy, C₂-C₄ arylalkoxy or C₂-C₄ arylalkyl, the latter two groups optionally substituted one or more halogens or —CF₃.

In another embodiment, in the general formula I, R¹, R², and R³ have the same meaning as defined in the preceding embodiment and R⁴ is C₅ alkyl, C₅ alkoxy, benzyl, phenoxy, or ethylpyridine, the latter three groups optionally substituted with one or more halogens or —CF₃.

In another embodiment, in the general formula I, R¹, R², and R³ have the same meaning as defined in the preceding embodiment and R⁴ is chlorobenzyl, methylpentane, methylpentanol, chlorophenylethanol, or fluorobenzyl, trifluoromethylbenzyl, trifluoromethyl-3-ethylpyridine.

In another embodiment, in the general formula I, R¹, R², and R³ have the same meaning as defined in the preceding embodiment and R⁴ is

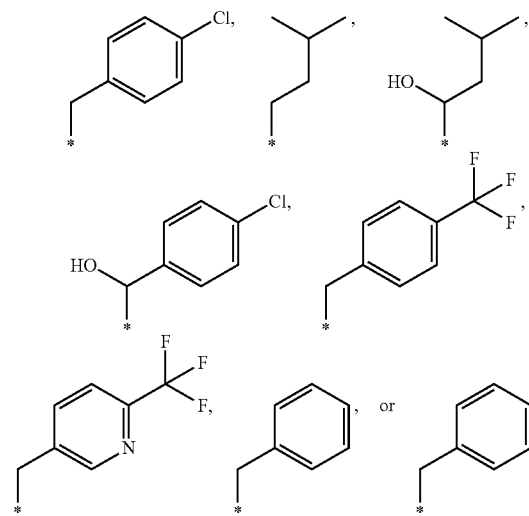

A further embodiment of the present invention comprises compounds of formula I in which R¹ is 3-hydroxypropyl;
R² is methyl;
R³ is

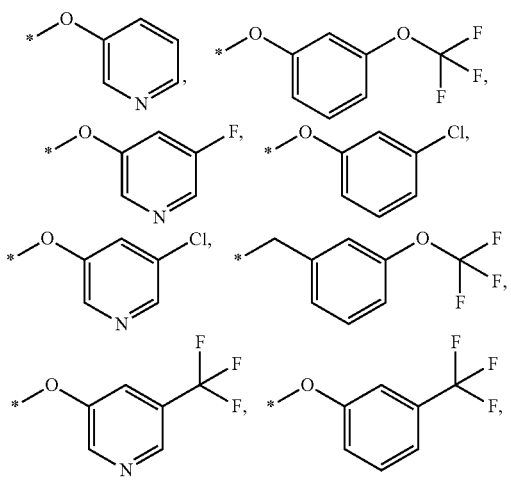

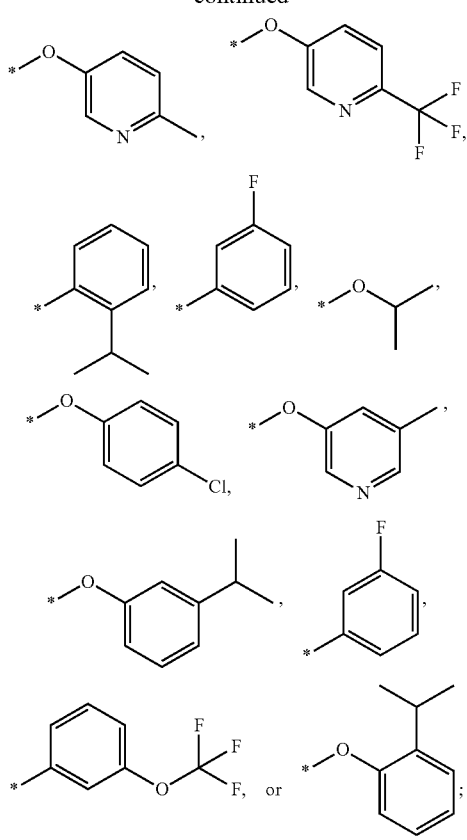

and
R⁴ is

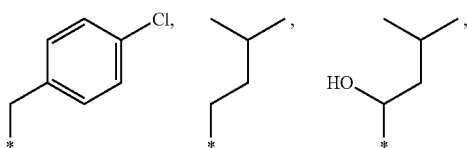

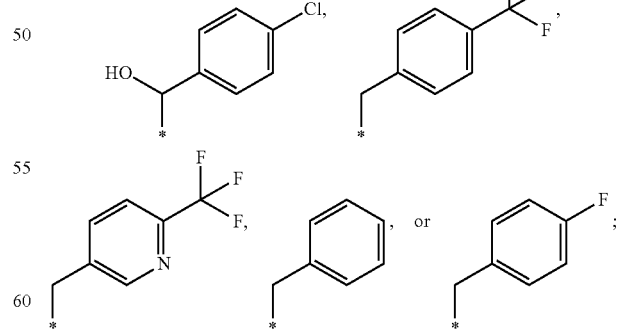

or a pharmaceutically acceptable salt thereof.

In certain embodiments, exemplary compounds of Formula (I) include the compounds described in Table 1 and in the Examples.

TABLE 1

| Compound Number | Structure |
|---|---|
| 14 | 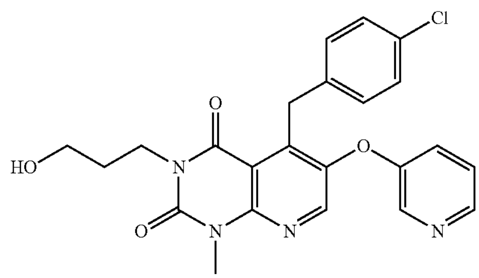 [SMILES: Cn1c(=O)n(CCCO)c(=O)c2c(Cc3ccc(Cl)cc3)c(Oc3cccnc3)cnc21] |
| 15 | 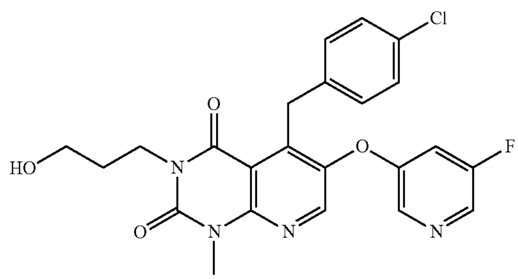 [SMILES: Cn1c(=O)n(CCCO)c(=O)c2c(Cc3ccc(Cl)cc3)c(Oc3cncc(F)c3)cnc21] |
| 16 | 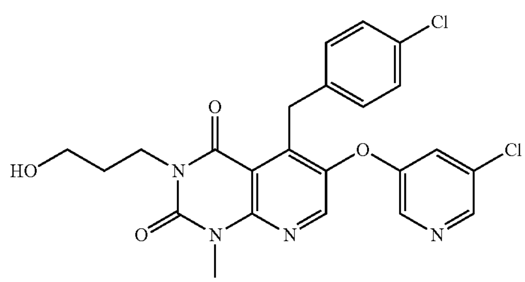 [SMILES: Cn1c(=O)n(CCCO)c(=O)c2c(Cc3ccc(Cl)cc3)c(Oc3cncc(Cl)c3)cnc21] |
| 17 | 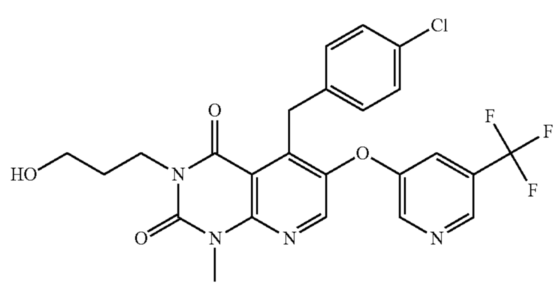 [SMILES: Cn1c(=O)n(CCCO)c(=O)c2c(Cc3ccc(Cl)cc3)c(Oc3cncc(C(F)(F)F)c3)cnc21] |
| 18 | 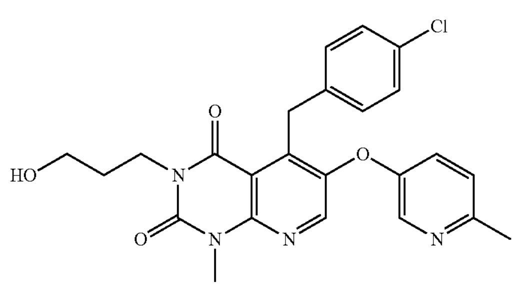 [SMILES: Cc1ccc(Oc2cnc3c(c2Cc2ccc(Cl)cc2)c(=O)n(CCCO)c(=O)n3C)cn1] |

TABLE 1-continued

| Compound Number | Structure |
| --- | --- |
| 19 | 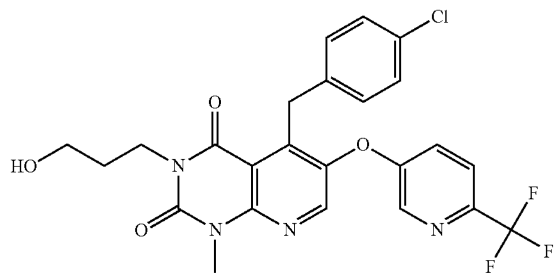 [SMILES: Cn1c(=O)n(CCCO)c(=O)c2c(Cc3ccc(Cl)cc3)c(Oc3ccc(C(F)(F)F)nc3)cnc21] |
| 20 | 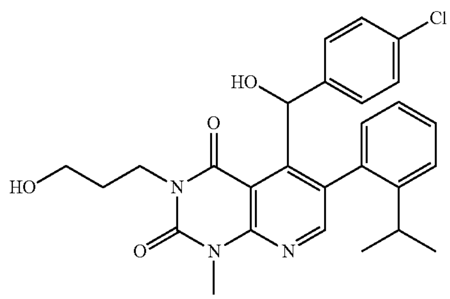 [SMILES: CC(C)c1ccccc1-c1cnc2c(c1C(O)c1ccc(Cl)cc1)c(=O)n(CCCO)c(=O)n2C] |
| 21 | 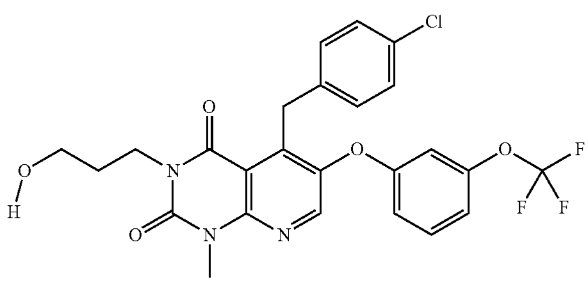 [SMILES: Cn1c(=O)n(CCCO)c(=O)c2c(Cc3ccc(Cl)cc3)c(Oc3cccc(OC(F)(F)F)c3)cnc21] |
| 22 | 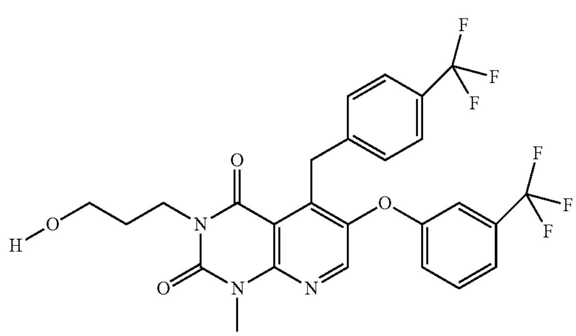 [SMILES: Cn1c(=O)n(CCCO)c(=O)c2c(Cc3ccc(C(F)(F)F)cc3)c(Oc3cccc(C(F)(F)F)c3)cnc21] |
| 23 | 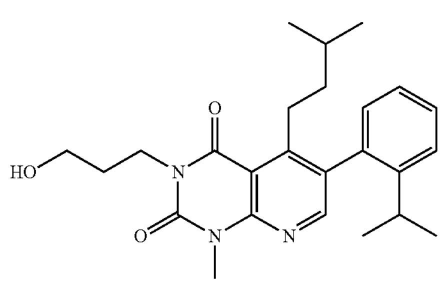 [SMILES: CC(C)CCc1c(-c2ccccc2C(C)C)cnc2c1c(=O)n(CCCO)c(=O)n2C] |

TABLE 1-continued

| Compound Number | Structure |
|---|---|
| 24 | (chemical structure) |
| 25 | (chemical structure) |
| 26 | (chemical structure) |
| 27 | (chemical structure) |
| 28 | (chemical structure) |

TABLE 1-continued

| Compound Number | Structure |
|---|---|
| 29 | 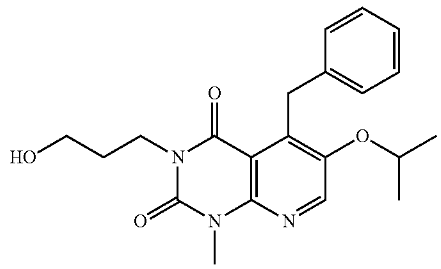 [SMILES: CC(C)Oc1cnc2c(c1Cc1ccccc1)c(=O)n(CCCO)c(=O)n2C] |
| 30 | 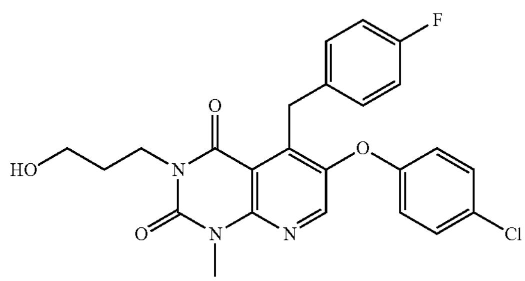 [SMILES: Cn1c(=O)n(CCCO)c(=O)c2c(Cc3ccc(F)cc3)c(Oc3ccc(Cl)cc3)cnc21] |
| 31 | 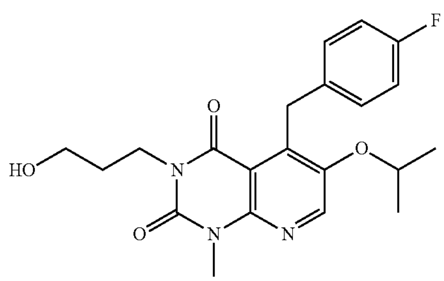 [SMILES: CC(C)Oc1cnc2c(c1Cc1ccc(F)cc1)c(=O)n(CCCO)c(=O)n2C] |
| 32 | 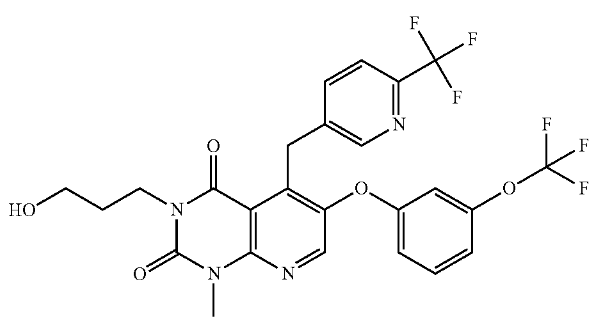 [SMILES: Cn1c(=O)n(CCCO)c(=O)c2c(Cc3ccc(C(F)(F)F)nc3)c(Oc3cccc(OC(F)(F)F)c3)cnc21] |
| 33 | 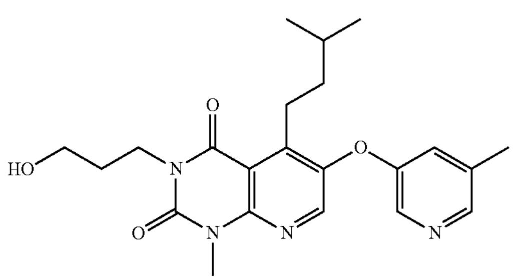 [SMILES: Cc1cncc(Oc2cnc3c(c2CCC(C)C)c(=O)n(CCCO)c(=O)n3C)c1] |

TABLE 1-continued

| Compound Number | Structure |
| --- | --- |
| 34 | 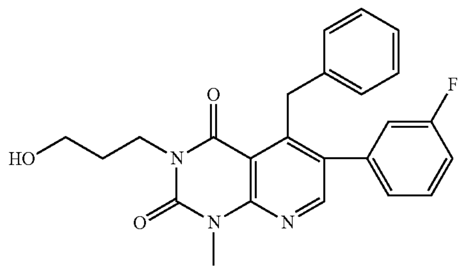 [SMILES: Cn1c(=O)n(CCCO)c(=O)c2c(Cc3ccccc3)c(-c3cccc(F)c3)cnc21] |
| 35 | 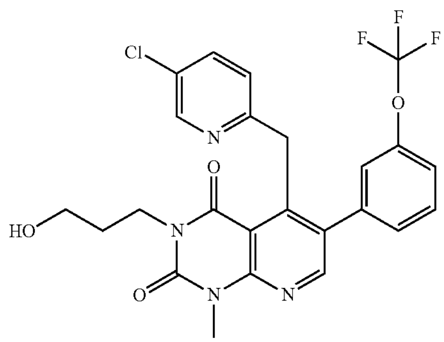 [SMILES: Cn1c(=O)n(CCCO)c(=O)c2c(Cc3ccc(Cl)cn3)c(-c3cccc(OC(F)(F)F)c3)cnc21] |
| 36 | 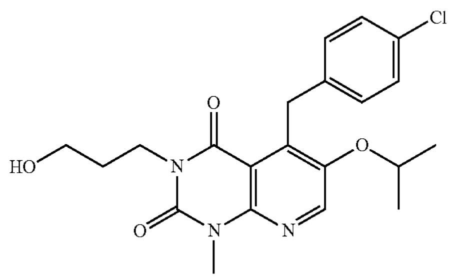 [SMILES: CC(C)Oc1cnc2c(c1Cc1ccc(Cl)cc1)c(=O)n(CCCO)c(=O)n2C] |
| 37 | 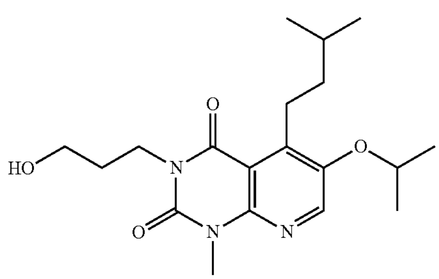 [SMILES: CC(C)CCc1c(OC(C)C)cnc2c1c(=O)n(CCCO)c(=O)n2C] |
| 38 | 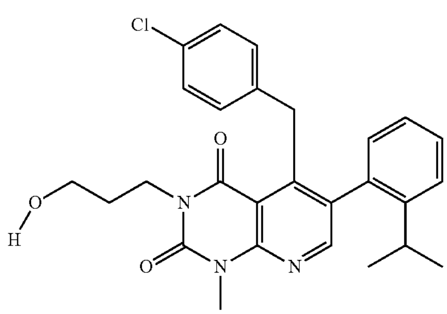 [SMILES: CC(C)c1ccccc1-c1cnc2c(c1Cc1ccc(Cl)cc1)c(=O)n(CCCO)c(=O)n2C] |

TABLE 1-continued

| Compound Number | Structure |
| --- | --- |
| 39 | 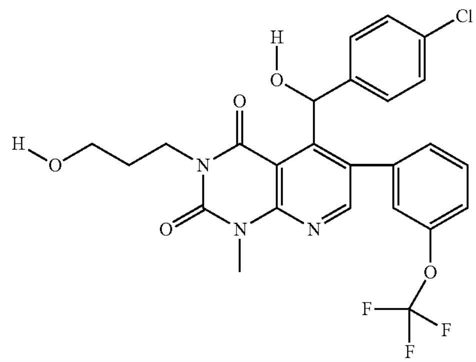 [SMILES: Cn1c(=O)n(CCCO)c(=O)c2c(C(O)c3ccc(Cl)cc3)c(-c3cccc(OC(F)(F)F)c3)cnc21] |
| 40 | 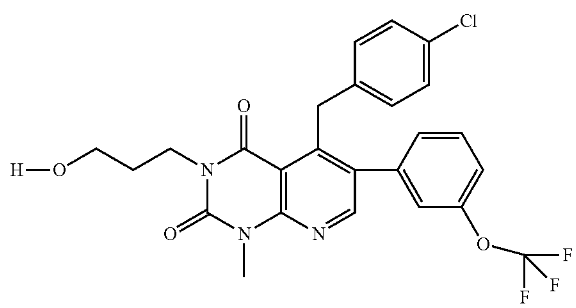 [SMILES: Cn1c(=O)n(CCCO)c(=O)c2c(Cc3ccc(Cl)cc3)c(-c3cccc(OC(F)(F)F)c3)cnc21] |
| 41 | 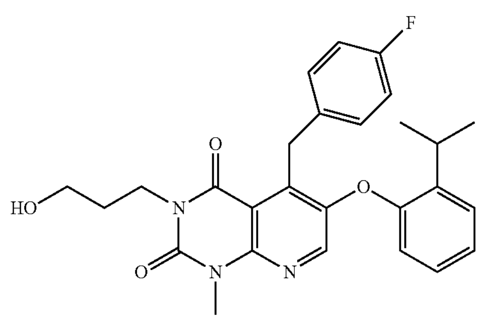 [SMILES: CC(C)c1ccccc1Oc1cnc2c(c1Cc1ccc(F)cc1)c(=O)n(CCCO)c(=O)n2C] |
| 42 | 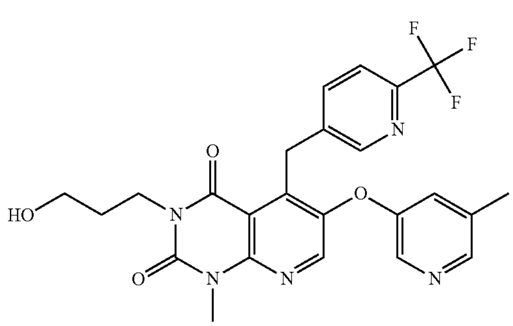 [SMILES: Cc1cncc(Oc2cnc3c(c2Cc2ccc(C(F)(F)F)nc2)c(=O)n(CCCO)c(=O)n3C)c1] |

TABLE 1-continued

| Compound Number | Structure |
|---|---|
| 43 | 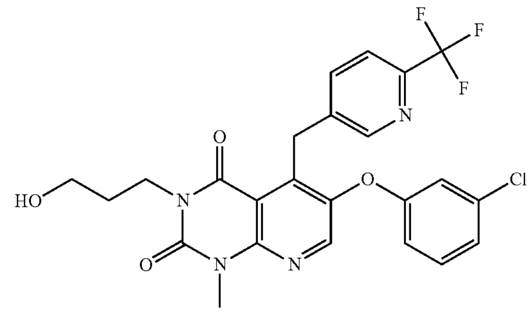 [SMILES: Cn1c(=O)n(CCCO)c(=O)c2c(Cc3ccc(C(F)(F)F)nc3)c(Oc3cccc(Cl)c3)cnc21] |
| 44 | 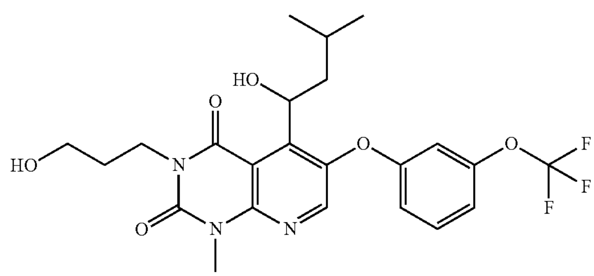 [SMILES: CC(C)CC(O)c1c(Oc2cccc(OC(F)(F)F)c2)cnc2c1c(=O)n(CCCO)c(=O)n2C] |
| 45 | 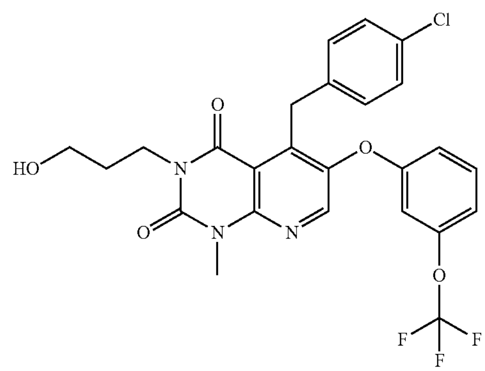 [SMILES: Cn1c(=O)n(CCCO)c(=O)c2c(Cc3ccc(Cl)cc3)c(Oc3cccc(OC(F)(F)F)c3)cnc21] |
| 46 | 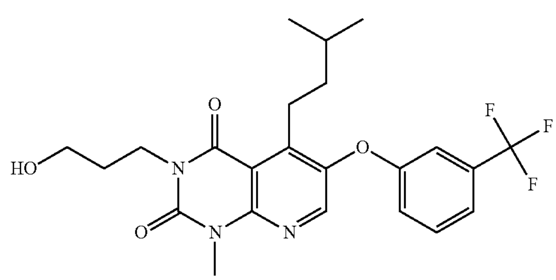 [SMILES: CC(C)CCc1c(Oc2cccc(C(F)(F)F)c2)cnc2c1c(=O)n(CCCO)c(=O)n2C] |
| 47 | 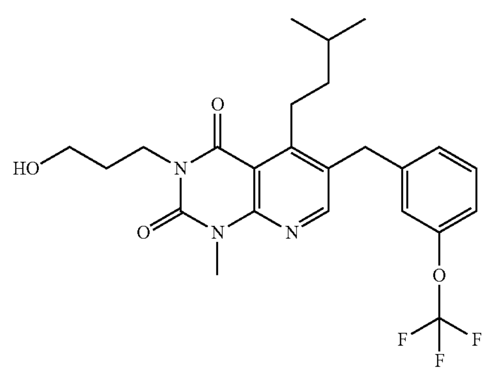 [SMILES: CC(C)CCc1c(Cc2cccc(OC(F)(F)F)c2)cnc2c1c(=O)n(CCCO)c(=O)n2C] |

TABLE 1-continued

| Compound Number | Structure |
|---|---|
| 48 | *(structure: pyrido-pyrimidine-2,4-dione with N-(3-hydroxypropyl), N-methyl, 5-isopentyl, 6-(3-chlorophenoxy) substituents)* |
| 49 | *(structure: pyrido-pyrimidine-2,4-dione with N-(3-hydroxypropyl), N-methyl, 5-isopentyl, 6-(3-trifluoromethoxyphenoxy) substituents)* |

The present invention further provides compositions comprising a compound of Formula (I) and a pharmaceutically acceptable carrier.

The present invention further provides methods of treating a TRPC5 mediated disorder in a subject, e.g. a human subject, comprising administering to the subject a compound or composition of a compound of Formula (I) or a pharmaceutically acceptable salt thereof, to thereby treat the subject, e.g., a human subject.

The present invention provides methods and compositions for treating conditions such as a neuropsychiatric disorder, a neurodegenerative disorder, nephropathy, and seizure disorder by modulating the activity of the transient receptor potential cation channel subfamily C, member 5 (TRPC5), which can exist in homomultimeric form as well as heteromultimeric form with other ion channels such as TRPC1 or TRPC3 (i.e., TRPC5-TRPC1 and TRPC1-TRPC3-TRPC5). The compound of Formula (I) modulate the function of TRPC5 by inhibiting a TRPC5-mediated ion flux or by inhibiting the inward current, the outward current, or both currents mediated by TRPC5. The inhibition of a particular current is the ability to inhibit or reduce such current (e.g., inward and/or outward) in an in vitro or an in vivo assay. The activation of a particular current is the ability to activate or increase such current (e.g., inward and/or outward) in an in vitro or an in vivo assay.

In one aspect, the invention relates to a method for treating a condition for which reduced TRPC5 activity can reduce the severity of the condition, by administering a TRPC5 antagonist, such as a compound of Formula (I), that inhibits TRPC5-mediated current and/or TRPC5-mediated ion flux. Described in greater detail herein are compounds of Formula (I), which are TRPC5 antagonists that have a measured $IC_{50}$ for inhibition of TRPC5 of 10 nanomolar or less. In certain embodiments, the compounds of Formula (I), which are TRPC5 antagonists inhibit one or both of inward and outward TRPC5-mediated currents with an $IC_{50}$ 10 nanomolar or less. In certain embodiments, the compounds of Formula (I) inhibit at least 95% of TRPC5-mediated current or TRPC5-mediated ion flux when administered at 1 micromolar or less.

In another aspect, compounds of Formula (I), which are TRPC5 antagonists, can be used to inhibit a function of TRPC5, for example a TRPC5-mediated current and/or a TRPC5-mediated ion flux. In some embodiments, compounds of Formula (I) can be used to inhibit a TRPC5 mediated current in vitro, for example in cells in culture. In other embodiments, compounds of Formula (I) can be used to inhibit a TRPC5 mediated current in vivo. In certain embodiments, compounds of Formula (I) inhibit both an inward and an outward TRPC5-mediated current.

Another aspect of the invention features a pharmaceutical preparation suitable for use in a human patient, or for veterinary use, comprising an effective amount of a compound of Formula (I) (or a salt thereof, or a solvate, hydrate, oxidative metabolite or prodrug of the compound or its salt), and one or more pharmaceutically acceptable excipients, diluents, or carriers. The invention further contemplates the use of compounds of Formula (I) in the manufacture of a medicament or pharmaceutical preparation to treat or reduce the symptoms of any of the diseases or conditions provided in the specification. The compounds of Formula (I) for use in treating a particular disease or condition can be formulated for administration via a route appropriate for the particular disease or condition.

Compounds of Formula (I) can be administered alone or in combination with another therapeutic agent. For instance, the compounds of Formula (I) can be administered conjointly with one or more of an anti-inflammatory agent, anti-acne agent, anti-wrinkle agent, anti-scarring agent, anti-psoriatic agent, anti-proliferative agent, anti-fungal agent, anti-viral agent, anti-septic agent, anti-migraine agent, keratolytic agent, or a hair growth inhibitor.

Compounds of Formula (I) can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally, sublingually, or by inhalation.

In some embodiments, compounds of Formula (I) can be administered topically.

In some embodiments, compounds of Formula (I) can be administered orally.

In some embodiments, compounds of Formula (I) can be administered parentally.

Definitions

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination. Compounds may be depicted by both chemical name and structure and in the event of conflict between the two the structure controls.

As used herein, "acyl" refers to the group ($C_1$-$C_6$ alkyl)-C(O)—.

As used herein, "alkyl," by itself or as part of another substituent, means, unless otherwise stated, a straight or branched chain, and can have a number of carbon atoms optionally designated (i.e., $C_1$-$C_6$ means one to six carbons). Examples of saturated hydrocarbon groups include, but are not limited to, groups such as methyl, ethyl, n-propyl, isopropyl, n-butyl, t-butyl, isobutyl, sec-butyl, n-pentyl, isopentyl, homologs and isomers of, for example, n-pentyl, n-hexyl, and the like.

As used herein, "alkenyl" can be a straight or branched hydrocarbon chain, containing at least one double bond, and having from two to six carbon atoms (i.e., $C_2$-$C_6$ alkenyl). Examples of alkenyl groups, include, but are not limited to, groups such as ethenyl (i.e., vinyl), prop-1-enyl (i.e., allyl), but-1-enyl, pent-1-enyl, penta-1,4-dienyl, and the like.

As used herein, "alkynyl" can be a straight or branched hydrocarbon chain, containing at least one triple bond, having from two to six carbon atoms (i.e., $C_2$-$C_6$ alkynyl). Examples of alkynyl groups, include, but are not limited to, groups such as ethynyl, propynyl, butynyl, pentynyl, hexynyl, and the like.

As used herein, "alkoxy" can be a straight chain or branched alkoxy group having from one to six carbon atoms (i.e., $C_1$-$C_6$ alkoxy). Examples of alkoxy groups, include, but are not limited to, groups such as methoxy, ethoxy, propyloxy, isopropyloxy, butyloxy, isobutyloxy, tert-butyloxy, pentyloxy, or hexyloxy, and the like.

As used herein, "amide" or "amido" refers to a chemical moiety with the formula —C(O)NR$^a$— or —NR$^a$C(O)— wherein R$^a$ is H or $C_1$-$C_6$ alkyl.

As used herein, "amino" or "amine" refers to a —NH$_2$ radical group.

As used herein, "alkylamino" refers to a group of formula —NH(alkyl), wherein the alkyl group each has 1 to 6 carbons.

As used herein, the term "dialkylamino" refers to a group of formula —N(alkyl)$_2$, wherein the two alkyl groups each independently have 1 to 6 carbons.

As used herein, "aryl" refers to a polyunsaturated, aromatic, hydrocarbon moiety which can be a single ring or multiple rings (e.g., 1 to 2 rings) which are fused together or linked covalently, having from six to twelve carbon atoms (i.e., $C_6$-$C_{12}$ aryl). Non-limiting examples of aryl groups include phenyl, 1-naphthyl, 2-naphthyl, and 4-biphenyl.

As used herein, "arylalkyl" refers to an (aryl)alkyl-radical wherein aryl and alkyl moieties are as disclosed herein. The arylalkyl may be represented as $C_6$-$C_{12}$ aryl-$C_1$-$C_6$ alkyl, a phenylalkyl, e.g. benzyl, and as structures such as the following non-limiting exemplary structures:

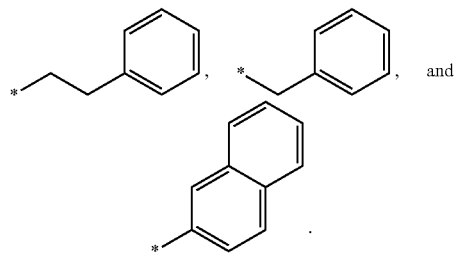

As used herein, "aryloxy" refers to —O-(aryl), wherein the aryl moiety is as defined herein. In one-non-limiting example, the may be phenoxy including the following exemplary structure.

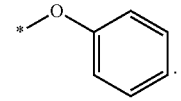

As used herein, "arylalkoxy" refers to —O-(arylalkyl), wherein the arylalkyl moiety is as defined herein e.g. —O—$C_6$-$C_{12}$ aryl-$C_1$-$C_6$ alkyl, —O—$C_1$-$C_6$ alkyl-$C_6$-$C_{12}$ aryl, and —$C_6$-$C_{12}$ aryl-$C_1$-$C_6$ alky-O.

As used herein, "carboxyl" refers to a —(C═O) radical.

As used herein, "cyano" refers to a —CN radical.

As used herein, "cycloalkyl" refers to a monocyclic or polycyclic radical that contains only carbon and hydrogen, and may be saturated, or partially unsaturated. Cycloalkyl groups include groups having from 3 to 10 ring atoms (i.e. $C_3$-$C_{10}$ cycloalkyl). Examples of cycloalkyl groups include, but are not limited to, groups such as cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

As used herein, "cycloalkyloxy" refers to —O-(cycloalkyl), wherein the cycloalkyl moiety is as defined herein e.g. —O—($C_3$-$C_{10}$ cycloalkyl).

As used herein, "halo" or "halogen," independently or as part of another substituent, mean, unless otherwise stated, a fluorine, chlorine, bromine, or iodine atom. The term "halide" by itself or as part of another substituent, refers to a fluoride, chloride, bromide, or iodide atom.

As used herein, "haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

As used herein, "heteroaryl" refers to a 5- to 14-membered aromatic radical (e.g., $C_2$-$C_{13}$ heteroaryl) that includes one or more ring heteroatoms selected from nitrogen, oxygen and sulfur, and which may be a monocyclic or bicyclic ring system. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like.

As used herein, "heteroarylalkyl" refers to refers to an (heteroaryl)alkyl-radical wherein the heteroaryl and alkyl moieties are as disclosed herein. A heteroarylalkyl may be represented as 5-14-membered heteroaryl-$C_1$-$C_6$ alkyl, by name such as a pyridylalkyl and may be depicted as a structure as in the following non-limiting structural example

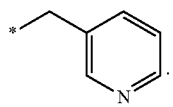

As used herein, "heteraryloxy" refers to —O-(heteroaryl), wherein the heteroaryl moiety is as defined herein. For example, such heteraryloxy may include a pyridyloxy as depicted in the following structural example

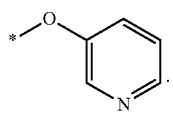

As used herein, "heterocycloalkyl" can be a stable 3- to 18-membered non-aromatic ring radical that comprises two to twelve carbon atoms and from one to six heteroatoms selected from nitrogen, oxygen and sulfur. Examples of heterocycloalkyl groups include, but are not limited to, groups such as dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, and the like.

As used herein, "hydroxy" or "hydroxyl" refers to —OH.

As used herein, "hydroxyalkyl" refers to an alkyl group having 1 to 10 carbon atoms, which is substituted with a hydroxyl group, e.g., hydroxypropyl.

As used herein, "keto" refers to a =O radical.

As used herein, "nitro" refers to —$NO_2$.

As used herein, "urea" refers to —$NR^a$—C(O)—$NR^a{}_2$ or —$NR^a$—C(O)$NR^a$—, wherein $R^a$ is H or $C_1$-$C_6$ alkyl.

As used herein, "sulfonyl" refers to —$S(O)_2$—$R^a$, wherein $R^a$ is $C_1$-$C_6$ alkyl.

As used herein, "sulfonylurea" refers to —$S(O)_2$—$NR^a$—C(O)—$NR^a$— or —$NR^a$—C(O)—$NR^a$—$SO_2$—, wherein $R^a$ is H or $C_1$-$C_6$ alkyl.

As used herein, "sulfonamidyl" refers to —$S(O)_2$—$NR^a$— or —$NR^a$—$S(O)_2$—, wherein $R^a$ is H or $C_1$-$C_6$ alkyl.

As used herein, "thionyl" refers to —S(O)—$R^a$, wherein $R^a$ is $C_1$-$C_6$ alkyl.

The terms "antagonist" and "inhibitor" are used interchangeably to refer to an agent that decreases or suppresses a biological activity, such as to repress an activity of an ion channel, such as TRPC5. TRPC5 ion channels as described herein include homomultimeric and heteromultimeric structures (e.g., homomultimeric TRPC5 and heteromeric TRPC5-TRPC1 or TRPC5-TRPC4). TRPC5 antagonists include inhibitors having any combination of the structural and/or functional properties disclosed herein.

An "effective amount" of, e.g., a TRPC5 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPC5 antagonist for use in the methods of the present invention includes an amount of a TRPC5 antagonist effective to decrease one or more in vitro or in vivo function of a TRPC5 channel. Exemplary functions include, but are not limited to, membrane polarization (e.g., an antagonist may promote hyperpolarization of a cell), ion flux, ion concentration in a cell, outward current, and inward current. Compounds that antagonize TRPC5 function include compounds that antagonize an in vitro or in vivo functional activity of TRPC5. When a particular functional activity is only readily observable in an in vitro assay, the ability of a compound to inhibit TRPC5 function in that in vitro assay serves as a reasonable proxy for the activity of that compound. In certain embodiments, an effective amount is an amount sufficient to inhibit a TRPC5-mediated current and/or the amount sufficient to inhibit TRPC5 mediated ion flux.

The TRPC5 antagonists for use in the methods of the present invention may be characterized according to their activity, or lack of activity, against one or more other ion channels. When other ion channels are referred to, inhibition of a function of such other ion channels is defined similarly. For example, inhibition of an ion channel or an activity of an ion channel means the antagonist inhibits one or more functional activities of the other ion channel. Such functions include the current mediated by the particular ion channel, ion flux, or membrane polarization.

The term "preventing" is art-recognized, and when used in relation to a condition, such as a local recurrence, a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "small molecule" refers to a compound having a molecular weight less than about 2500 amu, preferably less than about 2000 amu, even more preferably less than about 1500 amu, still more preferably less than about 1000 amu, or most preferably less than about 750 amu.

The terms "TRPC5", "TRPC5 protein", and "TRPC5 channel" are used interchangeably throughout the application. Unless expressly stated, the term TRPC5 includes homomultimeric structures (e.g., homomultimeric TRPC5) and heteromultimeric structures (e.g., heteromultimeric TRPC5-TRPC1).

The term "oxidative metabolite" is intended to encompass compounds that are produced by metabolism of the parent compound under normal physiological conditions. Specifically, an oxidative metabolite is formed by oxidation of the parent compound during metabolism. For example, a thioether group may be oxidized to the corresponding sulfoxide or sulfone.

The term "solvate" as used herein, refers to a compound formed by solvation (e.g., a compound formed by the combination of solvent molecules with molecules or ions of the solute).

The term "hydrate" as used herein, refers to a compound formed by the union of water with the parent compound.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

Contemplated equivalents of the compounds described above include compounds which otherwise correspond thereto, and which have the same general properties thereof (e.g., the ability to antagonize TRPC5 activity), wherein one or more simple variations of substituents are made which do not adversely affect the efficacy of the compound. In general, the compound of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art. Compounds of the invention also include tautomeric forms, such as keto-enol tautomers.

Compounds of the invention can exist in unsolvated forms as well as solvated forms, including hydrated forms. In general, the solvated forms are equivalent to unsolvated forms and are encompassed within the scope of the present invention.

The term "pharmaceutically acceptable salts" includes salts of a compound of Formula (I) which are prepared with relatively nontoxic acids or bases. Base addition salts can be obtained by contacting the neutral form of a compound of Formula (I) with a sufficient amount of the desired base, either neat or in a suitable inert solvent. Examples of pharmaceutically acceptable base addition salts include sodium, potassium, calcium, ammonium, organic amino, or magnesium salt, or a similar salt. Acid addition salts can be obtained by contacting the neutral form of a compound of Formula (I) with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, trifluoroacetic, propionic, isobutyric, maleic, malonic, benzoic, succinic, suberic, fumaric, lactic, mandelic, phthalic, benzensulfonic, p-tolylsulfonic, citric, tartaric, methanesulfonic, and the like. Also included are the salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19).

The neutral forms of a compound of Formula (I) is preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "low enough pyrogen activity", with reference to a pharmaceutical preparation, refers to a preparation that does not contain a pyrogen in an amount that would lead to an adverse effect (e.g., irritation, fever, inflammation, diarrhea, respiratory distress, endotoxic shock, etc.) in a subject to which the preparation has been administered. For example, the term is meant to encompass preparations that are free of, or substantially free of, an endotoxin such as, for example, a lipopolysaccharide (LPS).

Diseases, Disorders, or Conditions Related to TRPC5 Function

In certain embodiments, the invention provides methods and compositions for antagonizing a function of a TRPC5 channel in vitro or in vivo. Exemplary functions include, but are not limited to, TRPC5-mediated current. In certain embodiments, the invention provides methods for treating a disease or disorder or condition by administering a compound of the invention. In other embodiments, the compound as described herein selectively inhibits the expression level and/or activity of a TRPC5 protein. In other words, in certain embodiment, the compound as described herein inhibits the activity of a TRPC5 protein preferentially in comparison to the activity of one or more other ion channels.

Treatment of Anxiety and Fear-Related Disorders

In certain embodiments, the compounds of the invention can be used for preventing or treating anxiety and fear-related disorders (see, e.g., Riccio et al. (2009) Cell 137: 761-72). Examples of such disorders include post-traumatic stress disorder, panic disorder, agoraphobia, social phobias, generalized anxiety disorder, panic disorder, social anxiety disorder, obsessive-compulsive disorder, and separation anxiety.

Memory, Motion and Mood Disorders

A compound of Formula (I) is also useful for the treatment of Parkinson's disease, epilepsy, memory disorders, stroke, seizure, and mood disorders. Mood disorders include depression (e.g., major depression, psychiatric depression, dysthymia, and postpartum depression) and bipolar disorder (e.g., bipolar I, bipolar II, and cyclothymia). Memory disorders are conditions associated with any memory loss and may result from Alzheimer's disease, amnesia, aphasia, atherosclerosis, brain injury or disorder, brain tumor, chronic fatigue syndrome, Creutzfedt-Jacob disease, dissociative amnesia, depression, fuge amnesia, Huntington's disease, learning disorders, sleeping disorders, multiple personality disorder, pain, post-traumatic stress disorder, schizophrenia, sports injuries, stroke, and Wernicke-Korsakoff syndrome.

Treatment of Pain, Sensitivity to Pain and Touch, or Pain-Related Diseases or Disorders In certain embodiments, a compound of Formula (I) is used to treat or ameliorate pain. Exemplary classes of pain that can be treated using a compound of Formula (I) include, but are not limited to nociceptive pain, inflammatory pain, and neuropathic pain. The pain can be chronic or acute.

A compound of Formula (I) may be particularly useful in the treatment of pain associated with cancer, osteoarthritis, rheumatoid arthritis, post-herpetic neuralgia, burns, and other indications detailed above. To further illustrate, additional exemplary indications for which a compound of Formula (I) can be used include oral pain, pelvic pain, Fabry's disease, complex regional pain syndrome, pancreatitis, and fibromyalgia syndrome.

A compound of Formula (I) may also be used in connection with prevention or treatment of sensitivity to pain and touch. Pain or sensitivity to pain and touch may be indicated in a variety of diseases, disorders or conditions, including, but not limited to, diabetic neuropathy, breast pain, psoriasis, eczema, dermatitis, burn, post-herpetic neuralgia (shingles), nociceptive pain, peripheral neuropathic and central neuropathic pain, chronic pain, cancer and tumor pain, spinal cord injury, crush injury and trauma induced pain, migraine, cerebrovascular and vascular pain, sickle cell disease pain, rheumatoid arthritis pain, musculoskeletal pain including treating signs and symptoms of osteoarthritis and rheumatoid arthritis, orofacial and facial pain, including dental, temperomandibular disorder, and cancer related, lower back or pelvic pain, surgical incision related pain, inflammatory and non-inflammatory pain, visceral pain, psychogenic pain and soft tissue inflammatory pain, fibromyalgia-related pain, and reflex sympathetic dystrophy, and pain resulting from kidney stones or urinary tract infection.

The foregoing are merely exemplary of diseases and conditions that cause or lead to inflammation, lesions, ulcers, or other sources of oral pain. In other embodiments, the oral pain is due to an injury to the mouth, jaw, lips, gums, or teeth. In other embodiments, the oral pain is due to oral surgery, for example, surgery for cancer, tooth extraction, or jaw remodeling. Other conditions that may lead to oral ulcers, and thus oral pain, include, but are not limited to chickpox, herpes zoster, infectious mononucleosis, syphilis, tuberculosis, acute necrotizing gingivitis, and burning mouth syndrome.

Fibromyalgia (FMS; fibromyalgia syndrome) is a widespread musculoskeletal pain and fatigue disorder. Fibromyalgia is characterized by pain in the muscles, ligaments, and tendons. The condition affects more women than men, and occurs in people of all ages. Overall, FMS is estimated to afflict 3-6% of the population. Patients have described the pain associated with fibromylagia as deep muscular aching, throbbing, shooting, and stabbing. The pain sometimes includes an intense burning sensation. The pain and stiffness are often worse in the morning or after repetitive use of a particular muscle group.

Additionally, varying levels of fatigue ranging from mild to incapacitating are often associated with fibromylagia. Other symptoms of fibromylagia include gastrointestinal symptoms. Irritable bowel syndrome and IBS-like symptoms such as constipation, diarrhea, frequent abdominal pain, abdominal gas, and nausea occur in roughly 40 to 70% of FMS patients. Acid reflux or gastroesophogeal reflux disease (GERD) occurs at a similar frequency.

Complex Regional Pain Syndrome (CRPS; also known as chronic regional pain syndrome) is a chronic pain condition. CRPS was formerly known as reflex sympathetic dystrophy (RSD). CRPS is a chronic, painful, and progressive neurological condition that affects skin, muscles, joints, and bones. The syndrome usually develops in an injured limb, such as a broken leg or following surgery. However, many cases involve only a minor injury, such as a sprain, and sometimes no precipitating injurious event can be identified. CRPS involves continuous, intense pain that is disproportionate to the severity of the injury. The pain worsens, rather than improves, over time.

Although CRPS can affect a variety of regions of the body, it most often affects the arms, legs, hands, or feet. Often the pain begins in one portion of a limb, but spreads over time to include the entire limb or even to include a different limb. Typical features include dramatic changes in the color and temperature of the skin over the affected limb or body part, accompanied by intense burning pain, skin sensitivity, sweating, and swelling.

The compounds disclosed herein can also be used to treat endometriosis and the pain associated therewith.

Neurological or Neurodegenerative Diseases and Disorders

Neurodegenerative diseases and disorders include but are not limited to Alzheimer's disease (AD), Parkinson's disease, Huntington's disease, amyotrophic lateral sclerosis (ALS), and other brain disorders caused by trauma or other insults including aging.

Mechanisms associated with calcium signaling may be altered in many neurodegenerative diseases and in disorders resulting from brain injury. For example, fibroblasts or T-lymphocytes from patients with AD have consistently displayed an increase in $Ca^{2+}$ release from intracellular stores compared to controls (Ito et al. (1994) Proc. Natl. Acad. Sci. U.S.A. 91:534-538; Gibson et al. (1996) Biochem. Biophys. ACTA 1316:71-77; Etchenberrigaray et al. (1998) Neurobiology of Disease, 5:37-45). Consistent with these observations, mutations in presenilin genes (PS1 or PS2) associated with familial AD (FAD) have been shown to increase InsP3-mediated $Ca^{2+}$ release from internal stores (Guo et al. (1996) Neuro Report, 8:379-383; Leissring et al. (1999) J. Neurochemistry, 72:1061-1068; Leissring et al. (1999) J. Biol. Chem. 274 (46):32535-32538; Leissring et al. (2000) J. Cell Biol. 149 (4):793-797; Leissring et al. (2000) Proc. Natl. Acad. Sci. U.S.A. 97 (15):8590-8593). Furthermore, mutations in PS1 or PS2 associated with an increase in amyloidogenic amyloid β peptide generation in AD are reported to be associated with a decrease in intracellular calcium level (Yoo et al. (2000) Neuron, 27 (3):561-572).

Experimental traumatic brain injury has been shown to initiate massive disturbances in $Ca^{2+}$ concentrations in the brain that may contribute to further neuronal damage. Intracellular $Ca^{2+}$ may be elevated by many different ion channels. It has been further shown that channel blockers may be beneficial in the treatment of neurological motor dysfunction when administered in the acute posttraumatic period (Cheney et al. (2000) J. Neurotrauma, 17 (1):83-91).

Seizure

Excitotoxicity of a variety of origins leads to seizures. Commonly excess neuronal firing can drive seizure activity. Compounds that reduce the hyperexcitability of relevant neuronal populations have significant potential in reducing seizure activity.

Proteinuric Kidney Disease

TRPC5 is also expressed in the podocyte of the kidney. It has been proposed that there is an antagonistic regulation of actin dynamics and cell in the podocytes by TRPC5 and TRPC6 (Tian et al., (2010) Science Signaling). Thus, inhibiting TRPC5 may impact the reaction of the podocyte to injury.

Combination Therapy

The present invention provides a compound of Formula (I) for use in vitro and in vivo. The present invention also provides compositions and pharmaceutical compositions comprising a compound of Formula (I) that inhibits TRPC5 activity. In certain embodiments, the compound of Formula (I) is selective. In other words, in certain embodiments, the compound of Formula (I) inhibits TRPC5 activity preferentially over the activity of other ion channels. In certain embodiments, the compound of Formula (I) inhibits TRPC5 activity preferentially over TRPV1, TRPV2, TRPV3, TRPV4, TRPC3, TRPC6, TRPC7, TRPA1, and/or TRPM8 activity. For example, in certain embodiments, the compound of Formula (I) inhibits the activity of TRPC5 and also inhibits the activity of one or more of TRPC4, TRPV1, TRPV2, TRPV3, TRPV4, TRPC3, TRPC6, TRPC7, TRPA1, and TRPM8.

A compound of Formula (I) can be used alone or in combination with other pharmaceutically active agents. Examples of such other pharmaceutically active agents include, but are not limited to, anti-depressants, anti-anxiety agents, anti-epileptic agents, anti-inflammatory agents (e.g., NSAIDS, bradykinin receptor antagonists, hormones and autacoids such as corticosteroids), or anti-migraine agents. Certain active agents belong to more than one category.

In certain embodiments, a compound of Formula (I) is conjointly administered with an analgesic. Suitable analgesics include, but are not limited to, opioids, glucocorticosteroids, non-steroidal anti-inflammatories, naphthylalkanones, oxicams, para-aminophenol derivatives, propionic acids, propionic acid derivatives, salicylates, fenamates, fenamate derivatives, pyrozoles, and pyrozole derivatives. Examples of such analgesic compounds include, but are not limited to, codeine, hydrocodone, hydromorphone, levorphanol, morphine, oxycodone, oxymorphone, butorphanol, dezocine, nalbuphine, pentazocine, etodolac, indomethacin, sulindac, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid, mefanamic acid, prednisolone, and dexamethasone. Preferred analgesics are non-steroidal anti-inflammatories and opioids (preferably morphine).

In some embodiments, a compound of Formula (I) can be administered in conjunction with a therapeutic whose administration causes pain. For example, a compound of Formula (I) can be administered in conjunction with an anesthetic, to reduce the pain caused by the administration of the anaesthetic. A compound of Formula (I) can also be administered in conjunction with a chemotherapeutic agent, to reduce the pain caused by administration of the chemotherapeutic agent.

In certain embodiments, a compound of Formula (I) is conjointly administered with a non-steroidal anti-inflammatory. Suitable non-steroidal anti-inflammatory compounds include, but are not limited to, piroxicam, diclofenac, etodolac, indomethacin, ketoralac, oxaprozin, tolmetin, naproxen, flubiprofen, fenoprofen, ketoprofen, ibuprofen, mefenamic acid, sulindac, apazone, phenylbutazone, aspirin, celecoxib and rofecoxib.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds of the present invention with known excipients, for example inert diluents, carriers, disintegrants, adjuvants, surfactants, binders and/or lubricants. The tablets may also consist of several layers.

Dosages

The dose range of the compounds of the invention applicable per day is usually from 1 to 1000 mg, preferably from 5 to 800 mg, more preferably from 25 to 500 mg. Each dosage unit may conveniently contain from 1 to 1000 mg, preferably 25 to 500 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Disease and Injury Models

A compound of Formula (I) which antagonizes TRPC5 function may be useful in the prophylaxis and treatment of any of the foregoing injuries, diseases, disorders, or conditions. In addition to in vitro assays of the activity of the compound of Formula (I), its efficacy can be readily tested in one or more animal models. By way of example, numerous well known animal models exist. One or more suitable animal models (e.g., suitable in light of the particular indication) can be selected.

Fear-related behaviors can be measured as described, e.g., in Riccio et al. Pain behaviors can be studied using various agents or procedures to simulate pain resulting from injuries, diseases, or other conditions. Blackburn-Munro (2004) Trends in Pharmacological Sciences 25: 299-305. Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. Id. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the Chung model, the carageenan induced hyperalgesia model, the Freund's complete adjuvant induced hyperalgesia model, the thermal injury model, the formalin model and the Bennett Model. The Chung model of neuropathic pain (without inflammation) involves ligating one or more spinal nerves. Chung et al. (2004) Methods Mol Med 99: 35-45; Kim and Chung (1992) Pain 50: 355-363. Ligation of the spinal nerves results in a variety of behavioral changes in the animals including heat hyperalgesia, cold allodynia, and ongoing pain. Compounds that antagonize TRPC5 can be administered to ligated animals to assess whether they diminish these ligation-induced behavioral changes in comparison to that observed in the absence of compound.

Useful anxiety and depression models include the maternal separation model, the elevated plus-maze model, the forced swim test, the tail suspension test, the light/dark preference model, the light-enhanced startle model, and the ultrasonic vocalization model.

Useful seizure models include but are not limited to maximal electric shock (MES), acoustic startle in susceptible animals (e.g., DBA mice), and chemical induced seizure (with proconvulsant compounds such as pilocarpine, pentalene tetrazole, kainic acid, N-methyl-D-aspartic acid).

Useful models of kidney function include the LPS-induced proteinuria (waiting for a reference for others).

EXAMPLES

Example 1

High Throughput Screening Assay

The assay depended on detection of the rise in intracellular Ca2+ concentration ([Ca2+]i) following channel activation in cells inducibly expressing the TRPC5 channel. Ca2+ rise was quantified with the use of fluorescent Ca2+ indicators that were loaded into cells and thereafter indicated the [Ca2+]i Ca2+ influx followed activation of the TRPC5 channel. Compounds inhibiting the [Ca2+]i rise were considered hits for further investigation.

The commercially available HEK293/TREx line (Invitrogen) was stably transfected with a TRPC5 construct and screened by conventional calcium imaging to find clones with TRPC5 expression following stimulation with 1 μg/ml tetracycline. These cells were maintained in the growth medium recommended by the manufacturer supplemented with 100 μg/ml hygromycin to promote retention of the TRPC5 construct. After growing to near confluency, cells were plated at a density of ~35,000 cells/well in 384 well CellBind plates (Corning) in the presence of 1 μg/ml tetracycline, and allowed to grow for 20-30 hrs. A nearly confluent monolayer resulted. Cells were then loaded with Ca2+ dye: Fura-2/AM or Fluo4/AM was added to the wells to a final concentration of 4 μM or 0.5 μM, respectively, and incubated for 80 min or 60 min, respectively, at room temperature. Supernatant was then removed from the cells by inverting plates with a sharp flick, and 25 μl Hank's Balanced Salt Solution (HBSS; 0.185 g/l D-glucose, 0.9767 g/l MgSO4 (anhydrous), 0.4 g/l KCl, 0.06 g/l KH2PO4 (anhydrous), 0.35 g/l NaHCO3, 8.0 g/l NaCl, and 0.04788 g/l Na2HPO4 (anhydrous); pH 7.4) was then added to each well. Following ~0.5 hour for recovery from loading, cells were assayed using the Hamamatsu FDSS 6000 system, which permitted illumination alternately at 340 nm and 380 nm for Fura-2 experiments, or at 485 nm for Fluo4 experiments. Frames were acquired at a rate of 0.2 Hz. During the assay, the plates were continuously vortexed, with pipette mixing of wells following addition of each reagent. For the screening assay, 26 μl of a diluted compound stock (at 50 μM) was added to each well for 2 minutes following the collection of a short (4 frame) baseline. 13 μl 62 mM high-Ca2+Ringer solution (4.17 ml of normal ringer (with 2 mM Ca2+) plus 5.83 ml of isotonic calcium ringer (105 mM Ca2+; in this ringer all sodium has been replaced with calcium)) was then added to each well, achieving a final concentration of 14 mM Ca2+ and 10 μM test compound. Data was collected for ~3 minutes following addition of high Ca2+Ringer, where the fluorescent intensity (for Fluo4) and the F340/F380 ratio (for Fura-2) were proportional to the [Ca2+]i Negative controls consisted of HEK293/TREx TRPC5 cells exposed to high Ca2+ solution, but no compound. Positive control conditions consisted of addition of 2-APB, a promiscuous blocker of TRPC5 and other channels, to columns 23 and 24 of the plates, to a final concentration of 200 µM. These controls defined a screening window, and "hits" were defined as those compounds inhibiting the fluorescence response by at least 40%. IC50 values were determined for compounds defined as "hits." The Fluo4 cell-based fluorescence assay was used to determine the intracellular Ca2+ concentration in the presence of varying drug concentration. Final concentrations of compounds tested were 20 µM, 6.667 µM, 2.222 µM, 0.741 µM, 0.247 µM, 0.082 µM, and 0.027 µM. Compounds were tested in triplicate at all concentrations. Standard software was used to fit IC50 curves. A value of NF was assigned when no IC50 curves could not be fit.

Additionally or alternatively, efficacy can be represented as % inhibition in the presence (of a given concentration of compound) versus the absence of compound or in comparison to a control compound. For example, efficacy can be represented as % inhibition of ion flux in the presence versus the absence of compound. Exemplary compounds are shown in Table 2 below.

TABLE 2

| Compound Number | $IC_{50}$ (nM) |
| --- | --- |
| 14 | 3250 |
| 15 | 7530 |
| 16 | 3740 |
| 20 | 977 |
| 21 | 269 |
| 22 | 180 |
| 23 | 6490 |
| 24 | 1340 |
| 25 | 739 |
| 26 | 1290 |
| 27 | NF |
| 28 | 28.5 |
| 29 | 27 |
| 30 | 357 |
| 31 | 27 |
| 32 | 350 |
| 33 | NF |
| 34 | 154 |
| 30 | 357 |
| 31 | 27 |
| 32 | 350 |
| 33 | NF |
| 34 | 154 |
| 35 | 14 |
| 36 | 27 |
| 37 | 1160 |
| 38 | 215 |
| 41 | 33.8 |
| 42 | NF |
| 43 | 1420 |
| 44 | 3450 |
| 45 | 1310 |
| 46 | >20000 |
| 47 | NF |
| 48 | >10000 |
| 49 | >20000 |

Example 2

Patch Clamp Experiments

Patch clamp experiments permit the detection of currents through the TRPC5 channel in the cell line described above. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution. A perfusion system permits control of the extracellular solution, including the addition of blockers and activators of the current. The current can be activated by including 1.4 µM free $Ca^{2+}$ in the pipette (intracellular) solution, and 80 µM $LaCl_3$ in the extracellular solution.

TRPC5 cells were induced 20-48 hours, removed from growth plates, and replated at low density (to attain good single-cell physical separation) on glass coverslips for measurement. In some cases, cells were grown in low density overnight on glass coverslips. Patch clamp recordings were made in the whole-cell mode with a holding potential of −40 mV. Every 5 seconds, a voltage ramp was applied from −120 to +100 mV, 400 ms in duration. Currents elicited were quantified at −80 mV and +80 mV. The internal solution consisted of 140 mM cesium aspartate, 10 mM HEDTA, 2 mM $CaCl_2$, 2.27 mM $MgCl_2$ and 10 mM HEPES, pH 7.2, with 1,400 nM calculated free $Ca^{2+}$. The external solution consisted of 150 mM NaCl, 4.5 mM KCl, 1 mM $MgCl_2$, 2 mM $CaCl_2$, 10 mM HEPES, 10 mM glucose, 1 mM EGTA, pH 7.4. Upon addition of $LaCl_3$, TRPC5 current was induced only in TRPC5-expressing cells and not in parental HEK293 TREx cells. Removal of the $LaCl_3$ stimulus causes most of the current to go away. Potential blockers were tested for ability to block both inward and outward currents in the continued presence of $LaCl_3$.

$IC_{50}$ of a compound of Formula (I) was estimated by testing the compound at 5 µM and 500 nM. When 5 µM of a compound showed no block, $IC_{50}$ was estimated as >10 µM. When 5 µM of a compound showed 50% or less block, a rough estimate of $IC_{50}$ in the range of 5-10 µM could be made. $IC_{50}$ for a compound of Formula (I) between 500 nM and 5 µM was similarly estimated. Exemplary compounds are shown in Table 3 below.

TABLE 3

| Compound Number | $IC_{50}$ (nM) |
| --- | --- |
| 21 | <1 |
| 23 | 12.2 |
| 27 | 29 |
| 29 | 4.5 |
| 30 | <1 |
| 31 | 1.47 |
| 34 | 8.3 |
| 35 | 3.4 |
| 36 | 1.2 |
| 39 | 51.7 |
| 40 | 2.9 |

Example 3

General Experimental Procedures

General Procedures

All reagents were purchased from commercial suppliers and used without further purification unless otherwise stated. Reactions were monitored via thin layer chromatography (TLC) on silica gel plates and visualized using UV light (254 nm or 365 nm) and/or staining with a solution of DNP (12 g of 2,4-dinitrophenylhydrazine dissolved in $H_2SO_4$ (60 mL), water (80 mL) and ETOH (200 mL) and subsequent heating or monitored by LCMS. Preparative TLC plates used were Analtech Uniplate Silica Gel GF plates or Shanghia SANPONT PLC plate SGF254 20×20 cm size and 2000 um thickness.

All reactions were run under an inert atmosphere using either argon or nitrogen. All non-aqueous reactions were run using anhydrous solvents. All reactions were stirred either with a magnetic stir bar or with overhead mechanical stirring. All saturated extraction solutions are assumed to be aqueous ($NH_4Cl$ for example). All drying agents are anhydrous. Drying organic solutions with a drying agent implies that the drying agent was removed from the organic solution by filtration. Chromatography refers to column chromatography on silica gel. Concentration of reaction mixtures implies concentration under reduced pressure using of a Rotary Evaporation instrument. Drying of final products implies drying under high vacuum conditions. (MW) means using a microwave instrument with reaction carried out in a sealed microwave vial. Microwave reactions were carried out using a Biotage Smith Synthesizer.

LCMS were performed on a SHIMADZU LCMS-2010EV instrument using one of two sets of conditions. LCMS conditions one: (Chromolith SdeedROP, RP-18e column. 50×4.6 mm. mobile phase: Solvent A: $CH_3CN/H_2O/HCOOH=10/90/0.05$. Solvent B: $CH_3CN/H_2O/HCOOH=90/10/0.05$, 0.8 min @ 10% B. 2.7 min gradient (10-95% B), then 0.8 min @95% B. Flow rate: 3 mL/min. temperature: 40° C.). LCMS conditions two: (Zorbax. 3.5 micron. 2.1×50 mm C18 column. Mobile phase: Solvent A: 0.1% $HCOOH/CH_3CN$. Solvent B: 0.1% $HCOOH/H2O$. Gradient 5% to 95% B using a 5 min or 8 min runtime.

Preparative HPLC was performed either on a SHIMADZU LC-8A instrument. (Column: YMC Pack ODS-A (150*30 mm 10 um)) or LC-6AD (column: Shim=Pack PREP-ODS-H (250*20 mm, 10 um)) with UV detection which was controlled by LC solution Chemstation software. $H_2O$ (0.1% HCOOH) and methanol ($CH_3OH$) as mobile phase at the indicated flow rate.

Analytical HPLC was performed on a SHIMADZU LCMS-2010EV (Chromolith SpeedROD, RP-18e, 50×4.6 mm, mobile phase: Solvent A: $CH_3CN/H_2O/HCOOH=10/90/0.05$, Solvent B: $CH_3CN/H_2O/HCOOH=90/10/0.05$, 0.8 min@ 10% B, 2.7 min gradient (10-95% B), then 0.8 min@95% B, Flow rate: 3 mL/min, temperature: 40° C.

$^1H$ NMR spectra were recorded on either a Bruker Avance II 400 MHz or a Varian Unity Inova 400 MHz instrument. Chemical shifts (δ) are reported in ppm relative to tetramethylsilane (δ=0.00 ppm) and the spectra were calibrated to the residual solvent signal of Chloroform (δ=7.26). Dimethyl sulfoxide (δ=2.52), methanol (δ=3.34). Data for $^1H$ NMR spectra are reported as follows: chemical shift (multiplicity, J value, number of hydrogens). Abbreviations are as follows: s (singlet), d (doublet), t (triplet), td (doublet of triplets) q (quartet), quint (quintet), m (multiplet), brd (broad).

List of Abbreviations and Terms
AcONa sodium acetate
$Ac_2O$ acetic anhydride
aq. aqueous
Bn benzyl
Celite diatomaceous earth
$CDCl_3$ deuterated chloroform
CDI 1,1'-carbonyldiimidazole
$CD_3OD$ deuterated methanol
d deuterated
DCM dichloromethane
DHP dihydropyran
DIPEA diisopropylethylamine
DMA dimethylacetamide
DMAP 4-dimethylaminopyridine
DMF N,N-dimethylformamide
DMSO dimethyl sulfoxide
DMSO-$d_6$ deuterated DMSO
EA ethyl acetate
ETOH ethanol 200 proof
h hours
Hex hexanes
Hep heptanes
HPLC high pressure liquid chromatography
HOAc acetic acid
IBX 2-iodobenzoic acid
LAH lithium aluminum hydride
LCMS liquid chromatography-mass spectrometry
LDA lithium diisopropylamine
MeOH methanol
M molarity
mmol millimolar
mg milligrams
mL milliliters
min minutes
MW microwave reactor
MTBE methyl tert-butyl ether
Na sodium
n-BuLi n-butyllithium
N normality
NCS n-chlorosuccinimide
NBS n-bromosuccinimide
NMR nuclear magnetic resonance
Pd/C palladium on activated carbon
Pd(dppf)$Cl_2$ [1,1'Bis(diphenylphosphino)ferrocene]dichloropalladium(II)
Pd(PPh$_3$)$_4$ Bis(triphenylphosphine)palladium(II) dichloride
PE petroleum ether
PPTS pyridinium p-toluenesulfonate
Prep TLC preparative thin layer chromatography
Prep HPLC preparative high pressure liquid chromatography
psi pounds per square inch
RT room temperature
SEM 2-(trimethylsilyl)ethoxymethyl
TBAI tetrabutylammonium iodide
TBAF tetrabutylammonium fluoride
TBS t-butyldimethyl silyl
TEA triethylamine
TFA trifluoroacetic acid
THP tetrahydropyranyl
TLC thin layer chromatography
THF tetrahydrofuran
$T_r$ LCMS retention time Preparation of Compounds Compound 14

5-(4-chlorobenzyl)-3-(3-hydroxypropyl)-1-methyl-6-(pyridin-3-yloxy)pyrido[2,3-d]pyrimidine-2,4(1H,3H)-dione

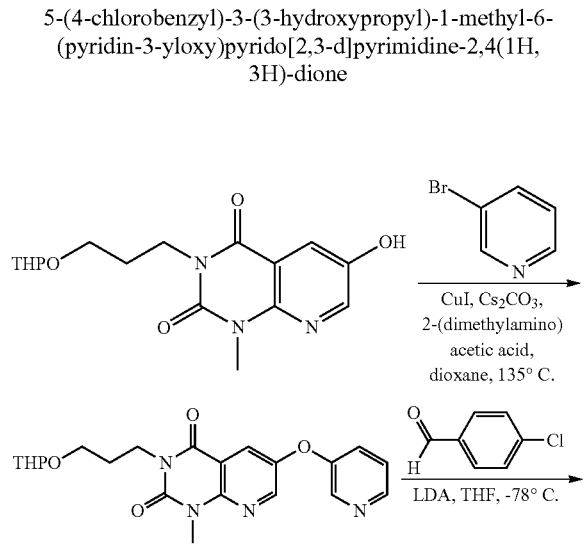

Step 1 1-methyl-6-(pyridin-3-yloxy)-3-(3-((tetrahydro-2H-pyran-2-yl)oxy)propyl)pyrido[2,3-d]pyrimidine-2,4(1H,3H)-dione

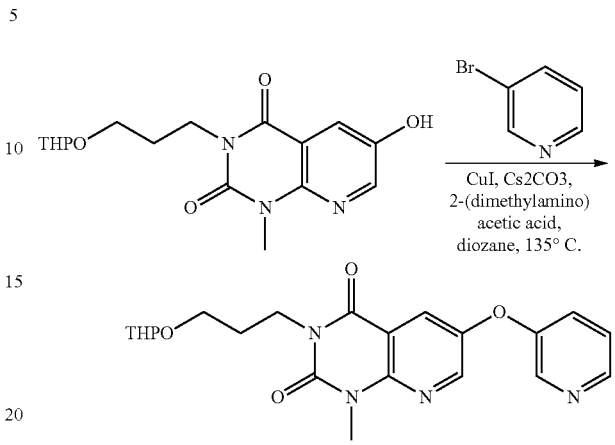

To a mixture of 6-hydroxy-1-methyl-3-(3-((tetrahydro-2H-pyran-2-yl)oxy)propyl)pyrido[2,3-d]pyrimidine-2,4(1H,3H)-dione (See Compound 36, step 2, 500 mg, 1.49 mmol), CuI (85.2 mg, 0.45 mmol), Cs$_2$CO$_3$ (971.6 mg, 2.98 mmol) and 2-(dimethylamino)acetic acid (76.87 mg, 0.75 mmol) in dioxane (20 mL) was added 3-bromopyridine (588.9 mg, 3.73 mmol). The reaction was heated at 135° C. for 5 h followed by heating at 100° C. for 18 h, cooled to RT then diluted with EA (25 mL) and water (10 mL). The organic layer was washed with water (20 mL) and brine (20 mL), dried over Na$_2$SO$_4$ and concentrated to a residue which was purified by chromatography eluted with PE/EA (10:1 to 1:1) to give 1-methyl-6-(pyridin-3-yloxy)-3-(3-((tetrahydro-2H-pyran-2-yl)oxy)propyl)pyrido[2,3-d]pyrimidine-2,4(1H,3H)-dione (450 mg, 73.2% yield) as a yellow oil. LCMS: [MH$^+$-THP] 329 and T$_R$=1.065 min.

Step 2 5-((4-chlorophenyl)(hydroxy)methyl)-1-methyl-6-(pyridin-3-yloxy)-3-(3-((tetrahydro-2H-pyran-2-yl)oxy)propyl)pyrido[2,3-d]pyrimidine-2,4(1H,3H)-dione

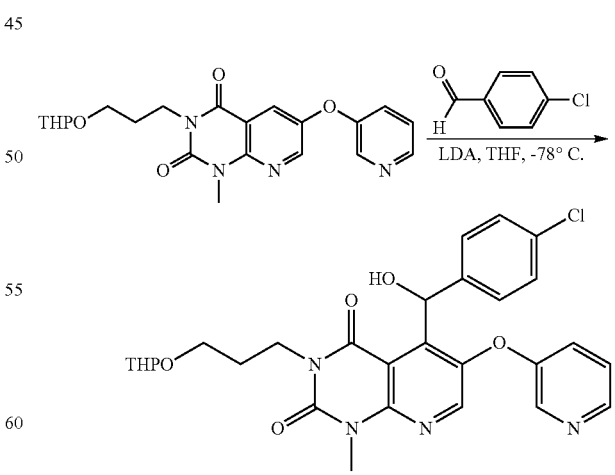

To a solution of 1-methyl-6-(pyridin-3-yloxy)-3-(3-((tetrahydro-2H-pyran-2-yl)oxy)propyl)pyrido[2,3-d]pyrimidine-2,4(1H,3H)-dione (400 mg, 0.97 mmol) in THF (8 mL) at −78° C. was added LDA (2M in THF, 1.94 mL, 3.88

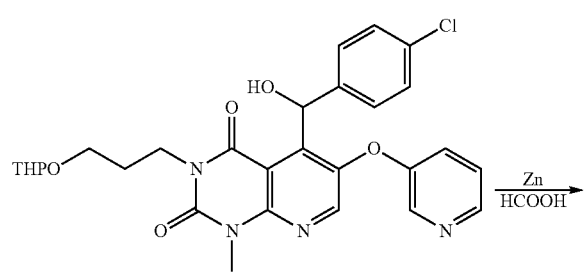

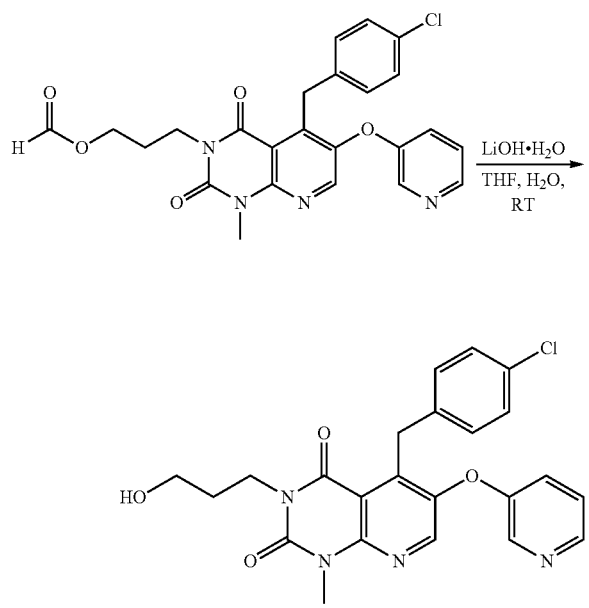

mmol) dropwise. The reaction was stirred at −78° C. for 1 h then a solution of 4-chlorobenzaldehyde (273.5 mg, 1.94 mmol) in THF (2 mL) was added dropwise. The reaction was stirred at −78° C. for 30 min. then diluted with EA (10 mL) and water (10 mL). The organic layer was dried over Na₂SO₄ and concentrated to a residue was purified by chromatography eluted with PE/EA (10:1 to 1:1) to give 5-((4-chlorophenyl) (hydroxy)methyl)-1-methyl-6-(pyridin-3-yloxy)-3-(3-((tetrahydro-2H-pyran-2-yl)oxy)propyl) pyrido[2,3-d]pyrimidine-2,4(1H,3H)-dione (71 mg, 13.2% yield) as an oil. LCMS: [MH⁺-THP] 469 and T$_R$=1.499 min.

Step 3 3-(5-(4-chlorobenzyl)-1-methyl-2,4-dioxo-6-(pyridin-3-yloxy)-1,2-dihydropyrido[2,3-d]pyrimidin-3(4H)-yl)propyl formate

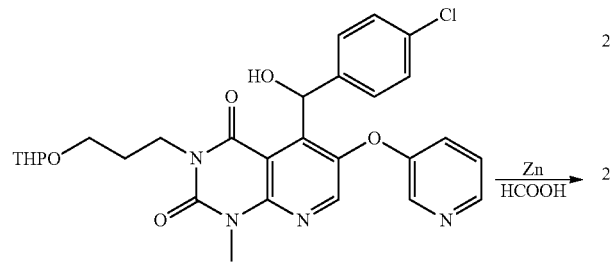

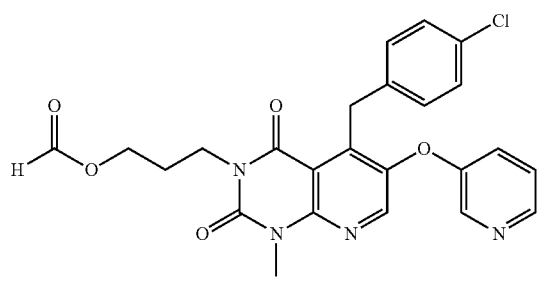

To a solution of 5-((4-chlorophenyl)(hydroxy)methyl)-1-methyl-6-(pyridin-3-yloxy)-3-(3-((tetrahydro-2H-pyran-2-yl)oxy)propyl)pyrido[2,3-d]pyrimidine-2,4(1H,3H)-dione (71 mg, 0.128 mmol) in HCOOH (3 mL) was added Zn dust (40.9 mg, 0.641 mmol). The reaction was heated at 50° C. for 2 h, cooled and filtered. The filtrate was concentrated to a residue which was purified by Prep TLC eluted with PE/EA (1:1) (three times) to give 3-(5-(4-chlorobenzyl)-1-methyl-2,4-dioxo-6-(pyridin-3-yloxy)-1,2-dihydropyrido[2,3-d]pyrimidin-3(4H)-yl)propyl formate (10.3 mg, 16.7% yield) as an oil. LCMS: MH⁺ 481 and T$_R$=1.399 min.

Step 4 5-(4-chlorobenzyl)-3-(3-hydroxypropyl)-1-methyl-6-(pyridin-3-yloxy)pyrido[2,3-d]pyrimidine-2,4 (1H,3H)-dione

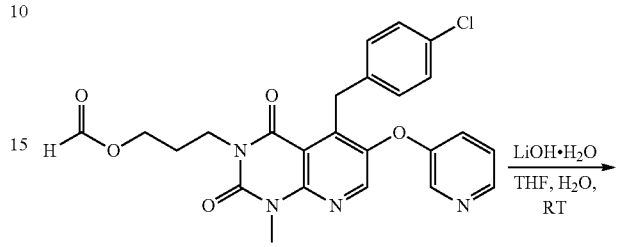

To a solution of 3-(5-(4-chlorobenzyl)-1-methyl-2,4-dioxo-6-(pyridin-3-yloxy)-1,2-dihydropyrido[2,3-d]pyrimidin-3(4H)-yl)propyl formate (10.3 mg, 0.021 mmol) in THF (5 mL) and water (5 mL), was added LiOH.H₂O (1.80 mg, 0.042 mmol) The reaction was stirred at RT for 30 min then diluted with EA (10 mL) and water (10 mL). The organic layer was dried over Na₂SO₄, filtered and concentrated to a residue which was purified by Prep HPLC to give 5-(4-chlorobenzyl)-3-(3-hydroxypropyl)-1-methyl-6-(pyridin-3-yloxy)pyrido[2,3-d]pyrimidine-2,4(1H,3H)-dione (6 mg, 61.8% yield) as a white solid. ¹H NMR (CDCl₃) δ: 8.39 (d, J=4.6 Hz, 1H), 8.33 (d, J=4.5 Hz, 2H), 7.24 (d, J=4.7 Hz, 1H), 7.17 (s, 4H), 7.10 (dd, J=8.4, 1.6 Hz, 1H), 4.75 (s, 2H), 4.24 (t, J=6.1 Hz, 2H), 3.71 (s, 3H), 3.62-3.49 (m, 2H), 2.99 (t, J=6.8 Hz, 1H), 2.00-1.84 (m, 2H). LCMS: MH⁺ 453 and T$_R$=1.963 min.

Compound 15

5-(4-chlorobenzyl)-6-((5-fluoropyridin-3-yl)oxy)-3-(3-hydroxypropyl)-1-methylpyrido[2,3-d]pyrimidine-2,4(1H,3H)-dione

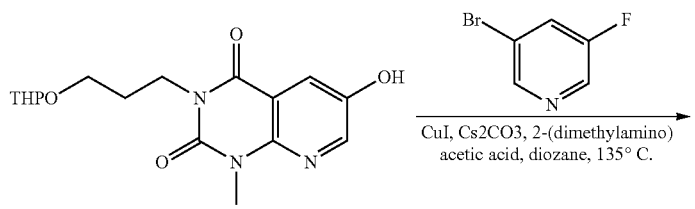

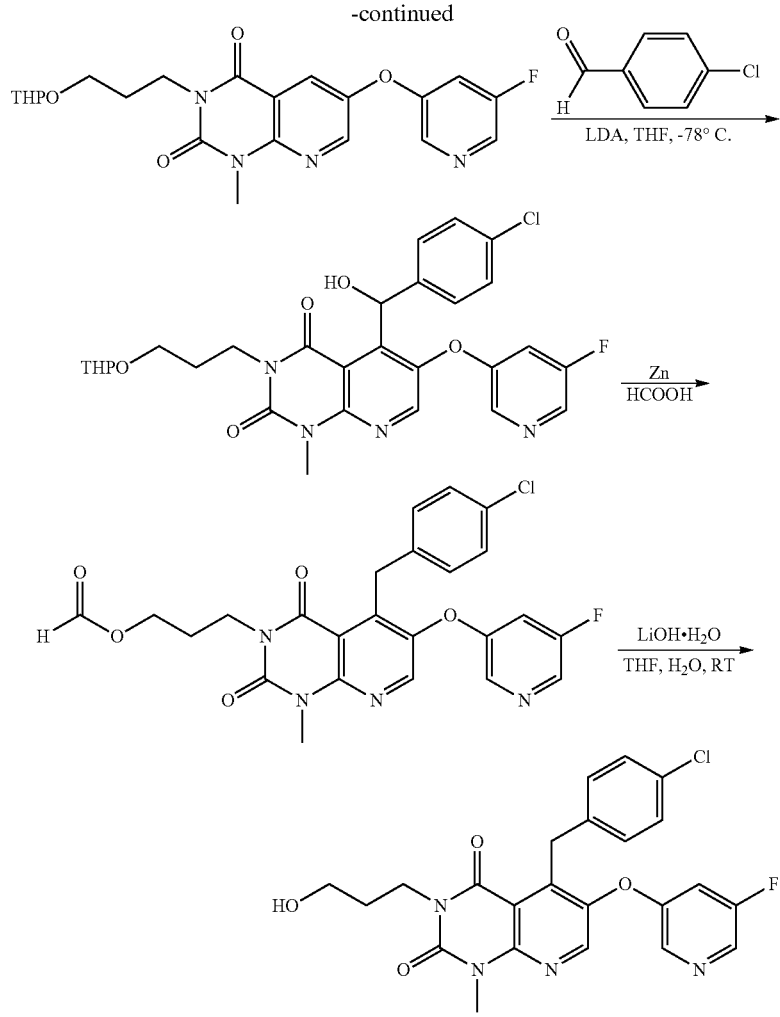

Step 1 6-((5-fluoropyridin-3-yl)oxy)-1-methyl-3-(3-((tetrahydro-2H-pyran-2-yl)oxy)propyl)-pyrido[2,3-d]pyrimidine-2,4(1H,3H)-dione

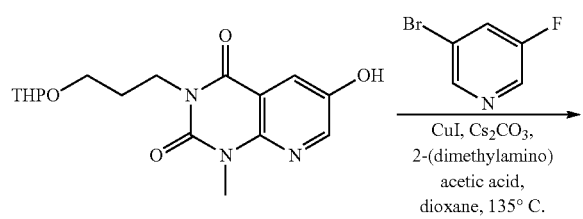

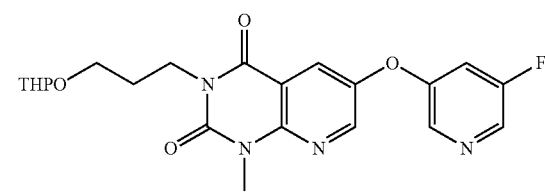

To a mixture of 6-hydroxy-1-methyl-3-(3-((tetrahydro-2H-pyran-2-yl)oxy)propyl)pyrido[2,3-d]pyrimidine-2,4 (1H,3H)-dione (See Compound 36, step 2, 300 mg, 0.90 mmol), CuI (22.5 mg, 0.19 mmol), $Cs_2CO_3$ (583.5 mg, 1.79 mmol) and 2-(dimethylamino)acetic acid (46.5 mg, 0.45 mmol) in dioxane (20 mL) was added 3-bromo-5-fluoropyridine (394 mg, 2.24 mmol). The reaction was heated at 140° C. for 5 h followed by heating at 100° C. for 18 h, cooled to RT then diluted with EA (25 mL) and water (10 mL). The organic layer was washed with water (20 mL) and brine (20 mL), dried over $Na_2SO_4$ and concentrated to a residue which was purified by chromatography eluted with PE/EA (10:1 to 1:1) to give 6-((5-fluoropyridin-3-yl)oxy)-1-methyl-3-(3-((tetrahydro-2H-pyran-2-yl)oxy) propyl) pyrido[2,3-d]pyrimidine-2,4(1H,3H)-dione (150 mg, 38.9% yield) as a white solid. LCMS: [MH$^+$-THP] 347 and $T_R$=1.482 min.

Step 2 5-((4-chlorophenyl)(hydroxy)methyl)-6-((5-fluoropyridin-3-yl)oxy)-1-methyl-3-(3-((tetrahydro-2H-pyran-2-yl)oxy)propyl)pyrido[2,3-d]pyrimidine-2,4(1H,3H)-dione

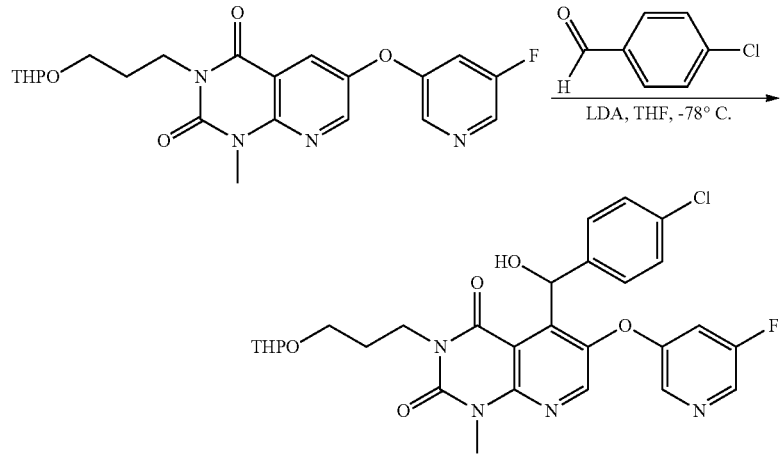

To a solution of 6-((5-fluoropyridin-3-yl)oxy)-1-methyl-3-(3-((tetrahydro-2H-pyran-2-yl)oxy) propyl)pyrido[2,3-d]pyrimidine-2,4(1H,3H)-dione (150 mg, 0.35 mmol) in THF (8 mL) at −78° C. was added LDA (2M in THF, 0.7 mL, 1.40 mmol) dropwise. The reaction was stirred at −78° C. for 1 h then 4-chlorobenzaldehyde (98 mg, 0.70 mmol) in THF (2 mL) was added. The reaction was stirred for 30 min at −78° C. then diluted with EA (10 mL) and water (10 mL). The organic layer was dried over $Na_2SO_4$ and concentrated to a residue which was purified by Prep TLC eluted with PE/EA (1:1) to give 5-((4-chlorophenyl)(hydroxy)methyl)-6-((5-fluoropyridin-3-yl)oxy)-1-methyl-3-(3-((tetrahydro-2H-pyran-2-yl)oxy)propyl)pyrido[2,3-d]pyrimidine-2,4(1H, 3H)-dione (50 mg, 25.1% yield) as an oil. LCMS: [MH$^+$-THP] 487 and $T_R$=1.423 min. Used without further purification.

Step 3 3-(5-(4-chlorobenzyl)-6-((5-fluoropyridin-3-yl)oxy)-1-methyl-2,4-dioxo-1,2-dihydropyrido[2,3-d]pyrimidin-3(4H)-yl)propyl formate

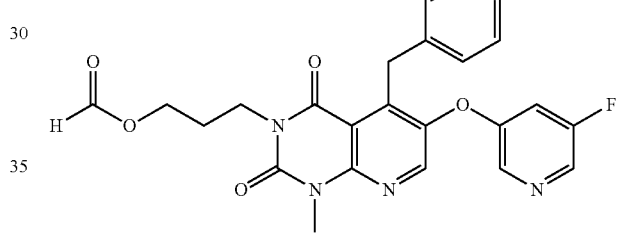

To a solution of 5-((4-chlorophenyl)(hydroxy)methyl)-6-((5-fluoropyridin-3-yl)oxy)-1-methyl-3-(3-((tetrahydro-2H-pyran-2-yl)oxy)propyl)pyrido[2,3-d]pyrimidine-2,4(1H, 3H)-dione (45 mg, 0.092 mmol) in HCOOH (5 mL) was added Zn dust (30.2 mg, 0.462 mmol). The reaction was heated at 70° C. for 1.5 h, cooled to RT and filtered. The filtrate was concentrated and dried to a residue which was purified by chromatography eluted with PE/EA (10:1 to 1:1) to give 3-(5-(4-chlorobenzyl)-6-((5-fluoropyridin-3-yl)oxy)-1-methyl-2,4-dioxo-1,2-dihydropyrido[2,3-d]pyrimidin-3(4H)-yl)propyl formate (32 mg, 69.4% yield) as an oil. LCMS: MH$^+$ 499 and $T_R$=1.513 min.

Step 4 5-(4-chlorobenzyl)-6-((5-fluoropyridin-3-yl)oxy)-3-(3-hydroxypropyl)-1-methylpyrido[2,3-d]pyrimidine-2,4(1H,3H)-dione

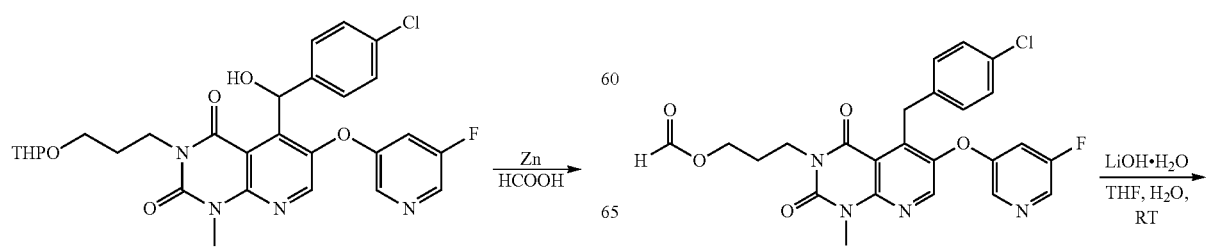

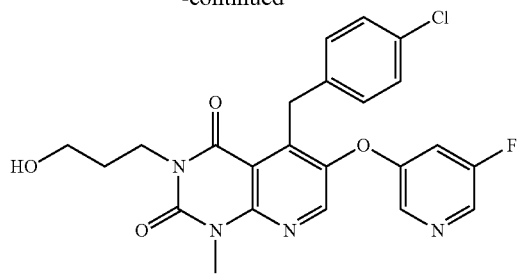

To a solution of 3-(5-(4-chlorobenzyl)-6-((5-fluoropyridin-3-yl)oxy)-1-methyl-2,4-dioxo-1,2-dihydropyrido[2,3-d]pyrimidin-3(4H)-yl)propyl formate (32 mg, 0.064 mmol) in THF (6 mL) and water (6 mL) was added LiOH.H$_2$O (5.38 mg, 0.128 mmol). The reaction was stirred at RT for 30 min then diluted with EA (10 mL) and water (10 mL). The organic layer was dried over Na$_2$SO$_4$ and concentrated to a residue which was purified by Prep TLC eluted with PE/EA (1:1) and then Prep HPLC to give 5-(4-chlorobenzyl)-6-((5-fluoropyridin-3-yl)oxy)-3-(3-hydroxypropyl)-1-methyl pyrido[2,3-d]pyrimidine-2,4(1H,3H)-dione (4 mg, 13.2% yield) as a white solid. $^1$H NMR (CDCl$_3$) δ: 8.47-8.35 (m, 2H), 8.03 (s, 1H), 7.76 (d, J=3.0 Hz, 1H), 7.18 (d, J=8.4 Hz, 2H), 7.12 (d, J=8.4 Hz, 2H), 4.24 (t, J=6.1 Hz, 2H), 4.06 (s, 2H), 3.73 (s, 3H), 3.57 (t, J=5.6 Hz, 2H), 2.01-1.88 (m, 2H). LCMS: MH$^+$ 471 and T$_R$=2.246 min.

Compound 16

5-(4-chlorobenzyl)-6-((5-chloropyridin-3-yl)oxy)-3-(3-hydroxypropyl)-1-methylpyrido[2,3-d]pyrimidine-2,4(1H,3H)-dione

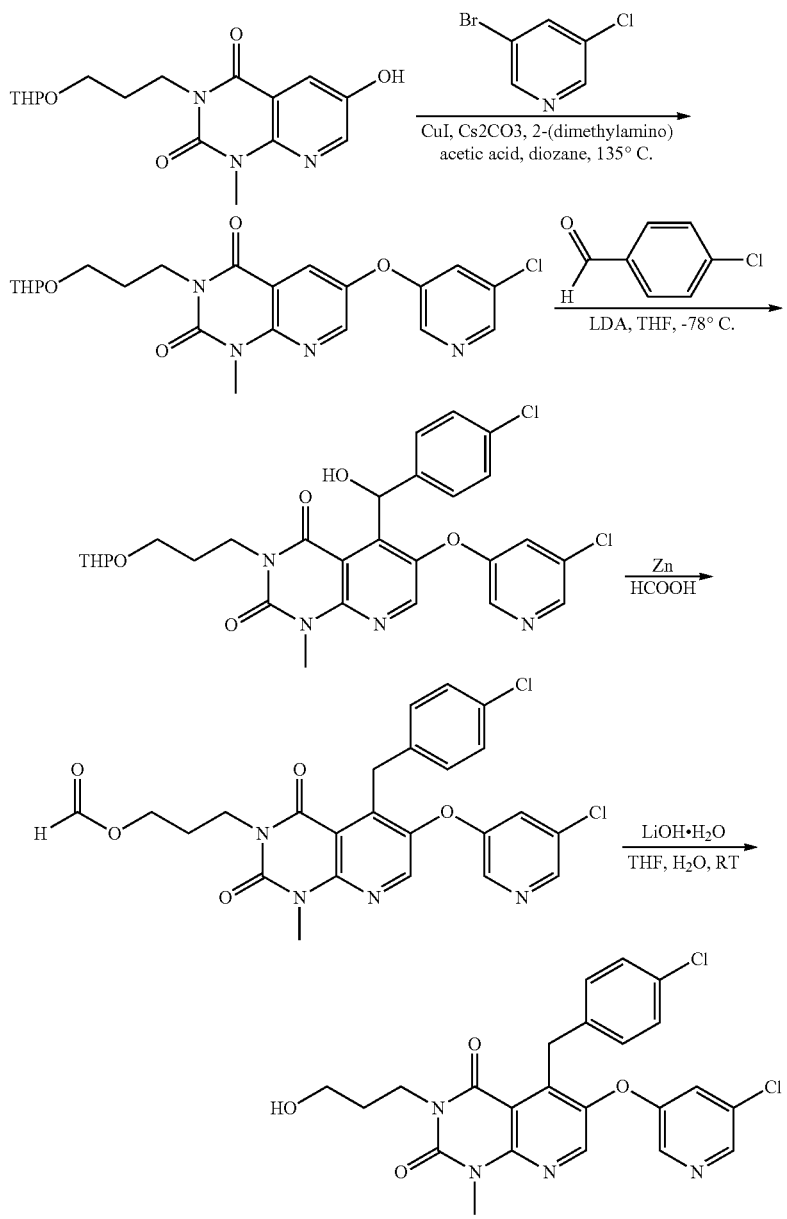

Step 1 6-((5-chloropyridin-3-yl)oxy)-1-methyl-3-(3-((tetrahydro-2H-pyran-2-yl)oxy)propyl)pyrido[2,3-d]pyrimidine-2,4(1H,3H)-dione

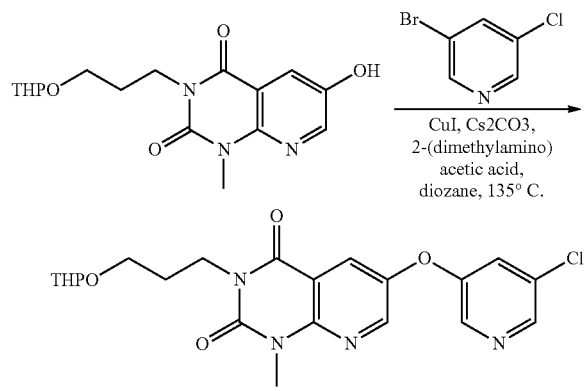

To a mixture of 6-hydroxy-1-methyl-3-(3-((tetrahydro-2H-pyran-2-yl)oxy)propyl)pyrido[2,3-d]pyrimidine-2,4(1H,3H)-dione (See Compound 36, step 2, 500 mg, 1.49 mmol), CuI (85.2 mg, 0.45 mmol), Cs$_2$CO$_3$ (971.6 mg, 2.98 mmol) and 2-(dimethylamino)acetic acid (76.87 mg, 0.75 mmol) in dioxane (20 mL) was added 3-bromo-5-chloropyridine (717.3 mg, 3.73 mmol). The reaction was heated at 135° C. for 5 h followed by heating at 100° C. for 18 h, cooled to RT then diluted with EA (25 mL) and water (10 mL). The organic layer was washed with water (20 mL) and brine (20 mL), dried over Na$_2$SO$_4$ and concentrated to a residue which was purified by chromatography eluted with PE/EA (10:1 to 1:1) to give 6-((5-chloropyridin-3-yl)oxy)-1-methyl-3-(3-((tetrahydro-2H-pyran-2-yl)oxy)propyl)pyrido[2,3-d]pyrimidine-2,4(1H,3H)-dione (525 mg, 78.8% yield) as a yellow oil. LCMS [MH$^+$-THP] 363 and T$_R$=1.403 min.

Step 2 5-((4-chlorophenyl)(hydroxy)methyl)-6-((5-chloropyridin-3-yl)oxy)-1-methyl-3-(3-((tetrahydro-2H-pyran-2-yl)oxy)propyl)pyrido[2,3-d]pyrimidine-2,4(1H,3H)-dione

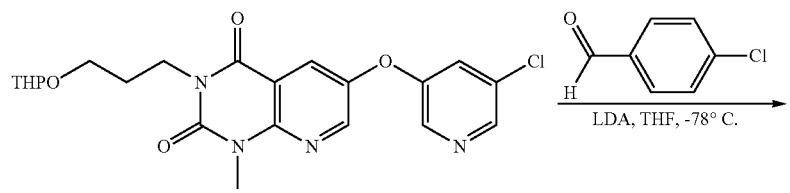

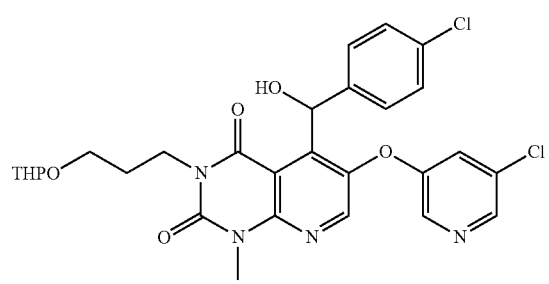

To a solution of 6-((5-chloropyridin-3-yl)oxy)-1-methyl-3-(3-((tetrahydro-2H-pyran-2-yl)oxy)propyl)pyrido[2,3-d]pyrimidine-2,4(1H,3H)-dione (470 mg, 1.06 mmol) in THF (10 mL) at −78° C. was added LDA (2M in THF, 2.12 mL, 4.24 mmol) dropwise. The reaction was stirred at −78° C. for 1 h then 4-chlorobenzaldehyde (298.8 mg, 2.12 mmol) in THF (2 mL) was added. The reaction was stirred at −78° C. for 30 min then diluted with EA (10 mL) and water (10 mL). The organic layer was dried over Na$_2$SO$_4$, and concentrated to a residue which was purified by chromatography eluted with PE/EA (10:1 to 1:1) to give 5-((4-chlorophenyl)(hydroxy)methyl)-6-((5-chloropyridin-3-yl)oxy)-1-methyl-3-(3-((tetrahydro-2H-pyran-2-yl)oxy)propyl)pyrido[2,3-d]pyrimidine-2,4 (1H,3H)-dione (120 mg, 19.4% yield) as an oil. LCMS: [MH$^+$-THP] 503 and T$_R$=1.508 min.

Step 3 3-(5-(4-chlorobenzyl)-6-((5-chloropyridin-3-yl)oxy)-1-methyl-2,4-dioxo-1,2-dihydropyrido[2,3-d]pyrimidin-3(4H)-yl)propyl formate To a solution of 5-((4-chlorophenyl)(hydroxy)methyl)-6-((5-chloropyridin-3-yl)oxy)-1-methyl-3-(3-((tetrahydro-2H- pyran-2-yl)oxy)propyl)pyrido[2,3-d]pyrimidine-2,4(1H,3H)-dione (120 mg, 0.204 mmol) in HCOOH (5 mL) was added Zn dust (66.8 mg, 1.02 mmol). The reaction was heated at 70° C. for 1.5 h, cooled to RT and filtered. The filtrate was concentrated to give 3-(5-(4-chlorobenzyl)-6-((5-chloropyridin-3-yl)oxy)-1-methyl-2,4-dioxo-1,2-dihydropyrido[2,3-d]pyrimidin-3(4H)-yl)propyl formate (40 mg, 38.0% yield) as an oil. LCMS MH⁺ 515 and $T_R$=1.696 min. Used without further purification.

Step 4 5-(4-chlorobenzyl)-6-((5-chloropyridin-3-yl)oxy)-3-(3-hydroxypropyl)-1-methylpyrido[2,3-d]pyrimidine-2,4(1H,3H)-dione

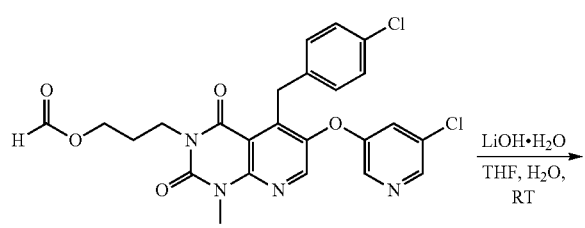

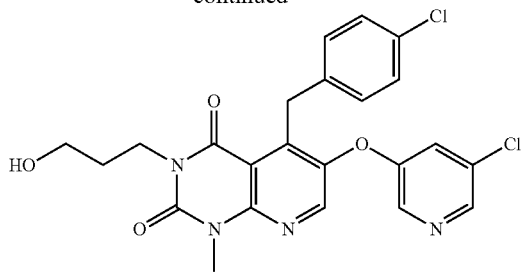

To a solution of 3-(5-(4-chlorobenzyl)-6-((5-chloropyridin-3-yl)oxy)-1-methyl-2,4-dioxo-1,2-dihydropyrido[2,3-d]pyrimidin-3(4H)-yl)propyl formate (40 mg, 0.078 mmol) in THF (6 mL) and water (6 mL) was added LiOH·H₂O (6.51 mg, 0.156 mmol) at 20° C. The reaction was stirred at RT for 30 min. then diluted with EA (10 mL) and water (10 mL). The organic layer was dried over Na₂SO₄ and concentrated to a residue which was purified by Prep HPLC to give 5-(4-chlorobenzyl)-6-((5-chloropyridin-3-yl)oxy)-3-(3-hydroxypropyl)-1-methylpyrido[2,3-d]pyrimidine-2,4(1H,3H)-dione (8 mg, 21.2% yield) as a white solid. ¹H NMR (CDCl₃) δ: 8.52 (s, 1H), 8.39 (d, J=3.0 Hz, 1H), 8.10 (s, 1H), 7.71 (d, J=3.0 Hz, 1H), 7.17 (d, J=8.5 Hz, 2H), 7.11 (d, J=8.4 Hz, 2H), 4.24 (t, J=6.1 Hz, 2H), 4.19 (s, 2H), 3.72 (s, 3H), 3.57 (d, J=5.0 Hz, 2H), 2.99 (s, 1H), 2.00-1.85 (m, 2H). LCMS MH⁺ 487 and $T_R$=2.436 min.

Compound 17

5-(4-chlorobenzyl)-3-(3-hydroxypropyl)-1-methyl-6-((5-(trifluoromethyl)pyridin-3-yl)oxy)pyrido[2,3-d]pyrimidine-2,4(1H,3H)-dione

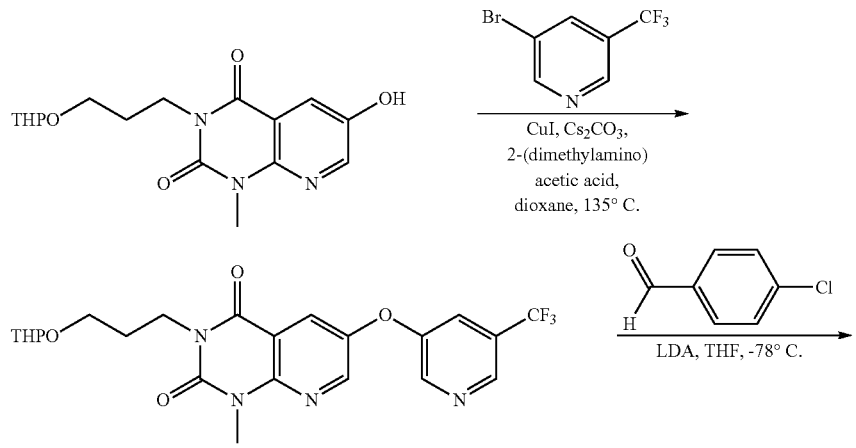

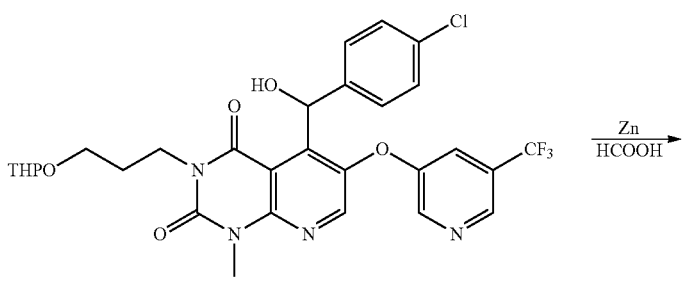

-continued

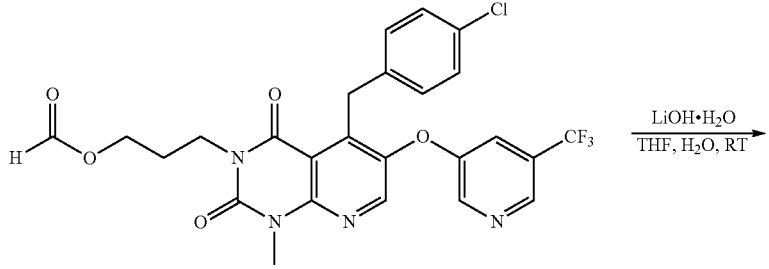

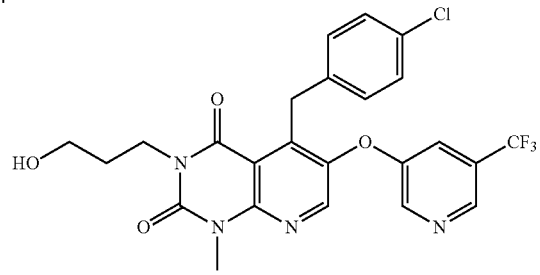

Step 1 1-methyl-3-(3-((tetrahydro-2H-pyran-2-yl)oxy)propyl)-6-((5-(trifluoromethyl)pyridin-3-yl)oxy)pyrido[2,3-d]pyrimidine-2,4(1H,3H)-dione

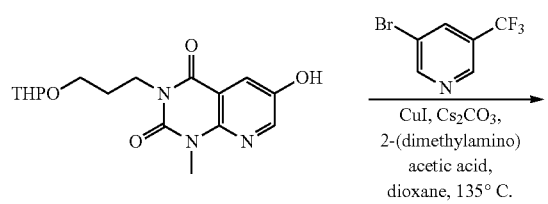

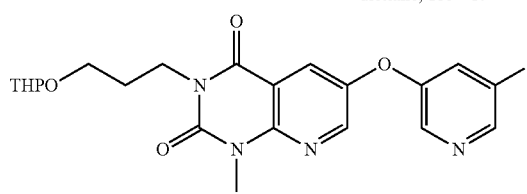

To a mixture of 6-hydroxy-1-methyl-3-(3-((tetrahydro-2H-pyran-2-yl)oxy)propyl)pyrido[2,3-d]pyrimidine-2,4(1H,3H)-dione (See Compound 36, step 2, 500 mg, 1.49 mmol), CuI (85.2 mg, 0.45 mmol), Cs$_2$CO$_3$ (971.6 mg, 2.98 mmol) and 2-(dimethylamino)acetic acid (76.87 mg, 0.75 mmol) in dioxane (20 mL) was added 3-bromo-5-(trifluoromethyl)pyridine (842.9 mg, 3.73 mmol). The reaction was heated at 135° C. for 5 hours, followed by heating at 100° C. for 18 h, cooled to RT and diluted with EA (25 mL) and water (10 mL). The organic layer was washed with water (20 mL) and brine (20 mL), dried over Na$_2$SO$_4$ and concentrated to a residue which was purified by chromatography eluted with PE/EA (10:1 to 1:1) to give 1-methyl-3-(3-((tetrahydro-2H-pyran-2-yl)oxy)propyl)-6-((5-(trifluoromethyl)pyridin-3-yl)oxy)pyrido[2,3-d]pyrimidine-2,4(1H,3H)-dione (460 mg, 64.2% yield) as a yellow oil. LCMS MH$^+$ 397 and T$_R$=1.540 min.

Step 2 5-((4-chlorophenyl)(hydroxy)methyl)-1-methyl-3-(3-((tetrahydro-2H-pyran-2-yl)oxy)propyl)-6-((5-(trifluoromethyl)pyridin-3-yl)oxy)pyrido[2,3-d]pyrimidine-2,4(1H,3H)-dione

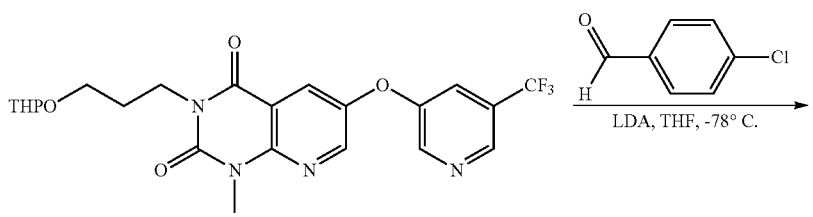

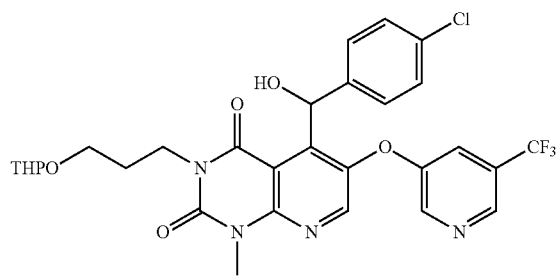

To a solution of 1-methyl-3-(3-((tetrahydro-2H-pyran-2-yl)oxy)propyl)-6-((5-(trifluoromethyl)pyridin-3-yl)oxy)pyrido[2,3-d]pyrimidine-2,4(1H,3H)-dione (340 mg, 0.708 mmol) in THF (8 mL) at −78° C. was added LDA (2M in THF, 1.42 mL, 2.83 mmol) dropwise. The reaction was stirred at −78° C. for 1 h then a solution of 4-chlorobenzaldehyde (199.7 mg, 1.42 mmol) in THF (2 mL) was added dropwise. The reaction was stirred for 30 min at −78° C. then diluted with EA (10 mL) and water (10 mL). The organic layer was dried over Na$_2$SO$_4$ and concentrated to a residue which was purified by chromatography eluted with PE/EA (10:1 to 1:1) to give 5-((4-chlorophenyl)(hydroxy)methyl)-1-methyl-3-(3-((tetrahydro-2H-pyran-2-yl)oxy)propyl)-6-((5-(trifluoromethyl)pyridin-3-yl)oxy)pyrido[2,3-d]pyrimidine-2,4(1H,3H)-dione (172 mg, 39.1% yield) as an oil. LCMS: [MH$^+$-THP] 537 and T$_R$=1.611 min.

Step 3 3-(5-(4-chlorobenzyl)-1-methyl-2,4-dioxo-6-((5-(trifluoromethyl)pyridin-3-yl)oxy)-1,2-dihydropyrido[2,3-d]pyrimidin-3(4H)-yl)propyl formate

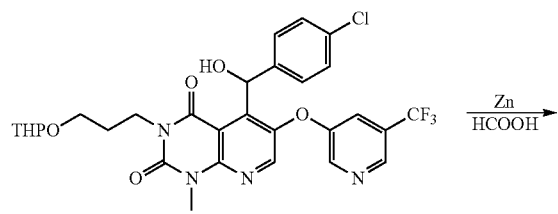

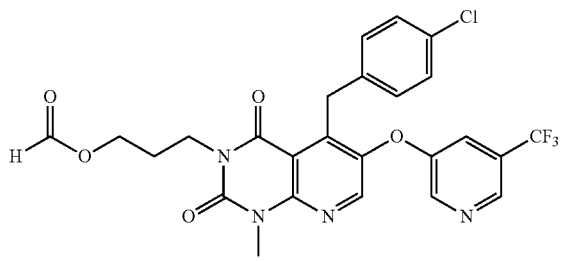

To a solution of 5-((4-chlorophenyl)(hydroxy)methyl)-1-methyl-3-(3-((tetrahydro-2H-pyran-2-yl)oxy)propyl)-6-((5-(trifluoromethyl)pyridin-3-yl)oxy)pyrido[2,3-d]pyrimidine-2,4(1H,3H)-dione (172 mg, 0.277 mmol) in HCOOH (5 mL) was added Zn dust (88.5 mg, 1.385 mmol) at 20° C. The reaction was heated at 50° C. for 2 h, cooled to RT and filtered. The filtrate was concentrated to a residue which was purified by Prep TLC eluted with PE/EA (1:1) to give 3-(5-(4-chlorobenzyl)-1-methyl-2,4-dioxo-6-((5-(trifluoromethyl)pyridin-3-yl)oxy)-1,2-dihydropyrido[2,3-d]pyrimidin-3(4H)-yl)propyl formate (45.3 mg, 29.8% yield) as an oil. LCMS: MH$^+$ 549 and T$_R$=1.471 min.

Step 4 5-(4-chlorobenzyl)-3-(3-hydroxypropyl)-1-methyl-6-((5-(trifluoromethyl)pyridin-3-yl)oxy)pyrido[2,3-d]pyrimidine-2,4(1H,3H)-dione

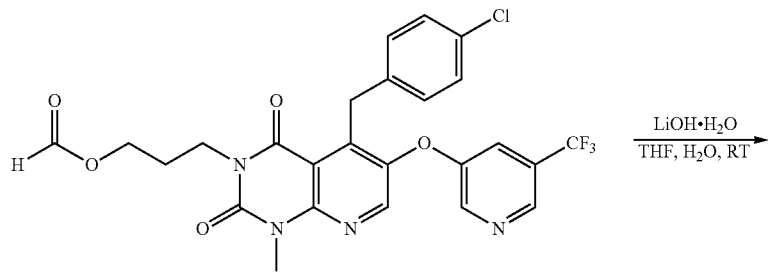

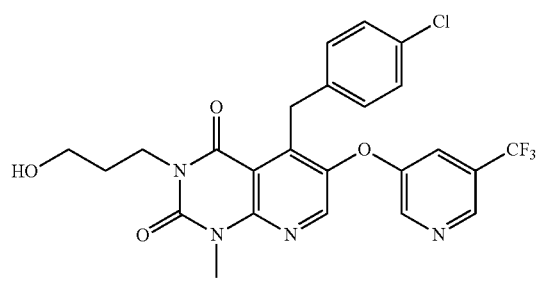

To a solution of 3-(5-(4-chlorobenzyl)-1-methyl-2,4-dioxo-6-((5-(trifluoromethyl)pyridin-3-yl)oxy)-1,2-dihydropyrido[2,3-d]pyrimidin-3(4H)-yl)propyl formate (45.3 mg, 0.083 mmol) in THF (5 mL) and water (5 mL) was added LiOH.H$_2$O (6.93 mg, 0.165 mmol). The reaction was stirred at RT for 30 min then diluted with EA (10 mL) and water (10 mL). The organic layer was dried over Na$_2$SO$_4$ and concentrated to a residue which was purified by Prep HPLC to give 5-(4-chlorobenzyl)-3-(3-hydroxypropyl)-1-methyl-6-((5-(trifluoromethyl)pyridin-3-yl)oxy)pyrido[2,3-d]pyrimidine-2,4(1H,3H)-dione (8 mg, 18.6% yield) as a white solid. $^1$H NMR (CDCl$_3$) δ: 8.82 (s, 1H), 8.35 (s, 1H), 8.26 (d, J=3.0 Hz, 1H), 7.53 (d, J=3.0 Hz, 1H), 7.12 (d, J=8.4 Hz, 2H), 7.01 (d, J=8.3 Hz, 2H), 4.26-4.20 (m, 4H), 3.71 (s, 3H), 3.58-3.54 (m, 2H), 2.97 (brd s, 1H), 1.96-1.90 (m, 2H). LCMS: MH$^+$ 521 and T$_R$=2.765 min.

Compound 18

5-(4-chlorobenzyl)-3-(3-hydroxypropyl)-1-methyl-6-((6-methylpyridin-3-yl)oxy)pyrido[2,3-d]pyrimidine-2,4(1H,3H)-dione

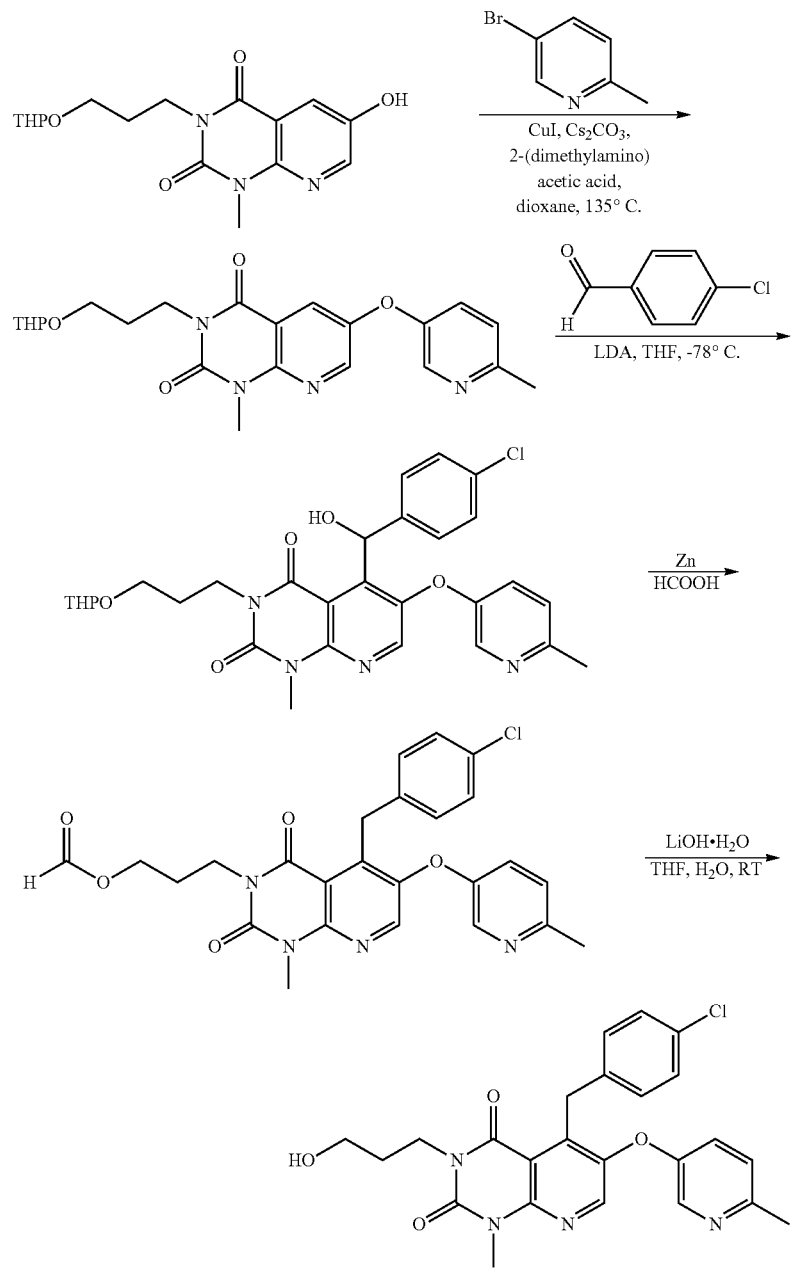

Step 1 1-methyl-6-((6-methylpyridin-3-yl)oxy)-3-(3-((tetrahydro-2H-pyran-2-yl)oxy)propyl)pyrido[2,3-d]pyrimidine-2,4(1H,3H)-dione

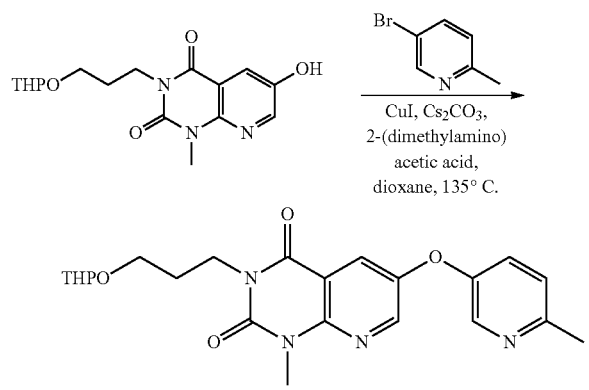

To a suspension of 6-hydroxy-1-methyl-3-(3-((tetrahydro-2H-pyran-2-yl)oxy)propyl)pyrido[2,3-d]pyrimidine-2,4(1H,3H)-dione (See Compound 36, step 2, 500 mg, 1.49 mmol), CuI (85.2 mg, 0.45 mmol), $Cs_2CO_3$ (971.6 mg, 2.98 mmol) and 2-(dimethylamino)acetic acid (76.87 mg, 0.75 mmol) in dioxane (20 mL) was added 5-bromo-2-methylpyridine (641.2 mg, 3.73 mmol). The reaction was heated at 135° C. for 5 h followed by heating at 100° C. for 18 h, cooled to RT then diluted with EA (25 mL) and water (10 mL). The organic layer was washed with water (20 mL) and brine (20 mL), dried over $Na_2SO_4$ and concentrated to residue which was purified by chromatography eluted with PE/EA (5:1 to 1:1) to give 1-methyl-6-((6-methylpyridin-3-yl)oxy)-3-(3-((tetrahydro-2H-pyran-2-yl)oxy)propyl)pyrido[2,3-d]pyrimidine-2,4(1H,3H)-dione (490 mg, 77.1% yield) as a yellow oil. LCMS: [$MH^+$-THP] 343 and $T_R$=1.215 min.

Step 2 5-((4-chlorophenyl)(hydroxy)methyl)-1-methyl-6-((6-methylpyridin-3-yl)oxy)-3-(3-((tetrahydro-2H-pyran-2-yl)oxy)propyl)pyrido[2,3-d]pyrimidine-2,4(1H,3H)-dione

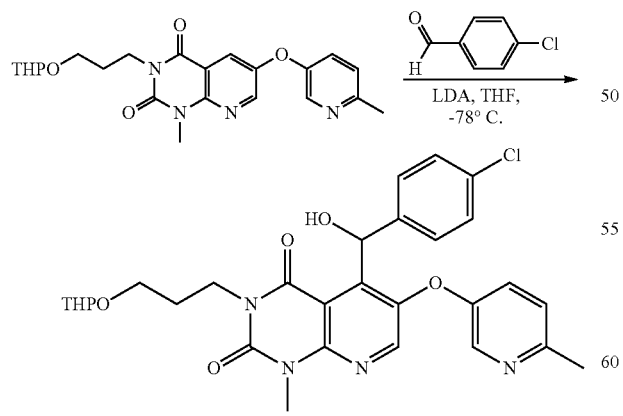

To a solution of 1-methyl-6-((6-methylpyridin-3-yl)oxy)-3-(3-((tetrahydro-2H-pyran-2-yl)oxy)propyl)pyrido[2,3-d]pyrimidine-2,4(1H,3H)-dione (450 mg, 1.06 mmol) in THF (8 mL) at −78° C. was added LDA (2M in THF, 2.11 mL, 4.24 mmol) dropwise. The reaction was stirred at −78° C. for 1 h. then a solution of 4-chlorobenzaldehyde (296.6 mg, 2.11 mmol) in THF (2 mL) was added dropwise. The reaction was stirred for 30 min at −78° C. then diluted with EA (10 mL) and water (10 mL). The organic layer was dried over $Na_2SO_4$ and concentrated to a residue which was purified by chromatography eluted with PE/EA (10:1 to 1:1) to give 5-((4-chlorophenyl)(hydroxy)methyl)-1-methyl-6-((6-methylpyridin-3-yl)oxy)-3-(3-((tetrahydro-2H-pyran-2-yl)oxy)propyl)pyrido[2,3-d]pyrimidine-2,4(1H,3H)-dione (40 mg, 6.7% yield) as an oil. LCMS: $MH^+$ 567 and $T_R$=1.400 min.

Step 3 3-(5-(4-chlorobenzyl)-1-methyl-6-((6-methylpyridin-3-yl)oxy)-2,4-dioxo-1,2-dihydropyrido[2,3-d]pyrimidin-3(4H)-yl)propyl formate

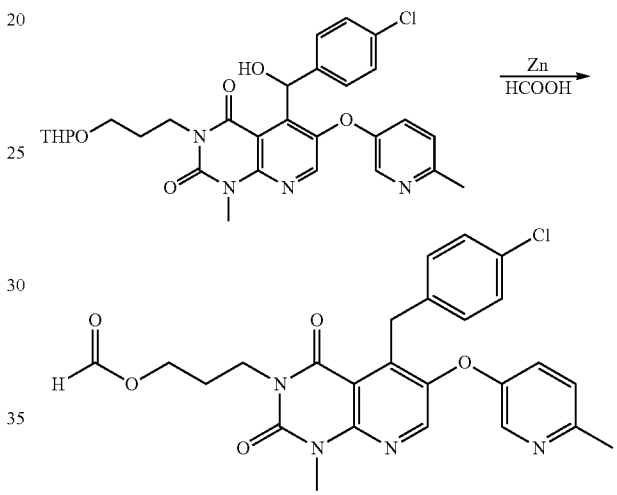

To a solution of 5-((4-chlorophenyl)(hydroxy)methyl)-1-methyl-6-((6-methylpyridin-3-yl)oxy)-3-(3-((tetrahydro-2H-pyran-2-yl)oxy)propyl)pyrido[2,3-d]pyrimidine-2,4(1H,3H)-dione (25 mg, 0.046 mmol) in HCOOH (3 mL) was added Zn dust (30.4 mg, 0.46 mmol). The reaction was heated at 70° C. for 40 min, cooled to RT and filtered. The filtrate was concentrated to a residue which was purified by Prep TLC eluted with PE/EA (1:1) to give 3-(5-(4-chlorobenzyl)-1-methyl-6-((6-methylpyridin-3-yl)oxy)-2,4-dioxo-1,2-dihydropyrido[2,3-d]pyrimidin-3(4H)-yl)propyl formate (10 mg, 45.8% yield) as a solid. LCMS: $MH^+$ 495 and $T_R$=1.316 min.

Step 4 5-(4-chlorobenzyl)-3-(3-hydroxypropyl)-1-methyl-6-((6-methylpyridin-3-yl)oxy)pyrido[2,3-d]pyrimidine-2,4(1H,3H)-dione

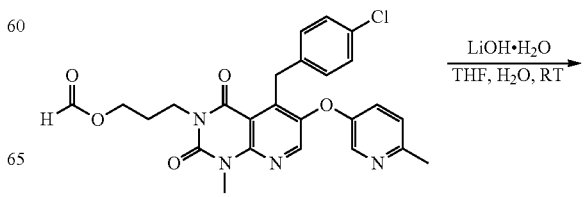

-continued

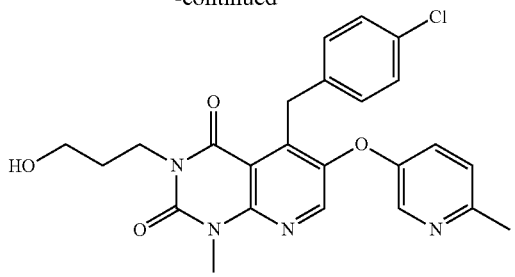

To a solution of 3-(5-(4-chlorobenzyl)-1-methyl-6-((6-methylpyridin-3-yl)oxy)-2,4-dioxo-1,2-dihydropyrido[2,3-d]pyrimidin-3(4H)-yl)propyl formate (10 mg, 0.020 mmol) in THF (5 mL) and water (5 mL) was added LiOH.H$_2$O (1.70 mg, 0.040 mmol). The reaction was stirred at RT for 30 min then diluted with EA (10 mL) and water (10 mL). The organic layer was dried over Na$_2$SO$_4$, and concentrated to a residue which was purified by Prep HPLC to give 5-(4-chlorobenzyl)-3-(3-hydroxypropyl)-1-methyl-6-((6-methylpyridin-3-yl)oxy)pyrido[2,3-d]pyrimidine-2,4(1H,3H)-dione (2 mg, 21.2% yield) as a white solid. $^1$H NMR (CDCl$_3$) δ: 8.29 (s, 1H), 8.20 (d, J=2.4 Hz, 1H), 7.16-7.18 (m, 4H), 7.10 (d, J=8.6 Hz, 1H), 7.03 (s, 1H), 4.76 (s, 2H), 4.24 (t, J=6.2 Hz, 2H), 3.70 (s, 3H), 3.53-3.57 (m, 2H), 3.04 (t, J=7.0 Hz, 1H), 2.54 (s, 3H), 1.92-1.96 (m, 2H). LCMS: MH$^+$ 467 and T$_R$=1.903 min.

Compound 19

5-(4-chlorobenzyl)-3-(3-hydroxypropyl)-1-methyl-6-(6-(trifluoromethyl)pyridin-3-yloxy)pyrido[2,3-d]pyrimidine-2,4(1H,3H)-dione

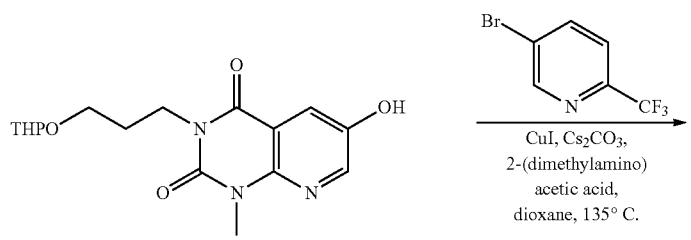

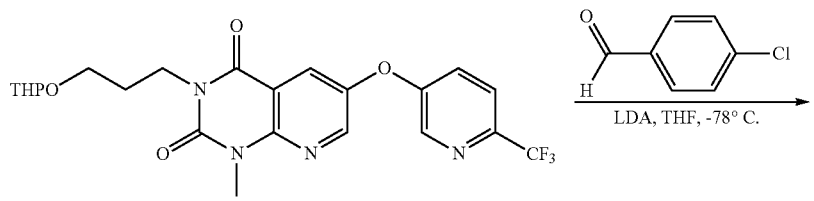

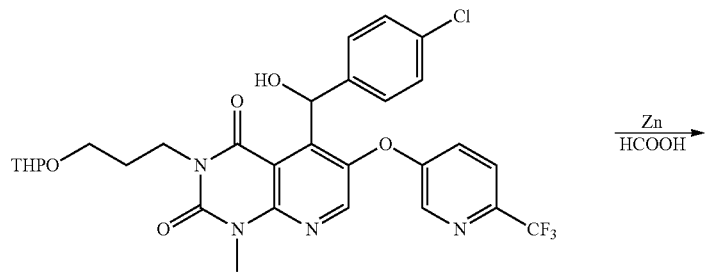

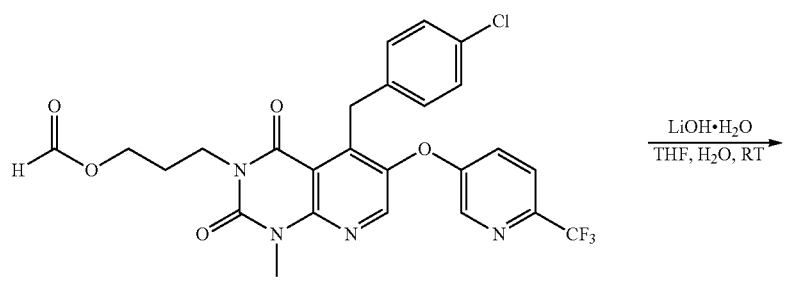

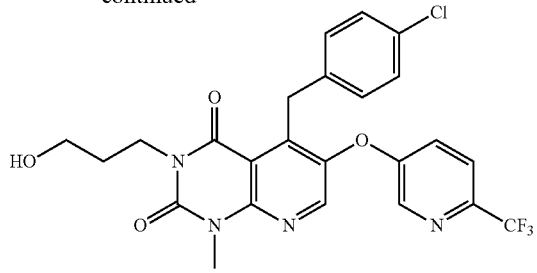

Step 1 1-methyl-3-(3-(tetrahydro-2H-pyran-2-yloxy)propyl)-6-(6-(trifluoromethyl)pyridin-3-yloxy)pyrido[2,3-d]pyrimidine-2,4(1H,3H)-dione

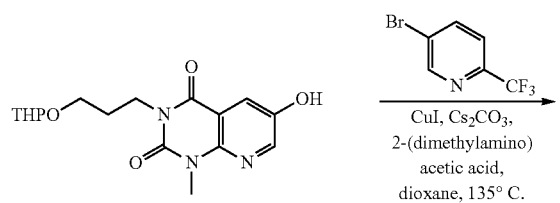

To a suspension of 6-hydroxy-1-methyl-3-(3-((tetrahydro-2H-pyran-2-yl)oxy)propyl)pyrido[2,3-d]pyrimidine-2,4(1H,3H)-dione (See Compound 36, step 2, 500 mg, 1.49 mmol), CuI (85.2 mg, 0.45 mmol), Cs₂CO₃ (973 mg, 2.99 mmol) and 2-(dimethylamino)acetic acid (76.87 mg, 0.75 mmol) in dioxane (20 mL) was added 5-bromo-2-(trifluoromethyl)pyridine (843 mg, 3.73 mmol). The reaction was heated at 135° C. for 8 hours, followed by heating at 100° C. for 18 h, cooled to RT then diluted with EA (25 mL) and water (10 mL). The organic layer was washed with water (20 mL) and brine (20 mL), dried over Na₂SO₄ and concentrated to a residue which was purified by chromatography eluted with PE/EA (10:1 to 1:1) to give 5-((4-chlorophenyl)(hydroxy)methyl)-1-methyl-3-(3-(tetrahydro-2H-pyran-2-yloxy)propyl)-6-(6-(trifluoromethyl)pyridin-3-yloxy)pyrido[2,3-d]pyrimidine-2,4(1H,3H)-dion (587 mg, 82.2% yield) as a yellow oil. LCMS: MH⁺ 481 and $T_R$=1.397 min.

Step 2 5-((4-chlorophenyl)(hydroxy)methyl)-1-methyl-3-(3-(tetrahydro-2H-pyran-2-yloxy)propyl)-6-(6-(trifluoromethyl)pyridin-3-yloxy)pyrido[2,3-d]pyrimidine-2,4(1H,3H)-dione

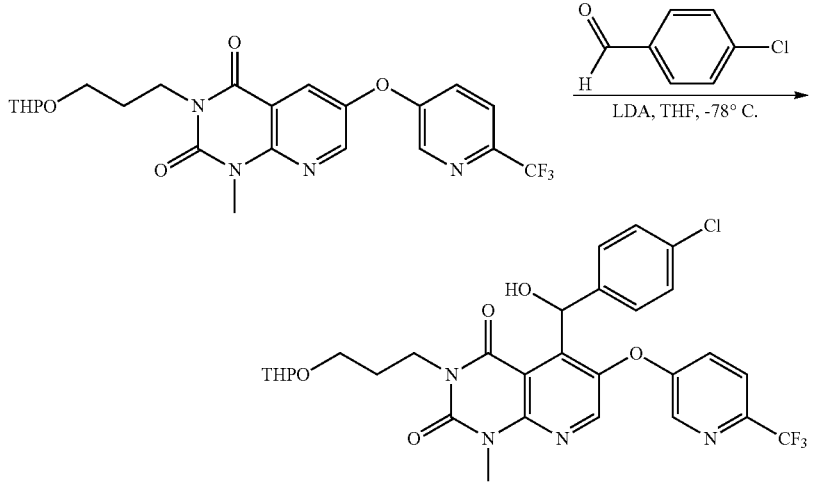

To a solution of 5-((4-chlorophenyl)(hydroxy)methyl)-1-methyl-3-(3-(tetrahydro-2H-pyran-2-yloxy)propyl)-6-(6-(trifluoromethyl)pyridin-3-yloxy)pyrido[2,3-d]pyrimidine-2,4(1H,3H)-dione (500 mg, 1.04 mmol) in THF (8 mL) at −78° C. was added LDA (2M in THF, 2.6 mL, 5.2 mmol) dropwise. The reaction was stirred at −78° C. for 1 h then a solution of 4-chlorobenzaldehyde (291 mg, 2.08 mmol) in THF (2 mL) was added. The reaction was stirred at −78° C. for 30 min then diluted with EA (10 mL) and water (10 mL). The organic layer was dried over Na₂SO₄ and concentrated to a residue which was purified by chromatography eluted with PE/EA (10:1 to 1:1) to give 5-((4-chlorophenyl)(hydroxy)methyl)-1-methyl-3-(3-(tetrahydro-2H-pyran-2-yloxy)propyl)-6-(6-(trifluoromethyl)pyridin-3-yloxy)pyrido

[2,3-d]pyrimidine-2,4(1H,3H)-dione (60 mg, 29.0% yield) LCMS: MH+ 621 and T$_R$=1.574 min.

Step 3 3-(5-(4-chlorobenzyl)-1-methyl-2,4-dioxo-6-(6-(trifluoromethyl)pyridin-3-yloxy)-1,2-dihydropyrido[2,3-d]pyrimidin-3(4H)-yl)propyl formate

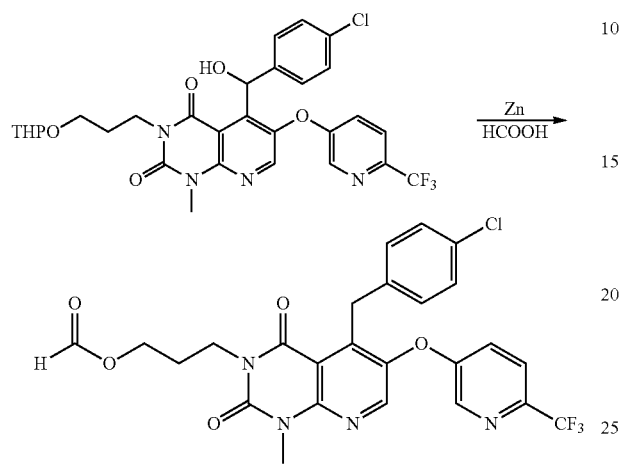

To a solution of 5-((4-chlorophenyl)(hydroxy)methyl)-1-methyl-3-(3-(tetrahydro-2H-pyran-2-yloxy)propyl)-6-(6-(trifluoromethyl)pyridin-3-yloxy)pyrido[2,3-d]pyrimidine-2,4(1H,3H)-dione (60 mg, 0.097 mmol) in HCOOH (5 mL) was added Zn dust (37.7 mg, 0.58 mmol). The reaction was heated at 70° C. for 1.5 h, cooled to RT and filtered. The filtrate was concentrated to give 3-(5-(4-chlorobenzyl)-1-methyl-2,4-dioxo-6-(6-(trifluoromethyl)pyridin-3-yloxy)-1,2-dihydropyrido[2,3-d]pyrimidin-3(4H)-yl)propyl formate (20 mg, 37.7% yield) as an oil. LCMS: MH+ 549 and T$_R$=1.799 min.

Step 4 5-(4-chlorobenzyl)-3-(3-hydroxypropyl)-1-methyl-6-(6-(trifluoromethyl)pyridin-3-yloxy)pyrido[2,3-d]pyrimidine-2,4(1H,3H)-dione

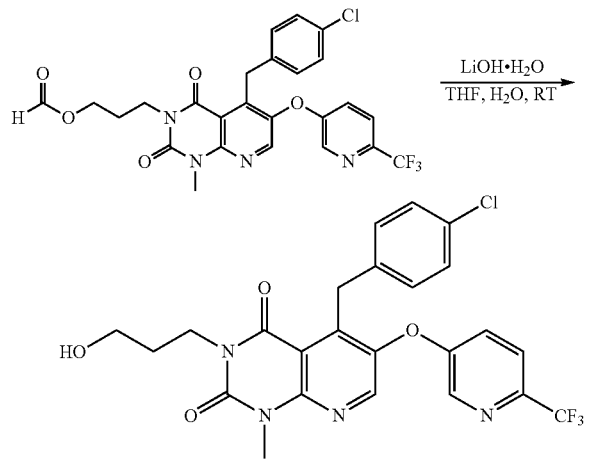

To a solution of 3-(5-(4-chlorobenzyl)-1-methyl-2,4-dioxo-6-(6-(trifluoromethyl)pyridin-3-yloxy)-1,2-dihydropyrido[2,3-d]pyrimidin-3(4H)-yl)propyl formate (20 mg, 0.036 mmol) in THF (2 mL) and water (2 mL) was added LiOH·H$_2$O (4.6 mg, 0.109 mmol). The reaction was stirred at RT for 30 min then diluted with EA (10 mL) and water (10 mL). The organic layer was dried over Na$_2$SO$_4$ filtered and concentrated to a residue which was purified by Prep HPLC to give 5-(4-chlorobenzyl)-3-(3-hydroxypropyl)-1-methyl-6-(6-(trifluoromethyl)pyridin-3-yloxy)pyrido[2,3-d]pyrimidine-2,4(1H,3H)-dione (6.5 mg, 34.2% yield) as a white solid. $^1$H NMR (CDCl$_3$) δ: 8.44 (d, J=3.2 Hz, 1H), 8.21 (s, 1H), 7.84 (d, J=3.2 Hz, 1H), 7.57 (s, 1H), 7.28-7.24 (overlap with CDCl3, 2H), 7.12 (t, J=8.8 Hz, 2H), 4.25 (t, J=6.0 Hz, 2H), 4.08 (s, 2H), 3.74 (s, 3H), 3.61-3.54 (m, 2H), 2.93 (brd s, 1H), 1.97-1.90 (m, 2H). LCMS: MH+ 521 and T$_R$=2.625 min.

Compound 20

5-((4-chlorophenyl)(hydroxy)methyl)-3-(3-hydroxypropyl)-6-(2-isopropylphenyl)-1-methylpyrido[2,3-d]pyrimidine-2,4(1H,3H)-dione

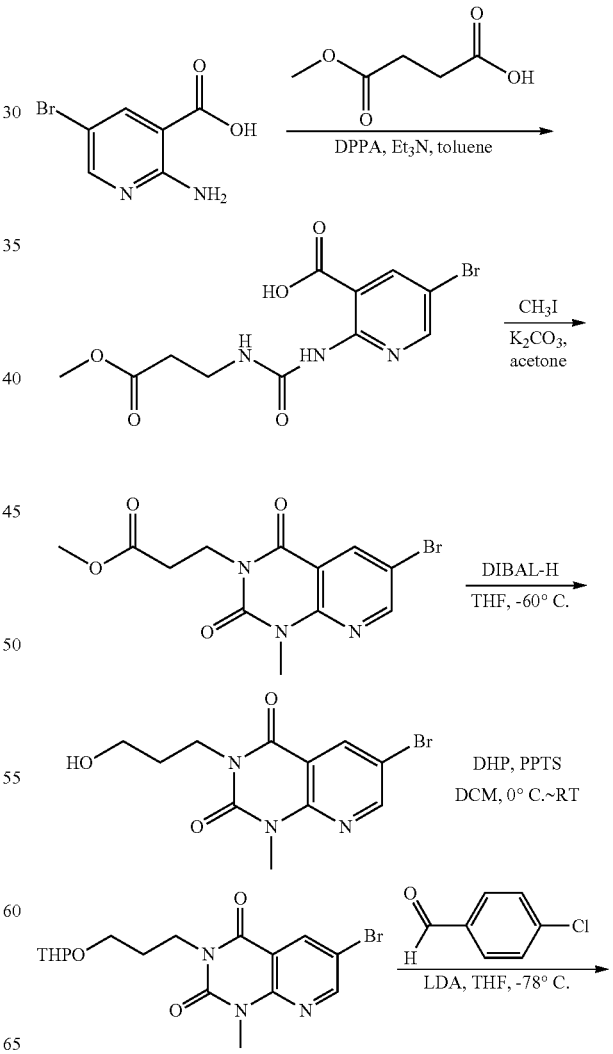

-continued

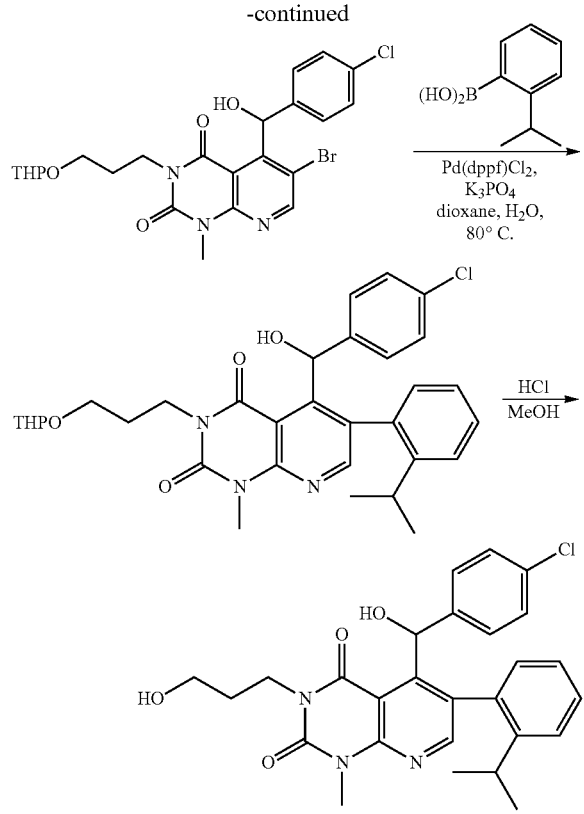

Step 1: 5-bromo-2-(3-(3-methoxy-3-oxopropyl) ureido)nicotinic acid

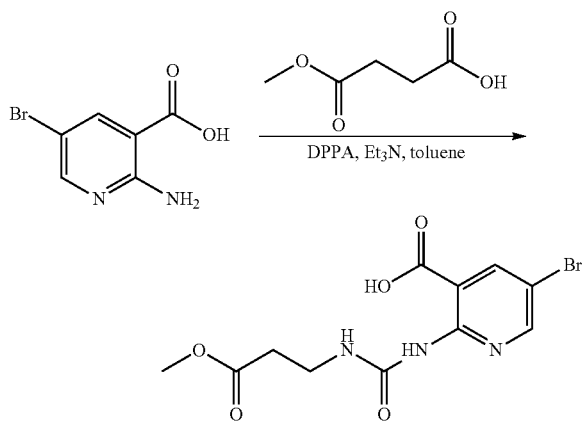

To a solution of 4-methoxy-4-oxobutanoic acid (14.6 g, 110.6 mmol) in toluene (530 mL) was added diphenylphosphoryl azide (30.4 g, 110.5 mmol) followed by triethylamine (18.3 g, 181.2 mmol). The reaction was stirred at RT for 30 min then 2-amino-5-bromonicotinic acid (15.9 g, 73.61 mmol) was added. The reaction was refluxed for 6 h, cooled to RT then diluted with EA (530 mL) and washed with brine (2×300 mL). The combined aqueous layers were acidified to PH 5 by adding aq. 2N HCl and a solid formed which was filtered off. The solid was dried to give 5-bromo-2-(3-(3-methoxy-3-oxopropyl)ureido)nicotinic acid (15 g, 39.3% yield) as pale yellow solid. LCMS: MH+ 347 and $T_R$=1.047 min. Used without further purification.

Step 2: methyl 3-(6-bromo-1-methyl-2,4-dioxo-1,2-dihydropyrido[2,3-d]pyrimidin-3(4H)-yl)propanoate

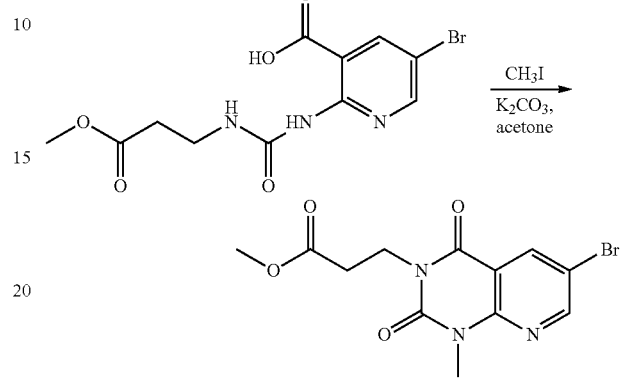

To a solution of 5-bromo-2-(3-(3-methoxy-3-oxopropyl) ureido)nicotinic acid (15 g, 43.5 mmol) in acetone (150 mL) was added $K_2CO_3$ (18 g, 130.4 mmol) followed by $CH_3I$ (18 mL, 263.1 mmol). The reaction was heated in a sealed flask at 40° C. for 24 h, cooled to RT, concentrated then diluted with EA (200 mL) and water (100 ml). The organic layer was washed with brine (100 mL), dried over $Na_2SO_4$, filtered and concentrated to a residue which was purified by chromatography PE/EA eluted with (10:1 to 2:1) to give methyl 3-(6-bromo-1-methyl-2,4-dioxo-1,2-dihydropyrido [2,3-d]pyrimidin-3(4H)-yl)propanoate (5.1 g, 34.4% yield) as a white solid. LCMS: MH+ 342 and $T_R$=1.266 min. Used without further purification.

Step 3: 6-bromo-3-(3-hydroxypropyl)-1-methyl-pyrido[2,3-d]pyrimidine-2,4(1H,3H)-dione

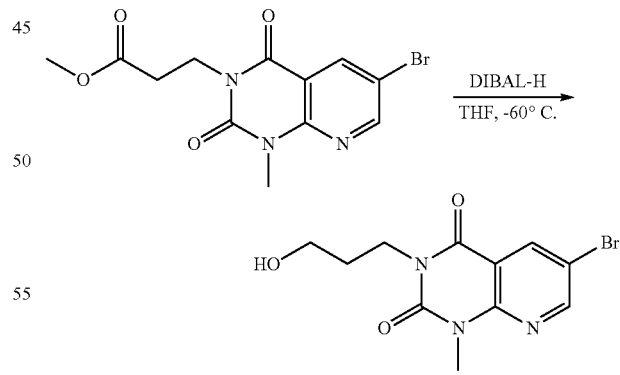

To a solution of methyl 3-(6-bromo-1-methyl-2,4-dioxo-1,2-dihydropyrido[2,3-d]pyrimidin-3(4H)-yl)propanoate (5.1 g, 14.96 mmol) in THF (500 mL) at −60° C., was added diisobutylaluminium hydride (1.5 M in toluene, 40 mL, 60 mmol) dropwise. The reaction was stirred at −60° C. for 3 h, warmed to 0° C., quenched with aq. $NH_4Cl$ (150 mL) then extracted with EA (200 mL). The organic layer was washed with brine (100 mL), dried over $Na_2SO_4$ and concentrated to give 6-bromo-3-(3-hydroxypropyl)-1-methylpyrido[2,3-d]pyrimidine-2,4 (1H,3H)-dione (6.2 g, >100% yield) as a yellow oil. LCMS: MH+ 314 and $T_R$=0.882 min. Used without further purification.

Step 4: 6-bromo-1-methyl-3-(3-(tetrahydro-2H-pyran-2-yloxy)propyl)pyrido[2,3-d]pyrimidine-2,4 (1H,3H)-dione

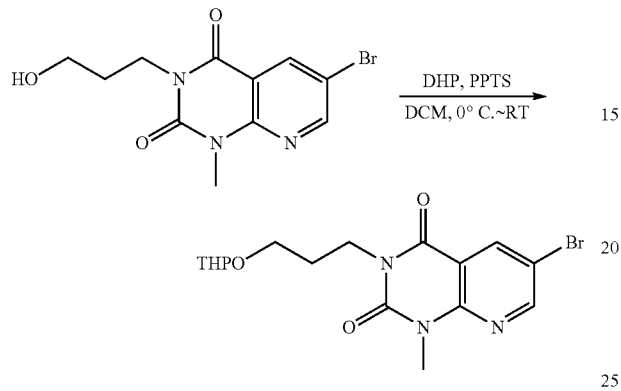

To a solution of 6-bromo-3-(3-hydroxypropyl)-1-methyl-pyrido[2,3-d]pyrimidine-2,4(1H,3H)-dione (6.2 g, 19.8 mmol) in DCM (100 mL) at 0° C. was added 3,4-dihydro-2H-pyran (6 mL, 65.7 mmol) and pyridinium p-toluenesulfonate (50 mg, 0.2 mmol). The reaction was stirred at RT for 16 h then diluted with DCM (100 mL). The organic layer was washed with brine (100 mL), dried over Na$_2$SO$_4$ and concentrated to a residue which was purified by chromatography PE/EA (8:1 to 2:1) to give 6-bromo-1-methyl-3-(3-(tetrahydro-2H-pyran-2-yloxy)propyl)pyrido[2,3-d]pyrimidine-2,4(1H,3H)-dione (2.5 g, 31.8% yield) as a white solid. $^1$H NMR (CDCl$_3$) δ: 8.68 (m, 1H), 8.54-8.53 (m, 1H), 4.57 (s, 1H), 4.26-4.17 (m, 2H), 3.87-3.80 (m, 2H), 3.68 (s, 3H), 3.52-3.47 (m, 2H), 2.04-1.97 (m, 2H), 1.76-1.63 (m, 2H), 1.49-1.46 (m, 2H). LCMS: [MH+-THP] 314 and $T_R$=1.626 min.

Step 5: 6-bromo-5-((4-chlorophenyl)(hydroxy)methyl)-1-methyl-3-(3-(tetrahydro-2H-pyran-2-yloxy)propyl)pyrido[2,3-d]pyrimidine-2,4(1H,3H)-dione

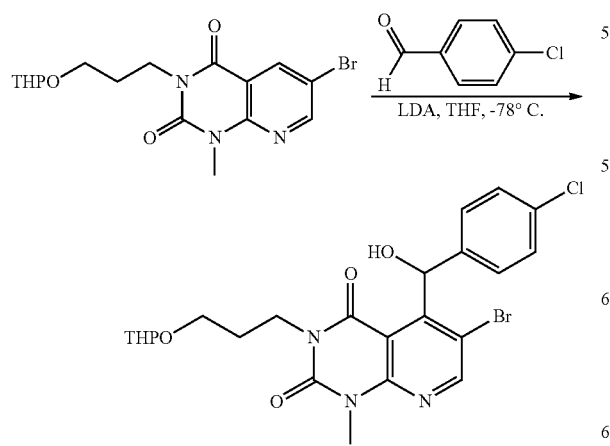

To a solution of 6-bromo-1-methyl-3-(3-(tetrahydro-2H-pyran-2-yloxy)propyl)pyrido[2,3-d]pyrimidine-2,4(1H, 3H)-dione (0.6 g, 1.51 mmol) in THF (10 mL) at −78° C. was added LDA (1.8 M in THF, 4.2 mL, 7.56 mmol) dropwise. The reaction was stirred at −78° C. for 30 min then a solution of 4-chlorobenzaldehyde (0.42 g, 3 mmol) in THF (2 mL) was added. The reaction was stirred at −78° C. for 1 h, quenched with aq. NaHCO$_3$ (5 mL) then diluted with EA (50 mL) and water (20 mL). The organic layer was dried over Na$_2$SO$_4$ and concentrated to a residue which was purified by chromatography PE/EA (4:1) to give 6-bromo-5-((4-chlorophenyl)(hydroxy)methyl)-1-methyl-3-(3-(tetrahydro-2H-pyran-2-yloxy)propyl)pyrido[2,3-d]pyrimidine-2,4(1H,3H)-dione (150 mg, 18.5% yield) as a white solid. LCMS: [M+-THP] 436 and $T_R$=1.900 min.

Step 6: 5-((4-chlorophenyl)(hydroxy)methyl)-6-(2-isopropylphenyl)-1-methyl-3-(3-(tetrahydro-2H-pyran-2-yloxy)propyl)pyrido[2,3-d]pyrimidine-2,4 (1H,3H)-dione

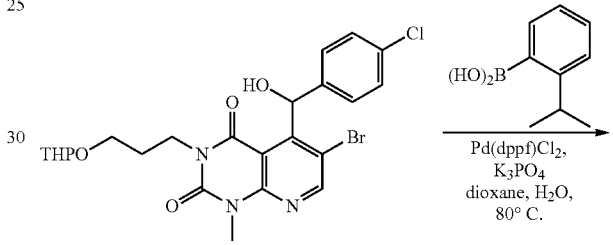

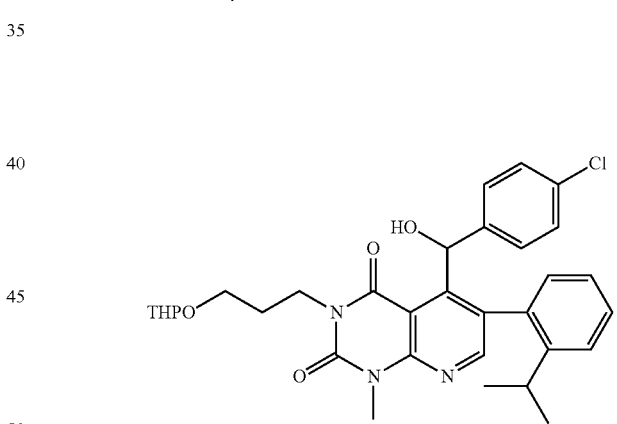

To a mixture of 6-bromo-5-((4-chlorophenyl)(hydroxy) methyl)-1-methyl-3-(3-(tetrahydro-2H-pyran-2-yloxy)propyl)pyrido[2,3-d]pyrimidine-2,4(1H,3H)-dione (50 mg, 0.093 mmol), Pd(dppf)Cl$_2$ (7 mg, 0.01 mmol) and aq. 2N K$_3$PO$_4$ (0.4 mL) in dioxane (2 mL) was added 2-isopropylphenylboronic acid (30 mg, 0.183 mmol). The reaction was heated at 80° C. for 18 h, cooled to RT and filtered. The filtrate was extracted with EA (2×20 mL). The combined organic layers were washed with water (20 mL) and brine (15 mL), dried over Na$_2$SO$_4$ and concentrated to a residue which was purified by Prep TLC eluted with PE/EA (1:1) to give 5-((4-chloro phenyl) (hydroxy)methyl)-6-(2-isopropylphenyl)-1-methyl-3-(3-(tetrahydro-2H-pyran-2-yloxy)propyl)pyrido[2,3-d]pyrimidine-2,4(1H,3H)-dione (50 mg, 93% yield) as a white solid.

Step 7: 5-((4-chlorophenyl)(hydroxy)methyl)-3-(3-hydroxypropyl)-6-(2-isopropylphenyl)-1-methyl-pyrido[2,3-d]pyrimidine-2,4(1H,3H)-dione To a solution of 5-((4-chlorophenyl)(hydroxy)methyl)-6-(2-isopropylphenyl)-1-methyl-3-(3-(tetrahydro-2H-pyran-2-yloxy)propyl)pyrido[2,3-d]pyrimidine-2,4(1H,3H)-dione (50 mg, 0.087 mmol) in MeOH (2 mL) was added saturated HCl/MeOH (2 mL, MeOH was saturated by HCl gas at 0° C.). The reaction was stirred at RT for 18 h, concentrated then diluted with EA (10 mL) and aq. NaHCO$_3$ (3 mL). The organic layer was dried over Na$_2$SO$_4$ and concentrated to a residue which was purified by Prep HPLC to give 5-((4-chlorophenyl)(hydroxy)methyl)-3-(3-hydroxypropyl)-6-(2-isopropylphenyl)-1-methylpyrido[2,3-d]pyrimidine-2,4(1H,3H)-dione (15 mg, 35% yield) as a white solid. $^1$H NMR (DMSO-d$_6$) δ: 8.61 (s, 1H), 7.48-7.35 (m, 2H), 7.24-7.15 (m, 3H), 7.11-6.96 (m, 3H), 6.74 (m, 0.3H), 6.35 (m, 0.8H), 6.10 (m, 0.3H), 5.66 (m, 0.7H), 3.93 (m, 2H), 3.68 (s, 3H), 3.38 (m, 2H), 2.72 (m, 1H), 1.64 (m, 2H), 1.15 (d, J=6.8 Hz, 2H), 1.08 (m, 3H), 0.81 (d, J=6.7 Hz, 1H). LCMS: [M$^+$—OH] 476 and T$_R$=2.931 min.

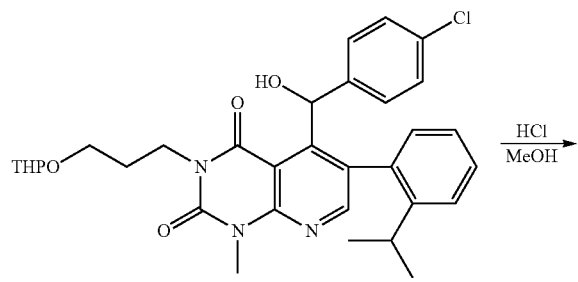

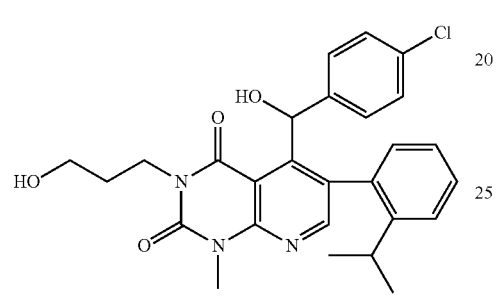

Compound 21

5-(4-chlorobenzyl)-3-(3-hydroxypropyl)-1-methyl-6-(3-(trifluoromethoxy)phenoxy)pyrido[2,3-d]pyrimidine-2,4(1H,3H)-dione

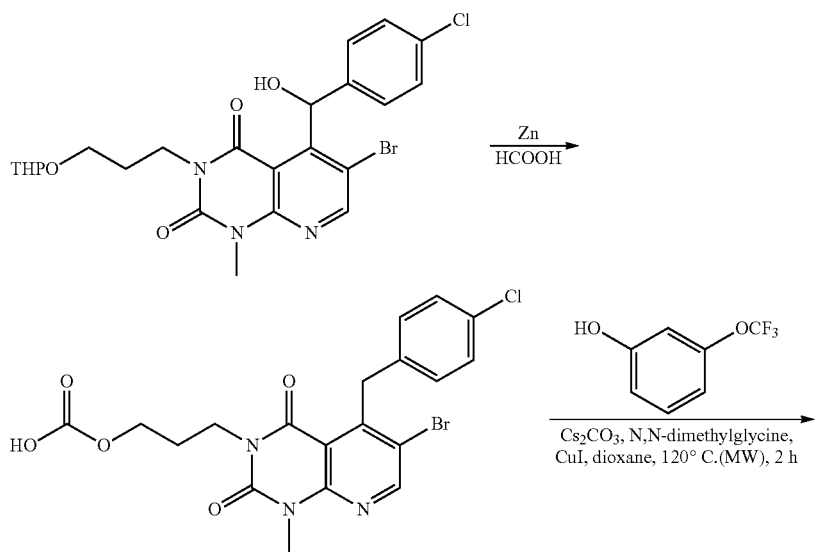

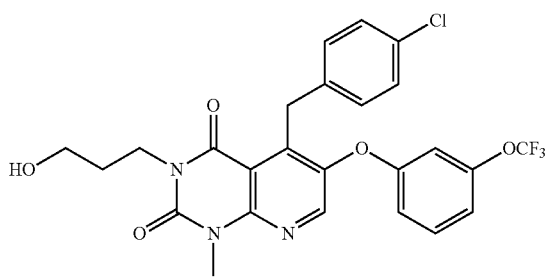

73

Step 1 3-(6-bromo-5-(4-chlorobenzyl)-1-methyl-2,4-dioxo-1,2-dihydropyrido[2,3-d]pyrimidin-3(4H)-yl) propyl formate

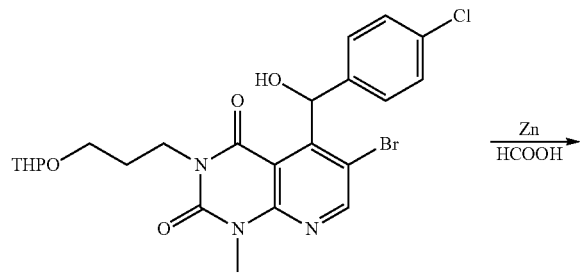

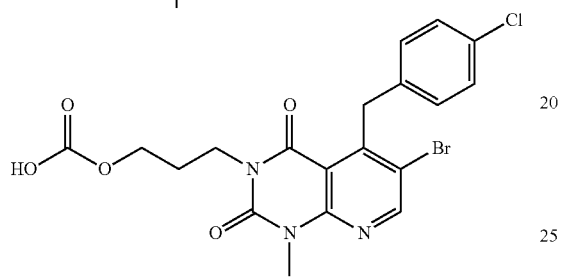

Step 2 5-(4-chlorobenzyl)-3-(3-hydroxypropyl)-1-methyl-6-(3-(trifluoromethoxy)phenoxy)-pyrido[2,3-d]pyrimidine-2,4(1H,3H)-dione

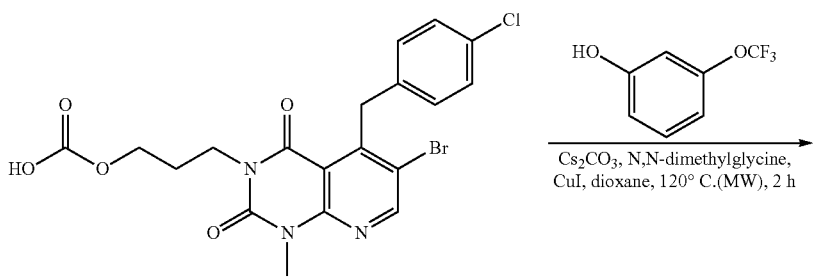

74

To a solution of 6-bromo-5-((4-chlorophenyl)(hydroxy)methyl)-1-methyl-3-(3-((tetrahydro-2H-pyran-2-yl)oxy)propyl)pyrido[2,3-d]pyrimidine-2,4(1H,3H)-dione (See Compound 20, step 5, 300 mg, 0.55 mmol) in HCOOH (10 mL) was added Zn dust (181 mg, 2.79 mmol). The reaction was heated at 50° C. for 2 h, cooled to RT and filtered. The filtrate was concentrated and dried to give 3-(6-bromo-5-(4-chlorobenzyl)-1-methyl-2,4-dioxo-1,2-dihydropyrido[2,3-d]pyrimidin-3(4H)-yl)propyl formate (214 mg, 83% yield) as an oil. LCMS: MH$^+$ 467 and T$_R$=2.016 min. Used without further purification.

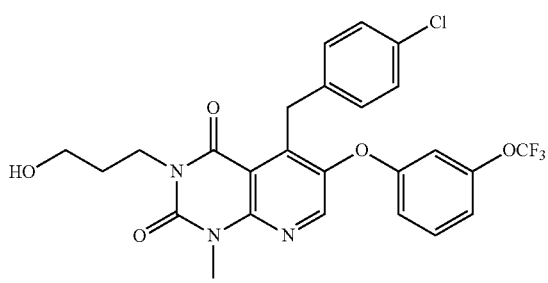

To a mixture of 3-(6-bromo-5-(4-chlorobenzyl)-1-methyl-2,4-dioxo-1,2-dihydropyrido[2,3-d]pyrimidin-3(4H)-yl) propyl formate (40 mg, 0.086 mmol), N,N-dimethylglycine (4.4 mg, 0.043 mmol), CuI (2.0 mg, 0.011 mmol), and $Cs_2CO_3$ (56 mg, 0.172 mmol) in dioxane (1 mL) was added 3-(trifluoromethoxy)phenol (23 mg, 0.130 mmol). The reaction was heated at 120° C. (MW) for 2 h, cooled to RT then diluted with EA (15 mL) and water (10 mL). The organic layer was washed with water (10 mL) and brine (10 mL), dried over $Na_2SO_4$ and concentrated to a residue which was purified by Prep HPLC to give 5-(4-chlorobenzyl)-3-(3-hydroxypropyl)-1-methyl-6-(3-(trifluoromethoxy)phenoxy)pyrido[2,3-d]pyrimidine-2,4(1H,3H)-dione (7 mg, 15% yield) as a white solid. $^1$H NMR ($CDCl_3$) δ: 8.36 (s, 1H), 7.32 (t, J=8.3 Hz, 1H), 7.16 (s, 4H), 6.98 (d, J=8.3 Hz, 1H), 6.75 (dd, J=13.0, 4.7 Hz, 2H), 4.71 (s, 2H), 4.24 (t, J=6.1 Hz, 2H), 3.72 (s, 3H), 3.55 (t, J=5.5 Hz, 2H), 1.98-1.87 (m, 2H). LCMS: $MH^+$ 536 and $T_R$=3.320 min.

Compound 22

3-(3-hydroxypropyl)-1-methyl-5-(4-(trifluoromethyl)benzyl)-6-(3-(trifluoromethyl)phenoxy)pyrido[2,3-d]pyrimidine-2,4(1H,3H)-dione

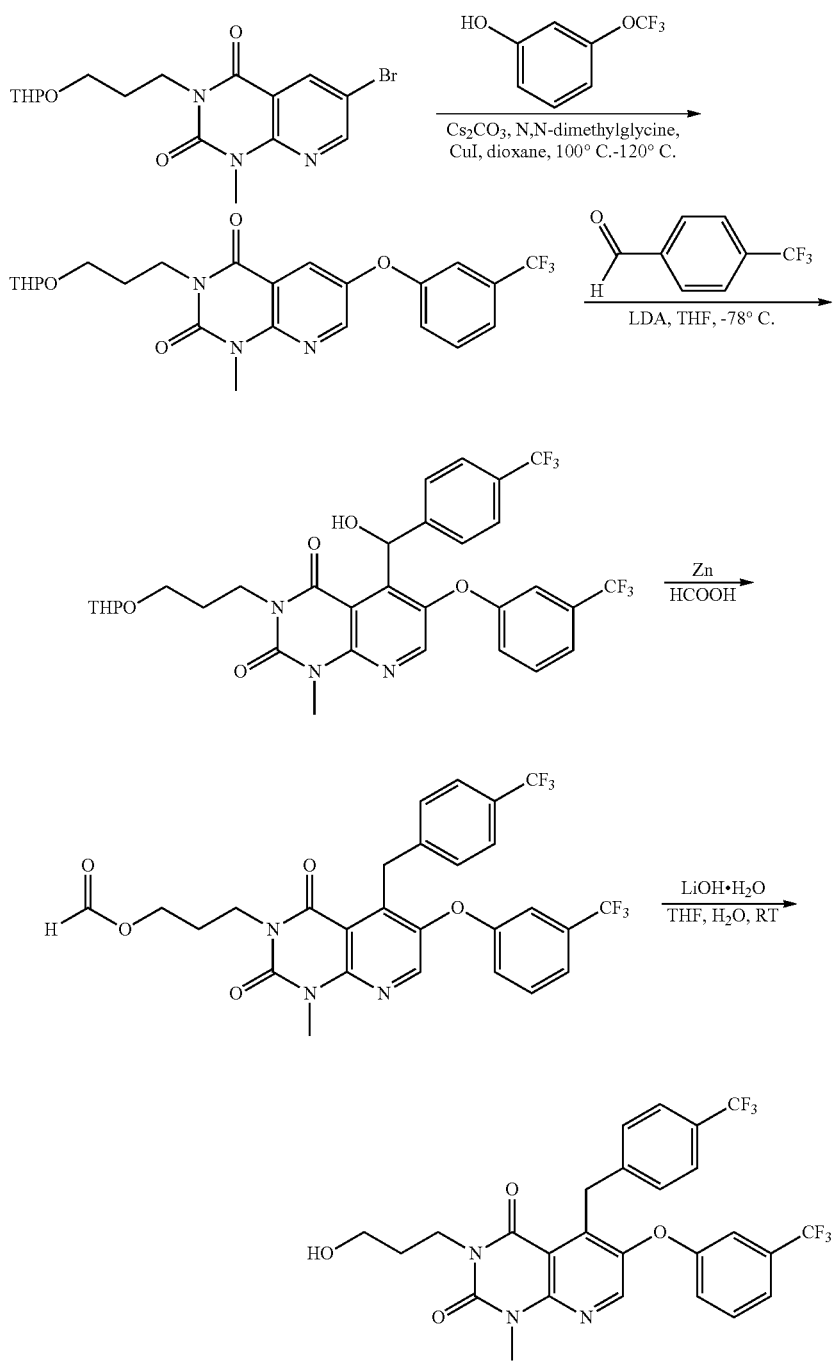

Step 1 1-methyl-3-(3-(tetrahydro-2H-pyran-2-yloxy) propyl)-6-(3-(trifluoromethyl)phenoxy)pyrido[2,3-d] pyrimidine-2,4(1H,3H)-dione

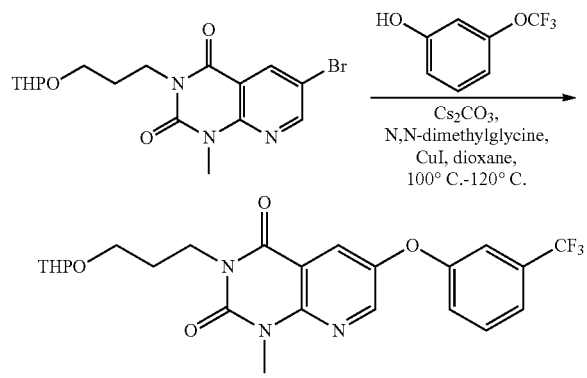

To a mixture of 6-bromo-1-methyl-3-(3-(tetrahydro-2H-pyran-2-yloxy)propyl)pyrido[2,3-d]pyrimidine-2,4(1H, 3H)-dione (See Compound 20, step 4, 500 mg, 1.26 mmol), N,N-dimethylglycine (65 mg, 0.631 mmol), CuI (30 mg, 0.158 mmol) and $Cs_2CO_3$ (821 mg, 2.52 mmol) in dioxane (10 mL) was added 3-(trifluoromethyl)phenol (306 mg, 1.89 mmol). The reaction was heated at 100° C. for 18 h followed by heating at 120° C. for 8 h, cooled to RT then diluted with EA (50 mL) and water (20 mL). The organic layer was washed with water (2×20 mL) and brine (20 mL), dried over $Na_2SO_4$ and concentrated to a residue which was purified by chromatography eluted with PE/EA (6:1) to give 1-methyl-3-(3-(tetrahydro-2H-pyran-2-yloxy)propyl)-6-(3-(trifluoromethyl)phenoxy)pyrido[2,3-d]pyrimidine-2,4(1H,3H)-dione (210 mg, 35% yield) as a white solid. LCMS: [M$^+$+Na] 502 and $T_R$=1.626 min.

Step 2 5-(hydroxy(4-(trifluoromethyl)phenyl) methyl)-1-methyl-3-(3-(tetrahydro-2H-pyran-2-yloxy) propyl)-6-(3-(trifluoromethyl)phenoxy) pyrido[2,3-d]pyrimidine-2,4(1H,3H)-dione

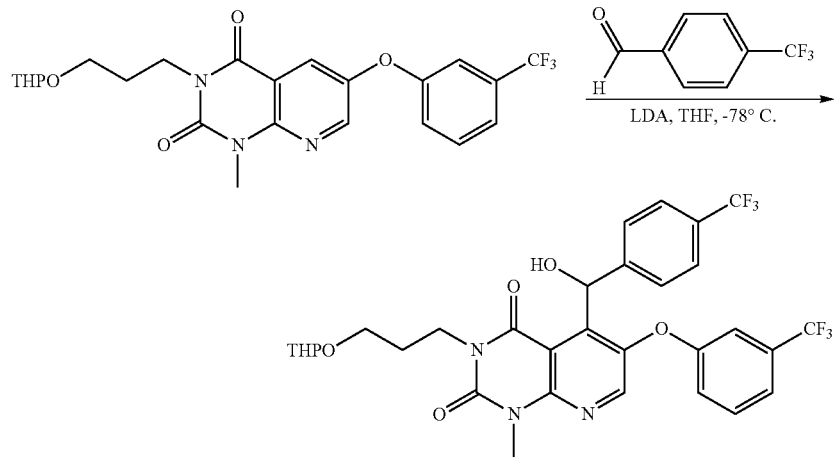

To a solution of 1-methyl-3-(3-(tetrahydro-2H-pyran-2-yloxy)propyl)-6-(3-(trifluoromethyl) phenoxy)pyrido[2,3-d]pyrimidine-2,4(1H,3H)-dione (210 mg, 0.438 mmol) in THF (5 mL) at −78° C. was added LDA (1.8 M in THF, 1.2 mL, 2.16 mmol). The reaction was stirred at −78° C. for 30 min then 4-(trifluoromethyl)benzaldehyde (153 mg, 0.879 mmol) was added. The reaction was stirred for 1 h, quenched with aq. $NaHCO_3$ (5 mL) then diluted with EA (10 mL) and water (10 mL). The organic layer was dried over $Na_2SO_4$ and concentrated to a residue which was purified by Prep TLC eluted with PE/EA (4:1) to give 5-(hydroxy(4-(trifluoromethyl)phenyl)methyl)-1-methyl-3-(3-(tetrahydro-2H-pyran-2-yloxy)propyl)-6-(3-(trifluoromethyl)phenoxy) pyrido[2,3-d]pyrimidine-2,4(1H,3H)-dione (200 mg, 69.9% yield) as a clear oil. LCMS: [MH$^+$-THP] 570 and $T_R$=1.933 min.

Step 3 3-(1-methyl-2,4-dioxo-5-(4-(trifluoromethyl) benzyl)-6-(3-(trifluoromethyl)phenoxy)-1,2-dihydro-pyrido[2,3-d]pyrimidin-3(4H)-yl)propyl formate

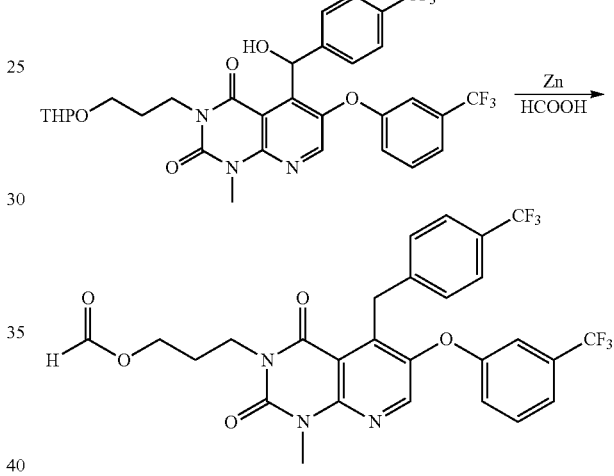

To a solution of 5-(hydroxy(4-(trifluoromethyl)phenyl) methyl)-1-methyl-3-(3-(tetrahydro-2H-pyran-2-yloxy)propyl)-6-(3-(trifluoromethyl)phenoxy)pyrido[2,3-d]pyrimidine-2,4(1H,3H)-dione (200 mg, crude) in HCOOH (5 mL)

was added Zn dust (100 mg, 1.54 mmol). The reaction was heated at 100° C. for 1 h, cooled to RT and filtered. The filtrate was concentrated to give 3-(1-methyl-2,4-dioxo-5-(4-(trifluoromethyl)benzyl)-6-(3-(trifluoromethyl)phenoxy)-1,2-dihydro pyrido[2,3-d]pyrimidin-3(4H)-yl)propyl formate (150 mg, 58.9 yield) as an oil. LCMS: MH+ 582 and $T_R$=1.746 min. Used without further purification.

Step 4 3-(3-hydroxypropyl)-1-methyl-5-(4-(trifluoromethyl)benzyl)-6-(3-(trifluoromethyl)phenoxy)pyrido[2,3-d]pyrimidine-2,4(1H,3H)-dione

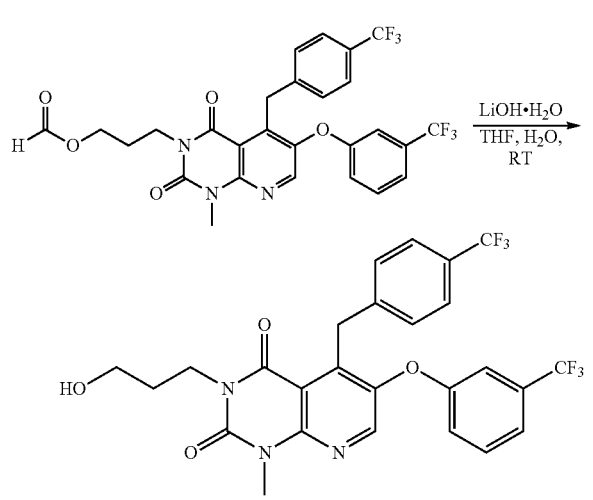

To a solution of 3-(1-methyl-2,4-dioxo-5-(4-(trifluoromethyl)benzyl)-6-(3-(trifluoromethyl) phenoxy)-1,2-dihydropyrido[2,3-d]pyrimidin-3(4H)-yl)propyl formate (150 mg, 0.258 mmol) in THF (2 mL) was added aq. LiOH.H$_2$O (1 mL, 0.5 M). The reaction was stirred at RT for 10 min then extracted with EA (50 mL). The organic layer was washed with brine (10 mL), dried over Na$_2$SO$_4$ and concentrated to a residue which was purified by Prep HPLC to give 3-(3-hydroxypropyl)-1-methyl-5-(4-(trifluoromethyl)benzyl)-6-(3-(trifluoromethyl)phenoxy)pyrido[2,3-d]pyrimidine-2,4(1H,3H)-dione (20 mg, 8% yield over 3 steps) as a white solid. $^1$H NMR (CDCl$_3$) δ: 8.37 (s, 1H), 7.42 (m, 3H), 7.35 (m, 1H), 7.31 (m, 2H), 7.02 (m, 2H), 4.83 (s, 2H), 4.24 (t, J=6.1 Hz, 2H), 3.73 (s, 3H), 3.56 (s, 2H), 2.95 (s, 1H), 1.98-1.87 (m, 2H). LCMS: MH+ 554 and $T_R$=3.39 min.

Compound 23

3-(3-hydroxypropyl)-5-isopentyl-6-(2-isopropylphenyl)-1-methylpyrido[2,3-d]pyrimidine-2,4(1H,3H)-dione

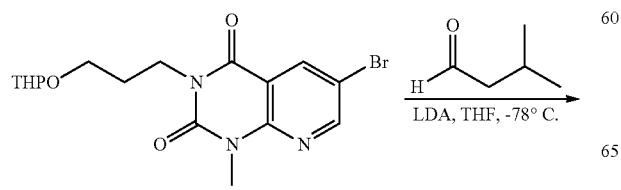

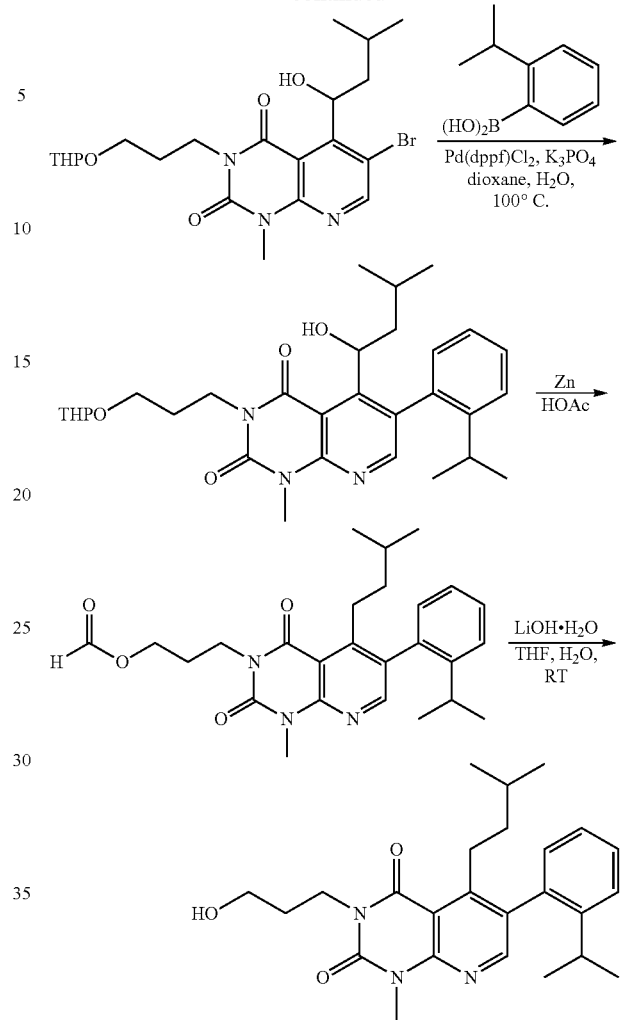

Step 1 6-bromo-5-(1-hydroxy-3-methylbutyl)-1-methyl-3-(3-((tetrahydro-2H-pyran-2-yl)oxy)propyl)pyrido[2,3-d]pyrimidine-2,4(1H,3H)-dione

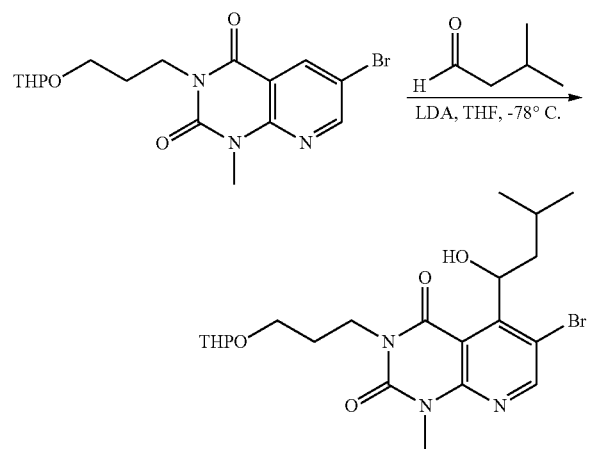

To a solution of 6-bromo-1-methyl-3-(3-((tetrahydro-2H-pyran-2-yl)oxy)propyl)pyrido[2,3-d]pyrimidine-2,4(1H,3H)-dione (See Compound 20, step 4, 300 mg, 0.753 mmol) in THF (10 mL) at −78° C. was added LDA (1.8M in THF, 2.1 mL, 3.765 mmol) dropwise. The reaction was stirred at −78° C. for 1 h then 3-methylbutanal (129.8 mg, 1.506 mmol) in THF (2 mL) was added. The reaction was stirred at −78° C. for 30 min then diluted with DCM (10 mL) and water (10 mL). The organic layer was dried over $Na_2SO_4$, and concentrated to a residue which was purified by chromatography eluted with PE/EA (10:1) to give 6-bromo-5-(1-hydroxy-3-methylbutyl)-1-methyl-3-(3-((tetrahydro-2H-pyran-2-yl)oxy)propyl)pyrido[2,3-d]pyrimidine-2,4(1H, 3H)-dione (65 mg, 17.8% yield) as a solid. LCMS: [M+-THP-OH] 382 and $T_R$=2.155 min.

Step 2 5-(1-hydroxy-3-methylbutyl)-6-(2-isopropylphenyl)-1-methyl-3-(3-((tetrahydro-2H-pyran-2-yl)oxy)propyl)pyrido[2,3-d]pyrimidine-2,4(1H,3H)-dione

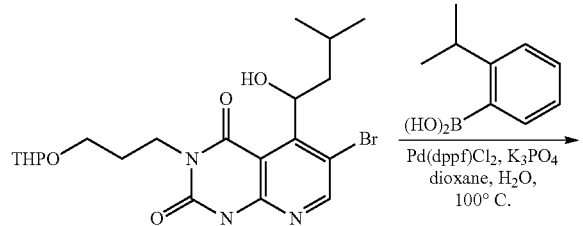

To a solution of 6-bromo-5-(1-hydroxy-3-methylbutyl)-1-methyl-3-(3-((tetrahydro-2H-pyran-2-yl)oxy)propyl)pyrido[2,3-d]pyrimidine-2,4(1H,3H)-dione (65 mg, 0.134 mmol) in dioxane (1 mL) was added (2-isopropylphenyl)boronic acid (88 mg, 0.536 mmol), Pd(dppf)Cl$_2$ (10 mg) and aq. 2N $K_3PO_4$ (0.2 mL). The mixture was heated at 100° C. for 5 h, cooled to RT and filtered. The filtrate was concentrated and dried to a residue which was purified by chromatography eluted with PE/EA (10:1 to 6:1) to give 5-(1-hydroxy-3-methylbutyl)-6-(2-isopropylphenyl)-1-methyl-3-(3-((tetrahydro-2H-pyran-2-yl)oxy)propyl)pyrido[2,3-d]pyrimidine-2,4(1H,3H)-dione (30 mg, 42.7% yield) as a solid. LCMS: [M+-THP-OH] 423 and $T_R$=2.047 min.

Step 3 3-(5-isopentyl-6-(2-isopropylphenyl)-1-methyl-2,4-dioxo-1,2-dihydropyrido[2,3-d]pyrimidin-3(4H)-yl)propyl formate

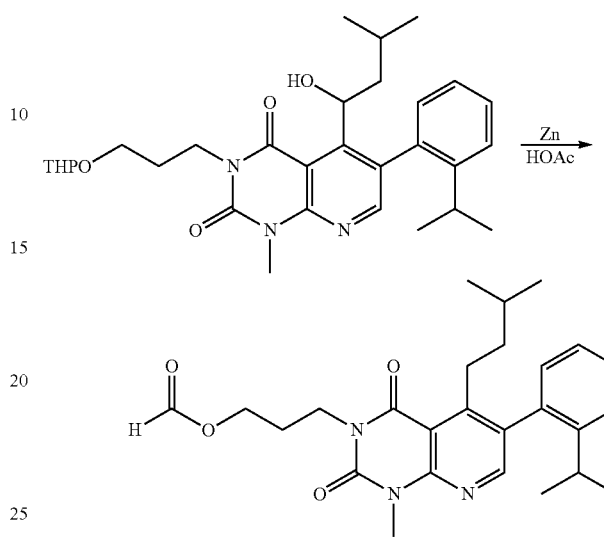

To a solution of 5-(1-hydroxy-3-methylbutyl)-6-(2-isopropylphenyl)-1-methyl-3-(3-((tetrahydro-2H-pyran-2-yl)oxy)propyl)pyrido[2,3-d]pyrimidine-2,4(1H,3H)-dione (30 mg, 0.057 mmol) in HCOOH (2 mL) was added Zn dust (18.7 mg, 0.285 mmol). The reaction was heated at 50° C. for 2 h, cooled to RT and filtered. The filtrate was concentrated and dried to give 3-(5-isopentyl-6-(2-isopropylphenyl)-1-methyl-2,4-dioxo-1,2-dihydropyrido[2,3-d]pyrimidin-3(4H)-yl)propyl formate (15 mg, 57.9% yield) as a solid. LCMS: MH+ 452 and $T_R$=2.286 min. Used without further purification.

Step 4 3-(3-hydroxypropyl)-5-isopentyl-6-(2-isopropylphenyl)-1-methylpyrido[2,3-d]pyrimidine-2,4(1H,3H)-dione

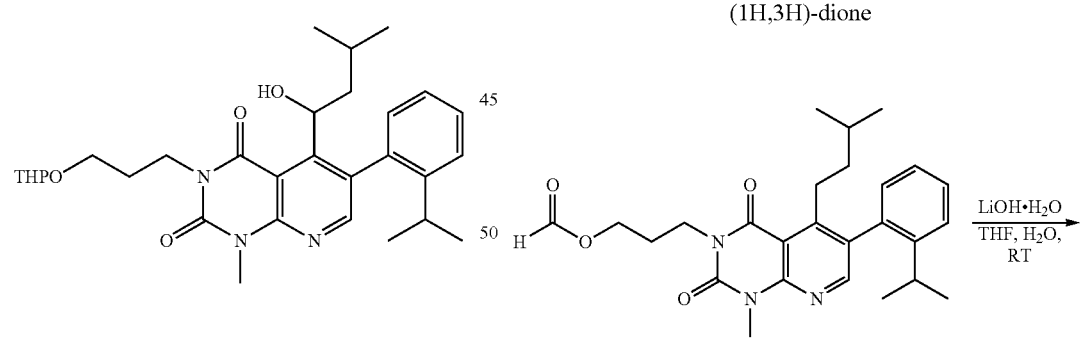

To a solution of 3-(5-isopentyl-6-(2-isopropylphenyl)-1-methyl-2,4-dioxo-1,2-dihydropyrido[2,3-d]pyrimidin-3

(4H)-yl)propyl formate (15 mg, 0.033 mmol) in THF (4 mL) and water (4 mL) was added LiOH.H$_2$O (2.79 mg, 0.066 mmol). The reaction was stirred at RT for 15 min then diluted with EA (5 mL) and water (5 mL). The organic layer was dried over Na$_2$SO$_4$ and concentrated to a residue which was purified by chromatography eluted with PE/EA (10:1) to give 3-(3-hydroxypropyl)-5-isopentyl-6-(2-isopropylphenyl)-1-methylpyrido[2,3-d]pyrimidine-2,4(1H,3H)-dione (8 mg, 56.8% yield) as a white solid. $^1$H NMR (CDCl$_3$) δ: 8.35 (s, 1H), 7.43-7.42 (d, J=4.0 Hz, 2H), 7.28-7.24 (m, 1H), 7.07-7.05 (m, 1H), 4.27 (m, 3H), 3.76 (s, 3H), 3.58 (s, 2H), 3.40-3.31 (m, 2H), 2.68-2.54 (m, 2H), 1.97-1.94 (m, 2H), 1.57 (m, 1H), 1.22-1.19 (m, 3H), 1.08-1.06 (m, 3H), 0.71-0.69 (m, 3H), 0.64-0.62 (d, J=8 Hz, 3H). LCMS: MH$^+$ 424 and T$_R$=3.546 min.

Compound 24

3-(3-hydroxypropyl)-1-methyl-6-(3-(trifluoromethyl)phenoxy)-5-((6-(trifluoromethyl)pyridin-3-yl)methyl)pyrido[2,3-d]pyrimidine-2,4(1H,3H)-dione

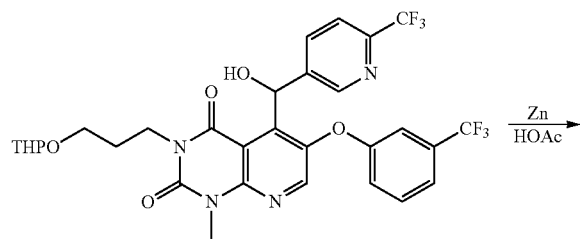

Step 1 3-(1-methyl-2,4-dioxo-6-(3-(trifluoromethyl)phenoxy)-5-((6-(trifluoromethyl)pyridin-3-yl)methyl)-1,2-dihydropyrido[2,3-d]pyrimidin-3(4H)-yl)propyl formate

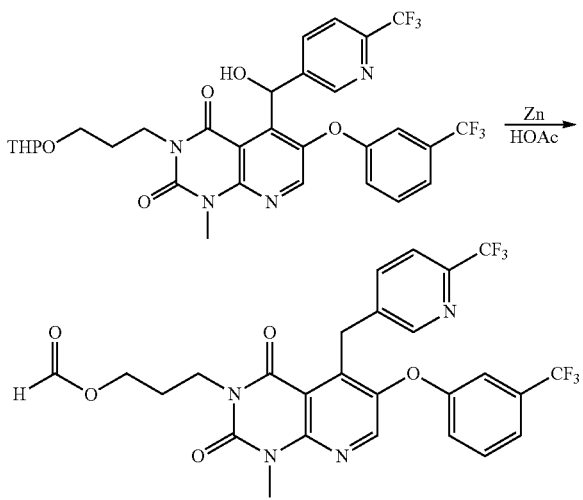

To a solution of 5-(hydroxy(6-(trifluoromethyl)pyridin-3-yl)methyl)-1-methyl-3-(3-((tetrahydro-2H-pyran-2-yl)oxy)propyl)-6-(3-(trifluoromethyl)phenoxy)pyrido[2,3-d]pyrimidine-2,4(1H,3H)-dione (See Compound 32, step 2, 75 mg, 0.114 mmol) in HCOOH (3 mL) was added Zn dust (37.5 mg, 0.573 mmol). The reaction was heated at 50° C. for 2 h, cooled to RT and filtered. The filtrate was concentrated and dried to give 3-(1-methyl-2,4-dioxo-6-(3-(trifluoromethyl)phenoxy)-5-((6-(trifluoromethyl)pyridin-3-yl)methyl)-1,2-dihydropyrido[2,3-d]pyrimidin-3(4H)-yl) propyl formate (35 mg, 52.4% yield) as a solid. LCMS: MH$^+$ 583 and T$_R$=1.979 min.

Step 2 3-(3-hydroxypropyl)-1-methyl-6-(3-(trifluoromethyl)phenoxy)-5-((6-(trifluoromethyl)pyridin-3-yl)methyl)pyrido[2,3-d]pyrimidine-2,4(1H,3H)-dione

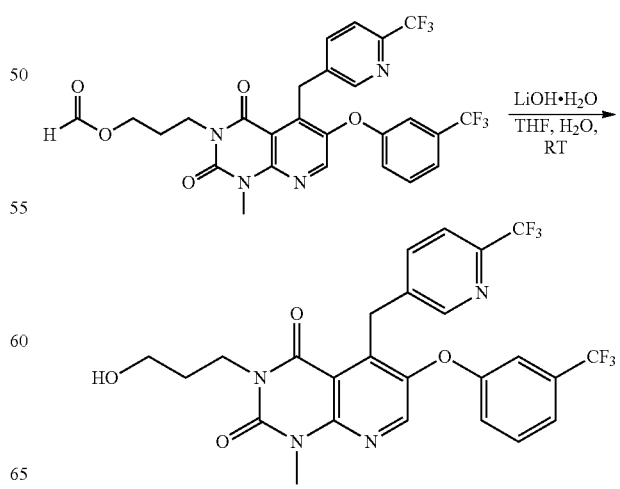

To a solution of 3-(1-methyl-2,4-dioxo-6-(3-(trifluoromethyl)phenoxy)-5-((6-(trifluoromethyl)pyridin-3-yl)methyl)-1,2-dihydropyrido[2,3-d]pyrimidin-3(4H)-yl)propyl formate (35 mg, 0.060 mmol) in THF (4 mL) and water (4 mL) was added LiOH.H₂O (5.04 mg, 0.12 mmol). The reaction was stirred for 15 min then diluted with EA (5 mL) and water (5 mL). The organic layer was dried over Na₂SO₄ and concentrated to a residue which was purified by Prep HPLC to give 3-(3-hydroxypropyl)-1-methyl-6-(3-(trifluoromethyl)phenoxy)-5-((6-(trifluoromethyl)pyridin-3-yl)methyl)pyrido[2,3-d]pyrimidine-2,4(1H,3H)-dione (13 mg, 39.0% yield) as a white solid. ¹H NMR (DMSO-d₆) δ: 8.63 (s, 1H), 8.51 (s, 1H), 7.75 (d, J=8.0 Hz, 1H), 7.62 (d, J=8.0 Hz, 1H), 7.51-7.49 (m, 1H), 7.36 (d, J=7.6 Hz, 1H), 7.23 (d, J=9.2 Hz, 1H), 6.98 (s, 1H), 4.78 (s, 2H), 4.50-4.48 (m, 1H), 4.00-3.96 (m, 2H), 3.61 (s, 3H), 3.48-3.43 (m, 2H), 1.75-1.71 (m, 2H). LCMS: MH⁺ 555 and $T_R$=3.087 min.

Compound 25

5-(4-chlorobenzyl)-6-(3-fluorophenyl)-3-(3-hydroxypropyl)-1-methylpyrido[2,3-d]pyrimidine-2,4(1H,3H)-dione

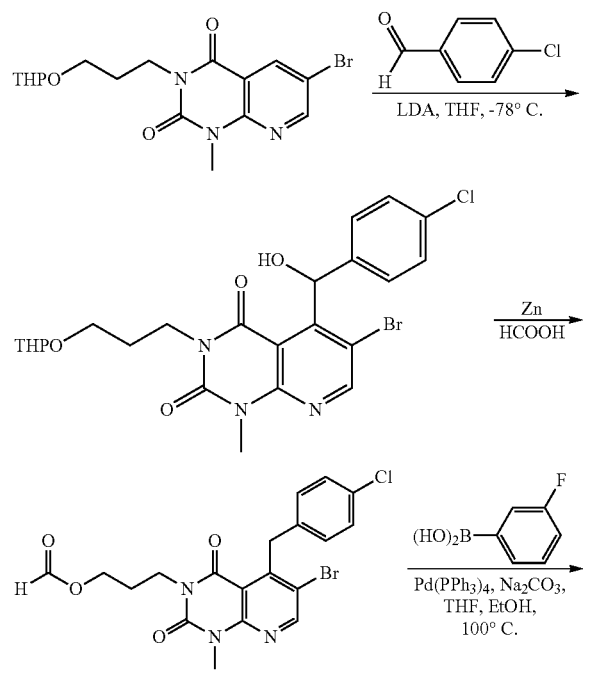

Step 1 6-bromo-5-((4-chlorophenyl)(hydroxy)methyl)-1-methyl-3-(3-(tetrahydro-2H-pyran-2-yloxy)propyl)pyrido[2,3-d]pyrimidine-2,4(1H,3H)-dione

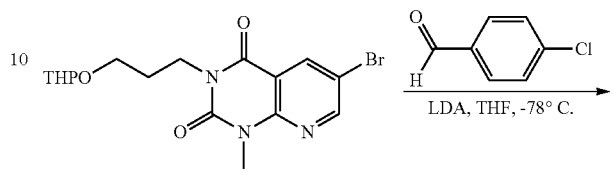

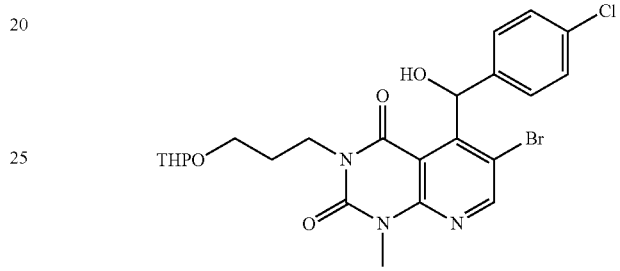

To a solution of 6-bromo-1-methyl-3-(3-(tetrahydro-2H-pyran-2-yloxy)propyl)pyrido[2,3-d]pyrimidine-2,4(1H,3H)-dione (See Compound 20, step 4, 4 g, 10.0 mmol) in THF (15 mL) at −78° C. was added LDA (2.0 M in THF, 25 mL, 50 mmol) dropwise. The reaction was stirred at −78° C. for 1 h then a solution of 4-chlorobenzaldehyde (2.8 g, 20 mmol) in THF (5 mL) was added. The reaction was stirred at −78° C. for 1 h, quenched with aq. NH₄Cl (15 mL) then diluted with EA (15 mL) and water (10 mL). The organic layer was dried over Na₂SO₄ and concentrated to a residue which was purified by chromatography PE/EA (7:1) to give 6-bromo-5-((4-chlorophenyl)(hydroxy)methyl)-1-methyl-3-(3-(tetrahydro-2H-pyran-2-yloxy)propyl)pyrido[2,3-d]pyrimidine-2,4(1H,3H)-dione (800 mg, 15% yield) as a solid. LCMS: MH⁺ 538 and $T_R$=1.825 min. Used without further purification.

Step 2 3-(6-bromo-5-(4-chlorobenzyl)-1-methyl-2,4-dioxo-1,2-dihydropyrido[2,3-d]pyrimidin-3(4H)-yl)propyl formate

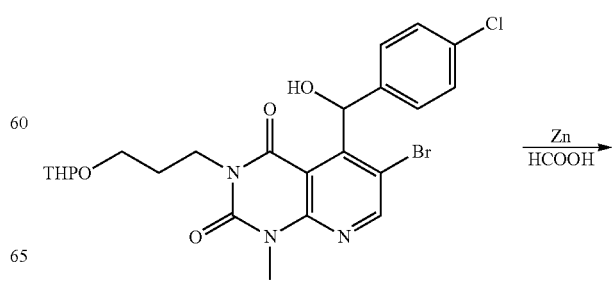

87

-continued

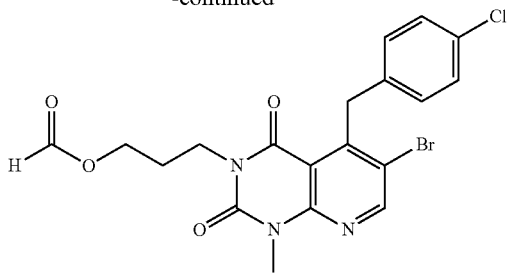

To a solution of 6-bromo-5-((4-chlorophenyl)(hydroxy)methyl)-1-methyl-3-(3-(tetrahydro-2H-pyran-2-yloxy)propyl)pyrido[2,3-d]pyrimidine-2,4(1H,3H)-dione (800 mg, 1.50 mmol) in HCOOH (10 mL) was added Zn dust (484 mg, 7.50 mmol). The reaction was heated at 60° C. for 2 h cooled to RT and filtered. The filtrate was concentrated to give 3-(6-bromo-5-(4-chlorobenzyl)-1-methyl-2,4-dioxo-1,2-dihydropyrido[2,3-d]pyrimidin-3(4H)-yl)propyl formate (70 mg, 10% yield) as an oil. LCMS: MH$^+$ 466 and T$_R$=1.753 min. Used without further purification.

Step 3 5-(4-chlorobenzyl)-6-(3-fluorophenyl)-3-(3-hydroxypropyl)-1-methylpyrido[2,3-d]pyrimidine-2,4(1H,3H)-dione

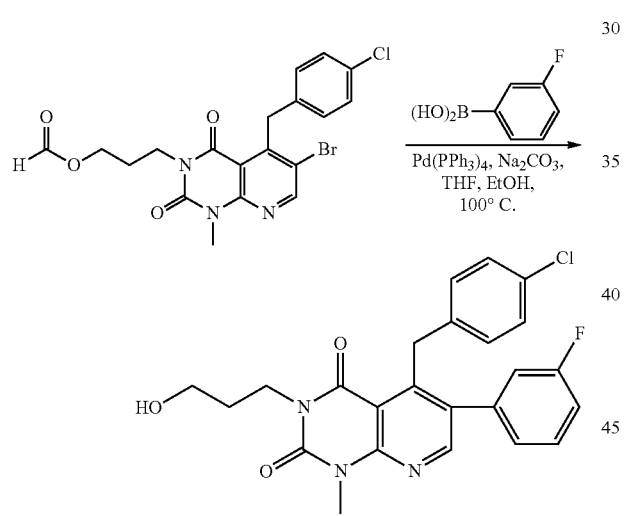

To a solution of 3-(6-bromo-5-(4-chlorobenzyl)-1-methyl-2,4-dioxo-1,2-dihydropyrido[2,3-d]pyrimidin-3(4H)-yl)propyl formate (70 mg, 0.15 mmol), 3-fluorophenylboronic acid (31 mg, 0.22 mmol), Na$_2$CO$_3$(0.6 ml) in THF (3.2 mL) and EtOH (1.6 mL) was added Pd(PPh$_3$)$_4$ (25 mg, 0.015 mmol). The reaction was heated at 100° C. for 18 h, cooled to RT then diluted with EA (20 mL) and water (20 mL). The organic layer was dried over Na$_2$SO$_4$, and concentrated to a residue which was purified by Prep HPLC to give 5-(4-chlorobenzyl)-6-(3-fluorophenyl)-3-(3-hydroxypropyl)-1-methylpyrido[2,3-d]pyrimidine-2,4(1H,3H)-dione (50 mg, 85% yield) as white solid. $^1$H NMR (CDCl$_3$) δ: 8.53 (s, 1H), 7.36 (dd, J=8.0, 6.0 Hz, 1H), 7.19-7.06 (m, 3H), 6.97-6.86 (m, 2H), 6.77 (d, J=8.3 Hz, 2H), 4.63 (s, 2H), 4.19 (t, J=6.1 Hz, 2H), 3.78 (s, 3H), 3.47 (dd, J=11.7, 6.1 Hz, 2H), 2.92 (t, J=6.9 Hz, 1H), 1.96-1.77 (m, 2H). LCMS: MH$^+$ 454 and T$_R$=3.00 min.

88

Compound 26

5-(4-chlorobenzyl)-6-(3-chlorophenoxy)-3-(3-hydroxypropyl)-1-methylpyrido[2,3-d]pyrimidine-2,4(1H,3H)-dione

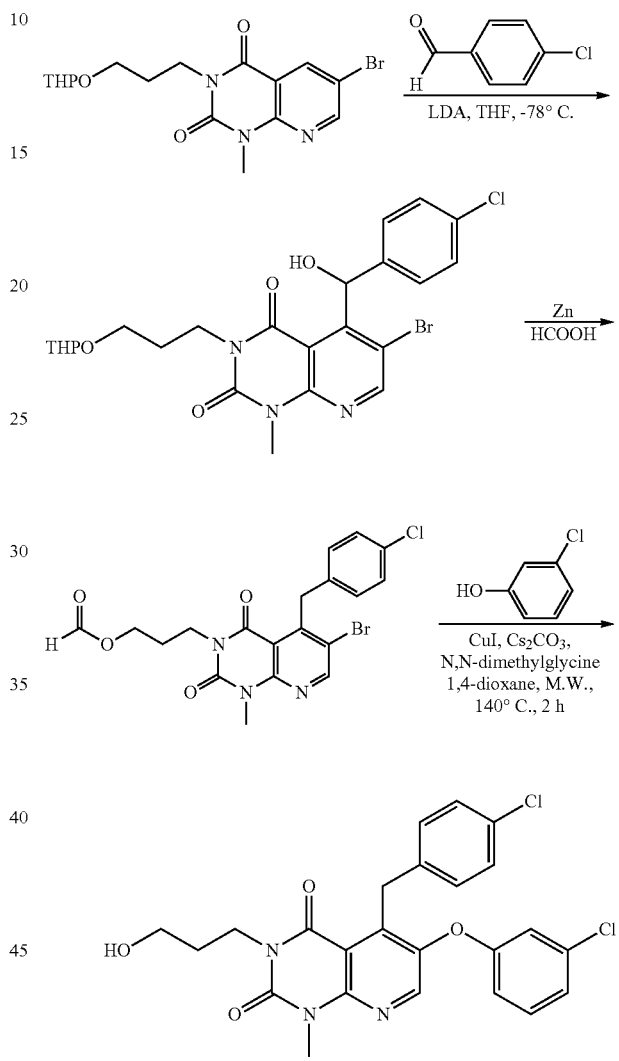

Step 1 6-bromo-5-((4-chlorophenyl)(hydroxy)methyl)-1-methyl-3-(3-(tetrahydro-2H-pyran-2-yloxy) propyl)pyrido[2,3-d]pyrimidine-2,4(1H,3H)-dione

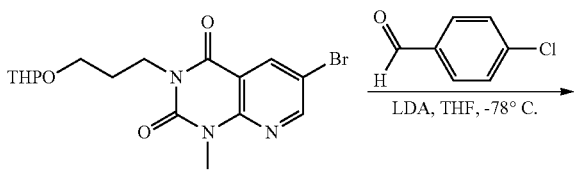

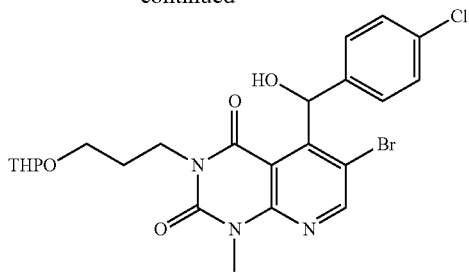

To a solution of 6-bromo-1-methyl-3-(3-(tetrahydro-2H-pyran-2-yloxy)propyl)pyrido[2,3-d]pyrimidine-2,4(1H,3H)-dione (See Compound 20, step 4, 1.0 g, 2.51 mmol) in THF (60 mL) at −78° C. was added LDA (2.0 M in THF, 2.26 mL, 4.52 mmol) dropwise. The reaction was stirred at −78° C. for 1 h then a solution of 4-chlorobenzaldehyde (0.7 g, 5.02 mmol) in THF (10 mL) was added dropwise. The reaction was stirred at −78° C. for 1 h, quenched with aq. NH$_4$Cl (30 mL) then diluted with EA (40 mL) and water (40 mL). The organic layer was dried over Na$_2$SO$_4$ and concentrated to a residue which was purified by Prep TLC eluted with PE/EA (1:2) to give 6-bromo-5-((4-chlorophenyl) (hydroxy)methyl)-1-methyl-3-(3-(tetrahydro-2H-pyran-2-yloxy)propyl)pyrido[2,3-d]pyrimidine-2,4(1H,3H)-dione (0.46 g, 34% yield) as a light yellow solid. LCMS: [M$^+$+Na] 560 and T$_R$=1.973 min.

Step 2 3-(6-bromo-5-(4-chlorobenzyl)-1-methyl-2,4-dioxo-1,2-dihydropyrido[2,3-d]pyrimidin-3(4H)-yl)propyl formate

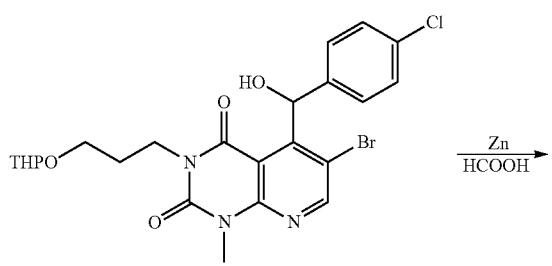

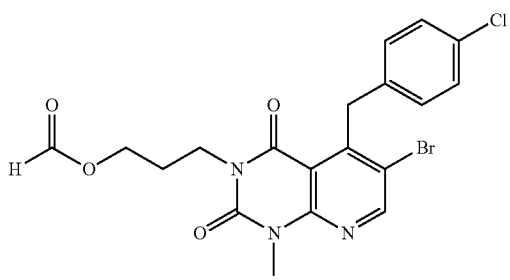

To a solution of 6-bromo-5-((4-chlorophenyl)(hydroxy)methyl)-1-methyl-3-(3-(tetrahydro-2H-pyran-2-yloxy)propyl)pyrido[2,3-d]pyrimidine-2,4(1H,3H)-dione (300 mg, 0.56 mmol) in HCOOH (10 mL) was added Zn dust (182 mg, 2.78 mmol). The reaction was heated at 60° C. for 1 h then cooled to RT and filtered. The filtrate was concentrated to a residue which was purified by Prep TLC eluted with PE/EA (1:2) to give 3-(6-bromo-5-(4-chlorobenzyl)-1-methyl-2,4-dioxo-1,2-dihydropyrido[2,3-d]pyrimidin-3(4H)-yl)propyl formate (190 mg, 73% yield) as a white solid. LCMS: MH$^+$ 468 and T$_R$=1.893 min.

Step 3 5-(4-chlorobenzyl)-6-(3-chlorophenoxy)-3-(3-hydroxypropyl)-1-methylpyrido[2,3-d]pyrimidine-2,4(1H,3H)-dione

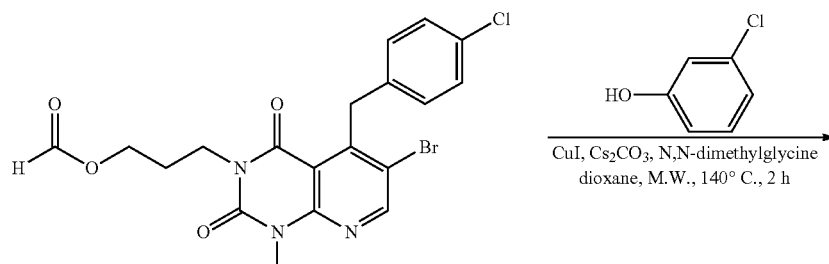

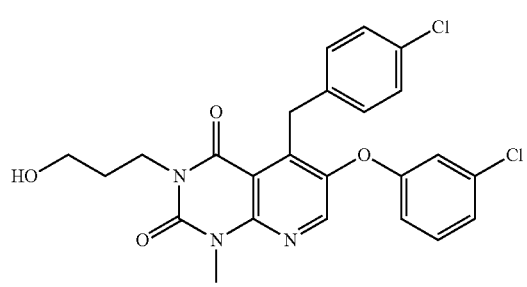

To a mixture of 3-(6-bromo-5-(4-chlorobenzyl)-1-methyl-2,4-dioxo-1,2-dihydropyrido[2,3-d]pyrimidin-3(4H)-yl) propyl formate (80 mg, 0.17 mmol), CuI (4.2 mg, 0.022 mmol), $Cs_2CO_3$ (167.6 mg, 0.51 mmol) and 2-(dimethylamino)acetic acid (8.8 mg, 0.085 mmol) in dioxane (2 mL) was added 3-chlorophenol (55.1 mg, 0.43 mmol). The reaction was heated at 140° C. (MW) for 2 h, cooled to RT then diluted with EA (15 mL) and water (10 mL). The organic layer was washed with water (20 mL) and brine (20 mL), dried over $Na_2SO_4$ and concentrated to a residue which was purified by Prep HPLC to give 5-(4-chlorobenzyl)-6-(3-chlorophenoxy)-3-(3-hydroxypropyl)-1-methylpyrido[2,3-d]pyrimidine-2,4(1H,3H)-dione (10.2 mg, 12% yield) as a white solid. $^1$H NMR (CDCl$_3$) δ: 8.35 (s, 1H), 7.23 (d, J=8.2 Hz, 1H), 7.17 (s, 4H), 7.09 (d, J=8.0 Hz, 1H), 6.84-6.73 (m, 2H), 4.71 (s, 2H), 4.24 (t, J=6.1 Hz, 2H), 3.72 (s, 3H), 3.55 (s, 2H), 3.02 (s, 1H), 2.00-1.86 (m, 2H). LCMS: MH$^+$ 486 and T$_R$=3.332 min.

Compound 27

5-(4-chlorobenzyl)-3-(3-hydroxypropyl)-1-methyl-6-(5-methylpyridin-3-yloxy)pyrido[2,3-d]pyrimidine-2,4(1H,3H)-dione

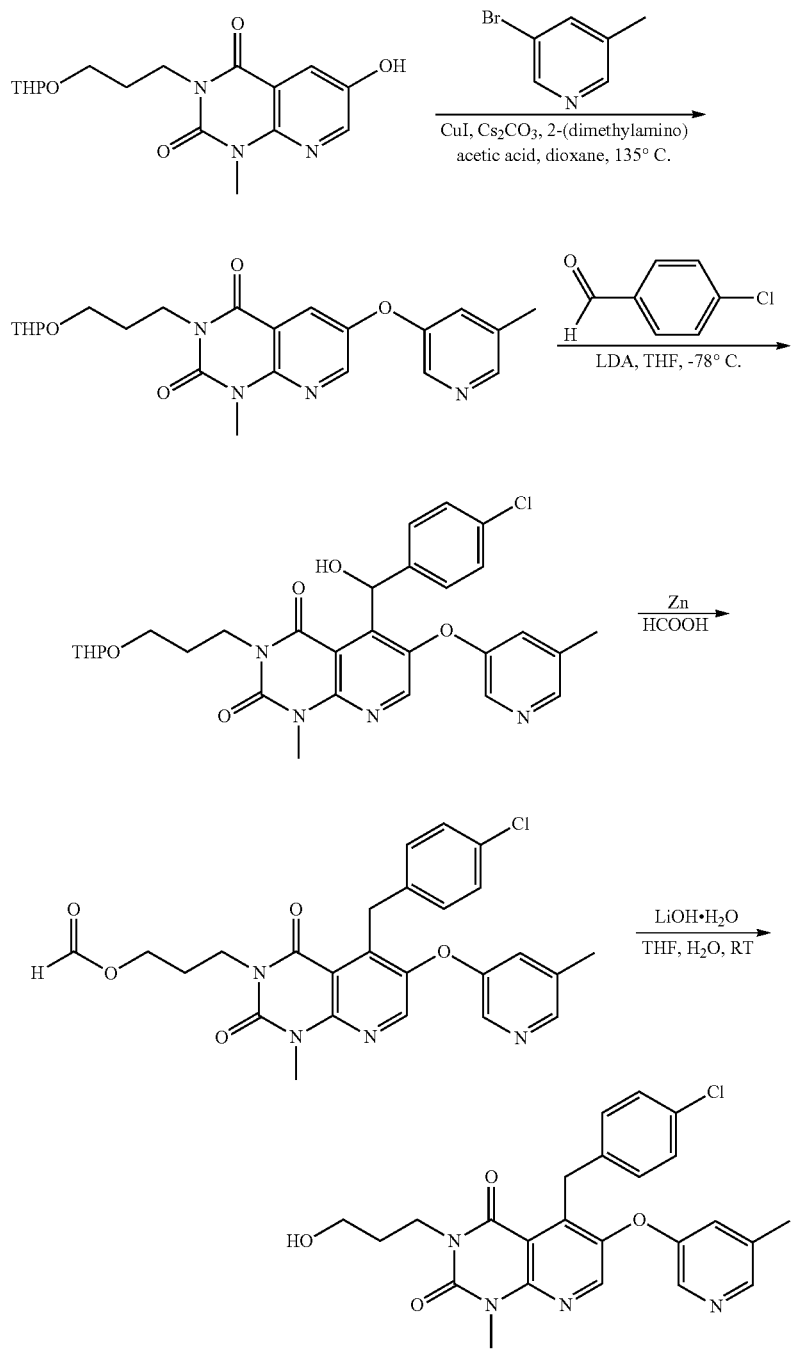

Step 1 1-methyl-6-((5-methylpyridin-3-yl)oxy)-3-(3-((tetrahydro-2H-pyran-2-yl)oxy)propyl)pyrido[2,3-d]pyrimidine-2,4(1H,3H)-dione

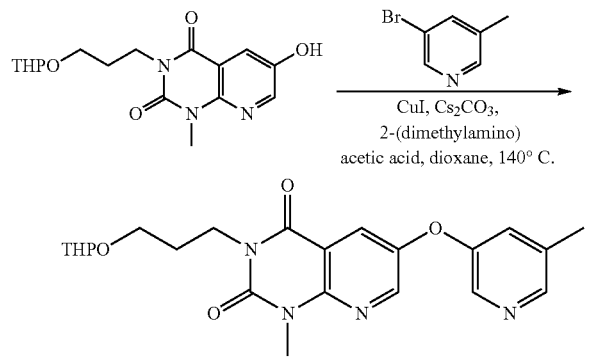

To a suspension of 6-hydroxy-1-methyl-3-(3-((tetrahydro-2H-pyran-2-yl)oxy)propyl)pyrido[2,3-d]pyrimidine-2,4(1H,3H)-dione (See Compound 36, step 2, 600 mg, 1.8 mmol), CuI (45 mg, 0.23 mmol), $Cs_2CO_3$ (1.69 mg, 5.4 mmol) and 2-(dimethylamino)acetic acid (93 mg, 0.9 mmol) in dioxane (10 mL) was added 3-bromo-5-methylpyridine (0.45 mL, 3.6 mmol). The reaction was heated at 140° C. (MW) in a sealed tube for 2 h, cooled to RT and diluted with EA (50 mL) and water (50 mL). The organic layer was washed with water (30 mL) and brine (50 mL), dried over $Na_2SO_4$ and concentrated to a residue which was purified by chromatography eluted with PE/EA (10:1) to give 1-methyl-6-(5-methylpyridin-3-yloxy)-3-(3-(tetrahydro-2H-pyran-2-yloxy)propyl)pyrido[2,3-d]pyrimidine-2,4(1H,3H)-dione (610 mg, 81% yield) as a yellow solid. LCMS $MH^+$ 427 and $T_R$=1.403 min.

Step 2 1-methyl-6-(5-methylpyridin-3-yloxy)-3-(3-(tetrahydro-2H-pyran-2-yloxy)propyl)-pyrido[2,3-d]pyrimidine-2,4(1H,3H)-dione

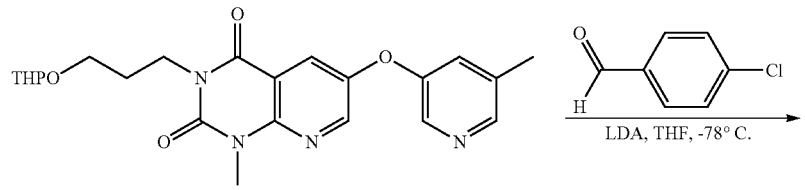

To a solution of 1-methyl-6-(5-methylpyridin-3-yloxy)-3-(3-(tetrahydro-2H-pyran-2-yloxy)propyl)pyrido[2,3-d]pyrimidine-2,4(1H,3H)-dione (150 mg, 0.35 mmol) in THF (10 mL) at −78° C. was added LDA (2.0 M in THF, 0.72 mL, 1.4 mmol) dropwise. The reaction was stirred at −78° C. for 1 h then a solution of 4-chlorobenzaldehyde (99 mg, 0.7 mmol) in THF (1 mL) was added. The reaction was stirred at −78° C. for 1 h, quenched with aq. $NH_4Cl$ (10 mL) then diluted with EA (20 mL) and water (20 mL). The organic layer was dried over $Na_2SO_4$ and concentrated to give a residue which was purified by Prep TLC eluted with PE/EA (1:2) to give 1-methyl-6-(5-methylpyridin-3-yloxy)-3-(3-(tetrahydro-2H-pyran-2-yloxy)propyl)pyrido[2,3-d]pyrimidine-2,4(1H,3H)-dione (110 mg, 55% yield) as a light yellow oil. LCMS: $MH^+$ 567 and $T_R$=1.727 min.

Step 3 3-(5-(4-chlorobenzyl)-1-methyl-6-(5-methylpyridin-3-yloxy)-2,4-dioxo-1,2-dihydropyrido[2,3-d]pyrimidin-3(4H)-yl)propyl formate

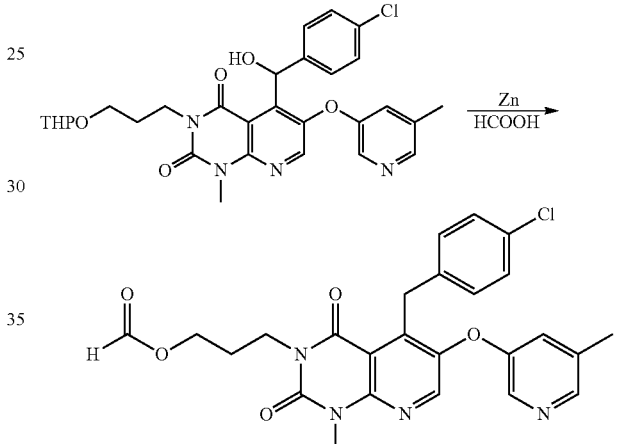

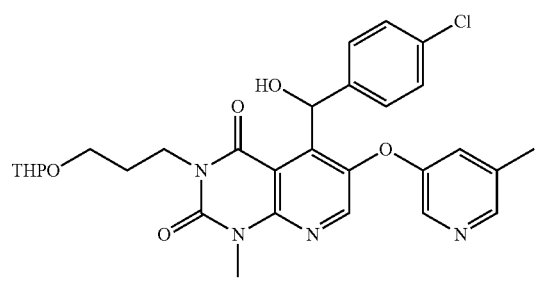

To a solution of 1-methyl-6-(5-methylpyridin-3-yloxy)-3-(3-(tetrahydro-2H-pyran-2-yloxy) propyl)pyrido[2,3-d]pyrimidine-2,4(1H,3H)-dione (100 mg, 0.176 mmol) in HCOOH (5 mL) was added Zn dust (57.7 mg, 0.881 mmol). The reaction was heated at 60° C. for 1 h, cooled to RT and filtered. The filtrate was concentrated to a residue which was purified by Prep TLC eluted with PE/EA (1:1) to give 3-(5-(4-chlorobenzyl)-1-methyl-6-(5-methylpyridin-3-yloxy)-2,4-dioxo-1,2-dihydropyrido[2,3-d]pyrimidin-3(4H)-yl)propyl formate (56 mg, 64% yield) as a colorless oil. LCMS: MH$^+$ 495 and T$_R$=1.833 min.

Step 4 5-(4-chlorobenzyl)-3-(3-hydroxypropyl)-1-methyl-6-(5-methylpyridin-3-yloxy)pyrido[2,3-d]pyrimidine-2,4(1H,3H)-dione

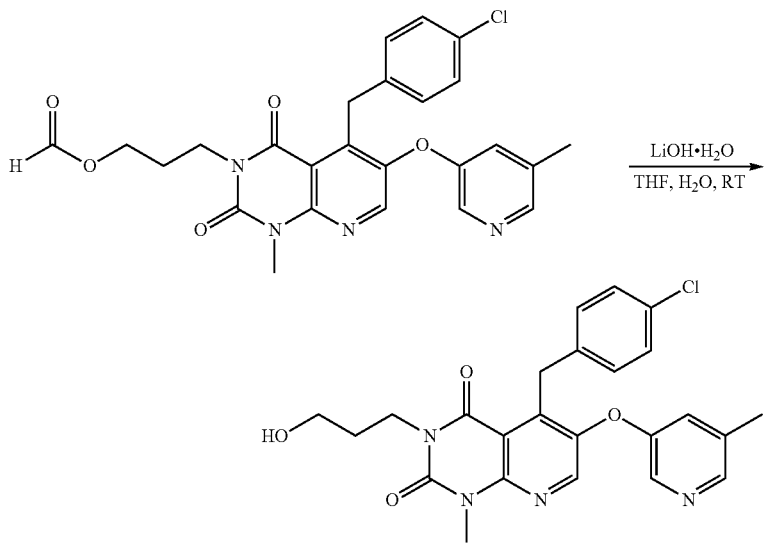

To a solution of 3-(5-(4-chlorobenzyl)-1-methyl-6-(5-methylpyridin-3-yloxy)-2,4-dioxo-1,2-dihydropyrido[2,3-d]pyrimidin-3(4H)-yl)propyl formate (56 mg, 0.113 mmol) in THF (3 mL) and water (3 mL) was added LiOH.H$_2$O (9.5 mg, 0.226 mmol). The reaction was stirred at RT for 15 min then diluted with EA (5 mL) and water (5 mL). The organic layer was dried over Na$_2$SO$_4$ and concentrated to a residue which was purified by Prep HPLC to give 5-(4-chlorobenzyl)-3-(3-hydroxypropyl)-1-methyl-6-(5-methylpyridin-3-yloxy)pyrido[2,3-d]pyrimidine-2,4(1H,3H)-dione (11 mg, 21% yield) as a white solid. $^1$H NMR (CD$_3$OD) δ: 8.43 (s, 1H), 8.13-7.95 (m, 2H), 7.22-7.05 (m, 4H), 6.94 (s, 1H), 4.81 (s, 2H), 4.18 (t, J=7.1 Hz, 2H), 3.72 (s, 3H), 3.65 (t, J=6.3 Hz, 2H), 2.24 (s, 3H), 1.98-1.84 (m, 2H). LCMS: MH$^+$ 467 and T$_R$=2.631 min.

Compound 28

6-(4-chlorophenoxy)-5-(4-fluorobenzyl)-3-(3-hydroxypropyl)-1-methylpyrido[2,3-d]pyrimidine-2,4(1H,3H)-dione

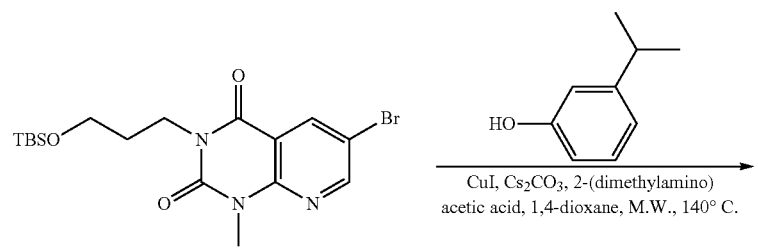

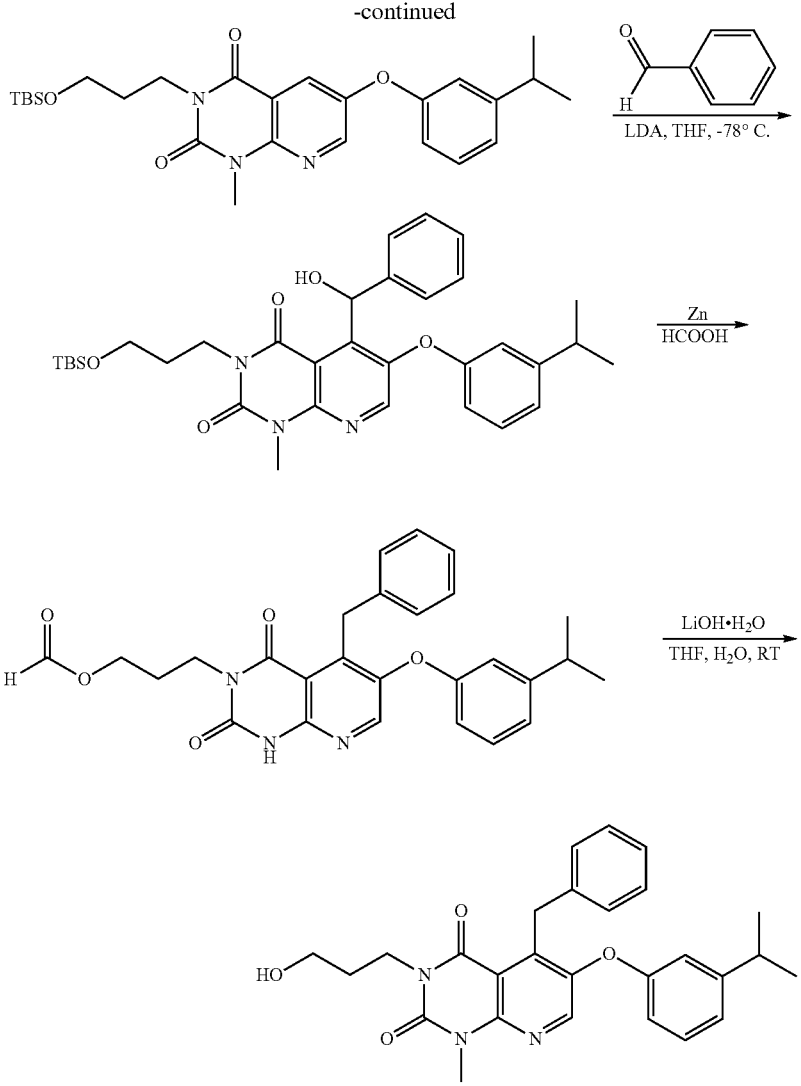

Step 1 6-(3-isopropylphenoxy)-1-methyl-3-(3-(tetrahydro-2H-pyran-2-yloxy)propyl)pyrido[2,3-d]pyrimidine-2,4(1H,3H)-dione

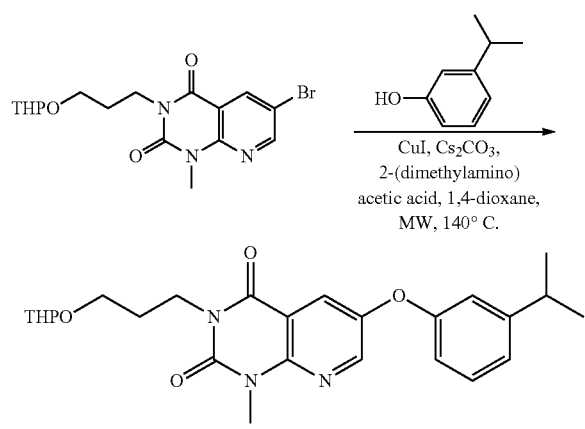

To a solution of 6-bromo-1-methyl-3-(3-(tetrahydro-2H-pyran-2-yloxy)propyl)pyrido[2,3-d]pyrimidine-2,4(1H,3H)-dione (See Compound 20, step 4, 400 mg, 1 mmol), CuI (24.7 mg, 0.13 mmol), $Cs_2CO_3$ (650 mg, 2 mmol) and 2-(dimethylamino)acetic acid (51.5 mg, 0.5 mmol) in dioxane (6 mL) was added 3-isopropylphenol (204 mg, 1.5 mmol). The reaction was heated at 140° C. (MW) for 1.5 h then cooled to RT and filtered. The filtrate was diluted with EA (5 mL) and water (5 mL). The organic layer was dried over $Na_2SO_4$ and concentrated to a residue which was purified by chromatography eluted with PE/EA (5:1) to give 6-(3-isopropylphenoxy)-1-methyl-3-(3-(tetra hydro-2H-pyran-2-yloxy)propyl)pyrido[2,3-d]pyrimidine-2,4(1H, 3H)-dione (250 mg, 55% yield) as a solid. LCMS: MH+ 454 and $T_R$=2.156 min.

Step 2 5-(hydroxy(phenyl)methyl)-6-(3-isopropyl-phenoxy)-1-methyl-3-(3-(tetrahydro-2H-pyran-2-yloxy)propyl)pyrido[2,3-d]pyrimidine-2,4(1H,3H)-dione

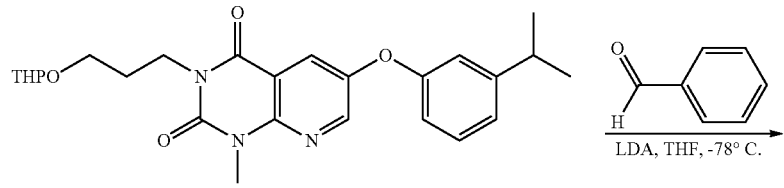

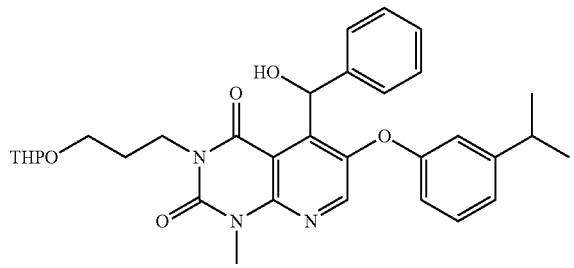

To a solution of 6-(3-isopropylphenoxy)-1-methyl-3-(3-(tetrahydro-2H-pyran-2-yloxy)propyl)pyrido[2,3-d]pyrimidine-2,4(1H,3H)-dione (220 mg, 0.50 mmol) in THF (10 mL) at −78° C. was added LDA (2.0 M in THF, 1.25 mL, 2.50 mmol) dropwise. The reaction was stirred at −78° C. for 1 h then a solution of benzaldehyde (106 mg, 1.00 mmol) in THF (2 mL) was added dropwise. The reaction was stirred at −78° C. for 1 h, quenched with aq. NH₄Cl (10 mL) then diluted with EA (20 mL) and water (20 mL). The organic layer was dried over Na₂SO₄ and concentrated to give a residue which was purified by chromatography PE/EA (7:1) to give 5-(hydroxy(phenyl)methyl)-6-(3-isopropylphenoxy)-1-methyl-3-(3-(tetrahydro-2H-pyran-2-yloxy)propyl)pyrido[2,3-d]pyrimidine-2,4(1H,3H)-dione (120 mg, 45% yield) as a solid. LCMS: MH⁺ 560 and T$_R$=1.869 min.

Step 3 3-(5-benzyl-6-(3-isopropylphenoxy)-1-methyl-2,4-dioxo-1,2-dihydropyrido[2,3-d]pyrimidin-3(4H)-yl)propyl formate

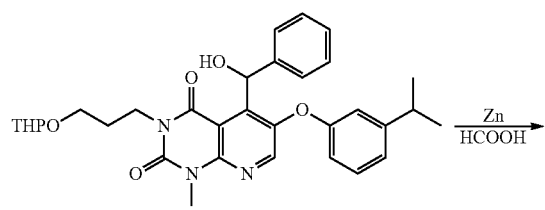

-continued

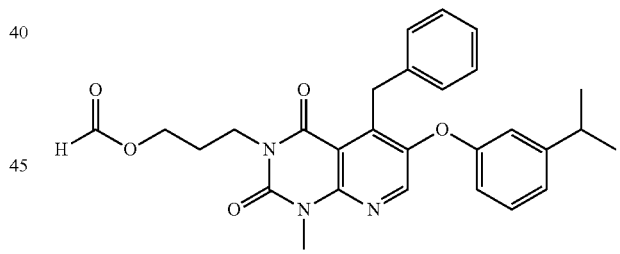

To a solution of 5-(hydroxy(phenyl)methyl)-6-(3-isopropylphenoxy)-1-methyl-3-(3-(tetrahydro-2H-pyran-2-yloxy) propyl)pyrido[2,3-d]pyrimidine-2,4(1H,3H)-dione (50 mg, 0.10 mmol) in HCOOH (3 mL) was added Zn dust (32.5 mg, 0.50 mmol). The reaction was heated at 60° C. for 2 h, cooled to RT and filtered. The filtrate was concentrated to give 3-(5-benzyl-6-(3-isopropyl phenoxy)-1-methyl-2,4-dioxo-1,2-dihydropyrido[2,3-d]pyrimidin-3(4H)-yl)propyl-formate (50 mg, 100% yield) as an oil. LCMS: MH⁺ 488 and T$_R$=1.568 min. Used without further purification.

Step 4 5-benzyl-3-(3-hydroxypropyl)-6-(3-isopropylphenoxy)-1-methylpyrido[2,3-d]pyrimidine-2,4(1H,3H)-dione

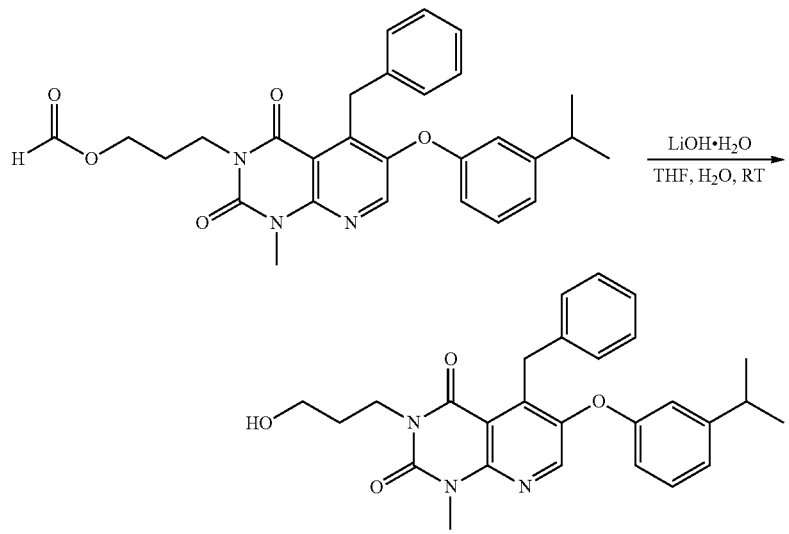

To a solution of 3-(5-benzyl-6-(3-isopropylphenoxy)-1-methyl-2,4-dioxo-1,2-dihydropyrido[2,3-d]pyrimidin-3(4H)-yl)propyl formate (50 mg, 0.10 mmol) in THF (3 ml) and water (3 mL) was added LiOH.H$_2$O (10 mg, 0.20 mmol). The reaction was stirred at RT for 15 min then diluted with EA (30 mL) and water (30 mL). The organic layer was dried over Na$_2$SO$_4$ and concentrated to give a residue which was purified by Prep HPLC to give 5-benzyl-3-(3-hydroxypropyl)-6-(3-isopropyl phenoxy)-1-methyl-pyrido[2,3-d]pyrimidine-2,4(1H,3H)-dione (15 mg, 45% yield) as a solid. $^1$H NMR (CDCl$_3$) δ: 8.32 (s, 1H), 7.29 (s, 2H), 7.25-7.12 (m, 4H), 6.99 (d, J=7.9 Hz, 1H), 6.76 (s, 1H), 6.68 (dd, J=8.0, 2.3 Hz, 1H), 4.80 (s, 2H), 4.24 (t, J=6.0 Hz, 2H), 3.70 (s, 3H), 3.52 (dd, J=11.8, 6.2 Hz, 2H), 3.10 (t, J=7.0 Hz, 1H), 2.85 (dt, J=13.9, 6.9 Hz, 1H), 1.98-1.83 (m, 2H), 1.22 (d, J=6.9 Hz, 6H). LCMS: MH$^+$ 460 and T$_R$=3.376 min.

Compound 29

5-benzyl-3-(3-hydroxypropyl)-6-isopropoxy-1-methylpyrido[2,3-d]pyrimidine-2,4(1H,3H)-dione

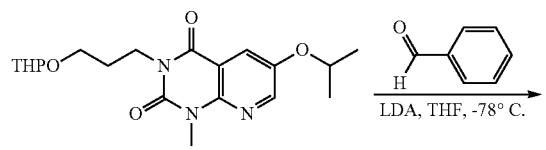

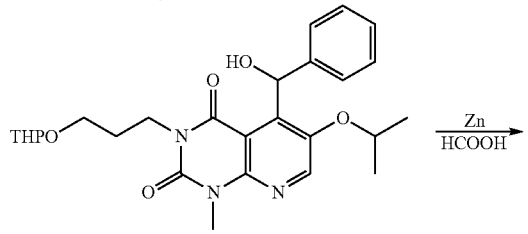

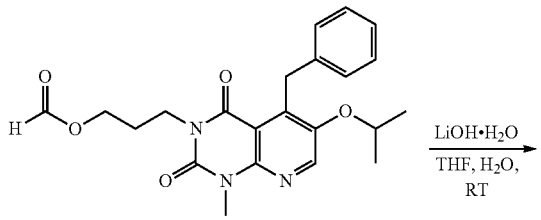

Step 1 5-(hydroxy(phenyl)methyl)-6-isopropoxy-1-methyl-3-(3-(tetrahydro-2H-pyran-2-yloxy)propyl)pyrido[2,3-d]pyrimidine-2,4(1H,3H)-dione

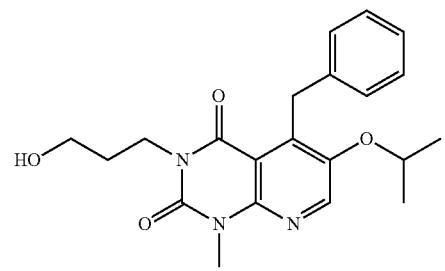

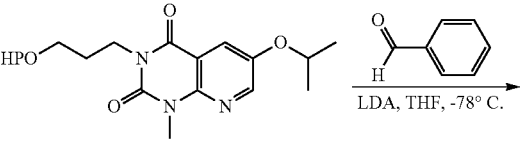

-continued

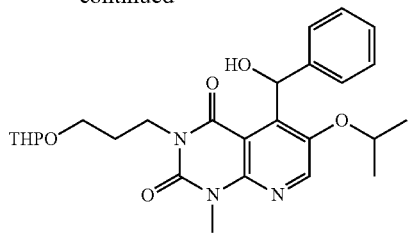

To a solution of 6-isopropoxy-1-methyl-3-(3-(tetrahydro-2H-pyran-2-yloxy)propyl)pyrido[2,3-d]pyrimidine-2,4(1H,3H)-dione (See Compound 36, step 3, 150 mg, 0.4 mmol) in THF (6 mL) at −78° C. was added LDA (2M in THF, 1.0 mL, 2 mmol) dropwise. The reaction was stirred at −78° C. for 1 h then benzaldehyde (84.8 mg, 0.8 mmol) in THF (1.5 mL) was added. The reaction was stirred at −78° C. for 1 h quenched with aq. NH$_4$Cl (8 mL) then diluted with EA (30 mL) and water (10 mL). The organic layer was dried over Na$_2$SO$_4$ and concentrated to a residue which was purified by Prep TLC eluted with PE/EA (2:1) to give 5-(hydroxy(phenyl)methyl)-6-isopropoxy-1-methyl-3-(3-(tetrahydro-2H-pyran-2-yloxy)propyl)pyrido[2,3-d]pyrimidine-2,4(1H,3H)-dione (100 mg, 51.8% yield) as a solid. LCMS: [M$^+$-THP-OH] 382 and T$_R$=1.855 min.

Step 2 3-(5-benzyl-6-isopropoxy-1-methyl-2,4-dioxo-1,2-dihydropyrido[2,3-d]pyrimidin-3(4H)-yl)propyl formate

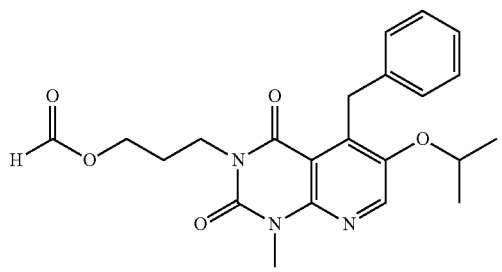

To a solution of 5-(hydroxy(phenyl)methyl)-6-isopropoxy-1-methyl-3-(3-(tetrahydro-2H-pyran-2-yloxy)propyl)pyrido[2,3-d]pyrimidine-2,4(1H,3H)-dione (100 mg, 0.207 mmol) in HCOOH (2 mL) was added Zn dust (67.2 mg, 1.034 mmol). The reaction was heated at 80° C. for 1 h then cooled to RT and filtered. The filtrate was concentrated and dried to a residue which was purified by Prep TLC eluted with PE/EA (2:1) to give 3-(5-benzyl-6-isopropoxy-1-methyl-2,4-dioxo-1,2-dihydropyrido[2,3-d]pyrimidin-3(4H)-yl)propyl formate (70 mg, 85% yield) as a white solid.

Step 3 5-benzyl-3-(3-hydroxypropyl)-6-isopropoxy-1-methylpyrido[2,3-d]pyrimidine-2,4(1H,3H)-dione

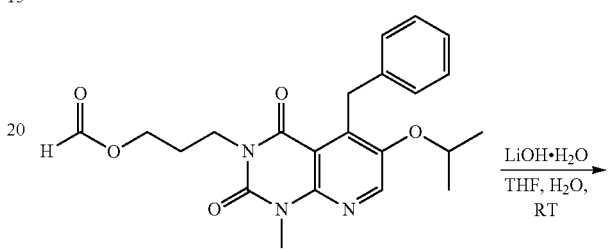

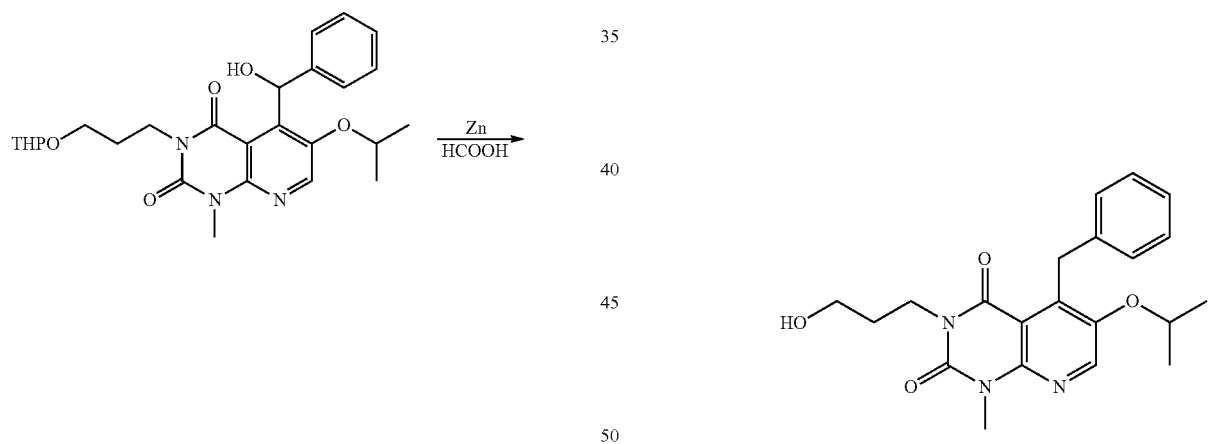

To a solution of 3-(5-benzyl-6-isopropoxy-1-methyl-2,4-dioxo-1,2-dihydropyrido[2,3-d]pyrimidin-3(4H)-yl)propyl formate (70 mg, 0.17 mmol) in THF (1 mL) and water (1 mL) was added LiOH.H$_2$O (14.2 mg, 0.34 mmol). The reaction was stirred at RT for 15 min then diluted with EA (5 mL) and water (5 mL). The organic layer was dried over Na$_2$SO$_4$ and concentrated to a residue which was purified by Prep HPLC to give 5-benzyl-3-(3-hydroxypropyl)-6-isopropoxy-1-methylpyrido[2,3-d]pyrimidine-2,4(1H,3H)-dione (18 mg, 39.0% yield) as a white solid. $^1$H NMR (CDCl$_3$) δ: 8.32 (s, 1H), 7.25-7.18 (m, 4H), 7.17-7.10 (m, 1H), 4.78 (s, 2H), 4.62 (dt, J=12.1, 6.1 Hz, 1H), 4.26-4.15 (m, 2H), 3.69 (s, 3H), 3.52-3.43 (m, 2H), 3.17 (t, J=7.0 Hz, 1H), 1.94-1.82 (m, 2H), 1.34 (d, J=6.0 Hz, 6H). LCMS: MH$^+$ 384 and T$_R$=2.708 min.

Compound 30
6-(4-chlorophenoxy)-5-(4-fluorobenzyl)-3-(3-hydroxypropyl)-1-methylpyrido[2,3-d]pyrimidine-2,4(1H,3H)-dione
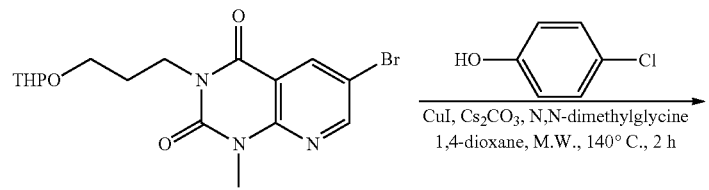
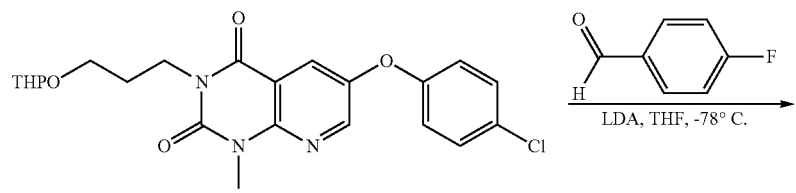
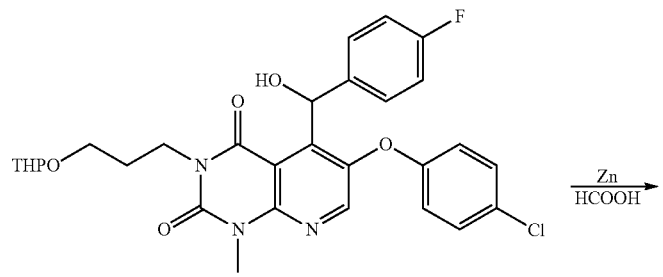
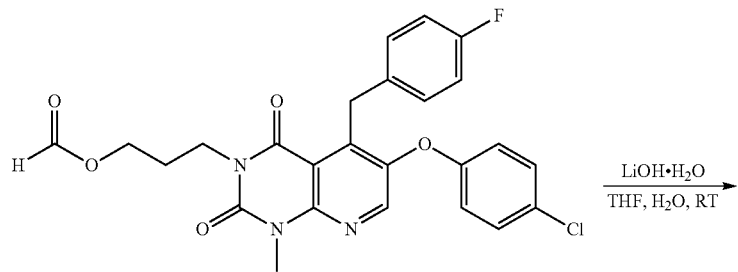
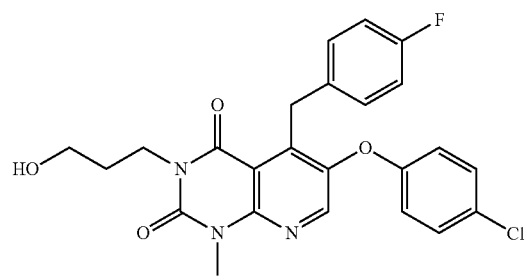

Step 1 6-(4-chlorophenoxy)-1-methyl-3-(3-(tetrahydro-2H-pyran-2-yloxy)propyl)pyrido[2,3-d]pyrimidine-2,4(1H,3H)-dione

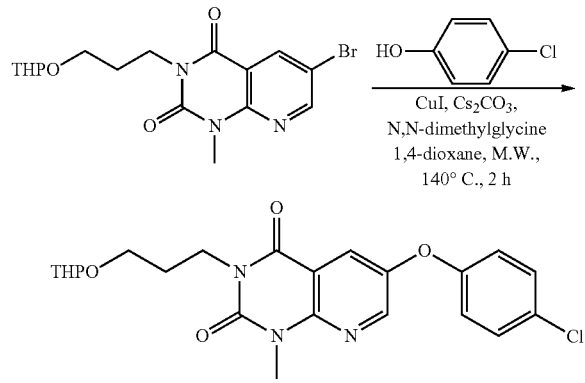

To a mixture of 6-(4-chlorophenoxy)-1-methyl-3-(3-(tetrahydro-2H-pyran-2-yloxy)propyl)pyrido[2,3-d]pyrimidine-2,4(1H,3H)-dione (See Compound 20, step 4400 mg, 1 mmol), CuI (24.7 mg, 0.13 mmol), Cs$_2$CO$_3$ (650 mg, 2 mmol), 2-(dimethylamino)acetic acid (51.5 mg, 0.5 mmol) in dioxane (6 mL) was added 4-chlorophenol (192 mg, 1.5 mmol). The reaction was heated at 140° C. (MW) for 1.5 h, cooled to RT and filtered. The filtrate was diluted with EA (5 mL) and water (5 mL). The organic layer was dried over Na$_2$SO$_4$ and concentrated to a residue which was purified by chromatography eluted with PE/EA (5:1) to give 6-(4-chlorophenoxy)-1-methyl-3-(3-(tetrahydro-2H-pyran-2-yloxy)propyl)pyrido[2,3-d]pyrimidine-2,4(1H,3H)-dione (250 mg, 56.2% yield) as an oil. LCMS: MH$^+$ 446 and T$_R$=3.000 min.

Step 2 6-(4-chlorophenoxy)-5-((4-fluorophenyl)(hydroxy)methyl)-1-methyl-3-(3-(tetrahydro-2H-pyran-2-yloxy)propyl)pyrido[2,3-d]pyrimidine-2,4(1H,3H)-dione

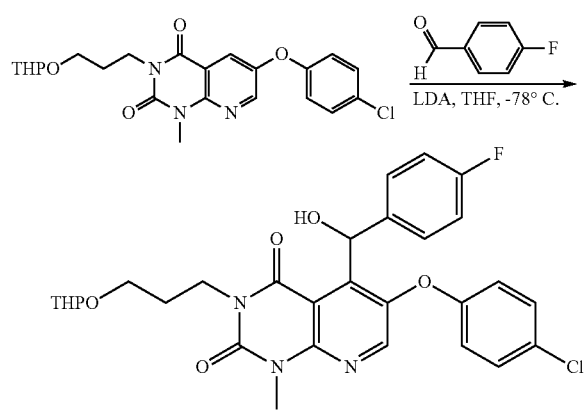

To a solution of 6-(4-chlorophenoxy)-1-methyl-3-(3-(tetrahydro-2H-pyran-2-yloxy)propyl)pyrido[2,3-d]pyrimidine-2,4(1H,3H)-dione (110 mg, 0.25 mmol) in THF (5 mL) at −78° C. was added LDA (2.0 M in THF, 0.63 mL, 1.25 mmol) dropwise. The reaction was stirred at −78° C. for 1 h then a solution of 4-fluorobenzaldehyde (62 mg, 0.50 mmol) in THF (1 mL) was added dropwise. The reaction was stirred at −78° C. for 1 h, quenched with sat. aq. NH$_4$Cl (5 mL) then diluted with EA (30 mL) and water (30 mL). The organic layer was dried over Na$_2$SO$_4$ and concentrated to give a residue which was purified by chromatography eluted with PE/EA (7:1) to give 6-(4-chlorophenoxy)-5-((4-fluorophenyl)(hydroxy)methyl)-1-methyl-3-(3-(tetrahydro-2H-pyran-2-yloxy)propyl)pyrido[2,3-d]pyrimidine-2,4(1H,3H)-dione (55 mg, 40% yield) as a solid. LCMS: [M$^+$+Na] 592 and T$_R$=3.372 min.

Step 3 3-(6-(4-chlorophenoxy)-5-(4-fluorobenzyl)-1-methyl-2,4-dioxo-1,2-dihydropyrido[2,3-d]pyrimidin-3(4H)-yl)propyl formate

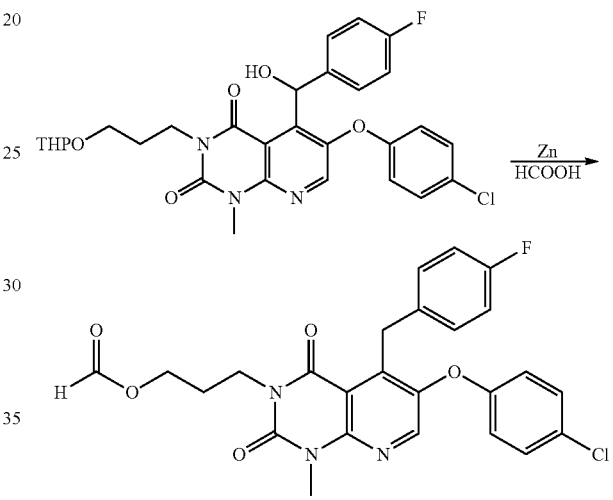

To a solution of 6-(4-chlorophenoxy)-5-((4-fluorophenyl)(hydroxy)methyl)-1-methyl-3-(3-(tetra hydro-2H-pyran-2-yloxy)propyl)pyrido[2,3-d]pyrimidine-2,4(1H,3H)-dione (55 mg, 0.10 mmol) in HCOOH (3 mL) was added Zn dust (40.4 mg, 0.62 mmol). The reaction was heated at 60° C. for 2 h then cooled to RT and filtered. The filtrate was concentrated to give 3-((6-(4-chlorophenoxy)-5-(4-fluorobenzyl)-1-methyl-2,4-dioxo-1,2-dihydropyrido[2,3-d]pyrimidin-3(4H)-yl)propylformate (50 mg, 100% yield) as a white solid. LCMS: MH$^+$ 498 and T$_R$=1.732 min. Used without further purification.

Step 4 6-(4-chlorophenoxy)-5-(4-fluorobenzyl)-3-(3-hydroxypropyl)-1-methylpyrido[2,3-d]pyrimidine-2,4(1H,3H)-dione

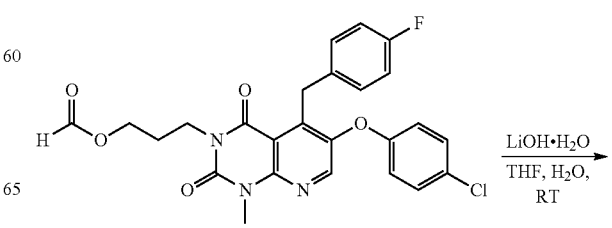

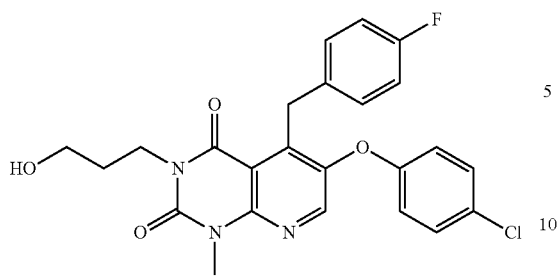

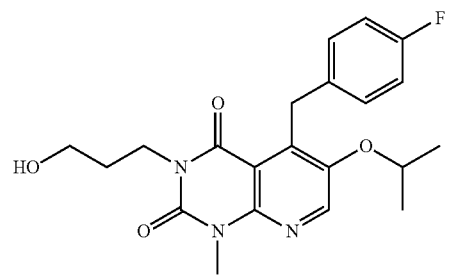

To a solution of 3-(6-(4-chlorophenoxy)-5-(4-fluorobenzyl)-1-methyl-2,4-dioxo-1,2-dihydro pyrido[2,3-d]pyrimidin-3(4H)-yl)propyl formate (50 mg, 0.10 mmol) in THF (3 mL) and water (3 mL) was added LiOH.H$_2$O (10 mg, 0.20 mmol). The reaction was stirred at RT for 15 min then diluted with EA (5 mL) and water (5 mL). The organic layer was dried over Na$_2$SO$_4$ and concentrated to a residue which was purified by Prep HPLC to give 6-(4-chlorophenoxy)-5-(4-fluorobenzyl)-3-(3-hydroxypropyl)-1-methylpyrido[2,3-d]pyrimidine-2,4(1H,3H)-dione (20 mg, 37% yield) as a white solid. $^1$H NMR (CDCl$_3$) δ: 8.31 (s, 1H), 7.31-7.27 (m, 2H), 7.22 (dd, J=8.6, 5.5 Hz, 2H), 6.89 (t, J=8.7 Hz, 2H), 6.83-6.77 (m, 2H), 4.72 (s, 2H), 4.24 (t, J=6.1 Hz, 2H), 3.70 (s, 3H), 3.55 (dd, J=11.7, 6.2 Hz, 2H), 3.04 (t, J=6.9 Hz, 1H), 2.01-1.86 (m, 2H). LCMS: MH$^+$ 470 and T$_R$=2.811 min Compound 31

5-(4-fluorobenzyl)-3-(3-hydroxypropyl)-6-isopropoxy-1-methylpyrido[2,3-d]pyrimidine-2,4(1H,3H)-dione

Step 1 5-((4-fluorophenyl)(hydroxy)methyl)-6-isopropoxy-1-methyl-3-(3-(tetrahydro-2H-pyran-2-yloxy) propyl)pyrido[2,3-d]pyrimidine-2,4(1H,3H)-dione

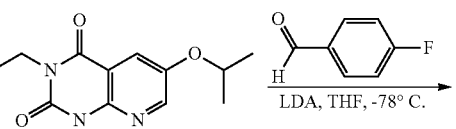

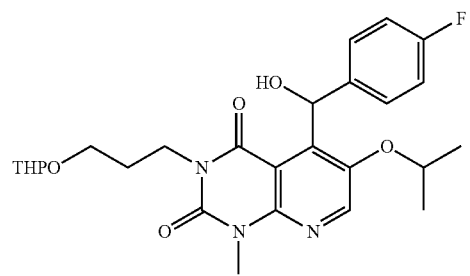

To a solution of 6-isopropoxy-1-methyl-3-(3-(tetrahydro-2H-pyran-2-yloxy)propyl)pyrido[2,3-d]pyrimidine-2,4(1H, 3H)-dione (See Compound 36, step 3, 150 mg, 0.4 mmol) in THF (6 mL) at −78° C. was added LDA (2.0 M in THF, 1.0 mL, 2.0 mmol) dropwise. The reaction was stirred at −78° C. for 1 h then a solution of 4-chlorobenzaldehyde (98.6 mg, 0.8 mmol) in THF (1 mL) was added dropwise. The reaction was stirred at −78° C. for 1 h, quenched with aq. NH$_4$Cl (5 mL) then diluted with EA (10 mL) and water (10 mL). The organic layer was dried over Na$_2$SO$_4$ and concentrated to a residue which was purified by Prep TLC eluted with PE/EA (1:1) to give 5-((4-fluorophenyl)(hydroxy)-methyl)-6-isopropoxy-1-methyl-3-(3-(tetrahydro-2H-pyran-2-yloxy)propyl)pyrido[2,3-d]pyrimidine-2,4 (1H,3H)-dione (128 mg, 62% yield) as a white solid. LCMS: [M$^+$-THP-OH] 401 and T$_R$=3.025 min.

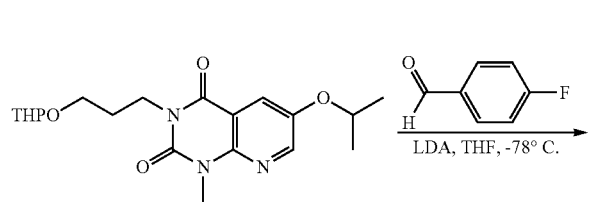

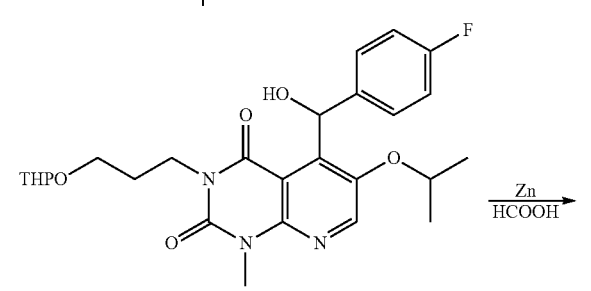

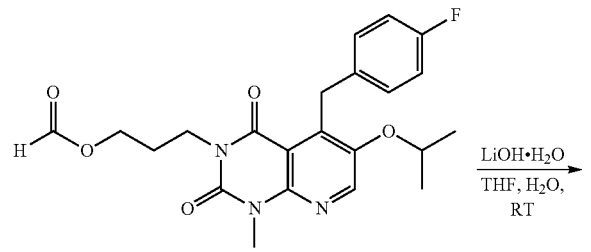

Step 2 3-(5-(4-fluorobenzyl)-6-isopropoxy-1-methyl-2,4-dioxo-1,2-dihydropyrido[2,3-d]pyrimidin-3(4H)-yl)propyl formate

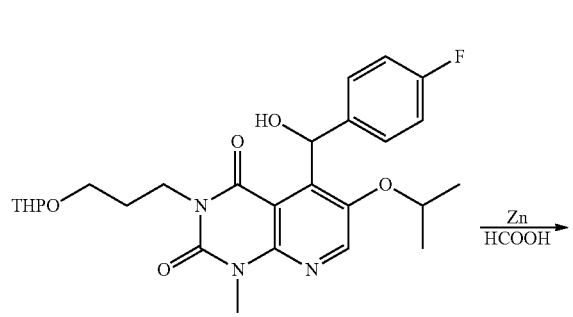

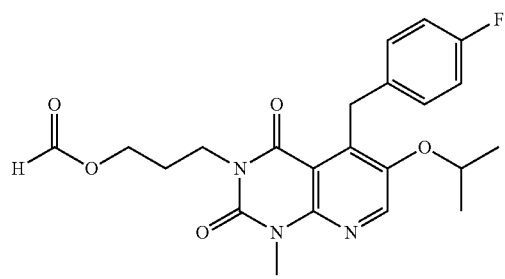

To a solution of 5-((4-fluorophenyl)(hydroxy)methyl)-6-isopropoxy-1-methyl-3-(3-(tetrahydro-2H-pyran-2-yloxy)propyl)pyrido[2,3-d]pyrimidine-2,4(1H,3H)-dione (128 mg, 0.26 mmol) in HCOOH (5 mL) was added Zn dust (83.5 mg, 1.28 mmol). The reaction was heated at 60° C. for 2 h, cooled to RT and filtered. The filtrate was concentrated to a residue which was purified by Prep TLC eluted with PE/EA (4:6) to give 3-(5-(4-fluorobenzyl)-6-isopropoxy-1-methyl-2,4-dioxo-1,2-dihydropyrido[2,3-d]pyrimidin-3(4H)-yl) propyl formate (89 mg, 81% yield) as a white solid. LCMS: MH$^+$ 430 and T$_R$=2.543 min.

Step 3 5-(4-fluorobenzyl)-3-(3-hydroxypropyl)-6-isopropoxy-1-methylpyrido[2,3-d]pyrimidine-2,4 (1H,3H)-dione

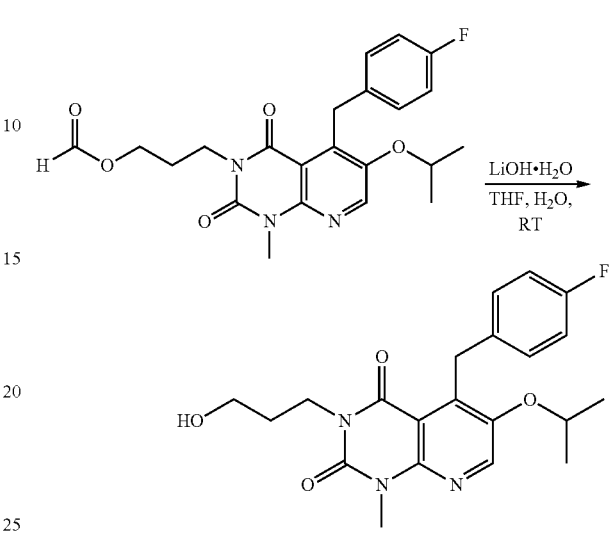

To a solution of 3-(5-(4-fluorobenzyl)-6-isopropoxy-1-methyl-2,4-dioxo-1,2-dihydropyrido[2,3-d]pyrimidin-3 (4H)-yl)propyl formate (89 mg, 0.21 mmol) in THF (3 mL) and water (3 mL) was added LiOH.H$_2$O (17.4 mg, 0.42 mmol). The reaction was stirred at RT for 15 min then diluted with EA (20 mL) and water (20 mL). The organic layer was dried over Na$_2$SO$_4$ and concentrated to a residue which was purified by Prep HPLC to give 5-(4-fluorobenzyl)-3-(3-hydroxypropyl)-6-isopropoxy-1-methylpyrido[2,3-d]pyrimidine-2,4(1H,3H)-dione (30 mg, 36% yield) as a white solid. $^1$H NMR (CDCl$_3$) δ: 8.33 (s, 1H), 7.22 (dd, J=8.6, 5.5 Hz, 2H), 6.95-6.84 (m, 2H), 4.73 (s, 2H), 4.64 (dt, J=12.1, 6.0 Hz, 1H), 4.27-4.15 (m, 2H), 3.69 (s, 3H), 3.52 (dd, J=11.6, 6.1 Hz, 2H), 3.19 (t, J=6.9 Hz, 1H), 1.96-1.84 (m, 2H), 1.35 (d, J=6.0 Hz, 6H). LCMS: MH$^+$ 402 and T$_R$=2.728 min.

Compound 32

3-(3-hydroxypropyl)-1-methyl-6-(3-(trifluoromethoxy)phenoxy)-5-((6-(trifluoromethyl)pyridin-3-yl)methyl)pyrido[2,3-d]pyrimidine-2,4(1H,3H)-dione

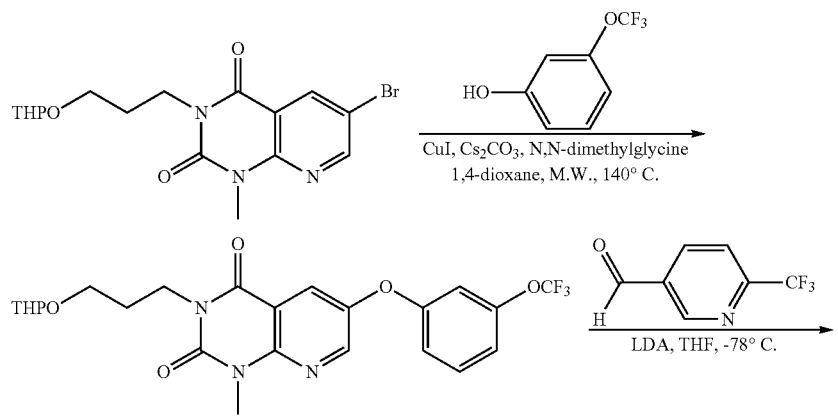

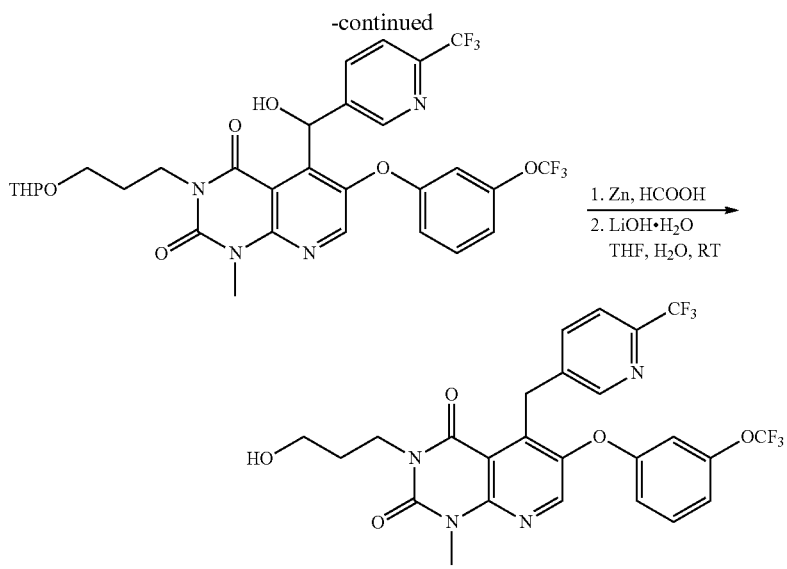

Step 1 3-(6-bromo-1-methyl-2,4-dioxo-5-((6-(trifluoromethyl)pyridin-3-yl)methyl)-1,2-dihydropyrido[2,3-d]pyrimidin-3(4H)-yl)propyl formate

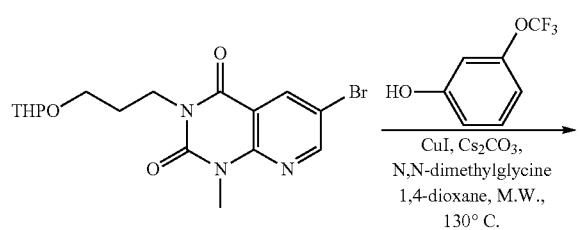

To a mixture of 6-bromo-1-methyl-3-(3-(tetrahydro-2H-pyran-2-yloxy)propyl)pyrido[2,3-d]pyrimidine-2,4(1H,3H)-dione (See Compound 20, step 4, 1.0 g, 2.5 mmol), CuI (62 mg, 0.325 mmol), $Cs_2CO_3$ (1.6 g, 5.0 mmol) and N,N-dimethylglycine (128.7 mg, 1.25 mmol) in dioxane (10 mL) was added 3-(trifluoromethoxy)phenol (1.12 g, 6.25 mmol). The reaction was degassed for 2 min with nitrogen then heated at 130° C. (MW) for 1.5 h, cooled to RT then diluted with EA (10 ml) and water (30 ml). The organic layer was washed with water (2×30 mL), dried over $Na_2SO_4$ and concentrated to a residue which was purified by chromatography eluted with PE/EA (1:1) to give 3-(6-bromo-1-methyl-2,4-dioxo-5-((6-(trifluoromethyl)pyridin-3-yl)methyl)-1,2-dihydro pyrido[2,3-d]pyrimidin-3(4H)-yl)propyl formate (600 mg, 50% yield) as a white solid. LCMS: $MH^+$ 496 and $T_R$=1.991 min.

Step 2 5-(hydroxy(6-(trifluoromethyl)pyridin-3-yl)methyl)-1-methyl-3-(3-(tetrahydro-2H-pyran-2-yloxy)propyl)-6-(3-(trifluoromethoxy)phenoxy)pyrido[2,3-d]pyrimidine-2,4(1H,3H)-dione

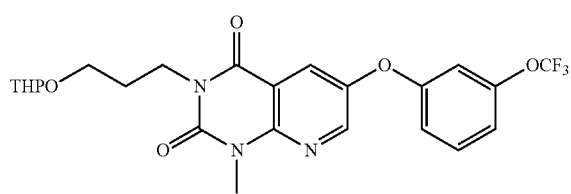

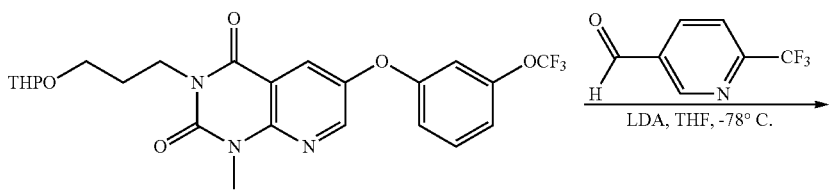

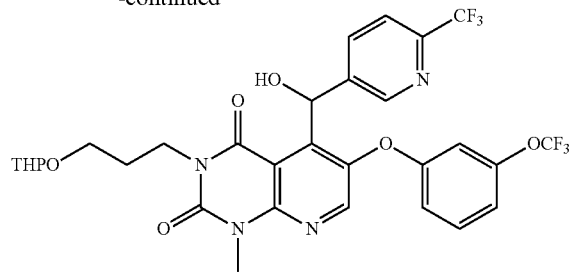

To a solution of 1-methyl-3-(3-(tetrahydro-2H-pyran-2-yloxy)propyl)-6-(3-(trifluoromethoxy) phenoxy)pyrido[2,3-d]pyrimidine-2,4(1H,3H)-dione (156 mg, 0.32 mmol) in THF (6 mL) at −78° C. was added LDA (0.8 mL, 1.6 mmol) dropwise. The reaction was stirred at −78° C. for 1 h then 6-(trifluoromethyl)nicotinaldehyde (112 mg, 0.64 mmol) in THF (3 mL) was added dropwise. The reaction was stirred at −78° C. for 45 min then diluted with DCM (10 mL) and water (10 mL). The organic layer was dried over $Na_2SO_4$ and concentrated to a residue which was purified by chromatography eluted with PE/EA (4:6) to give 5-(hydroxy(6-(trifluoromethyl)-pyridin-3-yl)methyl)-1-methyl-3-(3-(tetrahydro-2H-pyran-2-yloxy)propyl)-6-(3-(trifluoromethoxy)phenoxy)pyrido[2,3-d]pyrimidine-2,4(1H,3H)-dione (40 mg, 18.6% yield) as a solid. LCMS: [M+-THP-OH—H] 569 and $T_R$=2.162 min.

Step 3 3-(3-hydroxypropyl)-1-methyl-6-(3-(trifluoromethoxy)phenoxy)-5-((6-(trifluoromethyl)pyridin-3-yl)methyl)pyrido[2,3-d]pyrimidine-2,4(1H,3H)-dione

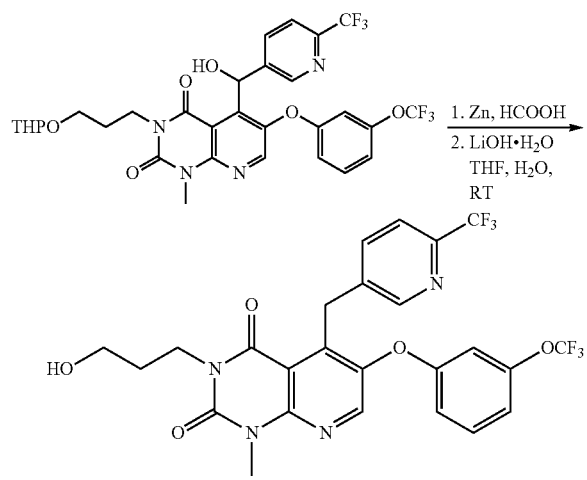

To a solution of 5-(hydroxy(6-(trifluoromethyl)pyridin-3-yl)methyl)-1-methyl-3-(3-(tetrahydro-2H-pyran-2-yloxy)propyl)-6-(3-(trifluoromethoxy)phenoxy)pyrido[2,3-d]pyrimidine-2,4(1H,3H)-dione (40 mg, 0.06 mmol) in HCOOH (2 mL) was added Zn dust (19.5 mg, 0.3 mmol). The reaction was heated at 100° C. for 1 h then cooled to RT and filtered. The filtrate was concentrated and dried to a residue which was dissolved in water (1 ml) and THF (1 mL). Next LiOH.H₂O (25 mg, 0.6 mmol) was added and the reaction was stirred at RT for 10 min then extracted with EA (3×5 mL). The combined organic layers were dried over $Na_2SO_4$ and concentrated to a residue which was purified by Prep HPLC to give 3-(3-hydroxypropyl)-1-methyl-6-(3-(trifluoromethoxy)phenoxy)-5-((6-(trifluoromethyl)pyridin-3-yl)methyl)pyrido[2,3-d]pyrimidine-2,4(1H,3H)-dione (10 mg, 29.4% yield) as clear oil. ¹H NMR (CDCl₃) δ: 8.65 (s, 1H), 8.40 (s, 1H), 7.78 (d, J=6.8 Hz, 1H), 7.53 (d, J=8.1 Hz, 1H), 7.36 (t, J=8.3 Hz, 1H), 7.01 (d, J=8.3 Hz, 1H), 6.81 (dd, J=8.3, 2.2 Hz, 1H), 6.75 (s, 1H), 4.82 (s, 2H), 4.23 (t, J=6.2 Hz, 2H), 3.57 (t, J=5.5 Hz, 2H), 2.93 (s, 1H), 2.00-1.87 (m, 2H). LCMS: MH⁺ 571 and $T_R$=3.069 min.

Compound 33

3-(3-hydroxypropyl)-5-isopentyl-1-methyl-6-(5-methylpyridin-3-yloxy)pyrido[2,3-d]pyrimidine-2,4(1H,3H)-dione

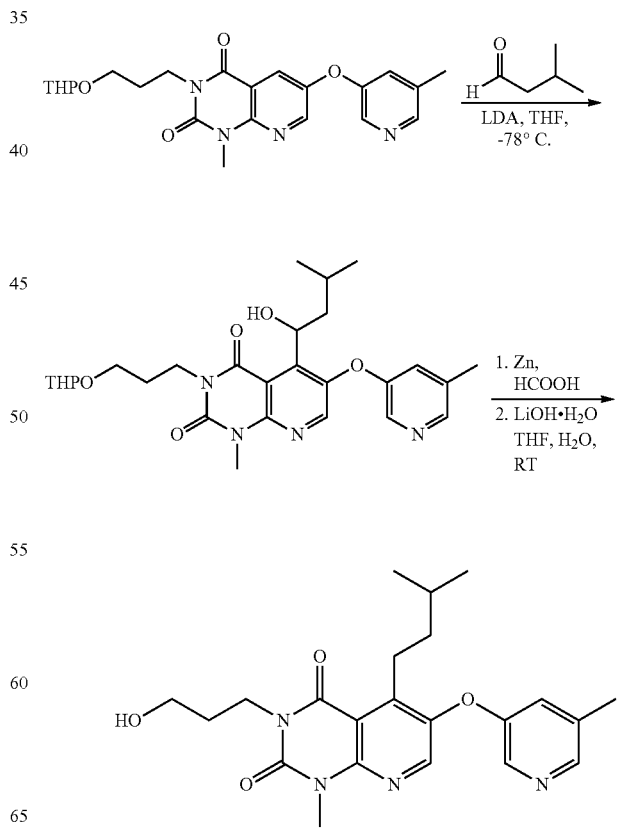

Step 1 5-(1-hydroxy-3-methylbutyl)-1-methyl-6-(5-methylpyridin-3-yloxy)-3-(3-(tetrahydro-2H-pyran-2-yloxy)propyl)pyrido[2,3-d]pyrimidine-2,4(1H,3H)-dione

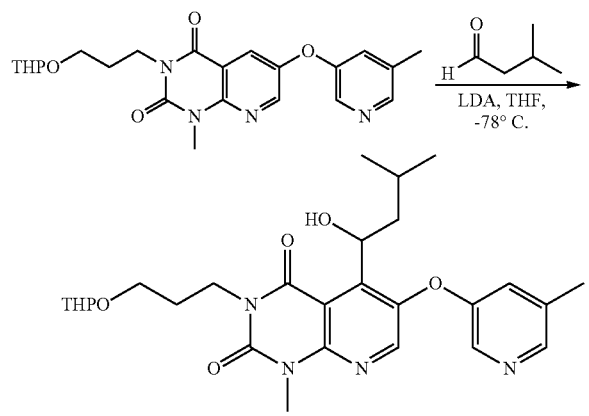

To a solution of 1-methyl-6-(5-methylpyridin-3-yloxy)-3-(3-(tetrahydro-2H-pyran-2-yloxy) propyl)pyrido[2,3-d]pyrimidine-2,4(1H,3H)-dione (See Compound 27, step 1, 100 mg, 0.23 mmol) in THF (5 mL) at −78° C. was added LDA (2M in THF, 0.48 mL, 0.940 mmol) dropwise. The reaction was stirred at −78° C. for 1 h then 3-methylbutanal (40 mg, 0.470 mmol) in THF (1 mL) was added. The reaction was stirred at −78° C. for 45 min then diluted with DCM (10 mL) and water (10 mL). The organic layer was dried over $Na_2SO_4$ and concentrated to give 5-(1-hydroxy-3-methylbutyl)-1-methyl-6-(5-methylpyridin-3-yloxy)-3-(3-(tetrahydro-2H-pyran-2-yloxy)propyl)pyrido[2,3-d]pyrimidine-2,4(1H,3H)-dione (120 mg, 90% yield) as a solid. LCMS: [M+-THP] 429 and $T_R$=1.769 min. Used without further purification.

Step 2 3-(3-hydroxypropyl)-5-isopentyl-1-methyl-6-(5-methylpyridin-3-yloxy)pyrido[2,3-d]pyrimidine-2,4(1H,3H)-dione

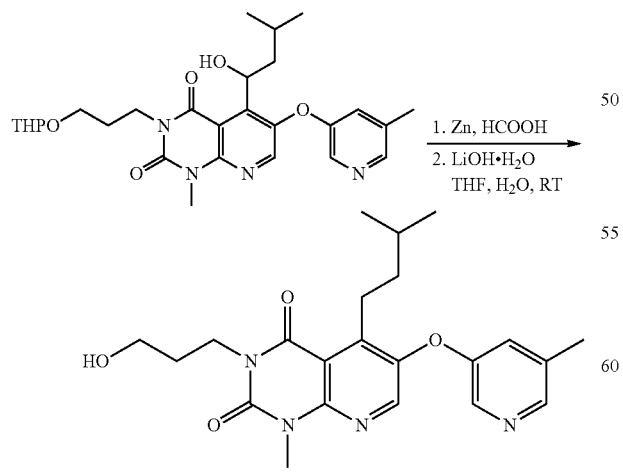

To a solution of 5-(1-hydroxy-3-methylbutyl)-1-methyl-6-(5-methylpyridin-3-yloxy)-3-(3-(tetrahydro-2H-pyran-2-yloxy)propyl)pyrido[2,3-d]pyrimidine-2,4(1H,3H)-dione (100 mg, 0.04 mmol) in HCOOH (2 mL) was added Zn dust (64 mg, 0.375 mmol). The reaction was heated at 100° C. for 1 h, cooled to RT and filtered. The filtrate was concentrated, dried to a residue then dissolved in THF (1 ml) and water (1 mL). Next LiOH.H2O (33.6 mg, 0.8 mmol) was added and the reaction was stirred at RT for 10 min then extracted with EA (3×5 mL). The combined organic layers were dried over $Na_2SO_4$ and concentrated to a residue which was purified by Prep HPLC to give 3-(3-hydroxypropyl)-5-isopentyl-1-methyl-6-(5-methylpyridin-3-yloxy)pyrido[2,3-d]pyrimidine-2,4(1H,3H)-dione (2.5 mg, 7% yield) as clear oil. $^1$H NMR (CDCl$_3$) δ: 8.29 (s, 1H), 8.22 (s, 1H), 8.16 (s, 1H), 6.99 (s, 1H), 4.26 (t, J=6.1 Hz, 2H), 3.72 (s, 3H), 3.56 (d, J=18.8 Hz, 2H), 3.33-3.23 (m, 2H), 3.20 (s, 1H), 2.33 (s, 3H), 1.99-1.92 (m, 2H), 1.68 (dt, J=11.9, 6.0 Hz, 1H), 1.40 (dt, J=10.7, 6.8 Hz, 2H), 0.91 (d, J=6.6 Hz, 6H). LCMS: MH+ 413 and $T_R$=2.549 min.

Compound 34

3-(6-bromo-5-(4-chlorobenzyl)-1-methyl-2,4-dioxo-1,2-dihydropyrido[2,3-d]pyrimidin-3(4H)-yl)propyl formate

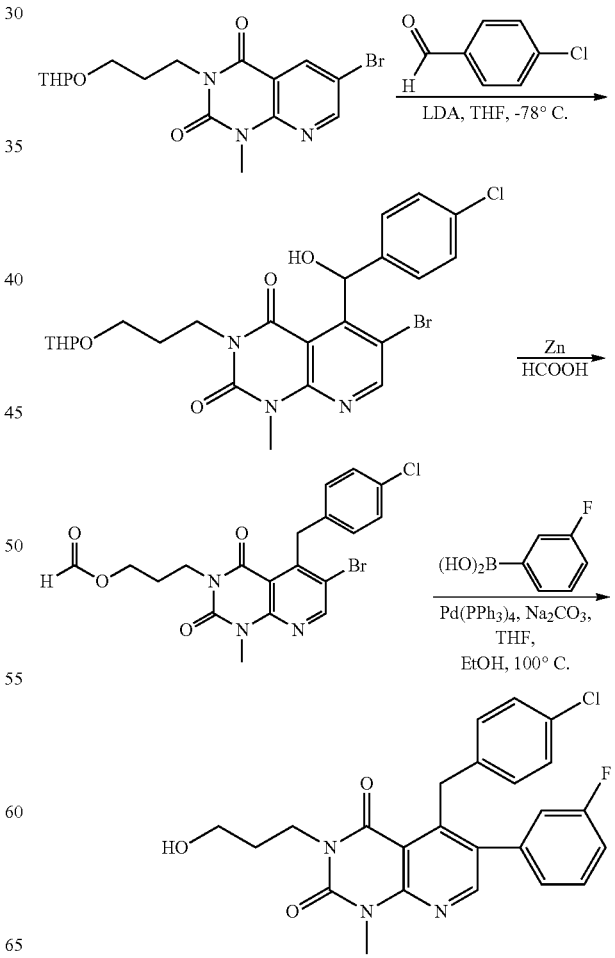

Step 1 6-bromo-5-((4-chlorophenyl)(hydroxy)
methyl)-1-methyl-3-(3-(tetrahydro-2H-pyran-2-
yloxy)propyl)pyrido[2,3-d]pyrimidine-2,4(1H,3H)-
dione

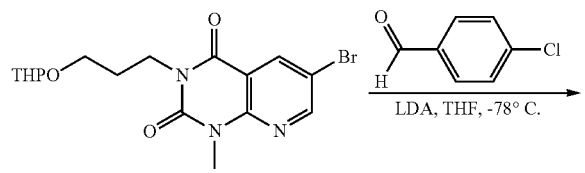

To a solution of 6-bromo-1-methyl-3-(3-(tetrahydro-2H-pyran-2-yloxy)propyl)pyrido[2,3-d]pyrimidine-2,4(1H,3H)-dione (See Compound 20, step 4, 4 g, 10.0 mmol) in THF (15 mL) at −78° C. was added LDA (2.0 M in THF, 25 mL, 50 mmol) dropwise. The reaction was stirred at −78° C. for 1 h then a solution of 4-chlorobenzaldehyde (2.8 g, 20 mmol) in THF (5 mL) was added dropwise. The reaction was stirred at −78° C. for 1 h, quenched with aq. NH$_4$Cl (15 mL) then diluted with EA (20 mL) and water (20 mL). The organic layer was dried over Na$_2$SO$_4$ and concentrated to a residue which was purified by chromatography eluted with PE/EA (7:1) to give 6-bromo-5-((4-chlorophenyl) (hydroxy) methyl)-1-methyl-3-(3-(tetrahydro-2H-pyran-2-yloxy)propyl)pyrido[2,3-d]pyrimidine-2,4(1H,3H)-dione (800 mg, 15% yield) as a solid. LCMS: MH$^+$ 538 and T$_R$=1.618 min.

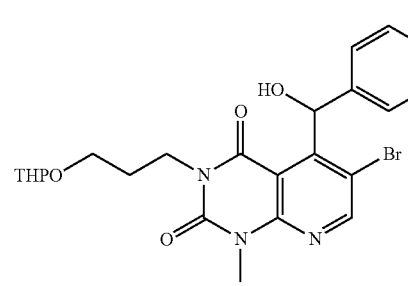

Step 2 3-(6-bromo-5-(4-chlorobenzyl)-1-methyl-2,4-
dioxo-1,2-dihydropyrido[2,3-d]pyrimidin-3(4H)-yl)
propyl formate

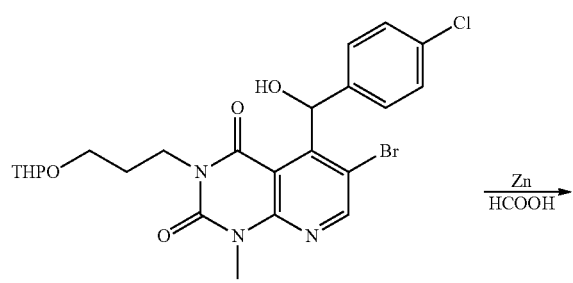

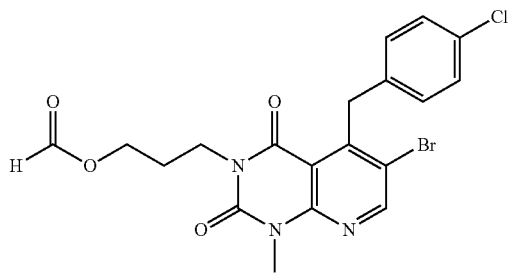

To a solution of 6-bromo-5-((4-chlorophenyl)(hydroxy) methyl)-1-methyl-3-(3-(tetrahydro-2H-pyran-2-yloxy)propyl)pyrido[2,3-d]pyrimidine-2,4(1H,3H)-dione (800 mg, 1.50 mmol) in HCOOH (10 mL) was added Zn dust (484 mg, 7.50 mmol). The reaction was heated at 60° C. for 2 h, cooled to RT and filtered. The filtrate was concentrated to give 3-(6-bromo-5-(4-chlorobenzyl)-1-methyl-2,4-dioxo-1,2-dihydropyrido[2,3-d]pyrimidin-3(4H)-yl)propyl formate (419 mg, 60% yield as a solid. LCMS: MH$^+$ 466 and T$_R$=1.589 min. Used without further purification.

Step 3 5-(4-chlorobenzyl)-6-(3-fluorophenyl)-3-(3-
hydroxypropyl)-1-methylpyrido[2,3-d]pyrimidine-2,
4(1H,3H)-dione

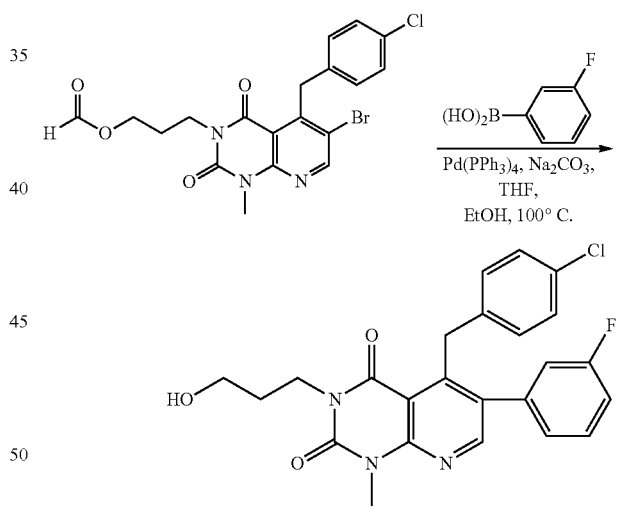

To a solution of 3-(6-bromo-5-(4-chlorobenzyl)-1-methyl-2,4-dioxo-1,2-dihydropyrido[2,3-d]pyrimidin-3 (4H)-yl)propyl formate (70 mg, 0.15 mmol), 3-fluorophenylboronic acid (31 mg, 0.22 mmol), Na$_2$CO$_3$ (0.6 ml) in THF (3.2 mL) and EtOH (1.6 mL) was added Pd(PPh$_3$)$_4$ (17 mg, 0.015 mmol). The reaction was heated at 100° C. for 18 h, cooled to RT then diluted with EA (20 mL) and water (20 mL). The organic layer was dried over Na$_2$SO$_4$ and concentrated to a residue which was purified by Prep HPLC to give 5-(4-chlorobenzyl)-6-(3-fluorophenyl)-3-(3-hydroxypropyl)-1-methylpyrido[2,3-d]pyramidine-2,4(1H,3H)-dione (50 mg, 85% yield) as a white solid. LCMS: MH$^+$ 454 and T$_R$=1.918 min.

Step 4 5-benzyl-6-(3-fluorophenyl)-3-(3-hydroxypropyl)-1-methylpyrido[2,3-d]pyrimidine-2,4(1H,3H)-dione

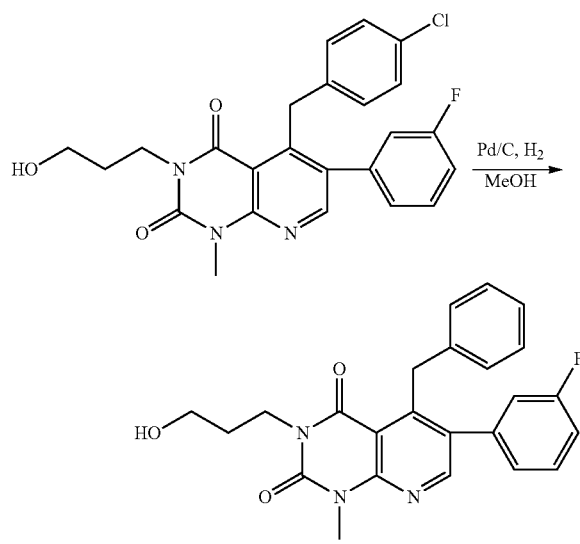

To a solution of 5-(4-chlorobenzyl)-6-(3-fluorophenyl)-3-(3-hydroxypropyl)-1-methylpyrido[2,3-d]pyrimidine-2,4 (1H,3H)-dione (25 mg, 0.06 mmol) in MeOH (1 mL) was added 10% Pd/C (10 mg). The reaction was hydrogenated (15 psi) at 70° C. for 1 h, cooled to RT then diluted with EA (30 mL) and water (30 mL). The organic layer was dried over $Na_2SO_4$ and concentrated to a residue which was purified by Prep HPLC to give 5-benzyl-6-(3-fluorophenyl)-3-(3-hydroxypropyl)-1-methylpyrido[2,3-d]pyrimidine-2,4 (1H,3H)-dione (10 mg, 43.5% yield) as a solid. $^1$H NMR ($CDCl_3$) δ: 8.52 (s, 1H), 7.35 (d, J=8.0, 6.0 Hz, 1H), 7.23-7.06 (m, 4H), 6.98 (t, J=8.0 Hz, 1H), 6.93-6.87 (m, 1H), 6.84 (d, J=6.9 Hz, 2H), 4.68 (s, 2H), 4.17 (dd, J=20.0, 13.9 Hz, 2H), 3.77 (s, 3H), 3.42 (t, J=5.2 Hz, 2H), 2.89 (s, 1H), 1.91-1.80 (m, 2H). LCMS: MH$^+$ 420 and $T_R$=2.83 min.

Compound 35

5-((5-chloropyridin-2-yl)methyl)-3-(3-hydroxypropyl)-1-methyl-6-(3-(trifluoromethoxy)phenyl)pyrido[2,3-d]pyrimidine-2,4(1H,3H)-dione

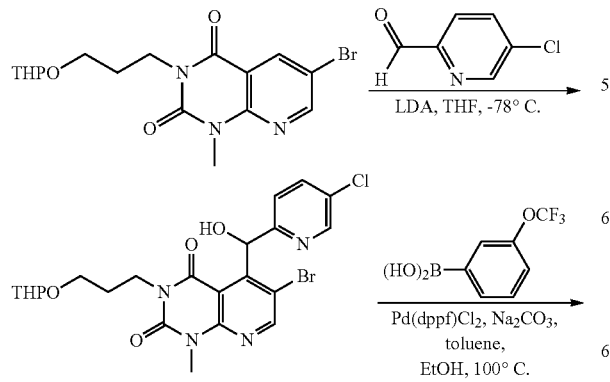

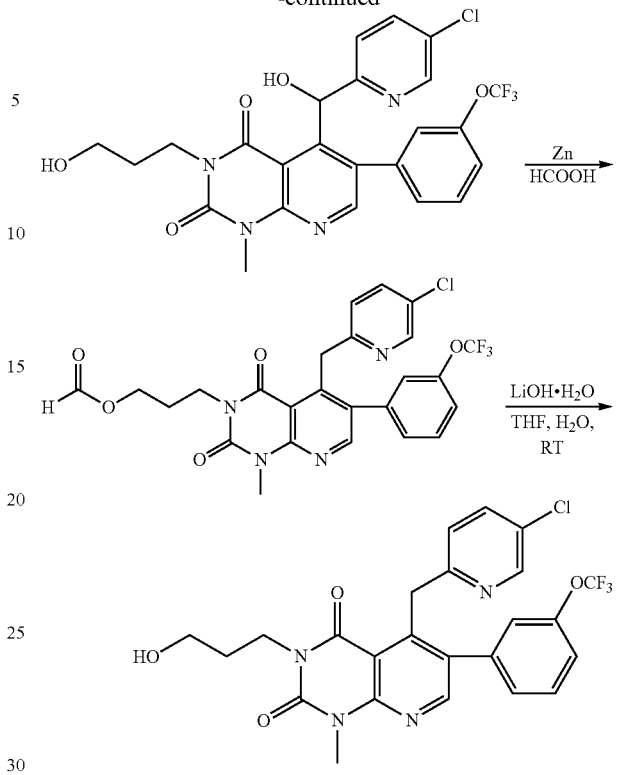

Step 1 6-bromo-5-((5-chloropyridin-2-yl)(hydroxy)methyl)-1-methyl-3-(3-(tetrahydro-2H-pyran-2-yloxy)propyl)pyrido[2,3-d]pyrimidine-2,4(1H,3H)-dione

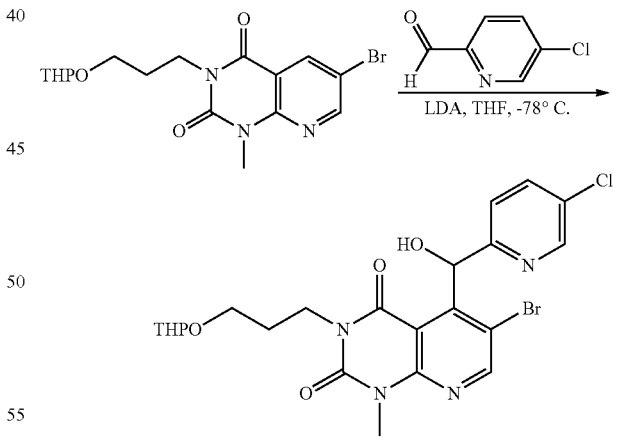

To a solution of 6-bromo-1-methyl-3-(3-((tetrahydro-2H-pyran-2-yl)oxy)propyl)pyrido[2,3-d]pyrimidine-2,4(1H, 3H)-dione (See Compound 20, step 4, 398 mg, 0.10 mmol) in THF (10 mL) at −78° C. was added LDA (2M in THF, 2.50 mL, 5.00 mmol) dropwise. The reaction was stirred at −78° C. for 1 h then 5-chloropicolinaldehyde (211 mg, 1.50 mmol) in THF (2 mL) was added. The reaction was stirred at −78° C. for 40 min then diluted with EA (20 mL) and water (10 mL). The organic layer was washed with brine (30 mL), dried over $Na_2SO_4$ and concentrated to a residue which was purified by chromatography eluted with PE/EA (8:1) to give 6-bromo-5-((5-chloropyridin-2-yl)(hydroxy)methyl)-1-methyl-3-(3-(tetrahydro-2H-pyran-2-yloxy)propyl)pyrido[2,3-d]pyrimidine-2,4(1H,3H)-dione (75 mg, 13.9% yield) as a solid. LCMS: MH+ 541 and $T_R$=1.773 min.

Step 2 5-((5-chloropyridin-2-yl)(hydroxy)methyl)-1-methyl-3-(3-(tetrahydro-2H-pyran-2-yloxy)propyl)-6-(3-(trifluoromethoxy)phenyl)pyrido[2,3-d]pyrimidine-2,4(1H,3H)-dione

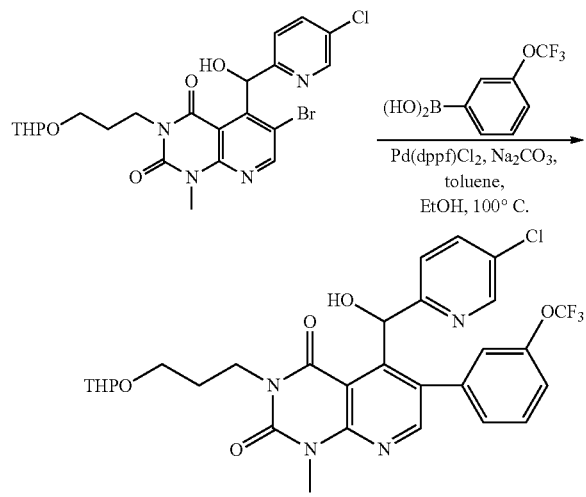

To a solution of 6-bromo-5-((5-chloropyridin-2-yl)(hydroxy)methyl)-1-methyl-3-(3-(tetrahydro-2H-pyran-2-yloxy)propyl)pyrido[2,3-d]pyrimidine-2,4(1H,3H)-dione (75 mg, 0.138 mmol) in toluene (4 mL) and EtOH 1.3 mL) was added 3-(trifluoromethoxy)phenylboronic acid (43 mg, 0.208 mmol), Pd(dppf)Cl₂ (10.7 mg) and aq. Na₂CO₃ (1M, 0.57 mL). The reaction was heated at 100° C. for 18 h, cooled to RT and filtered. The filtrate was concentrated and dried to a residue which was purified by Prep TLC eluted with PE/EA (4:1) to give 5-((5-chloropyridin-2-yl)(hydroxy)methyl)-1-methyl-3-(3-(tetrahydro-2H-pyran-2-yloxy)propyl)-6-(3-(trifluoromethoxy)phenyl)pyrido[2,3-d]pyrimidine-2,4(1H,3H)-dione (30 mg, 35.2% yield) as a solid. LCMS: MH+ 621 and $T_R$=2.047 min.

Step 3 3-(5-((5-chloropyridin-2-yl)methyl)-1-methyl-2,4-dioxo-6-(3-(trifluoromethoxy)phenyl)-1,2-dihydropyrido[2,3-d]pyrimidin-3(4H)-yl)propyl formate

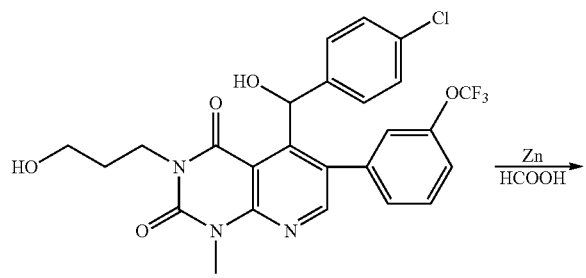

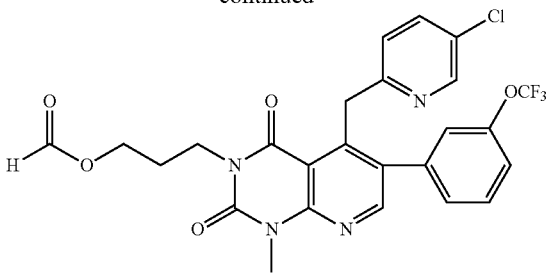

To a solution of 5-((5-chloropyridin-2-yl)(hydroxy)methyl)-1-methyl-3-(3-(tetrahydro-2H-pyran-2-yloxy)propyl)-6-(3-(trifluoromethoxy)phenyl)pyrido[2,3-d]pyrimidine-2,4(1H,3H)-dione (30 mg, 0.048 mmol) in HCOOH (1 mL) was added Zn dust (30 mg, 0.48 mmol). The reaction was heated at 80° C. for 30 min, cooled to RT then diluted with EA (2 mL) and water (2 mL). The organic layer was dried over Na₂SO₄ and concentrated to give 3-(5-isopentyl-6-(2-isopropyl phenyl)-1-methyl-2,4-dioxo-1,2-dihydropyrido[2,3-d]pyrimidin-3(4H)-yl)propylformate (30 mg, 90% yield) as a an oil. LCMS: MH+ 549 and $T_R$=2.286 min. Used without further purification.

Step 4 5-((5-chloropyridin-2-yl)methyl)-3-(3-hydroxypropyl)-1-methyl-6-(3-(trifluoromethoxy)phenyl)pyrido[2,3-d]pyrimidine-2,4(1H,3H)-dione

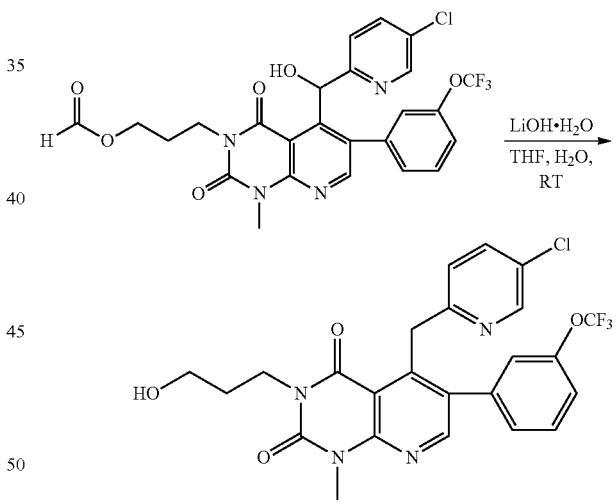

To a solution of 3-(5-isopentyl-6-(2-isopropylphenyl)-1-methyl-2,4-dioxo-1,2-dihydropyrido[2,3-d]pyrimidin-3 (4H)-yl)propyl formate (30 mg, 0.048 mmol) in THF (0.5 mL) and water (0.5 mL) was added LiOH.H₂O (4.2 mg, 0.1 mmol). The reaction was stirred at RT for 40 min then diluted with EA (5 mL) and water (5 mL). The organic layer was dried over Na₂SO₄ and concentrated to a residue which was purified by Prep HPLC to give 5-((5-chloropyridin-2-yl)methyl)-3-(3-hydroxypropyl)-1-methyl-6-(3-(trifluoromethoxy)phenyl)pyrido[2,3-d]pyrimidine-2,4(1H,3H)-dione (4 mg, 16% yield) as white solid. ¹H NMR (CDCl₃) δ: 8.56 (s, 1H), 8.31 (d, J=2.3 Hz, 1H), 7.56 (dd, J=8.4, 2.5 Hz, 1H), 7.42 (dd, J=14.2, 6.4 Hz, 1H), 7.26-7.19 (m, 3H), 7.10 (d, J=8.4 Hz, 1H), 4.68 (s, 2H), 4.14 (t, J=6.0 Hz, 2H), 3.77

(s, 3H), 3.43 (dd, J=11.4, 5.9 Hz, 2H), 2.93 (t, J=6.9 Hz, 1H), 1.90-1.76 (m, 2H). LCMS: MH⁺ 521 and $T_R$=3.546 min.

Compound 36

5-(4-chlorobenzyl)-3-(3-hydroxypropyl)-6-isopropoxy-1-methylpyrido[2,3-d]pyrimidine-2,4(1H,3H)-dione

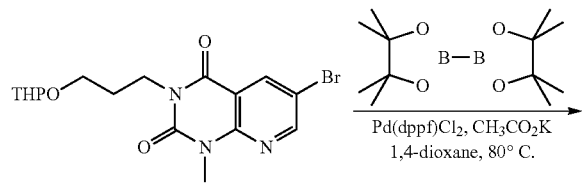

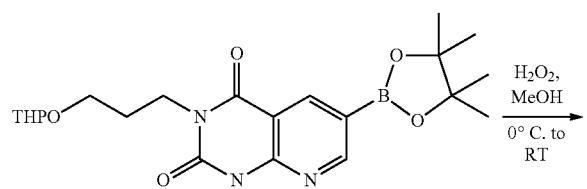

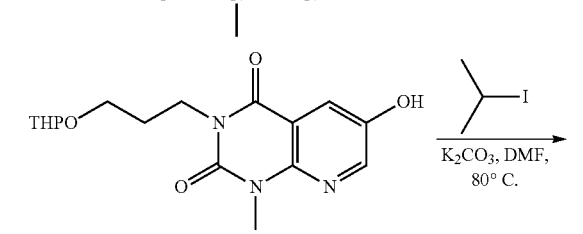

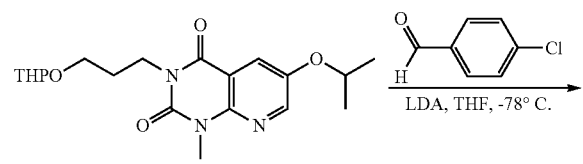

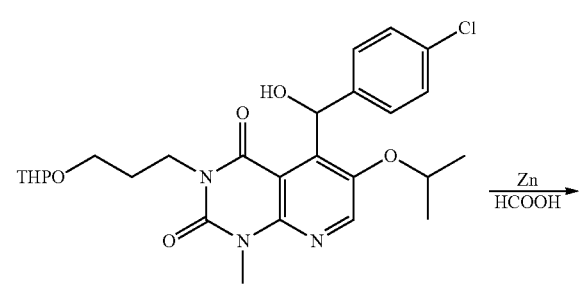

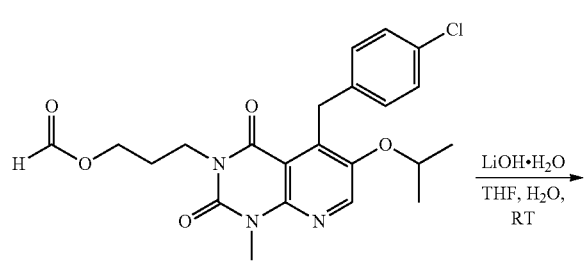

-continued

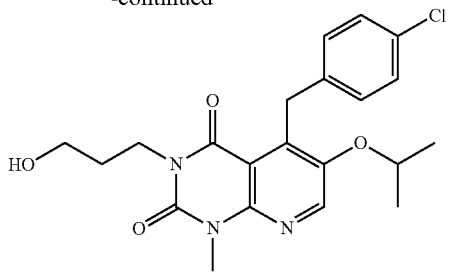

Step 1 1-methyl-3-(3-(tetrahydro-2H-pyran-2-yloxy)propyl)-6-(4,4,5,5-tetramethyl-1,3,2-dioxaborolan-2-yl)pyrido[2,3-d]pyrimidine-2,4(1H,3H)-dione

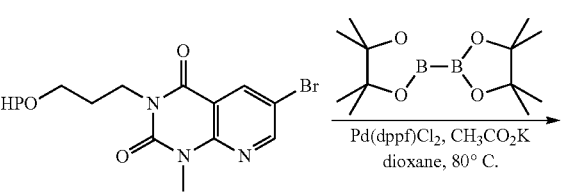

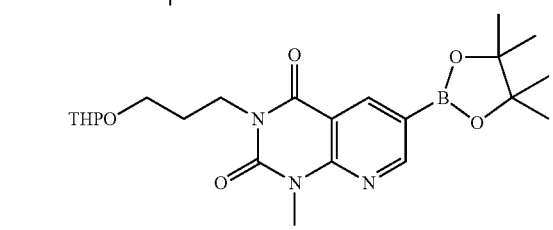

To a solution of 6-bromo-1-methyl-3-(3-(tetrahydro-2H-pyran-2-yloxy)propyl)pyrido[2,3-d]pyrimidine-2,4(1H,3H)-dione (See Compound 20, step 4, 2.5 g, 6.3 mmol) in dioxane (30 mL) was added 4,4,4',4',5,5,5',5'-octamethyl-2,2'-bi-1,3,2-dioxaborolane (1.75 g, 6.9 mmol), Pd(dppf)Cl₂ (0.46 g, 0.63 mmol) and CH₃CO₂K (1.85 g, 18.9 mmol). The reaction was heated at 80° C. for 2 h, cooled to RT and filtered through a pad of Celite and the pad was washed with the EA (2×50 mL). The filtrate was concentrated to give 1-methyl-3-(3-(tetrahydro-2H-pyran-2-yloxy)propyl)-6-(4,4,5,5-tetramethyl-1,3,2-dioxaborolan-2-yl)pyrido[2,3-d]pyrimidine-2,4(1H,3H)-dione (2.80, 100% yield) as an oil. LCMS: MH⁺ 446 and $T_R$=1.043 min. Used without further purification.

Step 2 6-hydroxy-1-methyl-3-(3-(tetrahydro-2H-pyran-2-yloxy)propyl)pyrido[2,3-d]pyrimidine-2,4(1H,3H)-dione

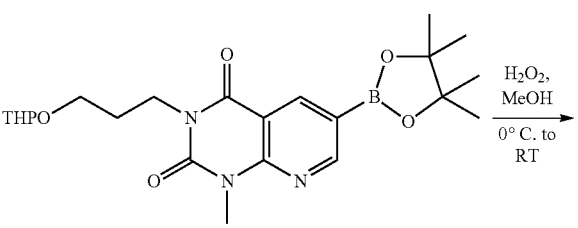

-continued

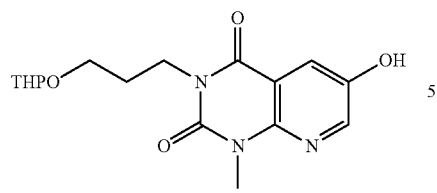

To a solution of 1-methyl-3-(3-(tetrahydro-2H-pyran-2-yloxy)propyl)-6-(4,4,5,5-tetramethyl-1,3,2-dioxaborolan-2-yl)pyrido[2,3-d]pyrimidine-2,4(1H,3H)-dione (2.8 g, 6.3 mmol) in MeOH (100 mL) at 0° C. was added $H_2O_2$ (30% in water, 1.4 mL, 10.6 mmol) dropwise over 5 min. The reaction was allowed to warm slowly to RT, stirred for 16 h, quenched with aq. 1M $Na_2SO_3$ solution (100 mL), stirred for 15 min then extracted with EA (3×75 mL). The combined organic layers were dried over $Na_2SO_4$ and concentrated to give a residue of 6-hydroxy-1-methyl-3-(3-(tetrahydro-2H-pyran-2-yloxy)propyl)pyrido[2,3-d]pyrimidine-2,4(1H,3H)-dione (2.1 g, 100% yield) as a solid. LCMS: [MH$^+$-THP] 252 and $T_R$=1.740 min. Used without further purification.

Step 3 6-isopropoxy-1-methyl-3-(3-(tetrahydro-2H-pyran-2-yloxy)propyl)pyrido[2,3-d]pyrimidine-2,4(1H,3H)-dione

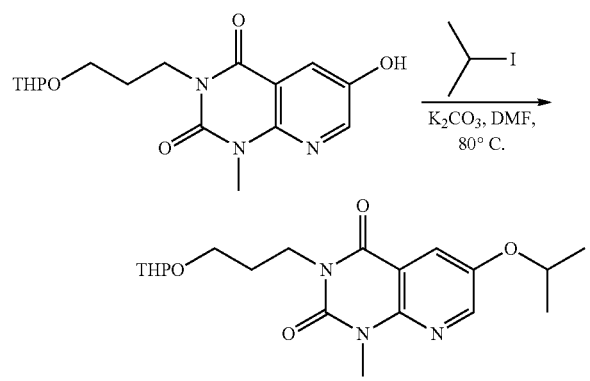

To a solution of 6-hydroxy-1-methyl-3-(3-(tetrahydro-2H-pyran-2-yloxy)propyl)pyrido[2,3-d]pyrimidine-2,4(1H,3H)-dione (2.1 g, 6.3 mmol) in DMF (20 mL) was added isopropyl iodide (2.14 g, 12.6 mmol) followed by $K_2CO_3$ (1.74 g, 12.6 mmol). The reaction was heated at 80° C. for 2 h, cooled to RT, diluted with water (100 mL) then extracted with EA (3×100 mL). The combined organic layers were washed with water (100 mL) then brine (100 mL), dried over $Na_2SO_4$ and concentrated to a residue which was purified by chromatography to give 6-isopropoxy-1-methyl-3-(3-(tetrahydro-2H-pyran-2-yloxy)propyl)pyrido[2,3-d]pyrimidine-2,4(1H,3H)-dione (1.08 g, 46% yield over 3 steps) as a solid. $^1$H NMR (CDCl$_3$) δ: 8.34 (d, J=3.1 Hz, 1H), 7.90 (d, J=3.1 Hz, 1H), 4.69-4.51 (m, 2H), 4.10-4.30 (m, 2H), 3.90-3.78 (m, 2H), 3.69 (s, 3H), 3.51, 3.40-3.70 (m, 2H), 2.01 (dd, J=13.4, 6.7 Hz, 2H), 1.86-1.45 (m, 6H), 1.38 (d, J=6.1 Hz, 6H), 1.26 (t, J=7.1 Hz, 2H). LCMS: [MH$^+$-THP] 294 and $T_R$=1.668 min.

Step 4 5-((4-chlorophenyl)(hydroxy)methyl)-6-isopropoxy-1-methyl-3-(3-(tetrahydro-2H-pyran-2-yloxy)propyl)pyrido[2,3-d]pyrimidine-2,4(1H,3H)-dione

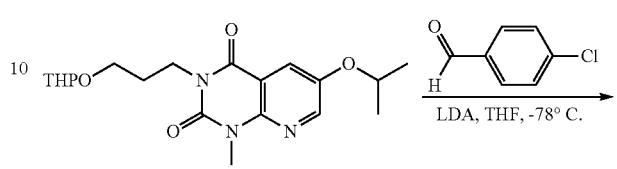

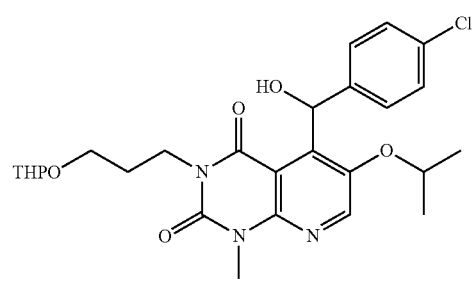

To a solution of 6-isopropoxy-1-methyl-3-(3-(tetrahydro-2H-pyran-2-yloxy)propyl)pyrido[2,3-d]pyrimidine-2,4(1H,3H)-dione (87 mg, 0.23 mmol) in THF (5 mL) cooled to −78° C. was added LDA (2.0 M in THF, 0.6 mL, 1.15 mmol) dropwise. The reaction was stirred at −78° C. for 1 h then a solution of 4-chlorobenzaldehyde (64.8 mg, 0.46 mmol) in THF (1 mL) was added dropwise. The reaction was stirred at −78° C. for 1 h, quenched with aq. NH$_4$Cl (5 mL), diluted with water (25 mL) then extracted with EA (3×25 mL). The combined organic layers were dried over $Na_2SO_4$ and concentrated to a residue which was purified by Prep TLC eluted with PE/EA (1:2) to give 5-((4-chlorophenyl)(hydroxy)methyl)-6-isopropoxy-1-methyl-3-(3-(tetrahydro-2H-pyran-2-yloxy) propyl)pyrido[2,3-d]pyrimidine-2,4(1H, 3H)-dione (64 mg, 53.6% yield) as a white solid. LCMS: [M$^+$-THP-OH] 416 and $T_R$=3.210 min. Used without further purification.

Step 5 3-(5-(4-chlorobenzyl)-6-isopropoxy-1-methyl-2,4-dioxo-1,2-dihydropyrido[2,3-d]pyrimidin-3(4H)-yl)propyl formate

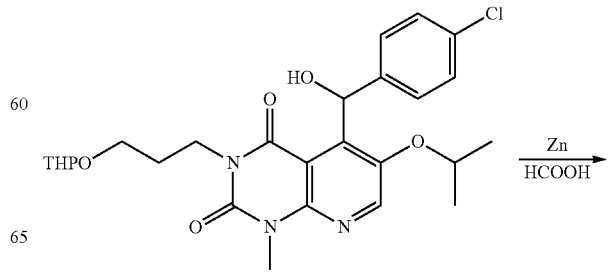

129

-continued

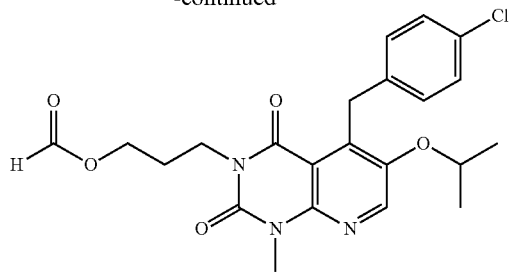

To a solution of 5-((4-chlorophenyl)(hydroxy)methyl)-6-isopropoxy-1-methyl-3-(3-(tetrahydro-2H-pyran-2-yloxy) propyl)pyrido[2,3-d]pyrimidine-2,4(1H,3H)-dione (64 mg, 0.12 mmol) in HCOOH (3 mL) was added Zn dust (40.4 mg, 0.62 mmol). The reaction was heated at 60° C. for 2 h, cooled to RT and filtered. The filtrate was concentrated to a residue which was purified by Prep TLC eluted with PE/EA (1:2) to give 3-(5-(4-chlorobenzyl)-6-isopropoxy-1-methyl-2,4-dioxo-1,2-dihydropyrido[2,3-d]pyrimidin-3(4H)-yl) propyl formate (55 mg, 99% yield) as a white solid. LCMS: MH$^+$ 446 and T$_R$=2.816 min.

Step 6 5-(4-chlorobenzyl)-3-(3-hydroxypropyl)-6-isopropoxy-1-methylpyrido[2,3-d]pyrimidine-2,4 (1H,3H)-dione

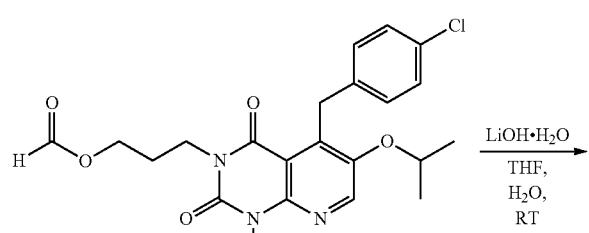

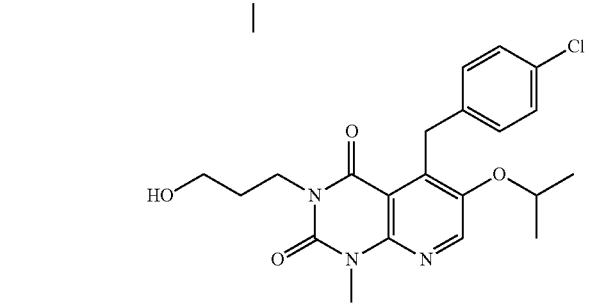

To a solution of 3-(5-(4-chlorobenzyl)-6-isopropoxy-1-methyl-2,4-dioxo-1,2-dihydropyrido[2,3-d]pyrimidin-3 (4H)-yl)propyl formate (55 mg, 0.13 mmol) in THF (6 mL) and water (6 mL) was added LiOH.H$_2$O (10.9 mg, 0.26 mmol). The reaction was stirred at RT for 15 min then diluted with water (20 mL) and extracted with EA (3×15 mL). The combined organic layers were dried over Na$_2$SO$_4$ and concentrated to a residue which was purified by Prep HPLC to give 5-(4-chlorobenzyl)-3-(3-hydroxypropyl)-6-isopropoxy-1-methylpyrido[2,3-d]pyrimidine-2,4(1H,3H)-dione (20 mg, 37% yield) as a white solid. $^1$H NMR (CDCl$_3$) δ: 8.33 (s, 1H), 7.18 (s, 4H), 4.73 (s, 2H),), 4.68-4.68 (m, 1H), 4.28-4.15 (m, 2H), 3.69 (s, 3H), 3.52 (dd, J=11.8, 6.2 Hz, 2H), 3.16 (t, J=7.0 Hz, 1H), 1.97-1.82 (m, 2H), 1.34 (d, J=6.0 Hz, 6H). LCMS: MH$^+$ 418 and T$_R$=2.915 min.

Compound 37

3-(3-hydroxypropyl)-5-isopentyl-6-isopropoxy-1-methylpyrido[2,3-d]pyrimidine-2,4(1H,3H)-dione

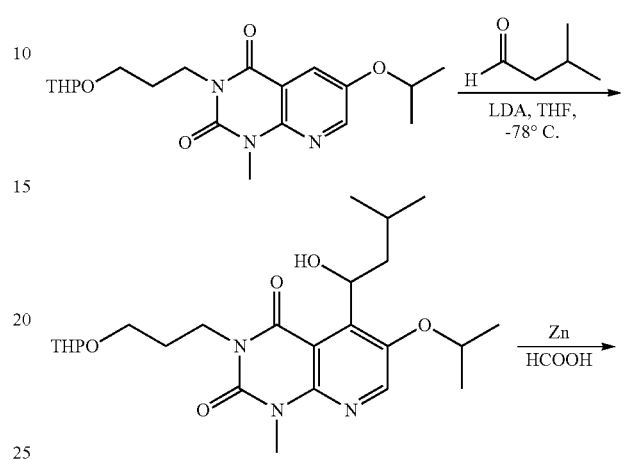

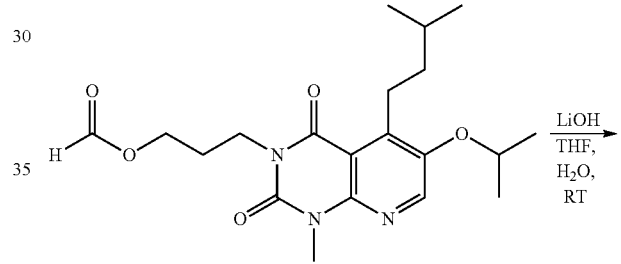

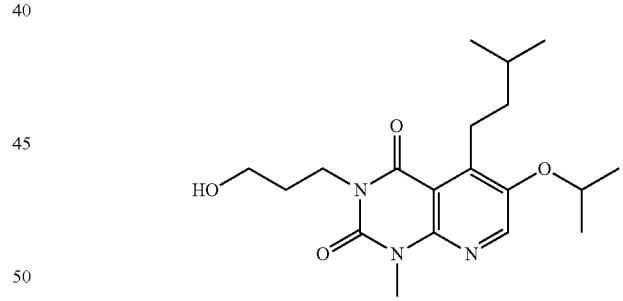

Step 1: 5-(1-hydroxy-3-methylbutyl)-6-isopropoxy-1-methyl-3-(3-(tetrahydro-2H-pyran-2-yloxy)propyl) pyrido[2,3-d]pyrimidine-2,4(1H,3H)-dione

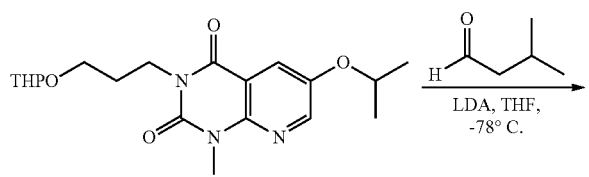

-continued

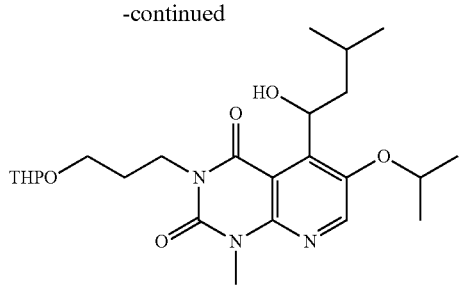

To a solution of 6-isopropoxy-1-methyl-3-(3-(tetrahydro-2H-pyran-2-yloxy)propyl)pyrido[2,3-d]pyrimidine-2,4(1H,3H)-dione (See Compound 36, step 3, 150 mg, 0.4 mmol) in THF (6 mL) at −78° C. was added LDA (2M in THF, 1.0 mL, 2.0 mmol) dropwise. The reaction was stirred at −78° C. for 1 h then 3-methylbutanal (68.8 mg, 0.8 mmol) in THF (1.5 mL) was added. The reaction was stirred at −78° C. for 1 h, quenched with aq. NH$_4$Cl (5 mL) diluted with water (13 mL) then extracted with EA (30 mL). The organic layer was dried over Na$_2$SO$_4$ and concentrated to a residue which was purified by Prep TLC eluted with PE/EA (2:1) to give 5-(1-hydroxy-3-methylbutyl)-6-isopropoxy-1-methyl-3-(3-(tetrahydro-2H-pyran-2-yloxy)propyl)pyrido[2,3-d]pyrimidine-2,4(1H,3H)-dione (60 mg, 32.4% yield) as a white solid. LCMS: [M$^+$-THP-OH] 362 and T$_R$=2.616 min.

Step 2: 3-(5-isopentyl-6-isopropoxy-1-methyl-2,4-dioxo-1,2-dihydropyrido[2,3-d]pyrimidin-3(4H)-yl) propyl formate

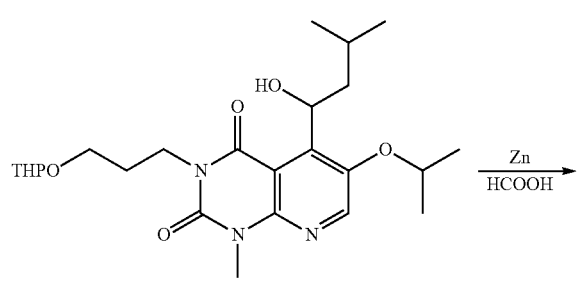

To a solution of 5-(1-hydroxy-3-methylbutyl)-6-isopropoxy-1-methyl-3-(3-(tetrahydro-2H-pyran-2-yloxy)propyl)pyrido[2,3-d]pyrimidine-2,4(1H,3H)-dione (60 mg, 0.13 mmol) in HCOOH (2 mL) was added Zn dust (42 mg, 0.65 mmol). The reaction was heated at 80° C. for 1 h, cooled to RT and filtered. The filtrate was concentrated and dried to a residue which was purified by Prep TLC eluted with PE/EA (2:1) to give 3-(5-isopentyl-6-isopropoxy-1-methyl-2,4-dioxo-1,2-dihydropyrido[2,3-d]pyrimidin-3(4H)-yl)propyl formate (48 mg, 82.7% yield) as a white solid. LCMS: MH$^+$ 392 and T$_R$=2.964 min.

Step 3: 3-(3-hydroxypropyl)-5-isopentyl-6-isopropoxy-1-methylpyrido[2,3-d]pyrimidine-2,4(1H,3H)-dione

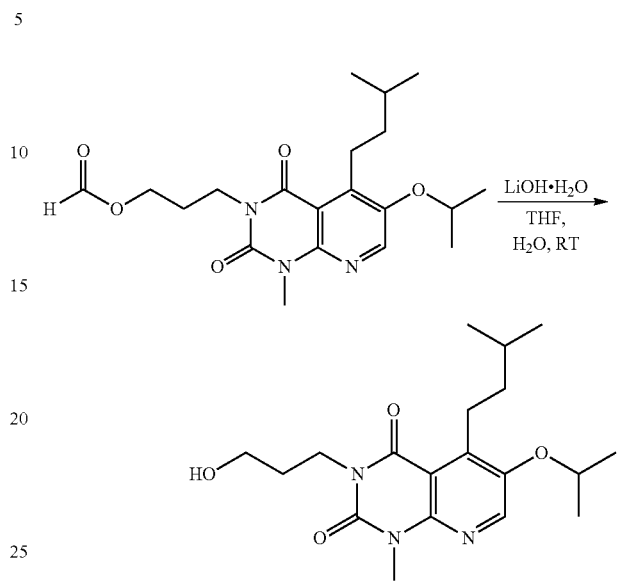

To a solution of 3-(5-isopentyl-6-isopropoxy-1-methyl-2,4-dioxo-1,2-dihydropyrido[2,3-d]pyrimidin-3(4H)-yl)propyl formate (48 mg, 0.123 mmol) in THF (1 mL) and water (1 mL) was added LiOH.H$_2$O (10.3 mg, 0.246 mmol). The reaction was stirred at RT for 15 min then diluted with EA (5 mL) and water (5 mL). The organic layer was dried over Na$_2$SO$_4$ and concentrated to a residue which was purified by Prep HPLC to give 3-(3-hydroxypropyl)-5-isopentyl-6-isopropoxy-1-methylpyrido[2,3-d]pyrimidine-2,4(1H,3H)-dione (22.6 mg, 50.5% yield) as a white solid. $^1$H NMR (CDCl$_3$) δ: 8.24 (s, 1H), 4.61-4.56 (m, 1H), 4.32-4.13 (m, 2H), 3.68 (s, 3H), 3.55 (d, J=5.3 Hz, 2H), 3.32 (dd, J=17.2, 9.1 Hz, 3H), 2.02-1.84 (m, 2H), 1.71 (dd, J=13.2, 6.6 Hz, 1H), 1.39 (d, J=6.0 Hz, 6H), 0.99 (d, J=6.6 Hz, 6H). LCMS: MH$^+$ 364 and T$_R$=3.032 min.

Compound 38

5-(4-chlorobenzyl)-3-(3-hydroxypropyl)-6-(2-isopropylphenyl)-1-methylpyrido[2,3-d]pyrimidine-2,4 (1H,3H)-dione

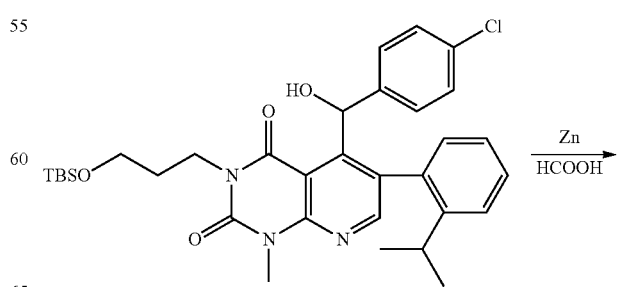

133
-continued

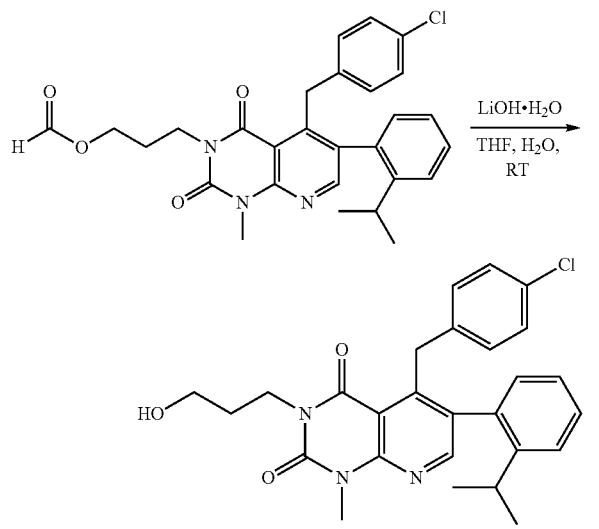

Step 1 3-(5-(4-chlorobenzyl)-6-(2-isopropylphenyl)-1-methyl-2,4-dioxo-1,2-dihydropyrido[2,3-d]pyrimidin-3(4H)-yl)propyl formate

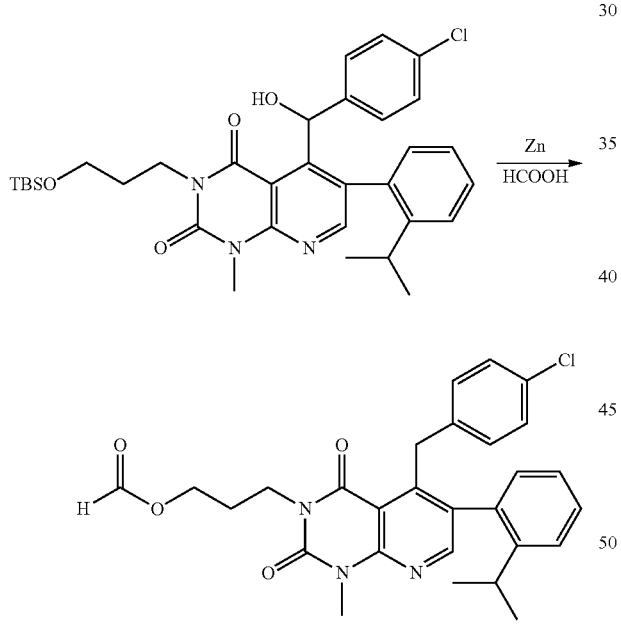

To a solution of 3-(3-((tert-butyldimethylsilyl)oxy)propyl)-5-((4-chlorophenyl) (hydroxy)methyl)-6-(2-isopropylphenyl)-1-methylpyrido[2,3-d]pyrimidine-2,4(1H,3H)-dione (See Compound 20, step 6, 50 mg, 0.086 mmol) in HCOOH (5 mL) was added Zn dust (56.6 mg, 0.86 mmol). The reaction was heated at 100° C. for 3 h, cooled to RT and filtered. The filtrate was concentrated and dried to give 3-(5-(4-chlorobenzyl)-6-(2-isopropylphenyl)-1-methyl-2,4-dioxo-1,2-dihydropyrido[2,3-d]pyrimidin-3(4H)-yl)propyl formate (20 mg, 48.0% yield) as a brown oil. LCMS: [MH+—OH] 506 and $T_R$=2.062 min. Used without further purification.

134

Step 2 5-(4-chlorobenzyl)-3-(3-hydroxypropyl)-6-(2-isopropylphenyl)-1-methylpyrido[2,3-d]pyrimidine-2,4(1H,3H)-dione

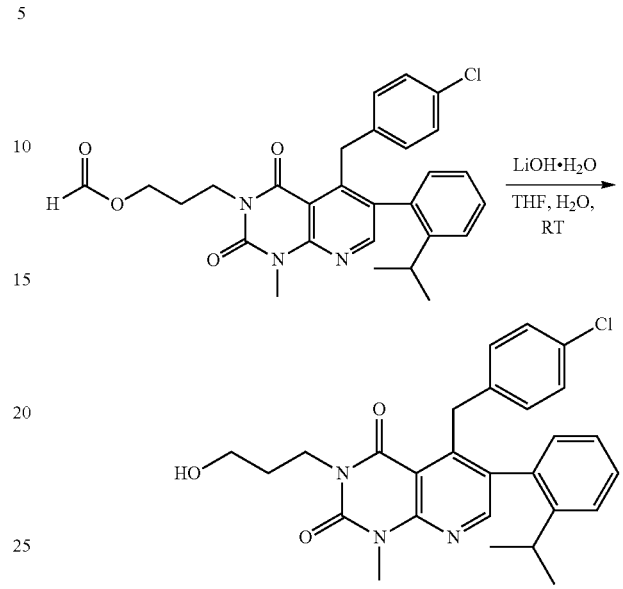

To a solution of 3-(5-(4-chlorobenzyl)-6-(2-isopropylphenyl)-1-methyl-2,4-dioxo-1,2-dihydro pyrido[2,3-d]pyrimidin-3(4H)-yl)propyl formate (35 mg, 0.069 mmol) in THF (6 mL) and water (6 mL) was added LiOH.H$_2$O (5.8 mg, 0.138 mmol). The reaction was stirred for 15 min then diluted with EA (10 mL) and water (10 mL). The organic layer was dried over Na$_2$SO$_4$ and concentrated to a residue which was purified by Prep HPLC to give 5-(4-chlorobenzyl)-3-(3-hydroxypropyl)-6-(2-isopropylphenyl)-1-methylpyrido[2,3-d]pyrimidine-2,4(1H,3H)-dione (15 mg, 45.4% yield) as white solid, $^1$H NMR (DMSO-d$_6$) δ: 8.49 (s, 1H), 7.40-7.38 (m, 2H), 7.18-7.14 (m, 3H), 6.93 (d, J=7.2 Hz, 1H), 6.75 (d, J=8.4 Hz, 2H), 4.68-4.65 (m, 1H), 4.45 (s, 1H), 4.24-4.20 (m, 1H), 3.95-3.91 (m, 2H), 3.64 (s, 3H), 3.42-3.40 (m, 2H), 2.40-2.36 (m, 1H), 1.70-1.66 (m, 2H), 1.01-1.00 (d, 3H), 0.85 (d, J=7.2 Hz, 3H). LCMS: [MH+—OH] 478 and $T_R$=3.454 min.

Compound 39

5-((4-chlorophenyl)(hydroxyl)methyl)-3-(3-hydroxypropyl)-1-methyl-6-(3-(trifluoromethoxy)phenyl)pyrido[2,3-d]pyrimidine-2,4(1H,3H)-dione

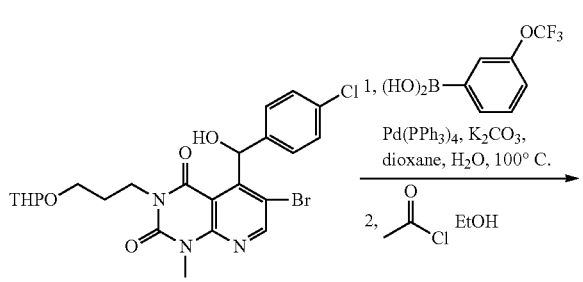

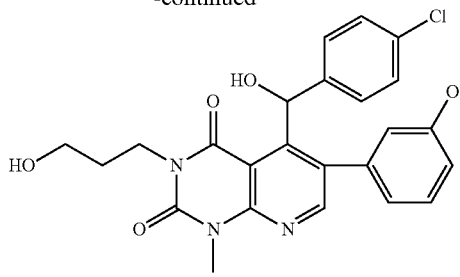

To a mixture of 6-bromo-5-((4-chlorophenyl)(hydroxy)methyl)-1-methyl-3-(3-(tetrahydro-2H-pyran-2-yloxy)propyl)pyrido[2,3-d]pyrimidine-2,4(1H,3H)-dione (See Compound 20, step 5, 120 mg, 0.22 mmol) and 3-(trifluoromethoxy)phenylboronic acid (60 mg, 0.33 mmol) in dioxane (3.2 ml) and water (0.8 mL) was added $K_2CO_3$ (92 mg, 0.67 mmol) and $Pd(PPh_3)_4$ (20 mg). The reaction was degassed with nitrogen (3×), heated at 100° C. for 18 h, cooled to RT, diluted with water (10 mL) then extracted with EA (2×10 mL). The combined organic layers were dried over $Na_2SO_4$ and concentrated to a residue which was purified by Prep TLC eluted with PE/EA (3:1) to give the intermediate 5-((4-chlorophenyl)(hydroxy)methyl)-1-methyl-3-(3-(tetrahydro-2H-pyran-2-yloxy) propyl)-6-(3-(trifluoromethoxy)phenyl)pyrido[2,3-d]pyrimidine-2,4(1H,3H)-dione (15 mg) as a white solid. The intermediate was dissolved in EtOH (3 mL) and acetyl chloride (0.3 mL) was added. The reaction was stirred at RT for 30 min then concentrated to a residue which was purified by Prep HPLC to give 5-((4-chlorophenyl)(hydroxy)methyl)-3-(3-hydroxypropyl)-1-methyl-6-(3-(trifluoromethoxy)phenyl)pyrido[2,3-d]pyrimidine-2,4(1H,3H)-dione (3 mg, 3% yield over 2 steps) as a white solid. $^1H$ NMR ($CDCl_3$) δ: 8.64 (s, 1H), 7.49 (t, J=8.0 Hz, 1H), 7.32 (d, J=8.4 Hz, 1H), 7.27 (d, J=7.2 Hz, 1H), 7.21-7.17 (m, 3H), 7.05 (d, J=8.0 Hz, 2H), 6.25 (s, 1H), 4.11-4.05 (m, 2H), 3.77 (s, 3H), 3.51 (t, J=6.4 Hz, 2H), 1.79-1.74 (m, 2H). LCMS: [$M^+$+Na] 558 and $T_R$=3.048 min.

Compound 40

5-(4-chlorobenzyl)-3-(3-hydroxypropyl)-1-methyl-6-(3-(trifluoromethoxy)phenyl)pyrido[2,3-d]pyrimidine-2,4(1H,3H)-dione

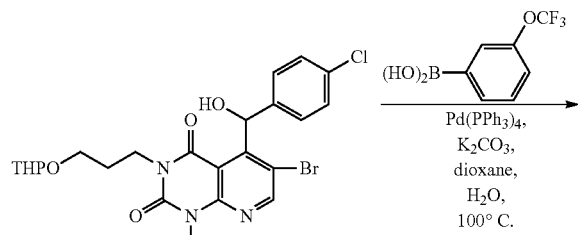

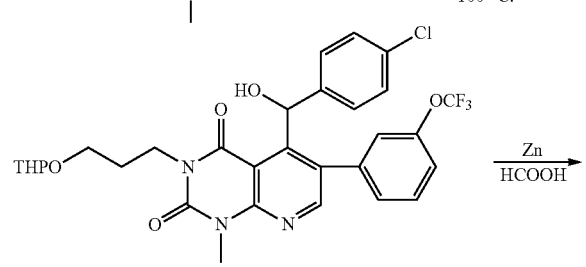

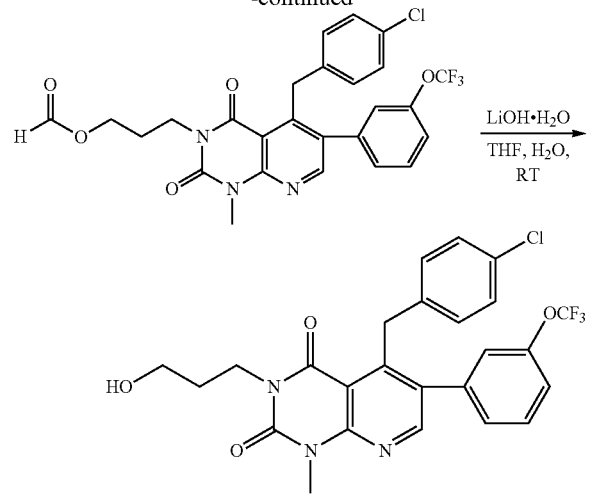

Step 1

5-((4-chlorophenyl)(hydroxy)methyl)-1-methyl-3-(3-((tetrahydro-2H-pyran-2-yl)oxy)propyl)-6-(3-(trifluoromethoxy)phenyl)pyrido[2,3-d]pyrimidine-2,4(1H,3H)-dione

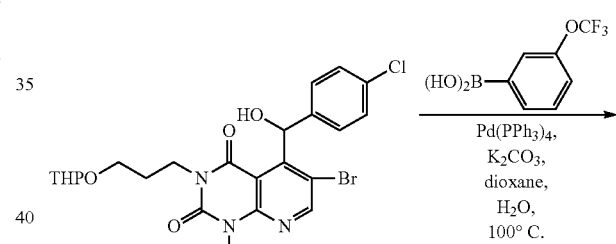

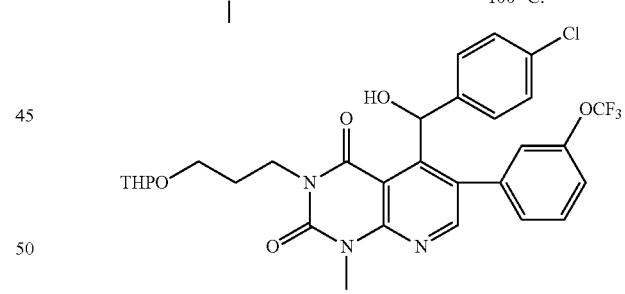

6-bromo-5-((4-chlorophenyl)(hydroxy)methyl)-1-methyl-3-(3-(tetrahydro-2H-pyran-2-yloxy)propyl)pyrido[2,3-d]pyrimidine-2,4(1H,3H)-dione (See Compound 20, step 5, 500 mg, 0.931 mmol) and 3-(trifluoromethoxy)phenylboronic acid (288 mg, 1.40 mmol) were combined in dioxane (15 ml) and water (4 mL) then $K_2CO_3$ (385 mg, 2.79 mmol) and $Pd(PPh_3)_4$ (60 mg) were added. The reaction was degassed with nitrogen (3×), heated at 100° C. for 18 h, cooled to RT, diluted with water (10 mL) and extracted with EA (2×50 mL). The combined organic layers were dried over $Na_2SO_4$ and concentrated to a residue which was purified by chromatography eluted with PE/EA (8:1) to give 5-((4-chlorophenyl)(hydroxy)methyl)-1-methyl-3-(3-(tetrahydro-2H-pyran-2-yloxy)propyl)-6-(3-(trifluoromethoxy)

phenyl)pyrido[2,3-d]pyrimidine-2,4(1H,3H)-dione (100 mg, 17.4% yield) as a yellow solid. LCMS: [MH⁺-THP] 536 and T_R=1.013 min.

Step 2

3-(5-benzyl)-1-methyl-2,4-dioxo-6-(3-(trifluoromethoxy)phenyl)-1,2-dihydropyrido[2,3-d]pyrimidin-3(4H)-yl)propyl formate

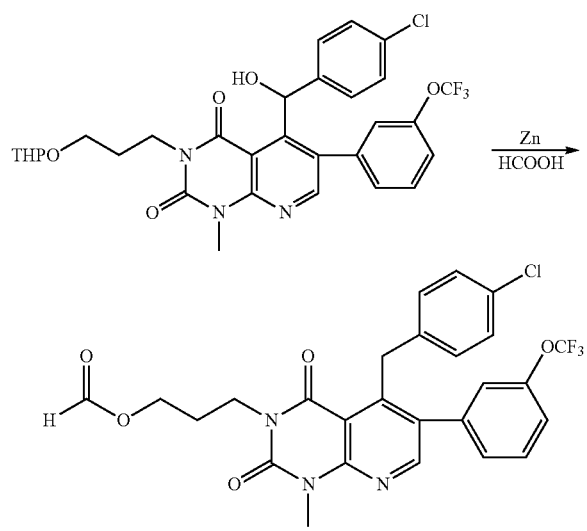

To a solution of 5-((4-chlorophenyl)(hydroxy)methyl)-1-methyl-3-(3-((tetrahydro-2H-pyran-2-yl)oxy)propyl)-6-(3-(trifluoromethoxy)phenyl)pyrido[2,3-d]pyrimidine-2,4 (1H, 3H)-dione (100 mg, 0.162 mmol) in formic acid (3 mL) was added Zn dust (40.9 mg, 0.641 mmol). The reaction was heated at 50° C. for 2 h, cooled to RT and filtered. The filtrate was concentrated to a residue which was purified by Prep TLC eluted with PE/EA (1:1) to give 3-(5-(4-chlorobenzyl)-1-methyl-2,4-dioxo-6-(3-(trifluoromethoxy)phenyl)-1,2-dihydropyrido[2,3-d]pyrimidin-3(4H)-yl)propyl formate (50 mg, 56.5% yield) as a white solid. LCMS: MH⁺ 548 and T_R=1.399 min.

Step 3

5-(4-chlorobenzyl)-3-(3-hydroxypropyl)-1-methyl-6-(3-(trifluoromethoxy)phenyl)pyrido[2,3-d]pyrimidine-2,4(1H,3H)-dione

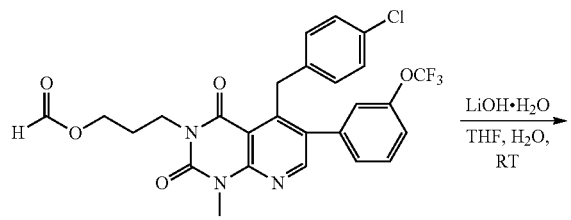

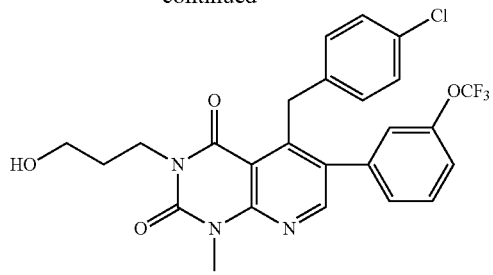

To a solution of 3-(5-(4-chlorobenzyl)-1-methyl-2,4-dioxo-6-(3-(trifluoromethoxy)phenyl)-1,2-dihydropyrido[2,3-d]pyrimidin-3(4H)-yl)propyl formate (50 mg, 0.091 mmol) in THF (2 ml) and water (2 mL) was added LiOH.H₂O (7.6 mg, 0.183 mmol). The reaction was stirred at RT for 30 min then diluted with EA (10 mL) and water (10 mL). The organic layer was dried over Na₂SO₄ and concentrated to a residue which was purified by Prep HPLC to give 5-(4-chlorobenzyl)-3-(3-hydroxypropyl)-1-methyl-6-(3-(trifluoromethoxy)phenyl)pyrido[2,3-d]pyrimidine-2,4(1H,3H)-dione (20 mg, 40.5% yield) as a white solid. ¹H NMR (CD₃OD) δ: 8.52 (s, 1H), 7.49 (t, J=8.0 Hz, 1H), 7.32 (d, J=8.0 Hz, 1H), 7.19 (d, J=8.0 Hz, 1H), 7.15-7.07 (m, 3H), 6.79 (d, J=8.4 Hz, 2H), 4.67 (s, 2H), 4.10 (t, J=6.8 Hz, 2H), 3.74 (s, 3H), 3.57 (t, J=6.4 Hz, 2H), 1.86-1.81 (m, 2H). LCMS: MH⁺ 520 and T_R=3.195 min.

Compound 41

5-(4-fluorobenzyl)-3-(3-hydroxypropyl)-6-(2-isopropylphenoxy)-1-methylpyrido[2,3-d]pyrimidine-2,4(1H,3H)-dione

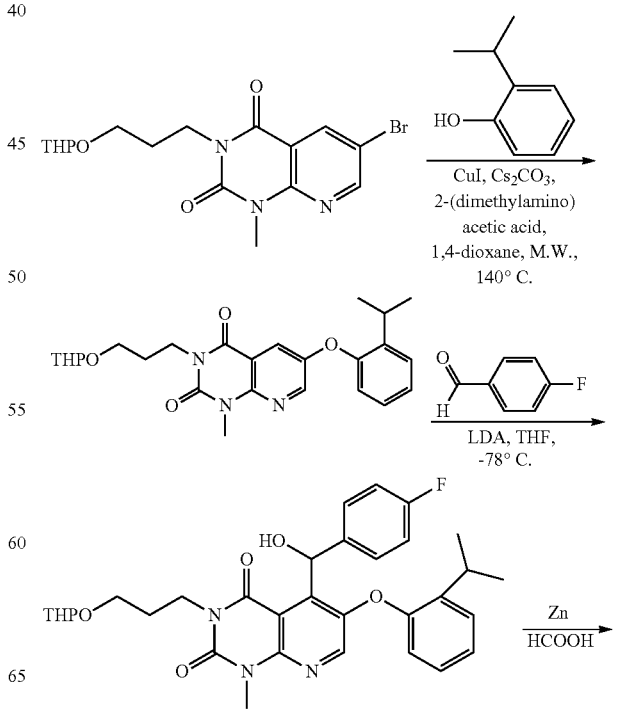

-continued

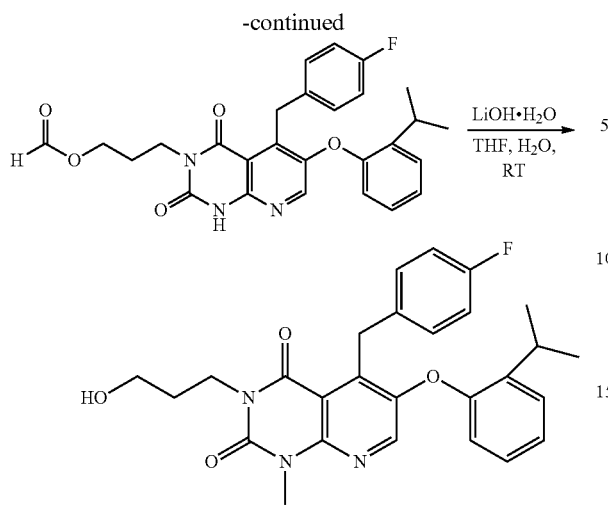

Step 1 6-(3-isopropylphenoxy)-1-methyl-3-(3-(tetra-hydro-2H-pyran-2-yloxy)propyl)pyrido[2,3-d]py-rimidine-2,4(1H,3H)-dione (FTY-000476-037)

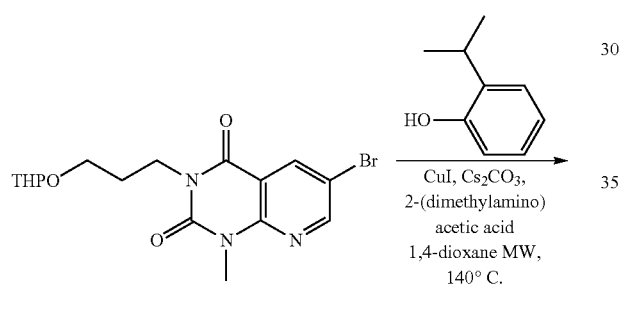

To a mixture of 6-bromo-1-methyl-3-(3-(tetrahydro-2H-pyran-2-yloxy)propyl)pyrido[2,3-d]pyrimidine-2,4(1H,3H)-dione (See Compound 20, step 4, 400 mg, 1 mmol), CuI (24 mg, 0.13 mmol), Cs$_2$CO$_3$ (650 mg, 2 mmol) and 2-(di-methylamino)acetic acid (51 mg, 0.5 mmol) in dioxane (6 mL) was added 2-isopropylphenol (204 mg, 1.5 mmol). The reaction was heated at 140° C. (MW) for 1.5 h then cooled to RT and filtered. The filtrate was diluted with EA (5 mL) and water (5 mL). The organic layer was dried over Na$_2$SO$_4$ and concentrated to a residue which was purified by chromatography eluted with PE/EA (1:1) to give 6-(2-isopropy-lphenoxy)-1-methyl-3-(3-(tetra hydro-2H-pyran-2-yloxy) propyl)pyrido[2,3-d]pyrimidine-2,4(1H,3H)-dione (250 mg, 55% yield) as a solid. LCMS: [MH$^+$-THP] 370 and T$_R$=0.918 min.

Step 2 5-((4-fluorophenyl)(hydroxy)methyl)-6-(2-isopropylphenoxy)-1-methyl-3-(3-((tetrandro-2H-pyran-2-ly)oxy)propyl)pyrido[2,3-d]pyrimidine-2,4 (1H,3H)-dione

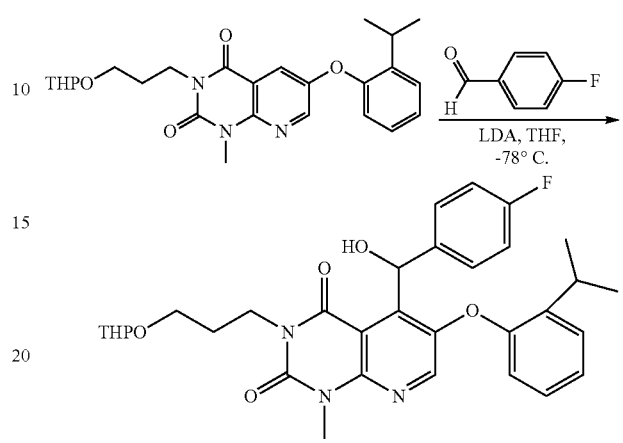

To a solution of 6-(2-isopropylphenoxy)-1-methyl-3-(3-(tetrahydro-2H-pyran-2-yloxy)propyl)pyrido[2,3-d]pyrimi-dine-2,4(1H,3H)-dione (260 mg, 0.574 mmol) in THF (15 mL) at −78° C. was added LDA (2.0 M in THF, 1.25 mL, 2.50 mmol) dropwise. The reaction was stirred at −78° C. for 1 h then a solution of 4-fluorobenzaldehyde (142 mg, 1.15 mmol) in THF (1 mL) was added drop wise. The reaction was stirred at −78° C. for 1 h, quenched with aq. NH$_4$Cl (10 mL) then diluted with EA (10 mL) and water (10 mL). The organic layer was dried over Na$_2$SO$_4$ and concentrated to a residue which was purified by chromatography eluted with PE/EA (7:1) to give 5-((4-fluorophenyl)(hydroxy)methyl)-6-(2-isopropylphenoxy)-1-methyl-3-(3-((tetrandro-2H-pyran-2-ly)oxy) propyl)pyrido[2,3-d]pyrimidine-2,4(1H, 3H)-dione (160 mg, 48.3% yield) as a solid. LCMS: [MH$^+$-THP] and T$_R$=1.611 min.

Step 3 3-(5-(4-fluorobenzyl)-6-(2-isopropylphe-noxy)-1-methyl-2,4-dioxo-1,2-dihydropyrido[2,3-d] pyrimidin-3(4H)-yl)propyl formate

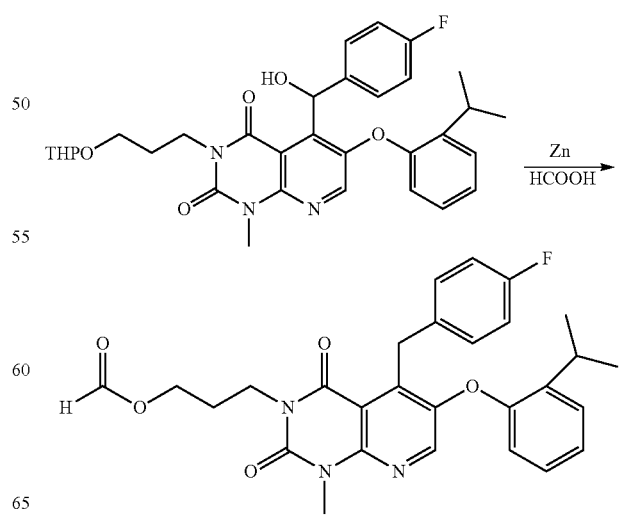

To a solution of 5-((4-fluorophenyl)(hydroxy)methyl)-6-(2-isopropylphenoxy)-1-methyl-3-(3-((tetrandro-2H-pyran-2-ly)oxy)propyl)pyrido[2,3-d]pyrimidine-2,4(1H,3H)-dione (80 mg, 0.139 mmol) in HCOOH (1.5 mL) was added Zn dust (45 mg, 0.692 mmol). The reaction was heated at 50° C. for 30 min, cooled to RT and filtered. The filtrate was concentrated to give 3-(5-(4-fluoro benzyl)-6-(2-isopropylphenoxy)-1-methyl-2,4-dioxo-1,2-dihydropyrido[2,3-d]pyrimidin-3(4H)-yl)propyl formate (68 mg, 97% yield) as an oil. LCMS: MH+ 506 and $T_R$=2.201 min. Used without further purification.

Step 4 5-(4-fluorobenzyl)-3-(3-hydroxypropyl)-6-(2-isopropylphenoxy)-1-methylpyrido[2,3-d]pyrimidine-2,4(1H,3H)-dione

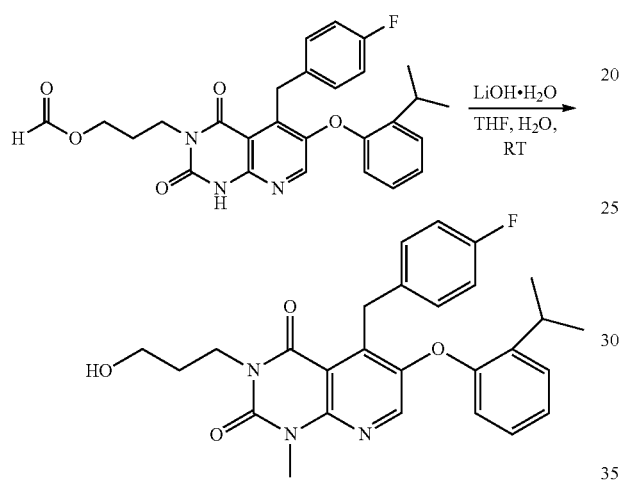

To a solution of 3-(5-(4-fluorobenzyl)-6-(2-isopropylphenoxy)-1-methyl-2,4-dioxo-1,2-dihydro pyrido[2,3-d]pyrimidin-3(4H)-yl)propyl formate (68 mg, 0.135 mmol) in THF (1 ml) and water (1 mL) was added LiOH.H₂O (14 mg, 0.33 mmol). The reaction was stirred at RT for 15 min then diluted with EA (10 mL) and water (10 mL). The organic layer was dried over Na₂SO₄ and concentrated to a residue which was purified by Prep HPLC to give 5-(4-fluorobenzyl)-3-(3-hydroxypropyl)-6-(2-isopropylphenoxy)-1-methylpyrido[2,3-d]pyrimidine-2,4(1H,3H)-dione (55 mg, 85.4% yield) as a white solid. ¹H NMR (DMSO-d₆) δ: 8.23 (s, 1H), 7.38-7.35 (m, 1H), 7.23-7.18 (m, 2H), 7.14-7.10 (m, 2H), 7.03 (t, J=8.8 Hz, 2H), 6.61-6.58 (m, 1H), 4.71 (s, 2H), 4.49 (t, J=5.2 Hz, 1H), 3.98 (t, J=7.2 Hz, 2H), 3.56 (s, 3H), 3.49-3.43 (m, 2H), 3.11-3.07 (m, 1H), 1.75-1.71 (m, 2H), 1.12 (d, J=6.4 Hz, 6H). LCMS: MH+ 478 and $T_R$=3.356 min.

Compound 42

3-(3-hydroxypropyl)-1-methyl-6-((5-methylpyridin-3-yl)oxy)-5-(((6-(trifluoromethyl)pyridine-3-yl)methyl)pyrido[2,3-d]pyrimidine-2,4(1H,3H)-dione

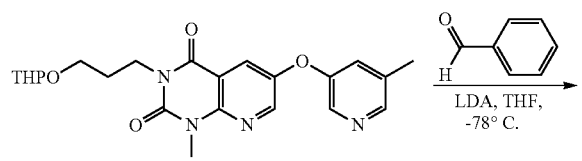

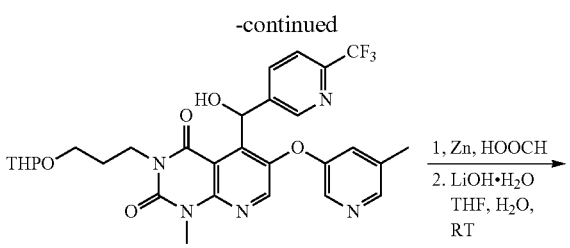

Step 1 5-(hydroxy(6-(trifluoromethyl)pyridin-3-yl)methyl)-1-methyl-6-(5-methylpyridin-3-yloxy)-3-(3-(tetrahydro-2H-pyran-2-yloxy)propyl)pyrido[2,3-d]pyrimidine-2,4(1H,3H)-dione

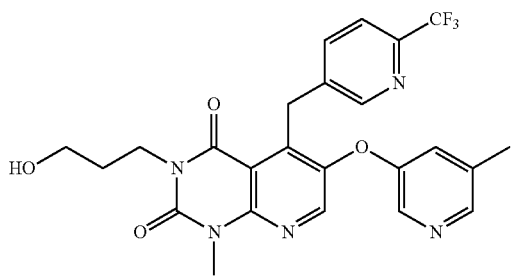

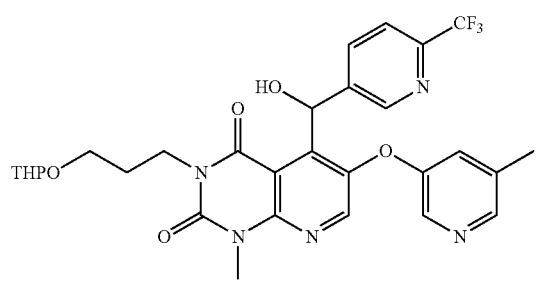

To a solution of 1-methyl-6-(5-methylpyridin-3-yloxy)-3-(3-(tetrahydro-2H-pyran-2-yloxy) propyl)pyrido[2,3-d]pyrimidine-2,4(1H,3H)-dione (See Compound 27, step 1, 140 mg, 0.330 mmol) in THF (10 mL) at −78° C. was added LDA (2M in THF, 0.84 mL, 1.65 mmol) dropwise The reaction was stirred at −78° C. for 1 h then a solution of 6-(trifluoromethyl) nicotinaldehyde (115 mg, 0.660 mmol) in THF (2 mL) was added. The reaction was stirred for 30 min at −78° C. then diluted with EA (10 mL) and water (10 mL). The organic layer was dried over Na₂SO₄ and concentrated to a residue which was purified by chromatography eluted with PE/EA (10:1 to 1:1) to give 5-(hydroxy(6-(trifluoromethyl)pyridin-3-yl)methyl)-1-methyl-6-(5-methylpyridin-3-yloxy)-3-(3-(tetrahydro-2H-pyran-2-yloxy)propyl)pyrido[2,3-d]pyrimidine-2,4 (1H,3H)-dione (24 mg, 12.1% yield) as a yellow oil. LCMS: [MH+-THP] 518 and $T_R$=1.494 min.

143

Step 2 3-(3-hydroxypropyl)-1-methyl-6-((5-methyl-pyridin-3-yl)oxy)-5-(((6-(trifluoromethyl)pyridin-3-yl)methyl)pyrido[2,3-d]pyrimidine-2,4(1H,3H)-dione

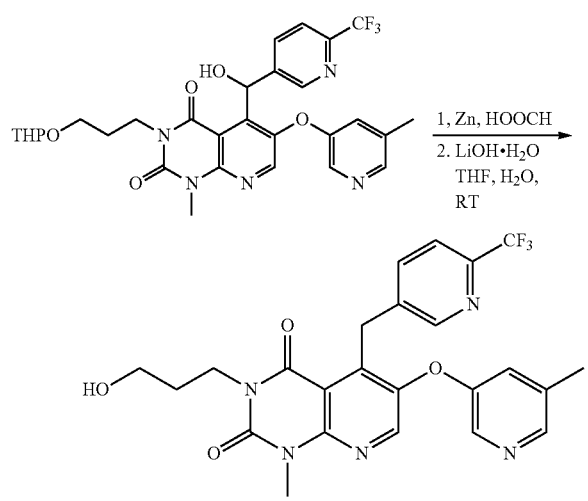

To a solution of 5-(hydroxy(6-(trifluoromethyl)pyridin-3-yl)methyl)-1-methyl-6-(5-methylpyridin-3-yloxy)-3-(3-(tetrahydro-2H-pyran-2-yloxy)propyl)pyrido[2,3-d]pyrimidine-2,4(1H,3H)-dione (24 mg, 0.04 mmol) in HCOOH (1 mL) was added Zn dust (13 mg, 0.2 mmol). The reaction was heated at 100° C. for 1 h, cooled to RT and filtered. The filtrate was concentrated to a crude intermediate which was dissolved in THF (2 mL) and water (2 mL) then LiOH·H₂O (33.6 mg, 0.8 mmol) was added. The reaction was stirred at RT for 30 min then diluted with EA (10 mL) and water (10 mL). The organic layer was dried over Na₂SO₄ and concentrated a residue which was purified by Prep HPLC to give 3-(3-hydroxypropyl)-1-methyl-6-(5-methylpyridin-3-yloxy)-5-(((6-(trifluoromethyl)pyridin-3-yl)methyl)pyrido[2,3-d]pyrimidine-2,4(1H,3H)-dione (4.0 mg, 20% yield) as a white solid. $^1$H NMR (CDCl$_3$) δ: 8.68 (s, 1H), 8.38 (s, 1H), 8.27 (s, 1H), 8.17 (d, J=2.4 Hz, 1H), 7.82 (d, J=8.0 Hz, 1H), 7.56 (d, J=7.6 Hz, 1H), 6.98 (s, 1H), 4.86 (s, 2H), 4.25 (t, J=6.0 Hz, 2H), 3.74 (s, 3H), 3.57-3.61 (m, 2H), 2.96 (brd s, 1H), 2.34 (s, 3H), 1.92-1.97 (m, 2H). LCMS: MH$^+$ 502 and T$_R$=2.285 min.

Compound 43

6-(3-chlorophenoxy)-3-(3-hydroxypropyl)-1-methyl-5-(((5-trifluoromethoxy)pyridine-3-yl)methyl)pyrido[2,3-d]pyrimidine-2,4(1H,3H)-dione

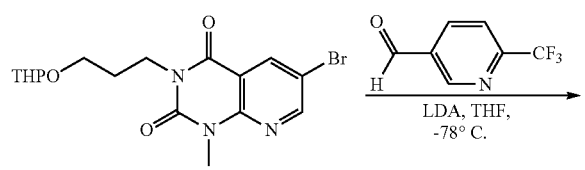

144

-continued

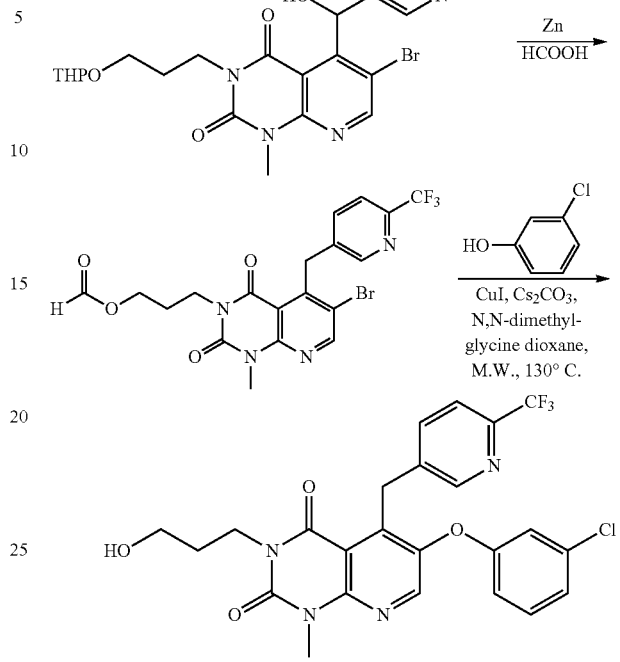

Step 1

6-bromo-5-(hydroxy(6-(trifluoromethyl)pyridin-3-yl)methyl)-1-methyl-3-(3-((tetrahydro-2H-pyran-2-yl)oxy)propyl)pyrido[2,3-d]pyrimidine-2,4(1H,3H)-dione

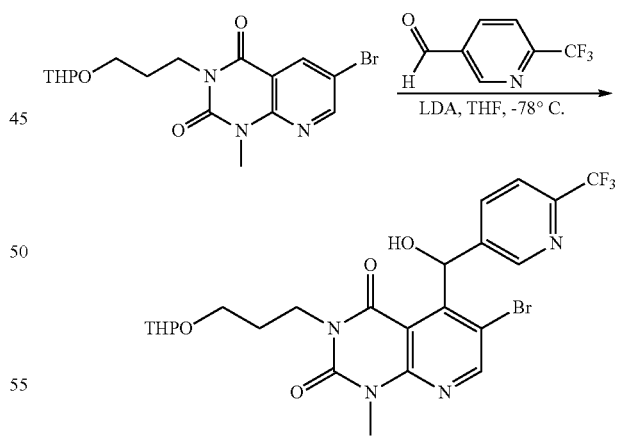

To a solution of 6-bromo-1-methyl-3-(3-((tetrahydro-2H-pyran-2-yl)oxy)propyl)pyrido[2,3-d]pyrimidine-2,4(1H,3H)-dione (See Compound 20, step 4, 1.0 g, 2.52 mmol) in THF (20 mL) at −78° C. was added LDA (2.0 M in THF, 6.3 mL, 12.6 mmol) dropwise. The reaction was stirred at −78° C. for 1 h then a solution of 6-(trifluoromethyl)nicotinaldehyde (880 mg, 5.04 mmol) in THF (5 mL) was added dropwise. The reaction was stirred at −78° C. for 30 min then diluted with EA (20 mL) and water (20 mL). The organic layer was dried over Na$_2$SO$_4$ and concentrated to a residue which was purified by chromatography eluted with PE/EA (10:1 to 1:1) to give 6-bromo-5-(hydroxy(6-(trifluoromethyl)pyridin-3-yl)methyl)-1-methyl-3-(3-((tetrahydro-2H-pyran-2-yl)oxy)propyl)pyrido[2,3-d]pyrimidine-2,4 (1H,3H)-dione (90 mg, 7.0% yield) as a white solid. LCMS: [MH$^+$-THP] 489 and T$_R$=1.786 min.

Step 2

3-(6-bromo-1-methyl-2,4-dioxo-5-((6-(trifluoromethyl)pyridin-3-yl)methyl)-1,2-dihydropyrido[2,3-d]pyrimidin-3(4H)-yl)propyl formate

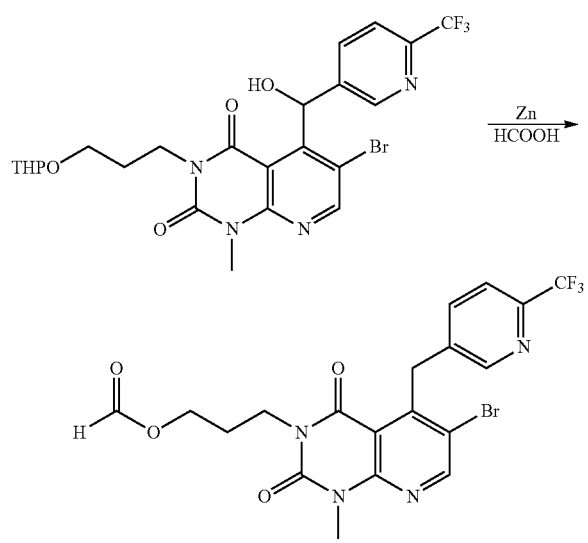

To a stirred solution of 6-bromo-5-(hydroxy(6-(trifluoromethyl)pyridin-3-yl)methyl)-1-methyl-3-(3-((tetrahydro-2H-pyran-2-yl)oxy)propyl)pyrido[2,3-d]pyrimidine-2,4 (1H,3H)-dione (160 mg, 0.280 mmol) in formic acid (2 mL) was added Zinc dust (40.9 mg, 0.64 mmol). The reaction was heated at 50° C. for 2 h, cooled to RT and filtered. The filtrate was concentrated to a residue which was purified by chromatography eluted with PE/EA (10:1) to give 3-(6-bromo-1-methyl-2,4-dioxo-5((6-(trifluoromethyl)pyridin-3-yl)methyl)-1,2-dihydropyrido[2,3-d]pyrimidin-3(4H)-yl)propylformate (80 mg, 57.1% yield). LCMS: MH$^+$ 501 and T$_R$=1.727 min.

Step 3

6-(3-chlorophenoxy)-3-(3-hydroxypropyl)-1-methyl-5-((5-trifluoromethoxy)pyridine-3-yl)methyl)pyrido[2,3-d]pyrimidine-2,4(1H,3H)-dione

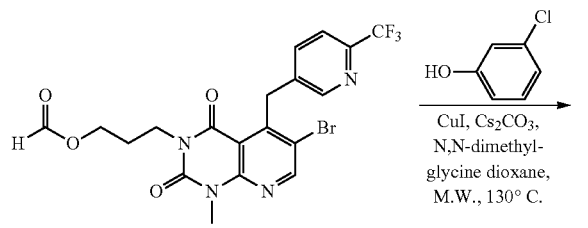

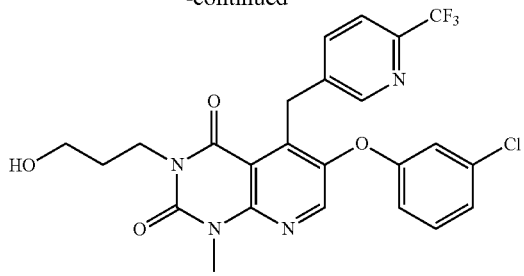

To a mixture of 3-(6-bromo-1-methyl-2,4-dioxo-5-((6-(trifluoromethyl)pyridin-3-yl)methyl)-1,2-dihydropyrido[2,3-d]pyrimidin-3(4H)-yl)propyl formate (40 mg, 0.08 mmol) and 3-chlorophenol (26 mg, 0.2 mmol) in dioxane (2 mL) was added Cs$_2$CO$_3$ (78 mg, 0.24 mmol), 2-(dimethylamino)acetic acid (4.1 mg, 0.04 mmol) and CuI (1.9 mg, 0.01 mmol). The reaction was degassed with nitrogen (3×), heated at 130° C. (MW) for 1.5 h, cooled to RT, diluted with water (10 mL) then extracted with EA (2×10 mL). The combined organic layers were dried over Na$_2$SO$_4$ and concentrated to a residue which was purified by Prep HPLC to give 6-(3-chlorophenoxy)-3-(3-hydroxypropyl)-1-methyl-5-((6-(trifluoromethyl)pyridin-3-yl)methyl)pyrido[2,3-d]pyrimidine-2,4(1H,3H)-dione (5.2 mg, 12.5% yield) as a white solid. $^1$H NMR (CDCl$_3$) δ: 8.66 (s, 1H), 8.39 (s, 1H), 7.79 (d, J=7.2 Hz, 1H), 7.54 (d, J=8.4 Hz, 1H), 7.30-7.25 (overlap with CDCl3, 1H), 7.12 (dd, J=8.0, 0.8 Hz, 1H), 6.87-6.79 (m, 2H), 4.81 (s, 2H), 4.23 (t, J=6.4 Hz, 2H), 3.72 (s, 3H), 3.55-3.58 (m, 2H), 2.95 (brd s, 1H), 1.95-1.90 (m, 2H). LCMS: MH$^+$ 521 and T$_R$=3.068 min.

Compound 44

5-(1-hydroxy-3-methylbutyl)-3-(3-hydroxypropyl)-1-methyl-6-(3-(trifluoromethoxy) phenoxy)pyrido[2,3-d]pyrimidine-2,4(1H,3H)-dione

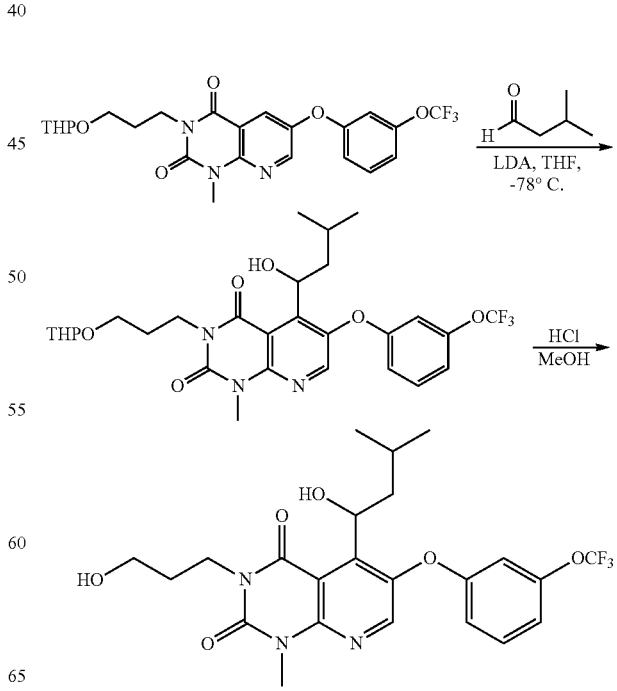

Step 1: 5-(1-hydroxy-3-methylbutyl)-1-methyl-3-(3-((tetrahydro-2H-pyran-2-yl)oxy)propyl)-6-(3-(trifluoromethoxy)phenoxy)pyrido[2,3-d]pyrimidine-2,4(1H,3H)-dione

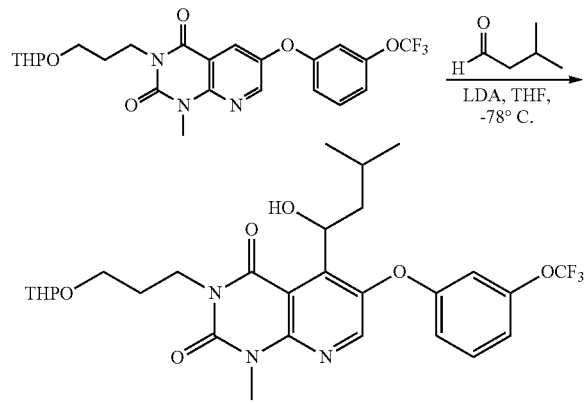

To a solution of 1-methyl-3-(3-((tetrahydro-2H-pyran-2-yl)oxy)propyl)-6-(3-(trifluoromethoxy) phenoxy)pyrido[2,3-d]pyrimidine-2,4(1H,3H)-dione (See Compound 45, step 1, 100 mg, 0.2 mmol) in THF (4 mL) at −78° C. was added LDA (2M in THF, 0.4 mL, 0.8 mmol) dropwise. The reaction was stirred at −78° C. for 1 h then 3-methylbutanal (34 mg, 0.4 mmol) in THF (1 mL) was added. The reaction was stirred at −78° C. for 1 h, quenched with aq. NH$_4$Cl (10 mL) then diluted with EA (10 mL) and water (10 mL). The organic layer was dried over Na$_2$SO$_4$ and concentrated to a residue which was purified by Prep TLC eluted with PE/EA (2:1) to give 5-(1-hydroxy-3-methylbutyl)-1-methyl-3-(3-((tetrahydro-2H-pyran-2-yl)oxy)propyl)-6-(3-(trifluoromethoxy)phenoxy)pyrido[2,3-d]pyrimidine-2,4(1H,3H)-dione (60 mg, 51.7% yield) as a solid. LCMS: [MH$^+$-THP] 498 and T$_R$=1.733 min.

Step 2: 5-(1-hydroxy-3-methylbutyl)-3-(3-hydroxypropyl)-1-methyl-6-(3-(trifluoromethoxy)phenoxy)pyrido[2,3-d]pyrimidine-2,4(1H,3H)-dione

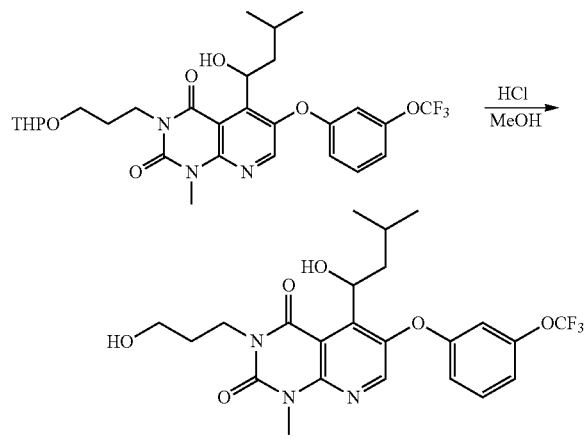

5-(1-hydroxy-3-methylbutyl)-1-methyl-3-(3-((tetrahydro-2H-pyran-2-yl)oxy)propyl)-6-(3-(trifluoromethoxy) phenoxy)pyrido[2,3-d]pyrimidine-2,4(1H,3H)-dione (60 mg, 0.104 mmol) was dissolved in 2N HCl/MeOH (5 mL). The reaction was stirred at RT for 1 h then diluted with EA (10 mL) and water (10 mL). The organic layer was washed with brine (10 mL), dried over Na$_2$SO$_4$ and concentrated to a residue which was purified by Prep HPLC to give 5-(1-hydroxy-3-methylbutyl)-3-(3-hydroxypropyl)-1-methyl-6-(3-(trifluoromethoxy)phenoxy)pyrido[2,3-d]pyrimidine-2,4(1H,3H)-dione (20 mg, 38.5% yield) as a white solid. $^1$H NMR (DMSO-d$_6$) δ: 8.59 (s, 1H), 7.48 (t, J=8.4 Hz, 1H), 7.09 (d, J=8.4 Hz, 1H), 6.98-6.92 (m, 3H), 5.62-5.60 (m, 2H), 4.54 (t, J=5.2 Hz, 1H), 4.06-4.01 (m, 2H), 3.60 (s, 3H), 3.46-3.52 (m, 2H), 1.92-1.90 (m, 1H), 1.80-1.72 (m, 3H), 1.24-1.19 (m, 1H), 0.83 (d, J=6.8 Hz, 3H), 0.75 (d, J=6.8 Hz, 3H). LCMS: MH$^+$ 498 and T$_R$=3.186 min.

Compound 45

5-(4-chlorobenzyl)-3-(3-hydroxypropyl)-1-methyl-6-(3-(trifluoromethoxy)benzyl)pyrido[2,3-d]pyrimidine-2,4(1H,3H)-dione

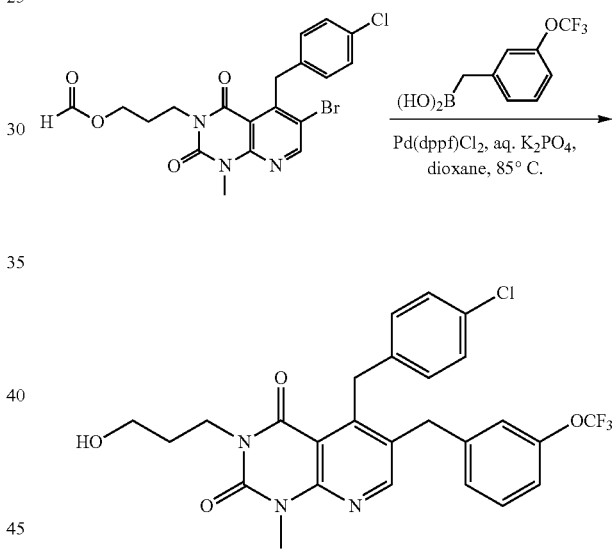

To a mixture of 3-(6-bromo-5-(4-chlorobenzyl)-1-methyl-2,4-dioxo-1,2-dihydropyrido[2,3-d]pyrimidin-3(4H)-yl)propyl formate (See Compound 34, step 2, 80 mg, 0.171 mmol) and 3-(trifluoromethoxy) benzylboronic acid (103 mg, 0.342 mmol) in dioxane (4 mL) was added aq. 2 M K$_3$PO$_4$ (0.8 mL) and Pd(dppf)Cl$_2$ (10 mg). The reaction was degassed with nitrogen (3×) and heated at 85° C. for 3 h, cooled to RT, diluted with water (10 mL) then extracted with EA (2×10 mL). The combined organic layers were dried over Na$_2$SO$_4$ and concentrated to a residue which was purified by Prep HPLC to give 6-(3-(trifluoromethoxy) benzyl)-5-(4-chlorobenzyl)-3-(3-hydroxy propyl)-1-methyl-pyrido[2,3-d]pyrimidine-2,4(1H,3H)-dione (15 mg, 16.5% yield) as a white solid. $^1$H NMR (CDCl$_3$) δ: 8.63 (s, 1H), 7.33 (t, J=8.0 Hz, 1H), 7.19 (d, J=8.4 Hz, 2H), 7.13 (d, J=8.4 Hz, 1H), 7.06 (d, J=7.6 Hz, 1H), 6.98-6.92 (m, 3H), 4.70 (s, 2H), 4.42-4.40 (m, 1H), 4.05 (s, 2H), 3.94-3.90 (m, 2H), 3.60 (s, 3H), 3.42-3.40 (m, 2H), 1.69-1.64 (m, 2H). LCMS: MH$^+$ 534 and T$_R$=3.262 min.

Compound 46

3-(3-hydroxypropyl)-5-isopentyl-1-methyl-6-(3-(trifluoromethyl)phenoxy)pyrido[2,3-d]pyrimidine-2,4(1H,3H)-dione

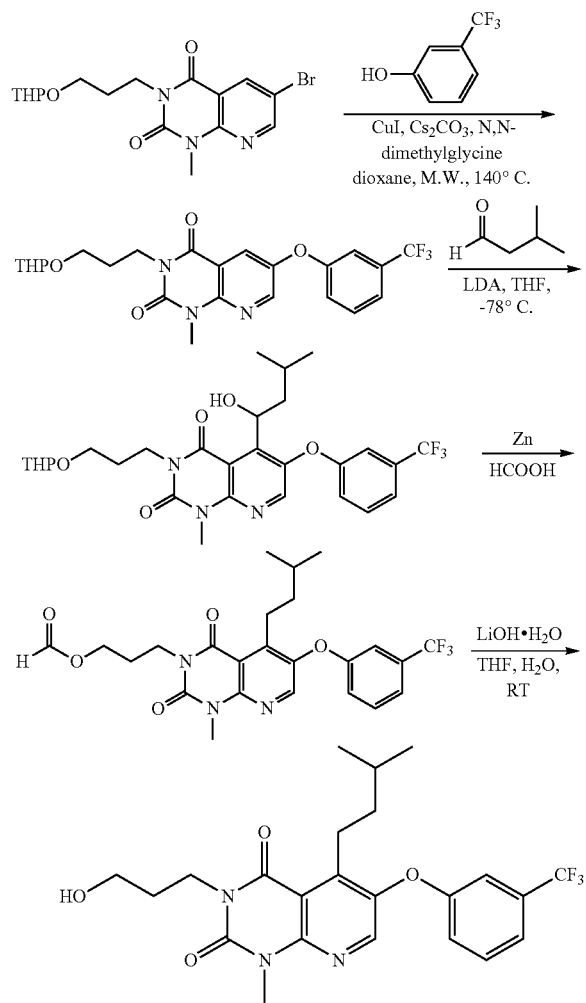

Step 1

1-methyl-3-(3-((tetrahydro-2H-pyran-2-yl)oxy)propyl)-6-(3-(trifluoromethyl)phenoxy)pyrido[2,3-d]pyrimidine-2,4(1H,3H)-dione

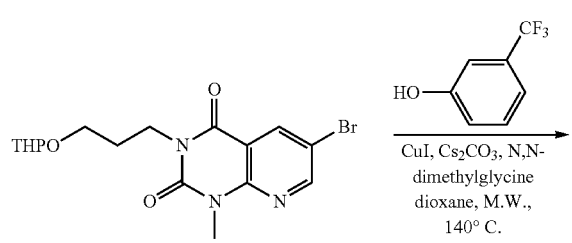

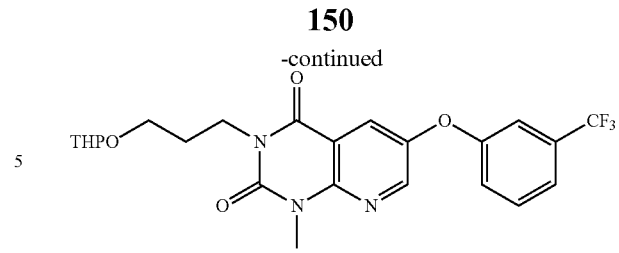

To a mixture of 6-bromo-1-methyl-3-(3-((tetrahydro-2H-pyran-2-yl)oxy)propyl)pyrido[2,3-d]pyrimidine-2,4(1H,3H)-dione (See Compound 20, step 4, 200 mg, 0.50 mmol), CuI (28.7 mg, 0.15 mmol), Cs₂CO₃ (327.2 mg, 1.00 mmol) and 2-(dimethylamino)acetic acid (10.4 mg, 0.10 mmol) in dioxane (3 mL) was added 3-(trifluoromethyl)phenol (162.8 mg, 1.00 mmol). The reaction was heated at 140° C. (MW) for 2 h, cooled to RT then diluted with EA (15 mL) and water (10 mL). The organic layer was washed with water (20 mL) and brine (20 mL), dried over Na₂SO₄ and concentrated to a residue which was purified by chromatography eluted with PE/EA (10:1 to 1:1) to give 1-methyl-3-(3-((tetrahydro-2H-pyran-2-yl)oxy)propyl)-6-(3-(trifluoromethyl)phenoxy)pyrido[2,3-d]pyrimidine-2,4(1H,3H)-dione (150 mg, 62.3% yield) as a white solid. LCMS: [MH⁺-THP] 396 and $T_R$=1.941 min.

Step 2

5-(1-hydroxy-3-methylbutyl)-1-methyl-3-(3-((tetrahydro-2H-pyran-2-yl)oxy)propyl)-6-(3-(trifluoromethyl)phenoxy)pyrido[2,3-d]pyrimidine-2,4(1H,3H)-dione

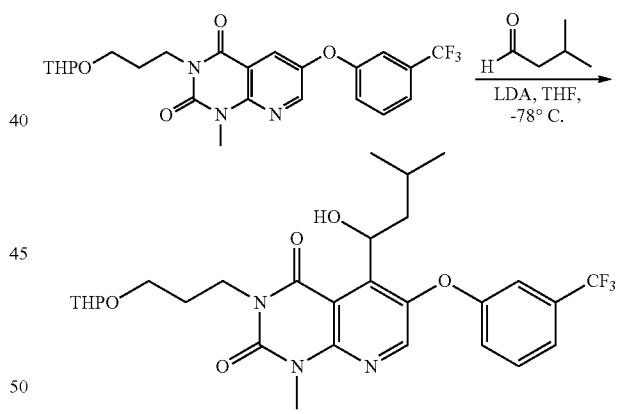

To a solution of 1-methyl-3-(3-((tetrahydro-2H-pyran-2-yl)oxy)propyl)-6-(3-(trifluoromethyl) phenoxy)pyrido[2,3-d]pyrimidine-2,4(1H,3H)-dione (100 mg, 0.21 mmol) in THF (8 mL) at −78° C. was added LDA (2M in THF, 0.4 mL, 0.82 mmol) dropwise. The reaction was stirred at −78° C. for 40 min then 3-methylbutanal (35.9 mg, 0.42 mmol) in THF (2 mL) was added. The reaction was stirred at −78° C. for 30 min then diluted with DCM (10 mL) and water (10 mL). The organic layer was dried over Na₂SO₄ and concentrated to a residue which was purified by chromatography eluted with PE/EA (10:1 to 5:1) to give 5-(1-hydroxy-3-methylbutyl)-1-methyl-3-(3-((tetrahydro-2H-pyran-2-yl)oxy)propyl)-6-(3-(trifluoromethyl)phenoxy)pyrido[2,3-d]pyrimidine-2,4(1H,3H)-dione (60 mg, 50.8% yield) as a solid. LCMS: [M⁺-THP-OH] 465 and $T_R$=2.180 min.

Step 3

3-(5-isopentyl-1-methyl-2,4-dioxo-6-(3-(trifluoromethyl)phenoxy)-1,2-dihydropyrido[2,3-d]pyrimidin-3(4H)-yl)propyl formate

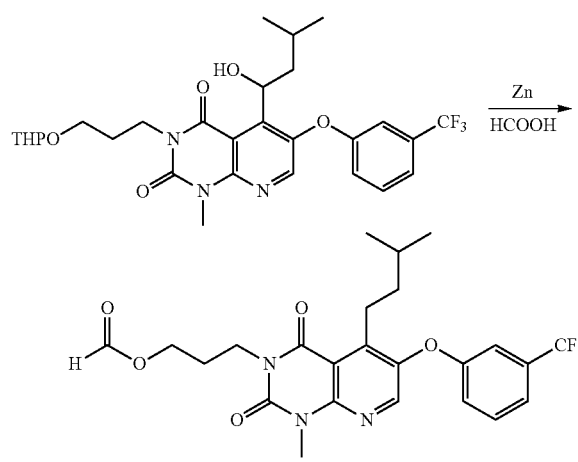

To a solution of 5-(1-hydroxy-3-methylbutyl)-1-methyl-3-(3-((tetrahydro-2H-pyran-2-yl)oxy) propyl)-6-(3-(trifluoromethyl)phenoxy)pyrido[2,3-d]pyrimidine-2,4(1H,3H)-dione (60 mg, 0.106 mmol) in HCOOH (5 mL) was added Zn dust (34.7 mg, 0.53 mmol). The reaction was heated at 50° C. for 2 h, cooled to RT and filtered. The filtrate was concentrated and dried to give 3-(5-isopentyl-1-methyl-2,4-dioxo-6-(3-(trifluoromethyl)phenoxy)-1,2-dihydropyrido[2,3-d]pyrimidin-3(4H)-yl)propyl formate (30 mg, 57.3% yield) as a solid. LCMS: MH$^+$ 494 and T$_R$=2.193 min.

Step 4

3-(3-hydroxypropyl)-5-isopentyl-1-methyl-6-(3-(trifluoromethyl)phenoxy)pyrido[2,3-d]pyrimidine-2,4(1H,3H)-dione

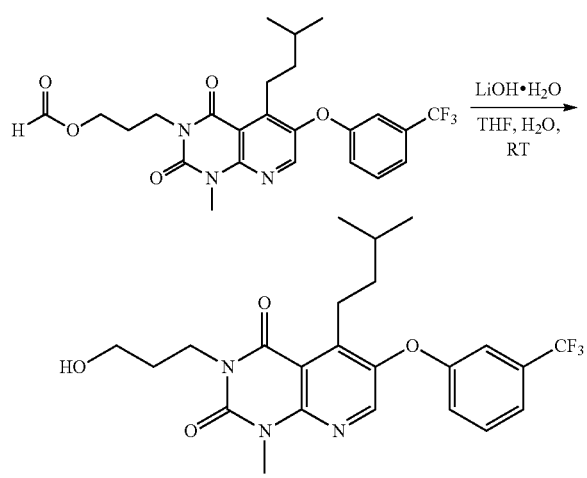

To a solution of 3-(5-isopentyl-1-methyl-2,4-dioxo-6-(3-(trifluoromethyl)phenoxy)-1,2-dihydropyrido[2,3-d]pyrimidin-3(4H)-yl)propyl formate (30 mg, 0.060 mmol) in THF (4 mL) and water (4 mL)) was added LiOH.H$_2$O (5.10 mg, 0.12 mmol). The reaction was stirred at RT for 15 min then diluted with EA (5 mL) and water (5 mL). The organic layer was dried over Na$_2$SO$_4$ and concentrated to a residue which was purified by Prep HPLC to give 3-(3-hydroxypropyl)-5-isopentyl-1-methyl-6-(3-(trifluoromethyl)phenoxy)pyrido[2,3-d]pyrimidine-2,4(1H,3H)-dione (13 mg, 45.9% yield) as a white solid. $^1$H NMR (DMSO-d$_6$) δ: 8.58 (s, 1H), 7.61 (t, J=7.8 Hz, 1H), 7.48 (d, J=7.6 Hz, 1H), 7.26 (d, J=8.6 Hz, 2H), 4.50 (t, J=5.2 Hz, 1H), 4.09-3.93 (m, 2H), 3.58 (s, 3H), 3.48 (q, J=6.3 Hz, 2H), 3.19-3.06 (m, 2H), 1.75 (dd, J=14.0, 6.8 Hz, 2H), 1.51 (dd, J=13.0, 6.6 Hz, 1H), 1.29 (dd, J=15.3, 7.2 Hz, 2H), 0.79 (d, J=6.6 Hz, 6H). LCMS: MH$^+$ 466 and T$_R$=3.373 min.

Compound 47

3-(3-hydroxypropyl)-5-isopentyl-1-methyl-6-(3-(trifluoromethoxy)benzyl)pyrido[2,3-d]pyrimidine-2,4(1H,3H)-dione

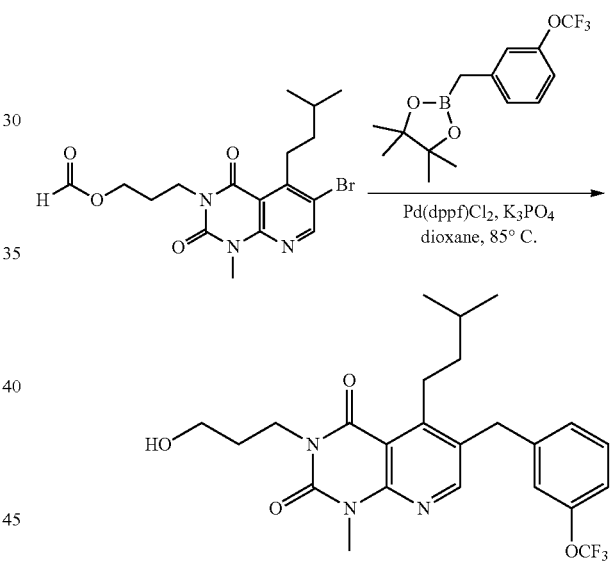

To a solution of 3-(6-bromo-5-isopentyl-1-methyl-2,4-dioxo-1,2-dihydropyrido[2,3-d]pyrimidin-3(4H)-yl)propyl formate (See Compound 48, step 2, 60 mg, 0.144 mmol) in dioxane (4 mL) was added 4,4,5,5-tetramethyl-2-(3-(trifluoromethoxy)benzyl)-1,3,2-dioxaborolane (90 mg, 0.288 mmol), Pd(dppf)Cl$_2$ (10 mg) and aq. 2M K$_3$PO$_4$ (0.8 mL). The reaction was heated at 85° C. for 2 h, cooled to RT and filtered. The filtrate was concentrated, dried to a residue which was purified by Prep HPLC to give 3-(3-hydroxypropyl)-5-isopentyl-1-methyl-6-(3-(trifluoromethoxy)benzyl)pyrido[2,3-d]pyrimidine-2,4(1H,3H)-dione (20 mg, 28.7% yield) as a white solid. $^1$H NMR (DMSO-d$_6$) δ: 8.61 (s, 1H), 7.43 (t, J=7.9 Hz, 1H), 7.19 (dd, J=25.5 and 8.5 Hz, 3H), 4.47 (s, 1H), 4.16 (s, 2H), 4.03-3.89 (m, 2H), 3.57 (s, 3H), 3.45 (dd, J=11.0 and 6.0 Hz, 2H), 3.12 (d, J=6.0 Hz, 2H), 1.81-1.64 (m, 2H), 1.51-1.56 (m, 1H), 1.03 (d, J=9.5 Hz, 2H), 0.81 (d, J=6.6 Hz, 6H). LCMS: MH$^+$ 480 and T$_R$=3.320 min.

Compound 48

6-(3-chlorophenyoxy)-3-(3-hydroxypropyl)-5-isopentyl-1-methylpyrido[2,3-d]pyrimidine-2,4(1H,3H)-dione

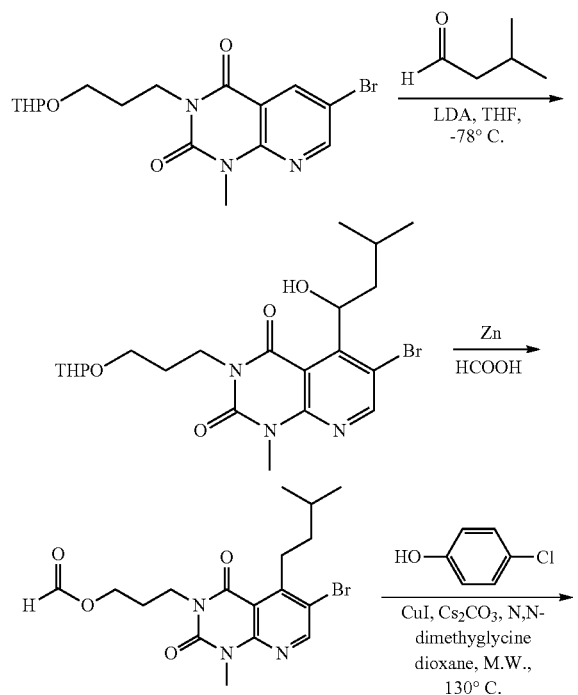

Step 1

6-bromo-5-(1-hydroxy-3-methylbutyl)-1-methyl-3-(3-(tetrahydro-2H-pyran-2-yloxy)propyl)pyrido[2,3-d]pyrimidine-2,4(1H,3H)-dione

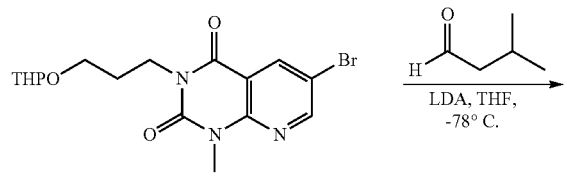

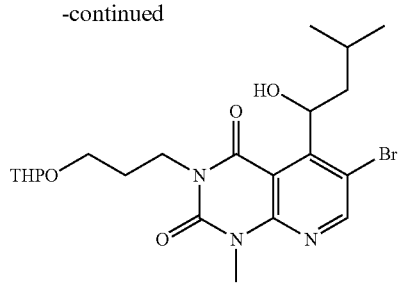

To a solution of 6-bromo-1-methyl-3-(3-(tetrahydro-2H-pyran-2-yloxy)propyl)pyrido[2,3-d]pyrimidine-2,4(1H,3H)-dione (See Compound 20, step 4, 500 mg, 1.26 mmol) in THF (5 mL) at −78° C. was added LDA (2.0 M in THF, 1.13 mL, 2.29 mmol) dropwise. The reaction was stirred at −78° C. for 1 h then a solution of 3-methylbutanal (216 mg, 2.52 mmol) in THF (1 mL) was added dropwise. The reaction was stirred at −78° C. for 1 h, quenched with aq. NH$_4$Cl (10 mL) then diluted with EA (10 mL) and water 10 mL). The organic layer was dried over Na$_2$SO$_4$ and concentrated to a residue which was purified by chromatography eluted with PE/EA (10:1) to give 6-bromo-5-(1-hydroxy-3-methylbutyl)-1-methyl-3-(3-(tetrahydro-2H-pyran-2-yloxy)propyl)pyrido[2,3-d]pyrimidine-2,4(1H,3H)-dione (70 mg, 11.5% yield) as a solid. LCMS: [MH$^+$-THP] and T$_R$=1.739 min.

Step 2

3-(6-bromo-5-isopentyl-1-methyl-2,4-dioxo-1,2-dihydropyrido[2,3-d]pyrimidin-3(4H)-yl)propyl formate

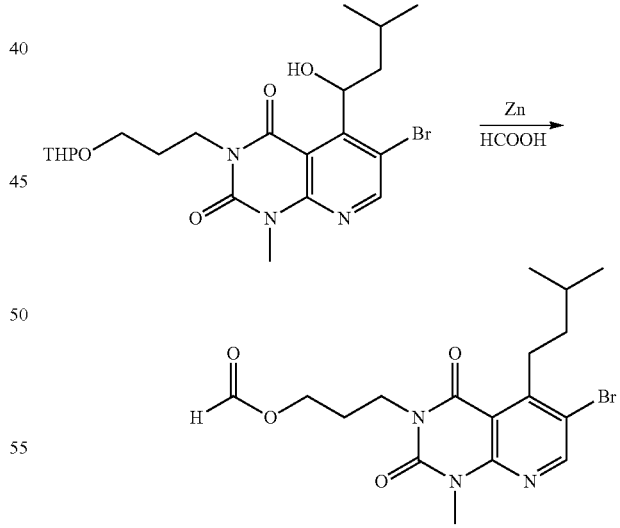

To a solution of 6-bromo-5-(1-hydroxy-3-methylbutyl)-1-methyl-3-(3-(tetrahydro-2H-pyran-2-yloxy)propyl)pyrido[2,3-d]pyrimidine-2,4(1H,3H)-dione (85 mg, 0.175 mmol) in HCOOH (1 mL) was added Zn dust (57 mg, 0.877 mmol). The reaction was heated at 50° C. for 2 h then cooled to RT and filtered. The filtrate was concentrated to give 3-(6-bromo-5-isopentyl-1-methyl-2,4-dioxo-1,2-dihydropyrido[2,3-d]pyrimidin-3(4H)-yl)propyl formate (40 mg, 47.0% yield) as a white solid. LCMS: MH⁺ 412 and $T_R$=2.076 min. Used without further purification.

Step 3

6-(3-chlorophenoxy)-5-(4-fluorobenzyl)-3-(3-hydroxypropyl)-1-methylpyrido[2,3-d]pyrimidine-2,4(1H,3H)-dione

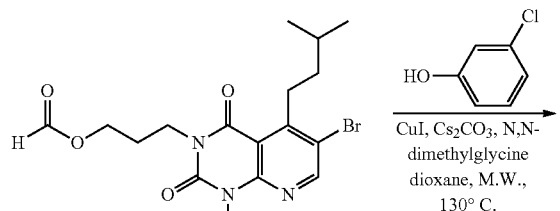

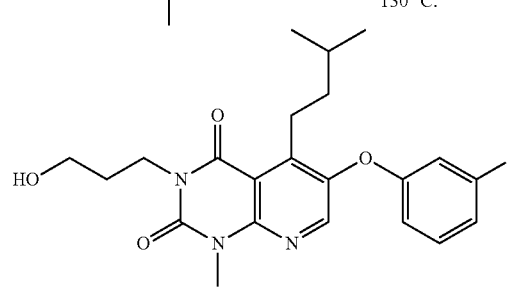

To a solution of 3-(6-bromo-5-isopentyl-1-methyl-2,4-dioxo-1,2-dihydropyrido[2,3-d]pyrimidin-3(4H)-yl)propyl formate (42 mg, 0.109 mmol) in dioxane (2 mL) was added 3-chlorophenol (28 mg, 0.218 mmol), CuI (6 mg, 0.0327 mmol), Cs₂CO₃ (71 mg, 0.218 mmol) and 3-(dimethylamino)propanoic acid (3 mg, 0.0327 mmol). The reaction was stirred at 130° C. (MW) for 2 h, cooled to RT then diluted with DCM (10 mL) and water (10 mL). The organic layer was dried over Na₂SO₄, and concentrated to a residue which was purified by Prep HPLC to give 6-(3-chlorophenoxy)-3-(3-hydroxypropyl)-5-isopentyl-1-methylpyrido[2,3-d]pyrimidine-2,4(1H,3H)-dione (8 mg, 15.5% yield) as a white solid. ¹H NMR (DMSO-d₆) δ: 8.57 (s, 1H), 7.39 (t, J=8.4 Hz, 1H), 7.17 (d, J=9.2 Hz, 1H), 7.02-7.00 (m, 1H), 6.93 (dd, J=8.0, 2.4 Hz, 1H), 4.50 (t, J=5.2 Hz, 1H), 4.00 (t, J=7.2 Hz, 2H), 3.58 (s, 3H), 3.45-3.50 (m, 2H), 3.15-3.10 (m, 2H), 1.77-1.72 (m, 2H), 1.57-1.52 (m, 1H), 1.23-1.34 (m, 2H), 0.82 (d, J=6.8 Hz, 6H). LCMS: MH⁺ 432 and $T_R$=3.366 min.

Compound 49

3-(3-hydroxypropyl)-5-isopentyl-1-methyl-6-(3-(trifluoromethoxy)phenoxy)pyrido[2,3-d]pyrimidine-2,4(1H,3H)-dione

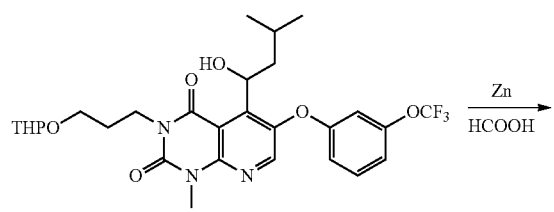

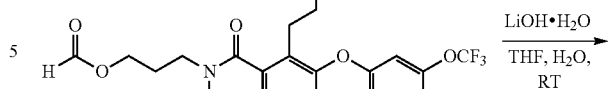

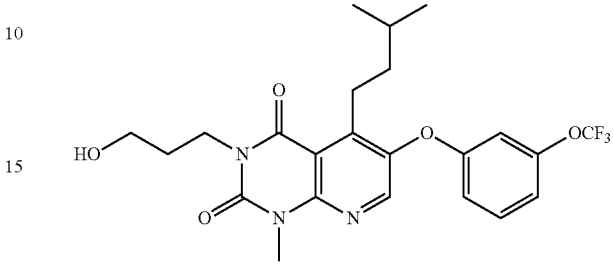

Step 1

5-(1-hydroxy-3-methylbutyl)-1-methyl-3(3-((tetrahydro-2H-pyran-2-yl)oxy)propyl)-6-(3-(trifluoromethoxyphenoxy)pyrido[2,3-d]pyrimidine-2,4(1H,3H)-dione

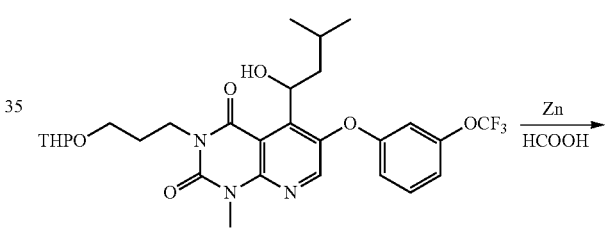

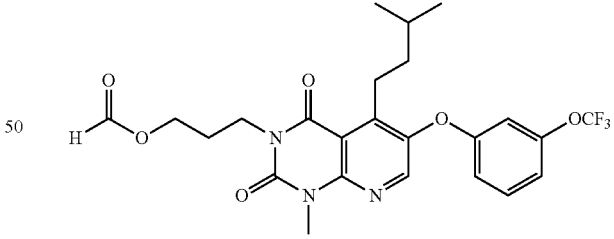

To a solution of 5-(1-hydroxy-3-methylbutyl)-1-methyl-3-(3-((tetrahydro-2H-pyran-2-yl)oxy) propyl)-6-(3-(trifluoromethoxy)phenoxy)pyrido[2,3-d]pyrimidine-2,4(1H,3H)-dione (See Compound 46, step 2, 60 mg, 0.103 mmol) in HCOOH (4 mL) was added Zn dust (34 mg, 0.515 mmol). The reaction was heated at 100° C. for 3 h, cooled to RT and filtered. The filtrate was concentrated and dried to give 3-(5-isopentyl-1-methyl-2,4-dioxo-6-(3-(trifluoromethoxy) phenoxy)-1,2-dihydropyrido[2,3-d]pyrimidin-3(4H)-yl)propyl formate (50 mg, 96.1% yield) as a solid. LCMS: MH⁺ 510 and $T_R$=2.446 min. Used without further purification.

Step 2

3-(3-hydroxypropyl)-5-isopentyl-1-methyl-6-(3-(trifluoromethoxy)phenoxy)pyrido[2,3-d]pyrimidine-2,4(1H,3H)-dione

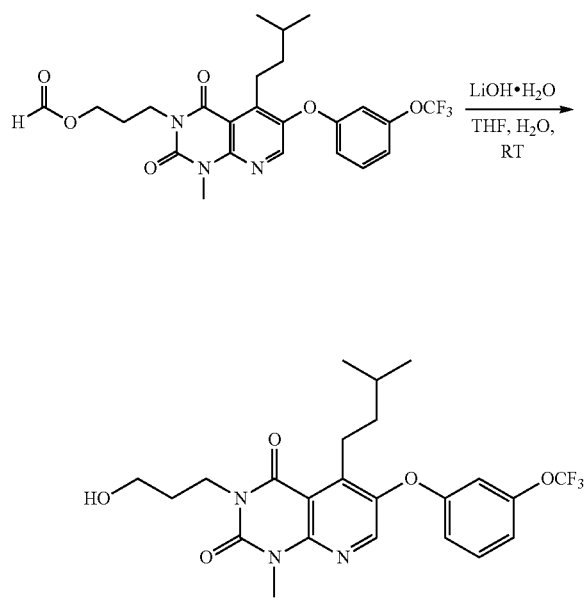

To a solution of 3-(5-isopentyl-1-methyl-2,4-dioxo-6-(3-(trifluoromethoxy)phenoxy)-1,2-dihydro pyrido[2,3-d]pyrimidin-3(4H)-yl)propyl formate (50 mg, 0.098 mmol) in THF (2 mL) and water (2 mL was added LiOH.H$_2$O (8.2 mg, 0.196 mmol). The reaction was stirred at RT for 30 min then diluted with EA (10 mL) and water (10 mL). The organic layer was dried over Na$_2$SO$_4$ and concentrated to a residue which was purified by Prep HPLC to give 3-(3-hydroxypropyl)-5-isopentyl-1-methyl-6-(3-(trifluoromethoxy)phenoxy)pyrido[2,3-d]pyrimidine-2,4(1H,3H)-dione (10 mg, 20.0% yield) as a white solid. $^1$H NMR (DMSO-d$_6$) δ: 8.57 (s, 1H), 7.49 (t, J=8.8 Hz, 1H), 7.11 (d, J=8.0 Hz, 1H), 6.98-6.95 (m, 2H), 4.51 (t, J=5.6 Hz, 1H), 4.02-3.97 (m, 2H), 3.58 (s, 3H), 3.50-3.45 (m, 2H), 3.15-3.10 (m, 2H), 1.77-1.70 (m, 2H), 1.54-1.50 (m, 1H), 1.32-1.23 (m, 2H), 0.79 (d, J=6.8 Hz, 6H). LCMS: MH$^+$ 482 and T$_R$=3.447 min.

INCORPORATION BY REFERENCE

All publications and patents mentioned herein, are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:
1. A compound of Formula (I):

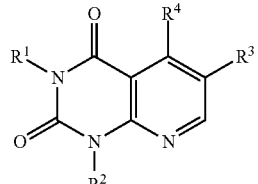

Formula (I)

or a pharmaceutically acceptable salt thereof, wherein:
R$^1$ is C$_2$-C$_{10}$ hydroxyalkyl, wherein one or more carbon atom of the alkyl portion of the hydroxylalkyl group is optionally substituted with 1-3 R$^6$;
R$^2$ is H, C$_1$-C$_6$ alkyl, C$_1$-C$_6$ hydroxyalkyl, C$_3$-C$_{10}$ cycloalkyl, C$_2$-C$_6$ alkenyl, C$_2$-C$_6$ alkynyl, or C$_1$-C$_6$ alkoxy;
R$^3$ is C$_1$-C$_6$ alkyl, C$_2$-C$_6$ alkenyl, C$_2$-C$_6$ alkynyl, C$_1$-C$_6$ acyl, C$_3$-C$_{10}$ cycloalkyl, C$_1$-C$_6$ alkoxy, C$_4$-C$_{10}$ cycloalkyloxy, halo, hydroxyl, alkylthio, thionyl, sulfonyl, sulfonamidyl, C$_6$-C$_{12}$ aryl, 5-14-membered heteroaryl, C$_6$-C$_{12}$ aryl-C$_1$-C$_6$ alkyl, 5-14-membered heteroaryl-C$_1$-C$_6$ alkyl, C$_6$-C$_{12}$ aryloxy, —O—C$_6$-C$_{12}$ aryl-C$_1$-C$_6$ alkyl, —O—C$_1$-C$_6$ alkyl-C$_6$-C$_{12}$ aryl, 5-14-membered heteroaryloxy, 3-18-membered heterocycloalkyl, amino, C$_1$-C$_6$ alkylamino, C$_2$-C$_{12}$ dialkylamino, —C(O)NH—R$^5$, —C(O)N—C$_1$-C$_6$ alkyl-R$^5$, —NHC(O)—R$^5$, —N—(C$_1$-C$_6$ alkyl)C(O)—R$^5$, urea, sulfonylurea, nitro, or cyano, wherein each alkyl, alkenyl, alkynyl, acyl, cycloalkyl, alkoxy, cycloalkyloxy, alkylthio, aryl, heteroaryl, aryloxy, heteroaryloxy, and heterocycloalkyl represented by R$^3$ is optionally and independently substituted with 1-5 R$^5$;
R$^4$ is C$_1$-C$_6$ alkyl, C$_1$-C$_6$ acyl, C$_3$-C$_{10}$ cycloalkyl, C$_1$-C$_6$ alkoxy, C$_4$-C$_{10}$ cycloalkyloxy, halo, hydroxyl, alkylthio, thionyl, sulfonyl, sulfonamidyl, C$_6$-C$_{12}$ aryl, 5-14-membered heteroaryl, C$_6$-C$_{12}$ aryl-C$_1$-C$_6$ alkyl, 5-14-membered heteroaryl-C$_1$-C$_6$ alkyl, C$_6$-C$_{12}$ aryloxy, —O—C$_6$-C$_{12}$ aryl-C$_1$-C$_6$ alkyl, —O—C$_1$-C$_6$ alkyl-C$_6$-C$_{12}$ aryl, 5-14-membered heteroaryl-C$_1$-C$_6$ alkyl, 5-14-membered heteroaryloxy, 3-18-membered heterocycloalkyl, amino, C$_1$-C$_6$ alkylamino, C$_2$-C$_{12}$ dialkylamino, —C(O)NH—R$^5$, —C(O)N—(C$_1$-C$_6$ alkyl)-R$^5$, —NHC(O)—R$^5$, —N—(C$_1$-C$_6$ alkyl)-C(O)—R$^5$, urea, sulfonylurea, nitro, or cyano, wherein each alkyl, acyl, cycloalkyl, alkoxy, cycloalkyloxy, alkylthio, aryl, heteroaryl, aryloxy, heteroaryloxy, and heterocycloalkyl represented by R$^4$ is optionally and independently substituted with 1-5 R$^5$;
each R$^5$ is independently C$_1$-C$_6$ alkyl, C$_2$-C$_6$ alkenyl, C$_2$-C$_6$ alkynyl, C$_1$-C$_6$ acyl, C$_1$-C$_6$ alkoxy, C$_4$-C$_{10}$ cycloalkyloxy, halo, hydroxy, amino, C$_6$-C$_{12}$ aryl, 5-14-membered heteroaryl, C$_6$-C$_{12}$ aryl-C$_1$-C$_6$ alkyl, C$_6$-C$_{12}$ aryloxy, O—C$_6$-C$_{12}$ aryl-C$_1$-C$_6$ alkyl, —O—C$_1$-C$_6$ alkyl-C$_6$-C$_{12}$ aryl, or 5-14-membered heteroaryloxy, wherein each alkyl, alkenyl, alkynyl, acyl, alkoxy, cycloalkyloxy, aryl, heteroaryl, aryloxy, and heteroaryloxy represented by R$^5$ is optionally and independently substituted with 1-5 R$^6$; and
each R$^6$ is independently C$_1$-C$_6$ alkyl, C$_1$-C$_6$ alkoxy, C$_3$-C$_{10}$ cycloalkyl, halo, C$_1$-C$_6$ haloalkyl, C$_1$-C$_6$haloalkoxy, hydroxyl, amino, C$_1$-C$_6$ alkylamino, C$_2$-C$_{12}$ dialkylamino, cyano, nitro, —C(O)NH$_2$, —C(O)NH—($C_1$-$C_6$ alkyl), —NHC(O)—($C_1$-$C_6$alkyl), —N—($C_1$-$C_6$ alkyl)-C(O)—($C_1$-$C_6$alkyl), —C(O)O—$C_1$-$C_6$ alkyl, —C(O)OH, —C(O)—$C_1$-$C_6$ alkyl, nitro, or cyano.

2. A compound according to claim 1, wherein $R^1$ is an unsubstituted 3-hydroxypropyl; or a pharmaceutically acceptable salt thereof.

3. A compound according to claim 1, wherein $R^2$ is $C_1$-$C_4$ alkyl.

4. A compound according to claim 1, wherein $R^2$ is methyl.

5. A compound according to claim 1, wherein $R^3$ is $C_1$-$C_4$ alkoxy, aryl-$C_2$alkoxy, aryl-$C_2$alkyl, or aryl, the latter three groups optionally substituted with one or more halogens, —$CF_3$, —$OCF_3$.

6. A compound according to claim 1, wherein $R^3$ is, propyloxy, methoxypyridine, phenoxy, propyloxy, phenyl or benzyl, the latter five groups optionally substituted with one or more halogens, —$CF_3$, —$OCF_3$.

7. A compound according to claim 1, wherein $R^3$ is

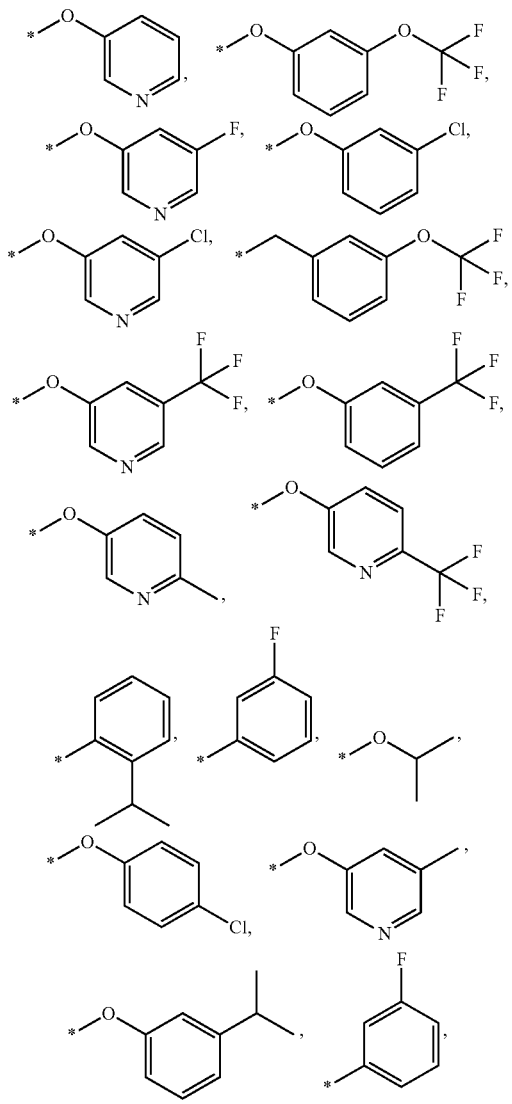

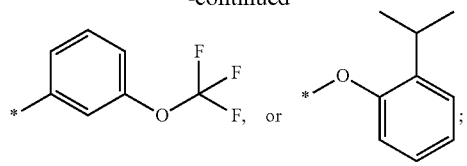

or a pharmaceutically acceptable salt thereof.

8. A compound according to claim 1, wherein $R^4$ is $C_2$-$C_6$ alkyl, $C_2$-$C_6$ alkoxy, aryl-$C_2$-$C_4$-alkoxy or aryl-$C_2$-$C_4$-alkyl, the latter two groups optionally substituted one or more halogens or —$CF_3$.

9. A compound according to claim 1, wherein $R^4$ is $C_5$ alkyl, $C_5$ alkoxy, benzyl, phenoxy, or ethylpyridine, the latter three groups optionally substituted with one or more halogens or —$CF_3$.

10. A compound according to claim 1, wherein $R^4$ is chlorobenzyl, methylpentane, methylpentanol, chlorophenylethanol, or fluorobenzyl, trifluoromethylbenzyl, trifluoromethyl-3-ethylpyridine.

11. A compound according to claim 1, wherein $R^4$ is

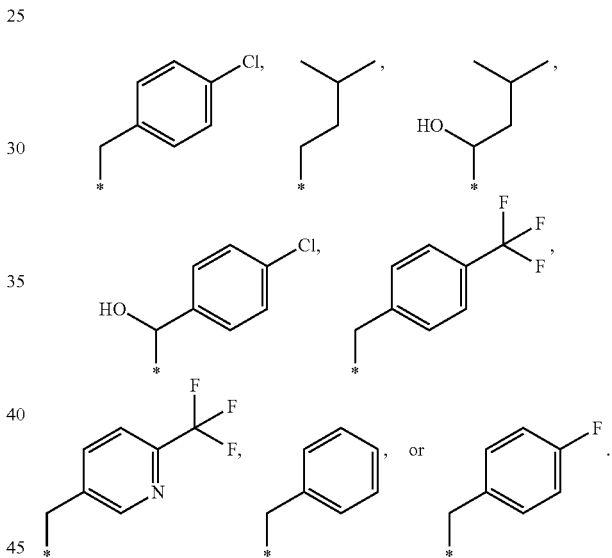

12. The compound according to claim 1, wherein:
$R^1$ is 3-hydroxypropyl;
$R^2$ is methyl;
$R^3$ is

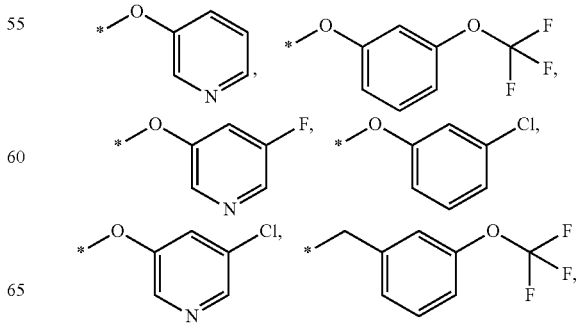

161
-continued
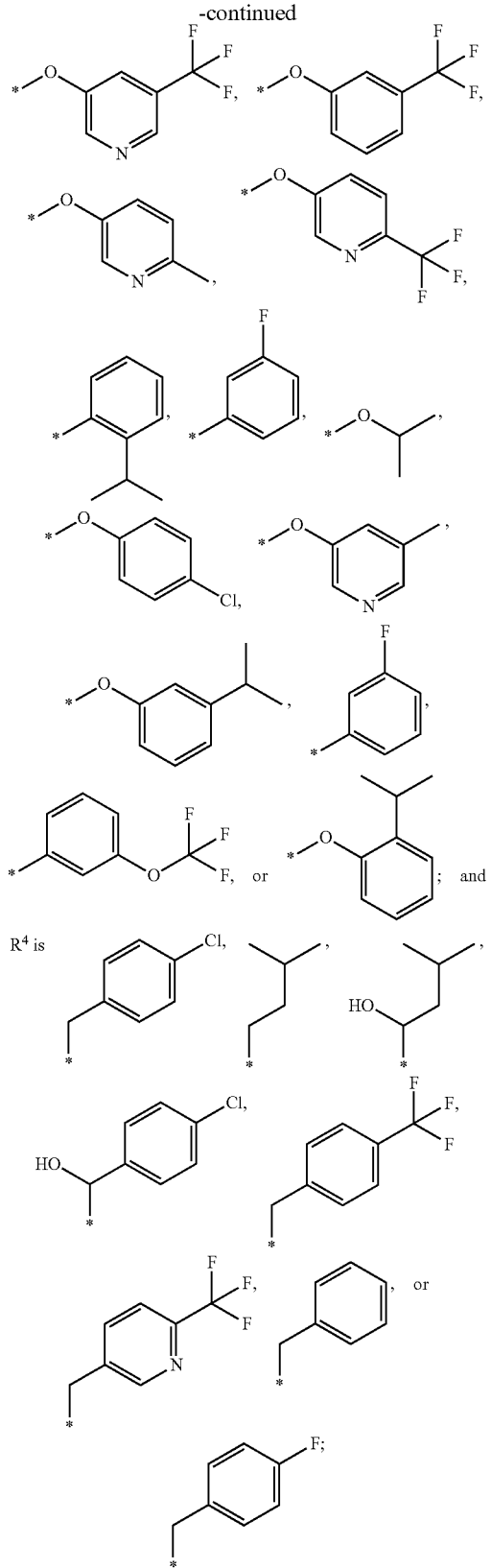
R⁴ is
or a pharmaceutically acceptable salt thereof.
13. The compound according to claim 1, wherein the compound is selected from the group consisting of:
162
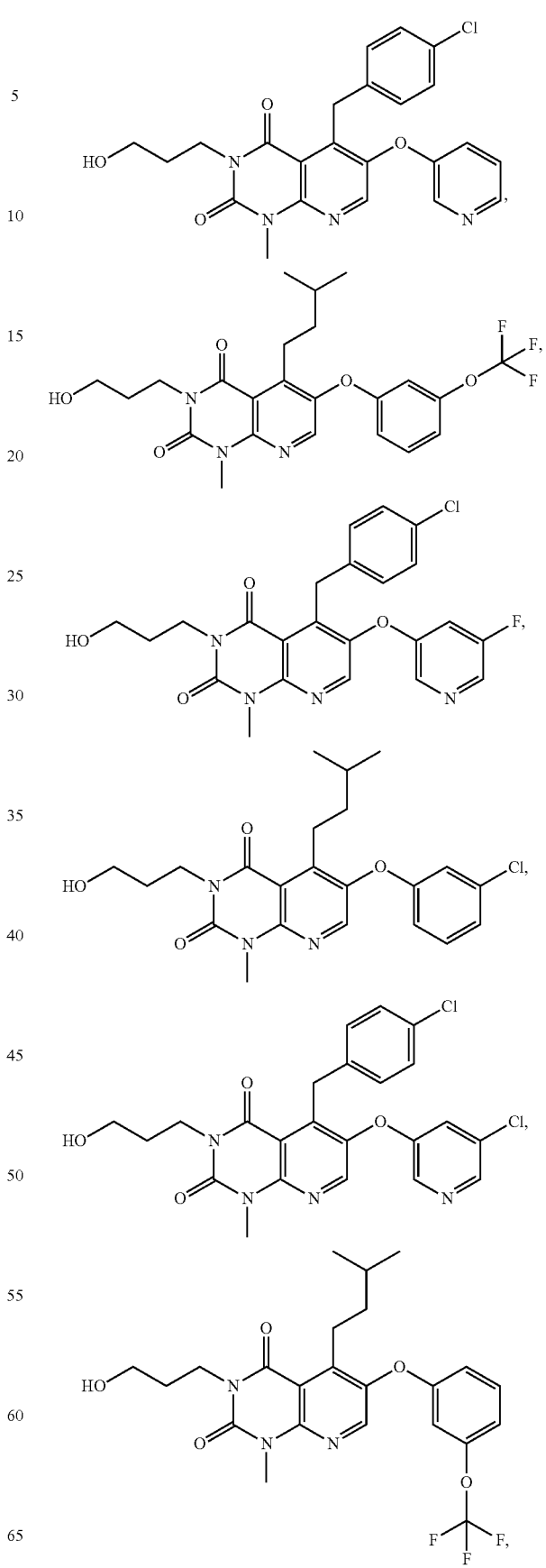

163
-continued
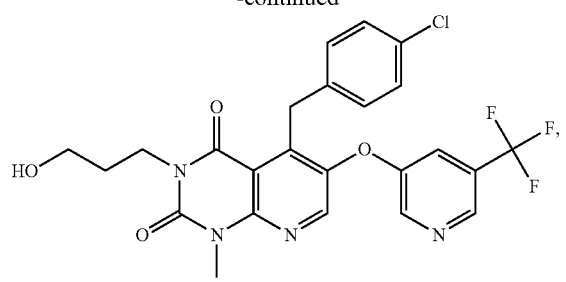
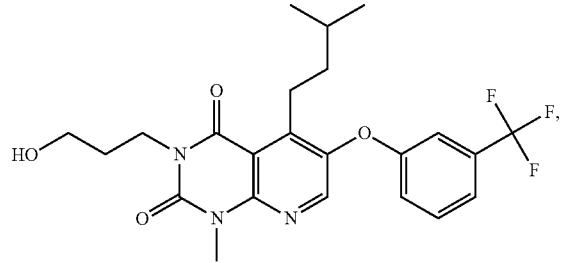
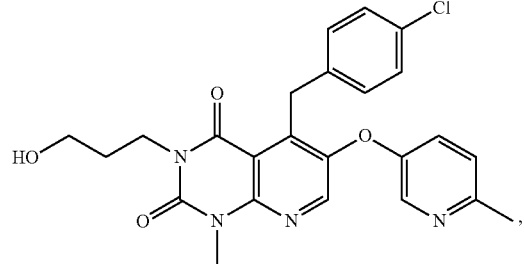
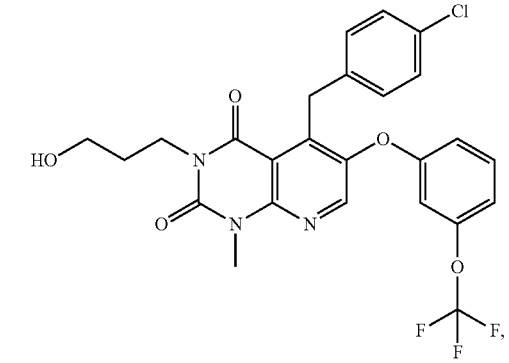
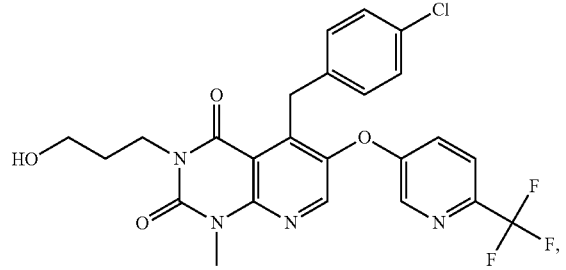
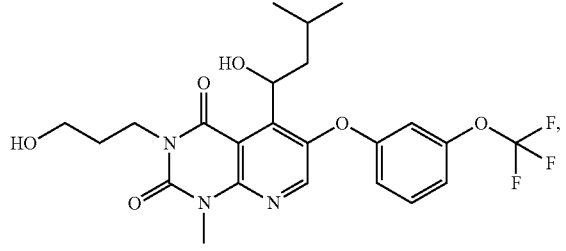
164
-continued
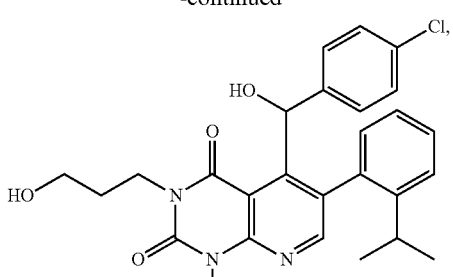
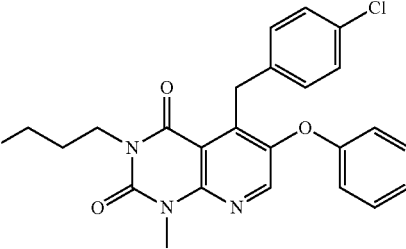
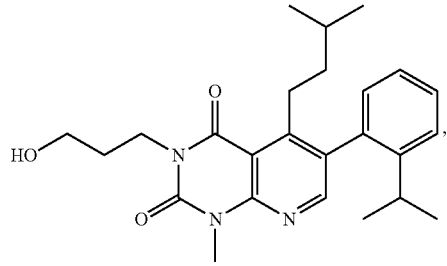
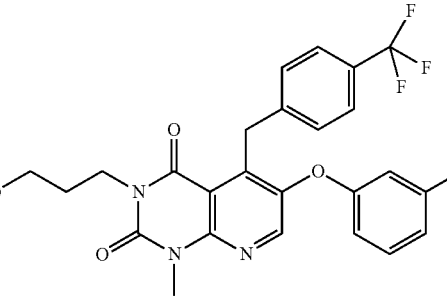
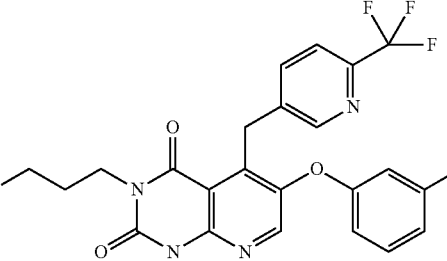
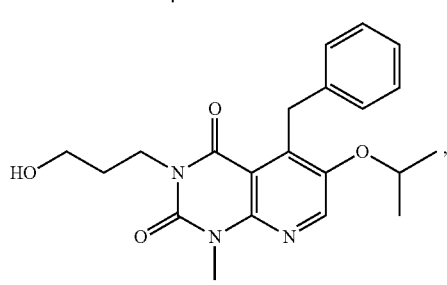

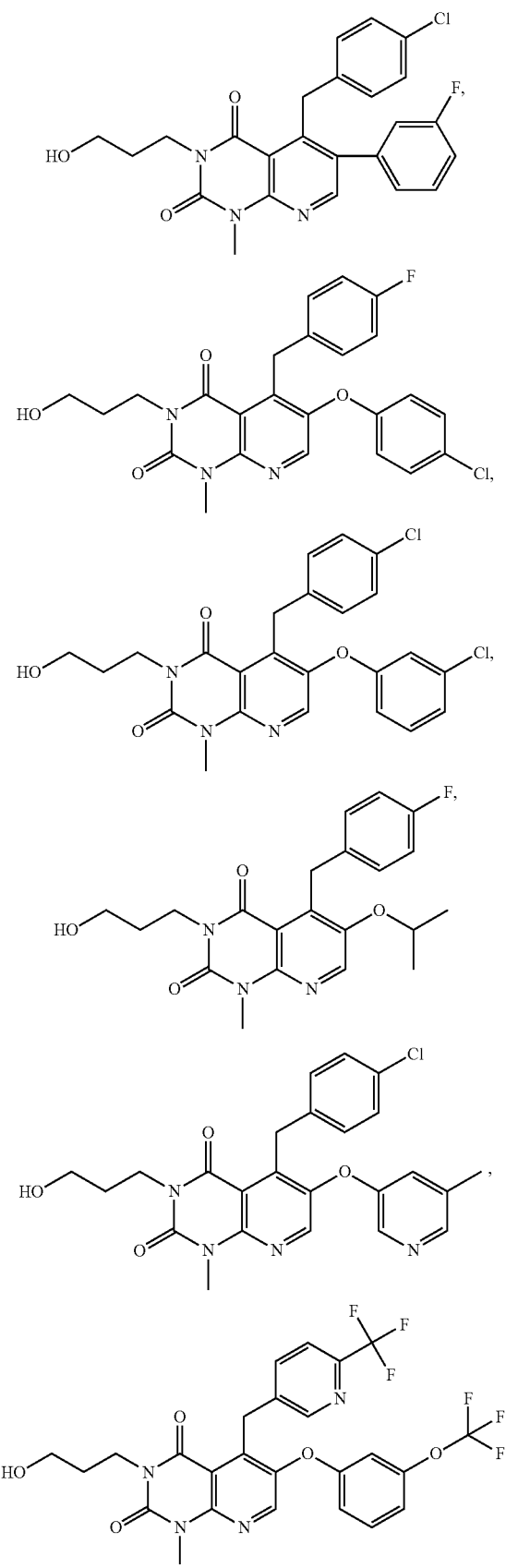
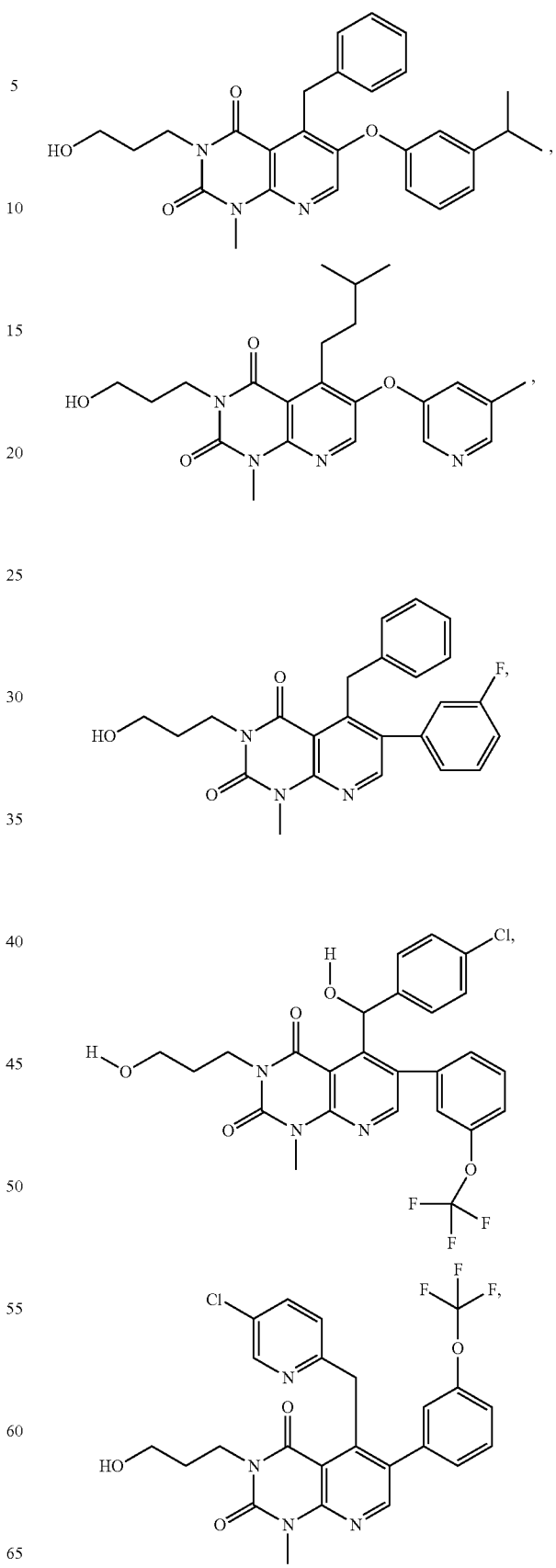

-continued

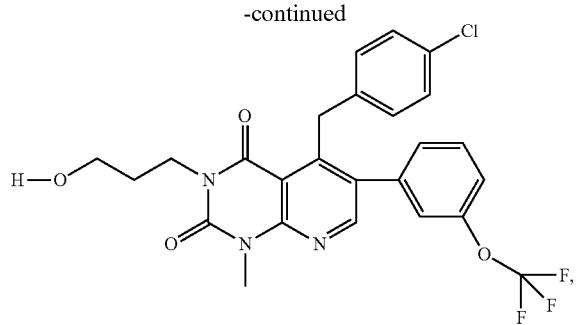

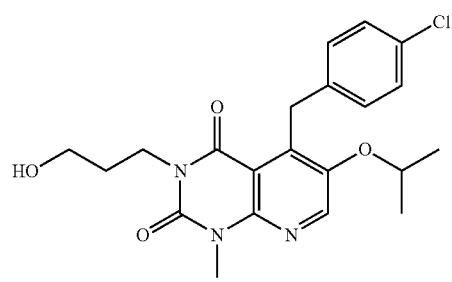

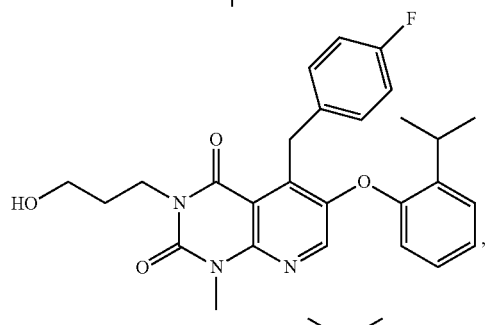

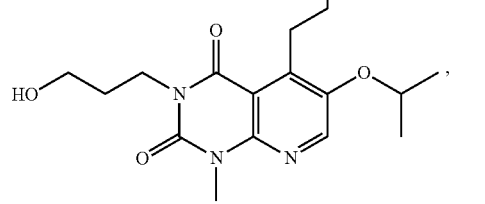

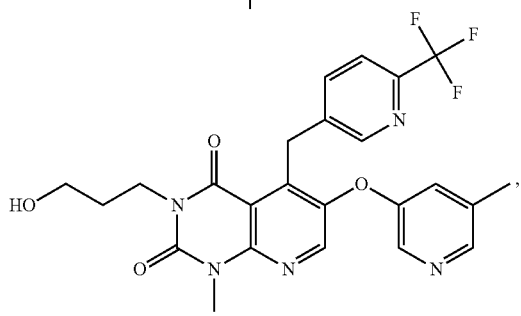

-continued

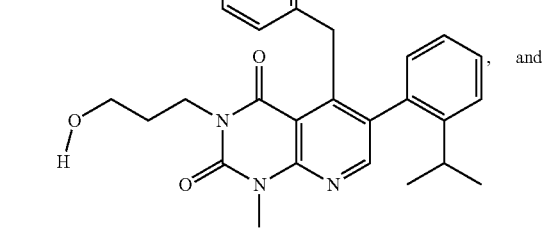

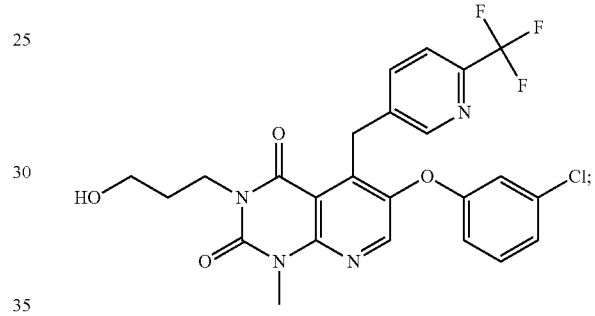

or a pharmaceutically acceptable salt thereof.

14. A pharmaceutical composition comprising at least one compound according to claim 1, or a pharmaceutically acceptable salt thereof, in a mixture with a pharmaceutically acceptable excipient, diluent or carrier.

15. A method of inhibiting TRPC5 comprising contacting a cell with the compound according to claim 1, or a pharmaceutically acceptable salt thereof.

16. A method of treating a TRCP5 mediated disorder in a subject in need thereof, comprising administering to the subject an effective amount of the compound according to claim 1, or a pharmaceutically acceptable salt thereof, wherein the TRPC5 mediated disorder is selected from the group consisting of: depression, anxiety disorders, Alzheimers disease, Parkinson s disease, Huntingtons disease, ALS, proteinuric kidney disease and seizure disorder.

* * * * *